US008877508B2

(12) United States Patent
Hyde et al.

(10) Patent No.: US 8,877,508 B2
(45) Date of Patent: *Nov. 4, 2014

(54) DEVICES AND SYSTEMS THAT DELIVER NITRIC OXIDE

(75) Inventors: Roderick A. Hyde, Redmond, WA (US); Muriel Y. Ishikawa, Livermore, CA (US); Leif T. Stordal, Isaquah, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1513 days.

This patent is subject to a terminal disclaimer.

(21) Appl. No.: 12/148,283

(22) Filed: Apr. 16, 2008

(65) Prior Publication Data
US 2009/0108777 A1      Apr. 30, 2009

Related U.S. Application Data

(63) Continuation-in-part of application No. 12/005,065, filed on Dec. 21, 2007, now Pat. No. 7,862,598, and a continuation-in-part of application No. 12/005,045, filed on Dec. 21, 2007, and a continuation-in-part of application No. 12/005,132, filed on Dec. 21, 2007, now Pat. No. 7,897,399, and a continuation-in-part of application No. 12/005,136, filed on Dec. 21, 2007, and a continuation-in-part of application No. 12/005,170, filed on Dec. 21, 2007, now Pat. No. 7,975,699, and a continuation-in-part of application No. 11/981,743, filed on Oct. 30, 2007, now Pat. No. 8,642,093, and a continuation-in-part of application No. 11/998,864, filed on Nov. 30, 2007, now Pat. No. 8,221,690.

(51) Int. Cl.
*B01J 19/00*  (2006.01)
*A61K 33/00*  (2006.01)
*A61K 9/70*  (2006.01)
*A61K 41/00*  (2006.01)

(52) U.S. Cl.
CPC .............. *A61K 33/00* (2013.01); *A61K 9/7084* (2013.01); *A61K 41/0042* (2013.01)
USPC ................................ 436/55; 424/423; 607/88

(58) Field of Classification Search
USPC ........ 607/88; 424/423–426; 422/186; 436/55
See application file for complete search history.

(56) References Cited

U.S. PATENT DOCUMENTS 3,918,967 A * 11/1975 Krohn et al. ................... 430/40
4,162,536 A    7/1979 Morley
4,210,697 A    7/1980 Adiletta
(Continued)

FOREIGN PATENT DOCUMENTS

DE    20115123 U1   6/2001
EP    1 704 877 A1   9/2006
(Continued)

OTHER PUBLICATIONS

U.S. Appl. No. 12/928,029, Hyde et al.
(Continued)

*Primary Examiner* — Tung X Le

(57) ABSTRACT

The present disclosure relates to dressings, such as patches and bandages, and other devices and systems that deliver nitric oxide.

40 Claims, 47 Drawing Sheets

(56) References Cited

U.S. PATENT DOCUMENTS

| | | | |
|---|---|---|---|
| 4,248,214 A | 2/1981 | Hannah et al. |
| 4,561,429 A | 12/1985 | Sato et al. |
| 4,611,594 A | 9/1986 | Grayhack et al. |
| 4,919,149 A | 4/1990 | Stang |
| 5,109,871 A | 5/1992 | Thornton |
| 5,279,294 A | 1/1994 | Anderson et al. |
| 5,351,698 A | 10/1994 | Wheeler et al. |
| 5,366,997 A | 11/1994 | Keefer et al. |
| 5,374,710 A | 12/1994 | Tsien et al. |
| 5,405,919 A | 4/1995 | Keefer et al. |
| 5,495,961 A | 3/1996 | Maestre |
| 5,530,263 A | 6/1996 | DiVincenzo |
| 5,567,302 A * | 10/1996 | Song et al. ................. 205/777.5 |
| 5,571,152 A | 11/1996 | Chen et al. |
| 5,580,433 A | 12/1996 | Baker et al. |
| 5,582,170 A | 12/1996 | Soller |
| 5,665,077 A | 9/1997 | Rosen et al. |
| 5,676,963 A | 10/1997 | Keefer et al. |
| 5,683,668 A | 11/1997 | Hrabie et al. |
| 5,690,777 A | 11/1997 | Kuethe et al. |
| 5,692,520 A | 12/1997 | Lavoisier |
| 5,736,152 A | 4/1998 | Dunn |
| 5,741,815 A | 4/1998 | Lai |
| 5,765,558 A | 6/1998 | Psaros et al. |
| 5,814,666 A | 9/1998 | Green et al. |
| 5,858,799 A | 1/1999 | Yee et al. |
| 5,900,433 A | 5/1999 | Igo et al. |
| 5,910,316 A | 6/1999 | Keefer et al. |
| 5,943,160 A | 8/1999 | Downing |
| 5,956,172 A | 9/1999 | Downing |
| 5,980,705 A | 11/1999 | Allen et al. |
| 5,994,444 A | 11/1999 | Trescony et al. |
| 6,000,398 A | 12/1999 | Alla et al. |
| 6,037,346 A | 3/2000 | Doherty, Jr. et al. |
| 6,080,110 A | 6/2000 | Thorgersen |
| 6,100,096 A | 8/2000 | Bollinger et al. |
| 6,103,765 A | 8/2000 | Neal |
| 6,127,363 A | 10/2000 | Doherty, Jr. et al. |
| 6,143,314 A | 11/2000 | Chandrashekar et al. |
| 6,149,606 A | 11/2000 | Alving et al. |
| 6,156,753 A | 12/2000 | Doherty, Jr. et al. |
| 6,182,661 B1 | 2/2001 | Solanki et al. |
| 6,190,704 B1 | 2/2001 | Murrell |
| 6,223,747 B1 | 5/2001 | Rudge et al. |
| 6,241,752 B1 | 6/2001 | Sheinman et al. |
| 6,265,420 B1 | 7/2001 | Lai |
| 6,280,604 B1 | 8/2001 | Allen et al. |
| 6,287,601 B1 | 9/2001 | Russell |
| 6,306,609 B1 | 10/2001 | Lai |
| 6,308,708 B2 | 10/2001 | Strauss et al. |
| 6,321,751 B1 | 11/2001 | Strauss et al. |
| 6,327,074 B1 | 12/2001 | Bass et al. |
| 6,341,607 B1 | 1/2002 | Couvreur |
| 6,369,071 B1 | 4/2002 | Haj-Yehia |
| 6,432,077 B1 | 8/2002 | Stenzler |
| 6,436,470 B1 | 8/2002 | Iacocca et al. |
| 6,440,498 B2 | 8/2002 | Schaller |
| 6,443,978 B1 | 9/2002 | Zharov |
| 6,451,337 B1 | 9/2002 | Smith et al. |
| 6,469,051 B2 | 10/2002 | Nagano et al. |
| 6,559,184 B2 | 5/2003 | Neal |
| 6,621,687 B2 | 9/2003 | Lewis, Jr. et al. |
| 6,635,273 B1 | 10/2003 | Loscalzo et al. |
| 6,635,415 B1 | 10/2003 | Bollinger et al. |
| 6,636,652 B1 | 10/2003 | Kopelman et al. |
| 6,639,007 B2 | 10/2003 | Plamthottam |
| 6,651,667 B2 | 11/2003 | Osterberg |
| 6,673,338 B1 | 1/2004 | Arnold et al. |
| 6,673,871 B2 | 1/2004 | Warneke et al. |
| 6,682,863 B2 * | 1/2004 | Rivers et al. ................. 430/22 |
| 6,696,072 B1 | 2/2004 | Podolski |
| 6,706,274 B2 | 3/2004 | Herrmann et al. |
| 6,743,249 B1 | 6/2004 | Alden |
| 6,747,062 B2 | 6/2004 | Murrell |
| 6,773,714 B2 | 8/2004 | Dunn et al. |
| 6,812,500 B2 | 11/2004 | Reeh et al. |
| 6,818,356 B1 | 11/2004 | Bates |
| 6,840,244 B2 | 1/2005 | Kemp |
| 6,841,166 B1 | 1/2005 | Zhang et al. |
| 6,900,891 B2 | 5/2005 | Kopelman et al. |
| 6,943,166 B1 | 9/2005 | Pullman et al. |
| 6,969,507 B2 | 11/2005 | Weiskoff et al. |
| 6,983,751 B2 | 1/2006 | Osterberg |
| 6,994,934 B2 | 2/2006 | Stanish et al. |
| 7,052,711 B2 | 5/2006 | West et al. |
| 7,088,040 B1 | 8/2006 | Ducharme et al. |
| 7,105,502 B2 | 9/2006 | Arnold et al. |
| 7,105,607 B2 | 9/2006 | Chen |
| 7,122,046 B2 | 10/2006 | Augustine et al. |
| 7,122,529 B2 | 10/2006 | Ruane et al. |
| 7,144,655 B2 | 12/2006 | Jenson et al. |
| 7,181,174 B2 | 2/2007 | Fitzgibbon et al. |
| 7,181,261 B2 | 2/2007 | Silver et al. |
| 7,183,001 B1 | 2/2007 | Ederle et al. |
| 7,189,471 B2 | 3/2007 | Jankowksi et al. |
| 7,194,801 B2 | 3/2007 | Jenson et al. |
| 7,206,605 B2 | 4/2007 | Hattori |
| 7,210,817 B2 | 5/2007 | Lee et al. |
| 7,215,687 B2 | 5/2007 | Kawai et al. |
| 7,215,887 B2 | 5/2007 | Ternullo et al. |
| 7,217,882 B2 | 5/2007 | Walukiewicz et al. |
| 7,218,900 B2 | 5/2007 | Suzuki |
| 7,220,258 B2 | 5/2007 | Myhr |
| 7,227,956 B1 | 6/2007 | Onishi |
| 7,235,189 B2 | 6/2007 | Höhn et al. |
| 7,235,361 B2 | 6/2007 | Bawendi et al. |
| 7,235,505 B2 | 6/2007 | Gromelski et al. |
| 7,236,595 B1 | 6/2007 | Bean et al. |
| 7,238,628 B2 | 7/2007 | Demaray et al. |
| 7,245,894 B2 | 7/2007 | Sekiguchi et al. |
| RE39,785 E | 8/2007 | Fuse |
| 7,253,953 B2 | 8/2007 | Browning |
| 7,254,160 B2 | 8/2007 | Kawamoto et al. |
| 7,256,923 B2 | 8/2007 | Liu et al. |
| 7,257,327 B2 | 8/2007 | Small |
| 7,260,155 B2 | 8/2007 | Stonick et al. |
| 7,260,402 B1 | 8/2007 | Ahmed |
| 7,260,764 B2 | 8/2007 | Chen |
| 7,260,768 B1 | 8/2007 | Matsumoto et al. |
| 7,261,693 B2 | 8/2007 | Wilcox et al. |
| 7,264,602 B1 | 9/2007 | Longsworth |
| 7,273,567 B1 | 9/2007 | Wellinghoff et al. |
| 7,280,811 B2 | 10/2007 | Sugiyama et al. |
| 7,283,710 B2 | 10/2007 | Sano et al. |
| 7,294,678 B2 | 11/2007 | McGlothlin et al. |
| 7,294,779 B2 | 11/2007 | Watabe et al. |
| 7,295,737 B2 | 11/2007 | Moorjani et al. |
| 7,295,741 B2 | 11/2007 | Sako et al. |
| 7,298,605 B2 | 11/2007 | Itoh et al. |
| 7,298,977 B2 | 11/2007 | Ohsawa et al. |
| 7,301,751 B2 | 11/2007 | Lee et al. |
| 7,301,754 B1 | 11/2007 | Knowles |
| 7,303,333 B2 | 12/2007 | Yu |
| 7,418,399 B2 | 8/2008 | Schaeffer et al. |
| 7,449,595 B2 | 11/2008 | Garvey et al. |
| 7,582,623 B2 | 9/2009 | Mascharak |
| 7,603,166 B2 | 10/2009 | Casscells, III et al. |
| 7,829,553 B2 | 11/2010 | Arnold et al. |
| 7,899,539 B2 | 3/2011 | Whitehurst et al. |
| 2001/0007080 A1 | 7/2001 | Sheinman et al. |
| 2002/0022046 A1 | 2/2002 | Tedeschi et al. |
| 2002/0026937 A1 | 3/2002 | Mault |
| 2002/0055702 A1 | 5/2002 | Atala et al. |
| 2002/0068365 A1 | 6/2002 | Kuhrts |
| 2002/0138051 A1* | 9/2002 | Hole et al. ................. 604/305 |
| 2002/0165179 A1 | 11/2002 | Baker, Jr. |
| 2002/0188323 A1 | 12/2002 | Penner et al. |
| 2003/0009127 A1 | 1/2003 | Trescony et al. |
| 2003/0039697 A1 | 2/2003 | Zhao et al. |
| 2003/0073133 A1 | 4/2003 | Leyland-Jones |
| 2003/0077243 A1 | 4/2003 | Fitzhugh et al. |
| 2003/0088191 A1 | 5/2003 | Freeman et al. |
| 2003/0093143 A1 | 5/2003 | Zhao et al. |
| 2003/0165578 A1 | 9/2003 | Murrell |

(56) References Cited

U.S. PATENT DOCUMENTS

| | | | |
|---|---|---|---|
| 2003/0203915 A1 | 10/2003 | Fang et al. | |
| 2004/0009238 A1 | 1/2004 | Miller et al. | |
| 2004/0013747 A1 | 1/2004 | Tucker et al. | |
| 2004/0072360 A1 | 4/2004 | Naaman et al. | |
| 2004/0081580 A1 | 4/2004 | Hole et al. | |
| 2004/0087831 A1 | 5/2004 | Michels et al. | |
| 2004/0158048 A1 | 8/2004 | Ruane et al. | |
| 2004/0166146 A1 | 8/2004 | Holloway et al. | |
| 2004/0193218 A1 | 9/2004 | Butler | |
| 2004/0202692 A1 | 10/2004 | Shanley et al. | |
| 2004/0209869 A1 | 10/2004 | Landau et al. | |
| 2004/0247640 A1* | 12/2004 | Zhao et al. | 424/423 |
| 2005/0053106 A1 | 3/2005 | Herron et al. | |
| 2005/0079148 A1 | 4/2005 | Fitzhugh et al. | |
| 2005/0136483 A1 | 6/2005 | Carlson | |
| 2005/0181026 A1 | 8/2005 | Davis et al. | |
| 2005/0197682 A1 | 9/2005 | Fox et al. | |
| 2005/0203069 A1 | 9/2005 | Arnold et al. | |
| 2005/0220838 A1 | 10/2005 | Zhao et al. | |
| 2005/0238704 A1 | 10/2005 | Zumbrunn et al. | |
| 2005/0249667 A1 | 11/2005 | Tuszynski et al. | |
| 2005/0267090 A1 | 12/2005 | Mascharak | |
| 2005/0286916 A1* | 12/2005 | Nakazato et al. | 399/16 |
| 2006/0074282 A1 | 4/2006 | Ward et al. | |
| 2006/0134728 A1 | 6/2006 | MacDonald et al. | |
| 2006/0206171 A1 | 9/2006 | Gertner et al. | |
| 2006/0206173 A1 | 9/2006 | Gertner et al. | |
| 2006/0235493 A1 | 10/2006 | Dotson | |
| 2006/0275350 A1 | 12/2006 | Davis et al. | |
| 2006/0280307 A1 | 12/2006 | Ikushima et al. | |
| 2007/0021382 A1 | 1/2007 | Assaf et al. | |
| 2007/0053996 A1 | 3/2007 | Boyden et al. | |
| 2007/0054319 A1* | 3/2007 | Boyden et al. | 435/7.1 |
| 2007/0059351 A1 | 3/2007 | Murrell et al. | |
| 2007/0065473 A1 | 3/2007 | Miller | |
| 2007/0088316 A1 | 4/2007 | Stenzler et al. | |
| 2007/0148117 A1 | 6/2007 | Davis et al. | |
| 2007/0166357 A1 | 7/2007 | Shaffer et al. | |
| 2007/0181444 A1 | 8/2007 | Bernstein et al. | |
| 2007/0190122 A1 | 8/2007 | Davis et al. | |
| 2007/0208395 A1 | 9/2007 | Leclerc et al. | |
| 2007/0233208 A1 | 10/2007 | Kurtz et al. | |
| 2007/0274874 A1 | 11/2007 | Miller et al. | |
| 2007/0298354 A1 | 12/2007 | Ding et al. | |
| 2008/0069863 A1 | 3/2008 | Peters | |
| 2008/0096805 A1 | 4/2008 | Tye | |
| 2008/0097282 A1 | 4/2008 | Hole et al. | |
| 2008/0220048 A1 | 9/2008 | Chen et al. | |
| 2008/0281383 A1* | 11/2008 | Butler | 607/80 |
| 2008/0286321 A1 | 11/2008 | Reneker et al. | |
| 2008/0311163 A1 | 12/2008 | Peters | |
| 2009/0024063 A1 | 1/2009 | Kalvatanond | |
| 2009/0081279 A1 | 3/2009 | Jezek et al. | |
| 2009/0118710 A1 | 5/2009 | Kortzeborn | |
| 2009/0202617 A1 | 8/2009 | Ward et al. | |
| 2009/0204057 A1 | 8/2009 | Woo et al. | |
| 2009/0214618 A1 | 8/2009 | Schoenfisch et al. | |
| 2009/0214624 A1 | 8/2009 | Smith et al. | |
| 2010/0081144 A1 | 4/2010 | Holmes et al. | |
| 2010/0098733 A1 | 4/2010 | Stasko | |
| 2010/0152683 A1 | 6/2010 | Lindgren et al. | |
| 2010/0197802 A1 | 8/2010 | Jezek et al. | |
| 2011/0008815 A1 | 1/2011 | Stamler et al. | |
| 2011/0033437 A1 | 2/2011 | Smith et al. | |

FOREIGN PATENT DOCUMENTS

| | | |
|---|---|---|
| WO | WO 92/09962 | 6/1992 |
| WO | WO 96/08966 A1 | 3/1996 |
| WO | WO 00/53193 | 9/2000 |
| WO | WO 01/10344 A1 | 2/2001 |
| WO | WO 02/17898 A2 | 3/2002 |
| WO | WO 02/057738 A2 | 7/2002 |
| WO | WO 03/006427 A1 | 1/2003 |
| WO | WO 03/086282 A2 | 10/2003 |
| WO | WO 2005/070008 A2 | 8/2005 |
| WO | WO 2005/112954 A1 | 12/2005 |
| WO | WO 2006/084912 A1 | 8/2006 |
| WO | WO 2006/095193 A2 | 9/2006 |
| WO | WO 2006/100155 A1 | 9/2006 |
| WO | WO 2006/107122 A1 | 10/2006 |
| WO | WO 2006/108420 A1 | 10/2006 |
| WO | WO 2006/128121 A2 | 11/2006 |
| WO | WO 2007/130702 A2 | 11/2007 |
| WO | WO 2008/046211 A1 | 4/2008 |
| WO | WO 2009/131931 A1 | 10/2009 |

OTHER PUBLICATIONS

U.S. Appl. No. 12/928,028, Hyde et al.
U.S. Appl. No. 12/927,610, Hyde et al.
U.S. Appl. No. 12/008,708, Hyde et al.
U.S. Appl. No. 12/008,694, Hyde et al.
U.S. Appl. No. 12/006,090, Hyde et al.
U.S. Appl. No. 12/006,069, Hyde et al.
U.S. Appl. No. 12/006,049, Hyde et al.
Andrews, Karen L. et al.; "A Photosensitive Vascular Smooth Muscle Store of Nitric Oxide in Mouse Aorta: No Dependence on Expression of Endothelial Nitric Oxide Synthase"; British Journal of Pharmacology; 2003; pp. 932-940; vol. 138; Nature Publishing Group.
Bonaventura, Daniella et al.; "A Macrocyclic Nitrosyl Ruthenium Complex is a NO Donor that Induces Rat Aorta Relaxation"; Nitric Oxide; Mar. 2004; pp. 83-91 (p. 1); vol. 10, Issue 2; located at: http://www.sciencedirect.com; printed on Oct. 26, 2007 (Abstract Only).
Burrell, María A. et al.; "Detection of Nitric Oxide Synthase (NOS) in Somatostatin-Producing Cells of Human and Murine Stomach and Pancreas"; The Journal of Histochemistry and Cytochemistry; 1996; pp. 339-346; vol. 44, No. 4; The Histochemical Society, Inc.
Chmura, Antonina et al.; "The Role of Photoinduced Electron Transfer Processes in Photodegradation of the $[Fe_4(\mu_3-S)_3(NO)_7]^-$ Cluster"; Nitric Oxide; Dec. 2006; pp. 370-379 (p. 1); vol. 15, Issue 4; located at: http://www.sciencedirect.com; printed on Oct. 26, 2007 (Abstract Only).
Chen, X; Gillis, CN; "Methylene Blue Enhanced Photorelaxation in Aorta, Pulmonary Artery and Corpus Cavernosum"; Biochem. Biophys. Res. Commun.; Jan. 29, 1993; pp. 559-563 (pp. 1-2); vol. 190, No. 2; located at: http://www.pubmed.gov; printed on Oct. 26, 2007 (Abstract Only).
Dujić, Željko et al; "Aerobic Exercise Before Diving Reduces Venous Gas Bubble Formation in Humans"; J. Physiol.; 2004; pp. 637-642; vol. 555.3; The Physiological Society.
"Easy Life II"; Photon Technology International; pp. 1-3; located at: http://www.pti-nj.com/EasyLife/easylife.html; printed on Oct. 6, 2007.
Ferezin, Camila Z. et al; "The Complex Trans-$[RuCl([15]aneN_4)NO]^{2+}$ Induces Rat Aorta Relaxation by Ultraviolet Light Irradiation"; Nitric Oxide; Nov. 2005; pp. 170-175 (p. 1); vol. 13, Issue 3; located at: http://www.sciencedirect.com; printed on Oct. 26, 2007 (Abstract Only).
Flitney, FW et al.; "Iron-Sulphur Cluster Nitrosyls, a Novel Class of Nitric Oxide Generator: Mechanism of Vasodilator Action on Rat Isolated Tail Artery"; Br. J. Pharmacol.; Nov. 1992; pp. 842-848 (pp. 1-2); vol. 107, No. 3; located at: http://www.pubmed.gov; printed on Oct. 26, 2007 (Abstract Only).
Flitney, Frederick Werner; Megson, Ian L.; "Nitric Oxide and the Mechanism of Rat Vascular Smooth Muscle Photorelaxation"; J. Physiol.; 2003; pp. 819-828; vol. 550.3; The Physiological Society.
Flitney, FW et al.; "Vasodilator Responses of Rat Isolated Tail Artery Enhanced by Oxygen-Dependent, Photochemical Release of Nitric Oxide from Iron-Sulphur-Nitrosyls"; Br. J. Pharmacol.; Apr. 1996; pp. 1549-1557 (pp. 1-2); vol. 117, No. 7; located at: http://www.pubmed.gov; printed on Oct. 26, 2007 (Abstract Only).
Fukuhara, Kiyoshi et al.; "Photochemical Generation of Nitric Oxide from 6-Nitrobenzo[α]pyrene"; J. Am. Chem. Soc.; 2001; pp. 8662-8666 (p. 1); vol. 123, No. 36, located at: http://pubs.acs.org/cgi-bin/abstract.cgi/jacsat/2001/123/i36/abs/ja0109038.html; printed on Oct. 26, 2007 (Abstract Only).

(56) References Cited

OTHER PUBLICATIONS

Gaston, Benjamin; "Summary: Systemic Effects of Inhaled Nitric Oxide"; Proceedings of the American Thoracic Society; 2006; pp. 170-172; vol. 3.

Gau, Jen-Jr et al.; "A MEMS Based Amperometric Detector for *E. coli* Bacteria Using Self-Assembled Monolayers"; Biosensors & Bioelectronics; 2001; pp. 745-755; vol. 16; Elsevier Science B.V.

Graham-Rowe, Duncan; "Photonic Fabrics Take Shape"; Nature Photonics; Jan. 2007; pp. 6-7; vol. 1; Nature Publishing Group.

Hardwick, J.B.J. et al.; "A Novel Method for the Delivery of Nitric Oxide Therapy to the Skin of Human Subjects Using a Semi-Permeable Membrane"; Clinical Science; 2001; pp. 395-400; vol. 100; The Biochemical Society and the Medical Research Society.

Hattenbach, Lars-Olof et al.; "Detection of Inducible Nitric Oxide Synthase and Vascular Endothelial Growth Factor in Choroidal Neovascular Membranes"; Ophthalmologica; 2002; pp, 209-214; vol. 216; S. Karger AG, Basel.

Hou, Yongchun et al.; "Nanomolar Scale Nitric Oxide Generation from Self-Assembled Monolayer Modified Gold Electrodes"; Chem. Commun.; 2000; pp. 1831-1832; The Royal Society of Chemistry.

Hrabie, Joseph A.; Keefer, Larry K.; "Chemistry of the Nitric Oxide-Releasing Diazeniumdiolate ("Nitrosohydroxylamine") Functional Group and Its Oxygen-Substituted Derivatives"; Chem. Rev.; 2002; pp. 1135-1154; vol. 102; American Chemical Society.

Ikeda, Osamu et al.; "Nitric Oxide Detection with Glassy Carbon Electrodes Coated with Charge-Different Polymer Films"; Sensors; Apr. 26, 2005; pp. 161-170; vol. 5; ISSN 1424-8220; MDPI.

"InNo-T Nitric Oxide Measurement System"; Warner Instruments; Bearing dates of 1998-2007; pp. 1-2; located at: http://www.warneronline.com/product_info.cfm?ID=220; printed on Oct. 24, 2007.

Keefer, Larry K.; "Nitric Oxide-Releasing Compounds: From Basic Research to Promising Drugs"; Chemtech; Aug. 1998; pp. 30-35 (pp. 1-8); vol. 28, No. 8; located at: http://pubs.acs.org/hotartcl/chemtech/98/aug/nitric.html; printed on Oct. 2, 2007; The American Chemical Society.

Khan, Ma et al.; "The Effect of Superoxide Dismutase on Nitric Oxide-Mediated and Electrical Field-Stimulated Diabetic Rabbit Cavernosal Smooth Muscle Relaxation"; BJU Int.; Jan. 2001; pp. 98-103 (p. 1); vol. 87, No. 1; located at: http://www.pubmed.gov; printed on Sep. 27, 2007 (Abstract Only).

Kim, SC et al.; "Effects of Ultraviolet Light on the Tension of Isolated Human Cavernosal Smooth Muscle from Non-Diabetic and Diabetic Impotent Men"; Urol. Res.; 1997; pp. 149-152 (p. 1); vol. 25, No. 2; located at: http://www.pubmed.gov; printed on Sep. 27, 2007 (Abstract Only).

Kim, JH et al; "Mechanism of UV Light-Induced Photorelaxation in Isolated Rat Aorta"; J. Vet. Sci.; Dec. 2000; pp. 81-86 (p. 1); vol. 1, No. 2; located at: http://www.pubmed.gov; printed on Oct. 26, 2007 (Abstract Only).

Li, Chang Ming et al.; "Electrochemical Detection of Nitric Oxide on a SWCNT/RTIL Composite Gel Microelectrode"; Electroanalysis; 2006; pp. 713-718; vol. 18, No. 7; Wiley-VCH Verlag GmbH & Co. KGaA, Weinheim.

"Light-Emitting Diode (LED)"; Fiber Optics; Bearing a date of 2005; pp. 1-10; located at: http://www.fiber-optics.info/articles/LEDs.htm; printed on Oct. 6, 2007.

Lin, Hong-Yu et al.; "Side-Polished Multimode Fiber Biosensor Based on Surface Plasmon Resonance with Halogen Light"; Applied Optics; Feb. 10, 2007; pp. 800-806; vol. 46, No. 5; Optical Society of America.

Matthews, EK et al.; "Photon Pharmacology of an Iron-Sulphur Cluster Nitrosyl Compound Acting on Smooth Muscle"; Br. J. Pharmacol.; Sep. 1994; pp. 87-94 (p. 1); vol. 113, No. 1; located at: http://www.pubmed.gov; printed on Oct. 26, 2007 (Abstract Only).

Mendioroz, A. et al.; "Infrared to Visible and Ultraviolet Upconversion Processes in $Nd^{3+}$-Doped Potassium Lead Chloride Crystal"; Optical Materials; Sep. 2004; pp. 351-357 (p. 1); vol. 26, Issue 4; located at: http://www.sciencedirect.com; printed on Oct. 29, 2007 (Abstract Only).

Nablo, Brian J. et al.; "Inhibition of Implant-Associated Infections Via Nitric Oxide Release"; Biomaterials; Dec. 2005; pp. 6984-6990 (p. 1); vol. 26, Issue 34; located at: http://www.sciencedirect.com; printed on Oct. 26, 2007 (Abstract Only).

"NO Electrodes"; WPI-Europe-Biosensing-NO Electrodes; Bearing a date of Nov. 29, 2007; pp. 1-5; World Precision Instruments; located at: http://www.wpi-europe.com/products/biosensing/noelectrodes.htm; printed on Nov. 29, 2007.

"OL 770-LED: High-Speed LED Measurement System"; Bearing a date of 2001; pp. 1-6; located at: http://www.optroniclabs.com; Optronic Laboratories, Inc.

"Particulate Effects on Immunologic Function"; OST 1997AR; Bearing a date of 1997; pp. 1-2; located at: http://www.fda.gov/cdrh/ost/rpt97/OST1997AR9.HTML; printed on Oct. 16, 2007.

Peng, H. et al.; "Ultraviolet Light-Emitting Diodes Operating in the 340 nm Wavelength Range and Application to Time-Resolved Fluorescence Spectroscopy"; Applied Physics Letters; Aug. 23, 2004; pp. 1436-1438 (p. 1); vol. 85, Issue 8; located at: http://scitation.aip.org; printed on Oct. 26, 2007 (Abstract Only).

Pou, SJ et al.; "Biological Studies of a Nitroso Compound that Releases Nitric Oxide Upon Illumination"; Molecular Pharmacology; Oct. 1, 1994; pp. 709-715 (p. 1); Vo. 46, Issue 4; located at: http://molpharm.aspetjournals.org/cgi/content/abstract/46/4/709; printed on Oct. 26, 2007 (Abstract Only).

"Probes for Nitric Oxide (NO) Research"; EMD-Calbiochem: Nitric Oxide Probes; Bearing a date of 2007; pp. 1-2; Calbiochem, Novabiochem, & Novagen; located at: http://www.emdbiosciences.com/html/cbc/nitric_oxide_probes.htm; printed on Nov. 29, 2007.

Räthel, Thomas R. et al.; "Application of 4,5-Diaminofluorescein to Reliably Measure Nitric Oxide Released from Endothelial Cells In Vitro"; Biological Procedures Online; Jun. 2, 2003; pp. 136-142; vol. 5, No. 1.

Rotta, J.C.G. et al.; "Nitric Oxide Release from the S-Nitrosothiol Zinc Phthalocyanine Complex by Flash Photolysis"; Brazilian Journal of Medical and Biological Research; 2003; pp. 587-594; vol. 36, No. 5; located at: http://www.scielo.br/pdf/bjmbr/v36n5/4604.pdf.

Seo, K.K. et al.; "Synergistic Effects of Sildenafil on Relaxation of Rabbit and Rat Cavernosal Smooth Muscles when Combined with Various Vasoactive Agents"; BJU International; 2001; pp. 596-601; vol. 88.

Singh, Ravinder Jit et al.; "Photosensitized Decomposition of S-Nitrosothiols and 2-Methyl-2-Nitrosopropane Possible Use for Site-Directed Nitric Oxide Production"; FEBS Letters; 1995; pp. 47-51; vol. 360; Federation of European Biochemical Societies.

Smith, DJ et al.; "Nitric Oxide-Releasing Polymers Containing the [N(O)NO]-Group"; J. Med. Chem.; Mar. 1, 1996; pp. 1148-1156 (p. 1); vol. 39, No. 5; located at: http://www.pubmed.gov; printed on Oct. 26, 2007 (Abstract Only).

Sonoki T. et al.; "Detection of Inducible Nitric Oxide Synthase (iNOS) mRNA by RT-PCR in ATL Patients and HTLV-1 Infected Cell Lines: Clinical Features and Apoptosis by NOS Inhibitor"; Leukemia; 1999; pp. 713-718; vol. 13; Stockton Press.

Wadsworth, Roger et al.; "Physiologically Relevant Measurements of Nitric Oxide in Cardiovascular Research Using Electrochemical Microsensors"; Journal of Vascular Research; 2006; pp. 70-85; vol. 43; S. Karger AG, Basel.

Wang, Peng George et al.; "Nitric Oxide Donors: Chemical Activities and Biological Applications"; Chem. Rev.; 2002; pp. 1091-1134 (pp. 1-53); vol. 102, No. 4; American Chemical Society; located at: http://pubs.acs.org/cgi-bin/abstract.cgi/chreay/2002/102/i04/abs/cr0000401.html; printed on Oct. 26, 2007.

Wang, Tianlong et al.; "Inhaled Nitric Oxide in 2003: A Review of its Mechanisms of Action"; Canadian Journal of Anesthesia; 2003; pp. 839-846; vol. 50, No. 8.

Williamson, David; "Study: Nitric Oxide-Releasing Materials Might Reduce Medical Implant Infections"; UNC News Services; Sep. 7, 2001; pp. 1-2; No. 416; located at: http://www.unc.edu/news/archives/sep01/schoen090701.htm; printed on Oct. 4, 2007.

Xie, Rong-Jun; "Highly Efficient White-Light-Emitting Diodes Fabricated with Short-Wavelength Yellow Oxynitride Phosphors"; Applied Physics Letters; Mar. 6, 2006; pp. 101104.1-101104.3 (pp. 1-2); vol. 88; located at: http://scitation.aip.org/; printed on Oct. 26, 2007 (Abstract Only).

(56) References Cited

OTHER PUBLICATIONS

Jamal, Sophie A. et al.; "Effect of Nitroglycerin Ointment on Bone Density and Strength in Postmenopausal Women"; JAMA; bearing a date of Feb. 23, 2011; pp. 800-807; vol. 305, No. 8; American Medical Association.

Khosla, Sundeep; "Is Nitroglycerin a Novel and Inexpensive Treatment for Osteoporosis?"; JAMA; bearing a date of Feb. 23, 2011; pp. 826-827; vol. 305, No. 8; American Medical Association.

Mims, Christopher; "Erectile Dysfunction Treatment to Save Soldiers' Lives"; Technology Review; bearing a date of Feb. 22, 2011; 2 pages; MIT; located at http://www.technologyreview.com/blog/mimssbits/26427/?pl=A5.

U.S. Appl. No. 12/930,351, Hyde et al.

Butler, P. et al.; "Cell Transplantation from Limb Allografts"; Plastic and Reconstructive Surgery; Bearing a date of Jul. 1998; pp. 161-168 (11 total pages); vol. 102, No. 1; American Society of Plastic Surgeons; located at: http://www.plasreconsurg.com; printed on Apr. 25, 2008.

Butler, A.R.; Nicholson, R.; Life, Death and Nitric Oxide; Bearing a date of Oct. 17, 2003; 1st edition; Royal Society of Chemistry, ISBN 978-0854046867 (Not Provided).

U.S. Appl. No. 12/148/284, Hyde et al.

De Lima, R.G. et al.; "Controlled Nitric Oxide Photo-Release From Nitro Ruthenium Complexes: The Vasodilator Response Produced by UV Light Irradiation"; Inorganica Chimica Acta; Bearing a date of 2005; pp. 2643-2650; vol. 358; Elsevier B.V.; located at: http://www.sciencedirect.com.

Frank, S. et al.; "Nitric Oxide Triggers Enhanced Induction of Vascular Endothelial Growth Factor Expression in Cultured Keratinocytes (HaCaT) and During Cutaneous Wound Repair"; The FASEB Journal; Bearing a date of 1999; pp. 2002-2014; vol. 13.

Ghaffari, A. et al.; "A Direct Nitric Oxide Gas Delivery System for Bacterial and Mammalian Cell Cultures"; Nitric Oxide; Bearing a date of 2005; pp. 129-140; vol. 12; Elsevier Inc.; located at: http://www.sciencedirect.com.

Ghaffari, A. et al.; "Efficacy of Gaseous Nitric Oxide in the Treatment of Skin and Soft Tissue Infections"; Wound Repair and Regeneration; Bearing a date of 2007; pp. 368-377; vol. 15; Wound Healing Society.

Ghaffari, A. et al.; "Potential Application of Gaseous Nitric Oxide as a Topical Antimicrobial Agent"; Nitric Oxide; Bearing a date of 2006; pp. 21-29; vol. 14; Elsevier Inc.; located at: http://www.sciencedirect.com.

Goldsmith, P.C. et al.; "Inhibitors of Nitric Oxide Synthase in Human Skin"; The Journal of Investigative Dermatology; Bearing a date of Jan. 1996; pp. 113-118; vol. 106, No. 1; The Society for Investigative Dermatology, Inc.

Govers, R.; Rabelink, T.J.; "Cellular Regulation of Endothelial Nitric Oxide Synthase"; Am. J. Physiol. Renal. Physiol.; Bearing a date of 2001; pp. F193-F206; vol. 280; The American Physiological Society; located at: http://www.ajprenal.org.

Guo, H.; "Two-and Three-Photon Upconversion of $LaOBr:Er^{3+}$"; Optical Materials; Bearing a date of 2007; pp. 1840-1843; vol. 29; Elsevier B.V.; located at: http://www.sciencedirect.com.

Hassett, D.J.; Imlay, J.A.; "Bactericidal Antibiotics and Oxidative Stress: A Radical Proposal"; ACS Chemical Biology; Bearing a date of 2007; pp. 708-710; vol. 2, No. 11; located at: http://www.acschemicalbiology.org.

Miller, C.C. et al.; "Treatment of Chronic Nonhealing Leg Ulceration with Gaseous Nitric Oxide: A Case Study"; Journal of Cutaneous Medicine and Surgery; Bearing a date of Aug. 2004; pp. 233-238; vol. 8, No. 4.

Pacher, P. et al.; "Nitric Oxide and Peroxynitrite in Health and Disease"; Physiol. Rev.; Bearing a date of Jan. 2007; pp. 315-424; vol. 87; The American Physiological Society; located at: http://www.prv.org.

Patel, D.N. et al.; "Spectroscopic and Two-Photon Upconversion Studies of $Ho^{3+}$-Doped $Lu_3Al_5O_{12}$"; Optical Materials; Bearing a date of Jul. 1998; pp. 225-234; vol. 10; Elsevier Science B.V.

Rapaport, A. et al.; "Review of the Properties of Up-Conversion Phosphors for New Emissive Displays"; Journal of Display Technology; Bearing a date of Mar. 2006; pp. 68-78; vol. 2, No. 1; IEEE.

Roméro-Graillet, C. et al.; "Nitric Oxide Produced by Ultraviolet-Irradiated Keratinocytes Stimulates Melanogenesis"; J. Clin. Invest.; Bearing a date of Feb. 1997; pp. 635-642; vol. 99, No. 4; The American Society of Clinical Investigation, Inc.

Seabra, A.B. et al.; "S-Nitrosoglutathione Incorporated in Poly(Ethylene Glycol) Matrix: Potential Use for Topical Nitric Oxide Delivery"; Nitric Oxide; Bearing a date of 2004; pp. 263-272; vol. 11; Elsevier Inc.; located at: http://www.sciencedirect.com.

Shabani, M. et al.; "Enhancement of Wound Repair with a Topically Applied Nitric Oxide-Releasing Polymer"; Wound Repair and Regeneration; Bearing dates of Jul.-Sep. 1996; pp. 353-362; vol. 4, No. 3; The Wound Healing Society.

Sussman, C.; Wound Care: A Collaborative Practice Manual; Bearing a date of Jan. 2007; ISBN 0781774446 (Not Provided).

Suzuki, H.; Hewitt, C.W.; "Cell Transplantation from Limb Allografts: Discussion"; Plastic and Reconstructive Surgery; Bearing a date of Jul. 1998; pp. 169-170 (2 total pages); vol. 102, No. 1; American Society of Plastic Surgeons; located at: http://www.plasreconsurg.com; printed on May 2, 2008.

Tamir, S.; Tannenbaum, S.R.; "The Role of Nitric Oxide (NO) in the Carcinogenic Process"; Biochimica et Biophysica Acta; Bearing a date of 1996; pp. F31-F36; vol. 1288; Elsevier Science B.V.

Tu, H. et al.; "A Novel Electrochemical Microsensor for Nitric Oxide Based on Electropolymerized Film of o-Aminobenzaldehyde-Ethylene-Diamine Nickel"; Electroanalysis; Bearing a date of 1999; pp. 70-74; vol. 11, No. 1; Wiley-VCH.

Van Faassen, E.; Vanin, A. (Eds); Radicals for Life: The Various Forms of Nitric Oxide; Bearing a date of Mar. 2007; 442 pages; ISBN 978-0-444-52236-8; Elsevier (Not Provided).

Weller, R. et al.; "Antimicrobial Effect of Acidified Nitrite on Dermatophyte Fungi, Candida and Bacterial Skin Pathogens"; Journal of Applied Microbiology; Bearing a date of 2001; pp. 648-652; vol. 90; The Society for Applied Microbiology.

Weller, R. et al.; "Nitric Oxide Is Generated on the Skin Surface by Reduction of Sweat Nitrate"; The Journal of Investigative Dermatology; Bearing a date of Sep. 1996; pp. 327-331; vol. 107, No. 3; The Society of Investigative Dermatology, Inc.

Yamasaki, K. et al.; "Reversal of Impaired Wound Repair in iNOS-Deficient Mice by Topical Adenoviral-Mediated iNOS Gene Transfer"; J. Clin. Invest.; Bearing a date of Mar. 1998; pp. 967-971; vol. 101, No. 5; The American Society for Clinical Investigation, Inc.; located at: http://www.jci.org.

Zhelyaskov, V.R.; Godwin, D.W.; "Photolytic Generation of Nitric Oxide Through a Porous Glass Partitioning Membrane"; Nitric Oxide: Biology and Chemistry; Bearing a date of 1998; pp. 454-459; vol. 2, No. 6; Article No. NO980195; Academic Press.

Stubbington, Tommy; "New Condom Nears Approval"; The Wall Street Journal Online; bearing at date of Apr. 20, 2011; pp. 1-2; 13:18; Dow Jones & Company, Inc.

"A Method of Nitric Oxide Delivery for Healing and Organ Preservation"; University of Texas at Dallas; bearing a date of May 18, 2009; p. 1; located at http://utdallas.technologypublisher.com/TechnologyProject.aspx?id=2302.

"Nanotechnology bandage speeds up healing"; Nanowerk News; Source: Akron Beacon Journal (Paula Schleis); bearing a date of Dec. 15, 2006; pp. 1-2; printed on Jul. 14, 2009; located at http://www.nanowerk.com/news/newsid=1156.php.

Dictionary.com; "Patch"; printed on Jul. 20, 2012; pp. 1-8; located at: http://dictionary.reference.com/browse/patch.

U.S. Appl. No. 13/452,502, Hyde et al.

Birkeland et al.; "On the Oxidation of Atmospheric Nitrogen in Electric Arcs"; Nature; bearing a date of 1898; pp. 98-116; No. 1,506, vol. 58.

Levine et al.; "A New, Highly Efficient Red-Emitting Cathodoluminescent Phosphor ($YVO_4:Eu$) for Color Television"; Applied Physics Letters; bearing a date of Sep. 15, 1964; pp. 1-3; vol. 5, No. 6.

Mellor, J.W.; "Modern Inorganic Chemistry"; excerpt from Modern Inorganic Chemistry; bearing a date of 1912; pp. 1-19; Longmans, Greene, and Co.

(56) References Cited

OTHER PUBLICATIONS

"The Shadow Mask and Aperture Grill"; The PC Guide; bearing a date of Apr. 17, 2001; pp. 1-3; © Copyright 1997-2004 Charles M. Kozierok; printed Oct. 6, 2009; located at http://www.pcguide.com/ref/crt/crtMask-c.html.

"Nanotechnology—the new Viagra?"; Nanowerk News; bearing a date of Apr. 26, 2009; p. 1; located at http://www.nanowerk.com/news/newsid=10273.php.

Liu et al.; "Novel Delivery System for the Bioregulatory Agent Nitric Oxide"; Chemistry of Materials; bearing a date of 2009; pp. 5032-5041; vol. 21, No. 21; © 2009 American Chemical Society.

"Nitric oxide-releasing wrap for donor organs and cloth for therapeutic socks"; e! Science News; bearing a date of Jan. 6, 2010; pp. 1-2; located at http://esciencenews.com/articles/2010/01/06/nitric.oxide.releasing.wrap.donor.organs.and.cloth.therapeutic. socks; printed on Jan. 19, 2010.

Walt et al.; "Biological Warfare"; Analytical Chemistry; Dec. 1, 2000; pp. 738 A-747 A.

\* cited by examiner

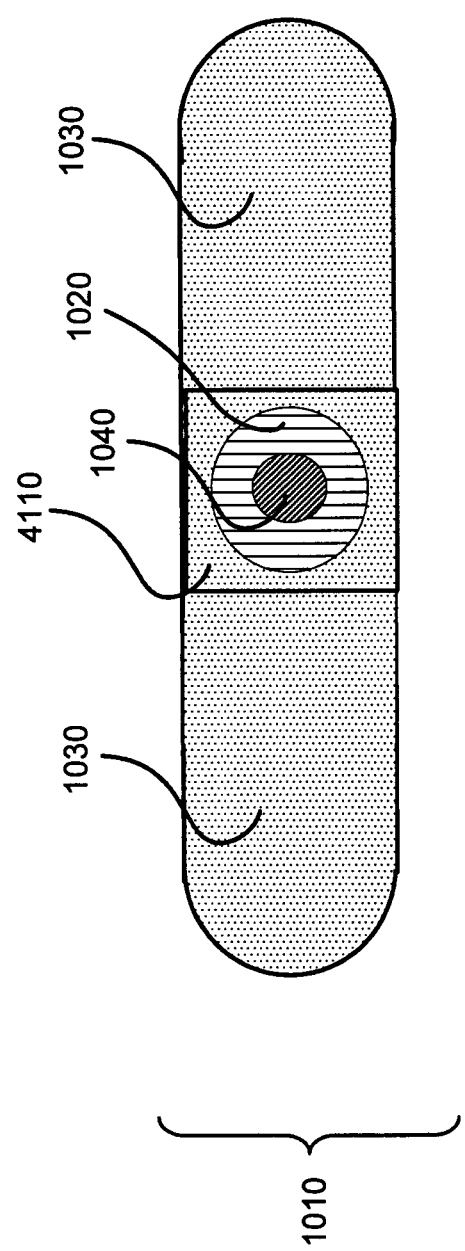

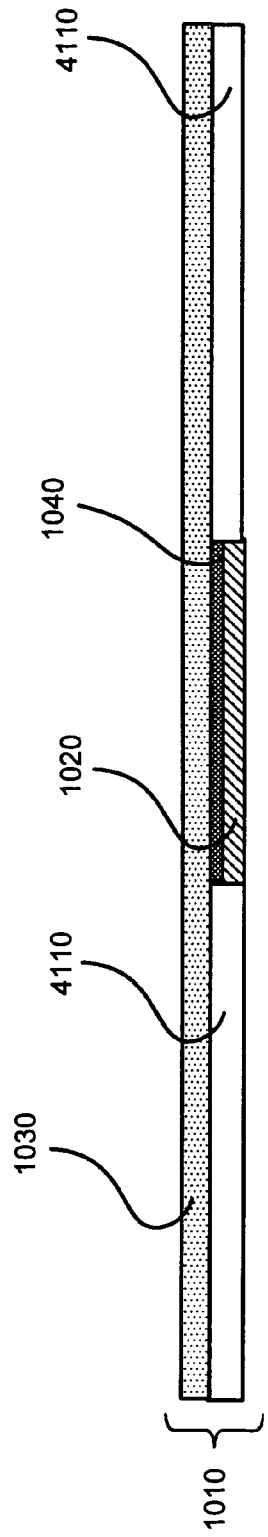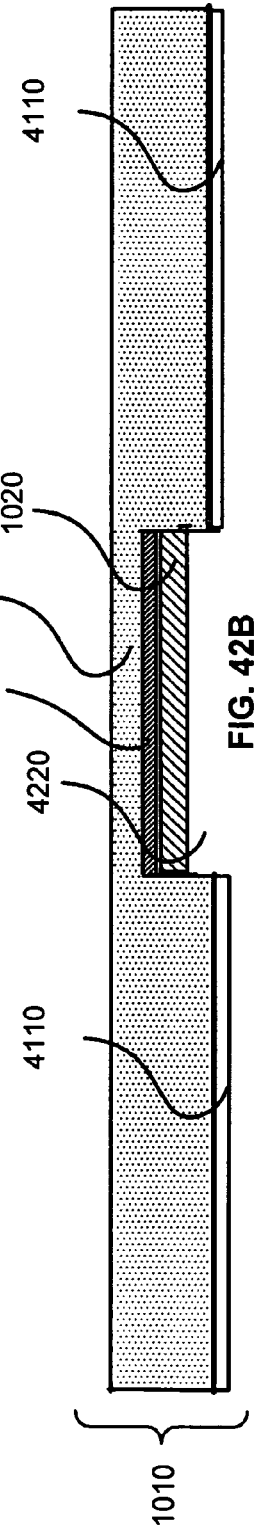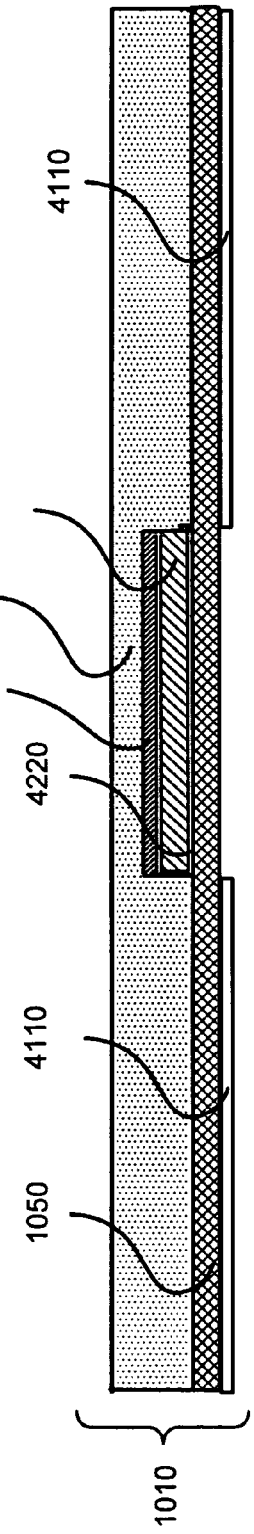
FIG. 42A-42C
FIG. 42A
FIG. 42B
FIG. 42C

4600 A system comprising:

4602 a signal-bearing medium bearing 4604 one or more instructions for operating one or more light sources that are operably associated with one or more backing sheets; and one or more instructions for operating one or more control units 4606 a computer-readable medium 4608 a recordable medium 4610 a communications medium

DEVICES AND SYSTEMS THAT DELIVER NITRIC OXIDE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 12/005,065, entitled Devices and Systems that Deliver Nitric Oxide, naming Roderick A. Hyde, Muriel Y. Ishikawa, Leif T. Stordal and Lowell L. Wood, Jr. as inventors, filed 21 Dec. 2007 now U.S Pat. No. 7,862,598, or is an application of which a currently co-pending application is entitled to the benefit of the filing date.

For purposes of the USPTO extra-statutory requirements, the present application constitutes a continuation-in-part of U.S. patent application Ser. No. 11/981,743, entitled Methods and Systems for Use of Photolyzable Nitric Oxide Donors, naming Roderick A. Hyde, Muriel Y. Ishikawa and Lowell L. Wood, Jr. as inventors, filed 30 Oct. 2007 now U.S Pat. No. 8,642,093, or is an application of which a currently co-pending application is entitled to the benefit of the filing date.

For purposes of the USPTO extra-statutory requirements, the present application constitutes a continuation-in-part of U.S. patent application Ser. No. 11/998,864, entitled Systems and Devices that Utilize Photolyzable Nitric Oxide Donors, naming Roderick A. Hyde, Muriel Y. Ishikawa and Lowell L. Wood, Jr. as inventors, filed 30 Nov. 2007 now U.S. Pat. No. 8,221,690, or is an application of which a currently co-pending application is entitled to the benefit of the filing date.

For purposes of the USPTO extra-statutory requirements, the present application constitutes a continuation-in-part of U.S. patent application Ser. No. 12/005,045, entitled Systems and Devices Related to Nitric Oxide Releasing Materials, naming Roderick A. Hyde, Muriel Y. Ishikawa, Leif T. Stordal and Lowell L. Wood, Jr. as inventors, filed 21 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,132, entitled Nitric Oxide Sensors and Systems, naming Roderick A. Hyde, Muriel Y. Ishikawa, Leif T. Stordal and Lowell L. Wood, Jr. as inventors, filed 21 Dec. 2007 now U.S Pat. No. 7,897,399, or is an application of which a currently co-pending application is entitled to the benefit of the filing date.

For purposes of the USPTO extra-statutory requirements, the present application constitutes a continuation-in-part of U.S. patent application Ser. No. 12/005,136, entitled Devices Configured to Facilitate Release of Nitric Oxide, naming Roderick A. Hyde, Muriel Y. Ishikawa and Lowell L. Wood, Jr. as inventors, filed 21 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,170, entitled Condoms Configured to Facilitate Release of Nitric Oxide, naming Roderick A. Hyde, Muriel Y. Ishikawa and Lowell L. Wood, Jr. as inventors, filed 21 Dec 2007 now U.S Pat. No. 7,975,699, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present disclosure relates to dressings, such as patches and bandages, and other devices and systems that deliver nitric oxide.

SUMMARY

In some embodiments one or more dressings are provided that include one or more backing sheets and one or more photolyzable nitric oxide donors associated with the one or more backing sheets. The dressings may optionally include one or more nitric oxide permeable layers. In addition to the foregoing, other aspects are described in the claims, drawings, and text forming a part of the present disclosure.

In some embodiments one or more dressings are provided that include one or more backing sheets, one or more light sources operably associated with the one or more backing sheets, and one or more photolyzable nitric oxide donors operably associated with the one or more light sources. The dressings may optionally include one or more nitric oxide permeable layers. The dressings may optionally include one or more control units. The dressings may optionally include one or more nitric oxide permeable layers. The dressings may optionally include one or more sensors. In addition to the foregoing, other aspects are described in the claims, drawings, and text forming a part of the present disclosure.

In some embodiments one or more systems are provided that include circuitry for operating one or more light sources that are operably associated with one or more photolyzable nitric oxide donors and one or more backing sheets. The system may optionally include circuitry for operating one or more control units. The system may optionally include circuitry for operating one or more sensors. In addition to the foregoing, other aspects are described in the claims, drawings, and text forming a part of the present disclosure.

In some embodiments one or more systems are provided that include means for operating one or more light sources that are operably associated with one or more backing sheets. The system may optionally include means for operating one or more control units. The system may optionally include means for operating one or more sensors. In addition to the foregoing, other aspects are described in the claims, drawings, and text forming a part of the present disclosure.

In some embodiments one or more systems are provided that include one or more instructions for operating one or more light sources that are operably associated with one or more backing sheets. The system may optionally include one or more instructions for operating one or more control units. The system may optionally include one or more instructions for operating one or more sensors. In addition to the foregoing, other aspects are described in the claims, drawings, and text forming a part of the present disclosure.

In some embodiments, means include but are not limited to circuitry and/or programming for effecting the herein referenced functional aspects; the circuitry and/or programming can be virtually any combination of hardware, software, and/or firmware configured to effect the herein referenced functional aspects depending upon the design choices of the system designer. In addition to the foregoing, other system aspects means are described in the claims, drawings, and/or text forming a part of the present disclosure.

In some embodiments, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects; embodiments, and features will become apparent by reference to the drawings, claims, and the following detailed description.

BRIEF DESCRIPTION OF THE FIGURES

FIG. 41 illustrates embodiment of dressing 1010 within system 1000.

FIG. 42A illustrates a side-view of an embodiment of dressing 1010 within system 1000 as illustrated in FIG. 41.

FIG. 42B illustrates a side-view of an embodiment of dressing 1010 within system 1000 as illustrated in FIG. 41.

FIG. 42C illustrates a side-view of an embodiment of dressing 1010 within system 1000 as illustrated in FIG. 41.

DETAILED DESCRIPTION

Figure 1:
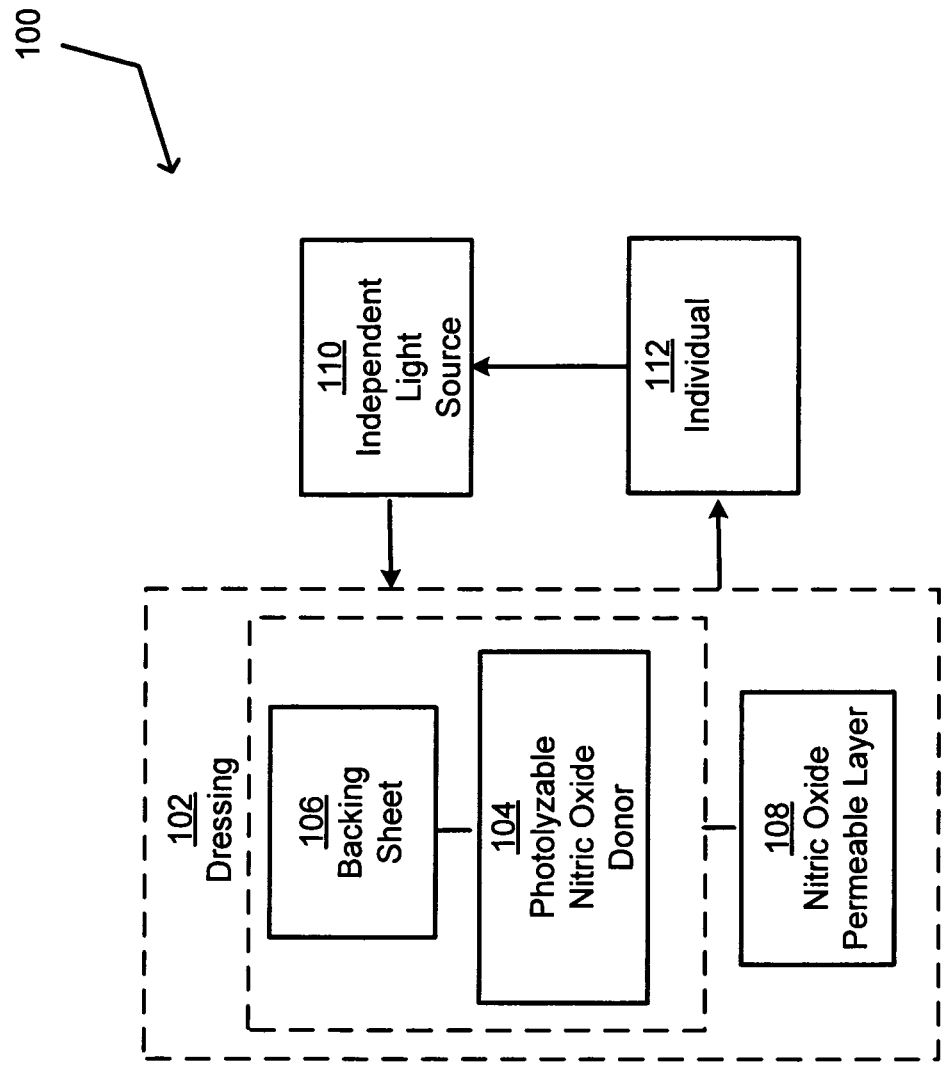
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates a system 100 in which embodiments may be implemented. System 100 may include one or more dressings 102 that include one or more backing sheets 106 and one or more photolyzable nitric oxide donors 104. In some embodiments, dressing 102 may include one or more nitric oxide permeable layers 108. In some embodiments, system 100 may include one or more independent light sources 110.

Dressing

System 100 includes one or more dressings 102. A dressing 102 may be configured in numerous ways. In some embodiments, a dressing 102 may be configured to deliver nitric oxide to a surface of an individual 112. In some embodiments, a dressing 102 may be configured for application to an outside surface of an individual 112. For example, in some embodiments, a dressing 102 may be configured to deliver nitric oxide to the skin of an individual 112. Accordingly, a dressing 102 may be configured in numerous ways to deliver nitric oxide to a surface or region of an individual 112. In some embodiments, a dressing 102 may be configured to deliver nitric oxide as a therapeutic agent (e.g. U.S. Patent Application No.: 2007/0088316). For example, in some embodiments, a dressing 102 may be configured to deliver nitric oxide to a person to combat infection. In some embodiments, a dressing 102 may be configured to deliver nitric oxide to a person to assist in removal of necrotic tissue. In some embodiments, a dressing 102 may be configured to deliver nitric oxide to a person to reduce inflammation. In some embodiments, a dressing 102 may be configured to deliver nitric oxide to a person to upregulate the expression of collagenase. In some embodiments, a dressing 102 may be configured to deliver nitric oxide to a person to facilitate vascularisation. In some embodiments, a dressing 102 may be configured to deliver nitric oxide to a person suffering from diabetes. For example, in some embodiments, a dressing 102 may be configured to deliver nitric oxide to tissue lesions. In some embodiments, a dressing 102 may be configured to deliver nitric oxide as a sanitizing agent. In some embodiments, a dressing 102 may be configured to deliver nitric oxide to an accident victim. For example, in some embodiments, a dressing 102 may be configured as a bandage and/or patch that may be applied to an individual 112.

In some embodiments, a dressing 102 may be applied to an individual 112 and then irradiated with light to facilitate release of nitric oxide from one or more photolyzable nitric oxide donors 104 associated with the dressing 102. For example, in some embodiments, a dressing 102 may be applied to an individual 112 and then an independent light source 110 may be used to irradiate the dressing 102 to facilitate release of nitric oxide from one or more photolyzable nitric oxide donors 104 associated with the dressing 102. In some embodiments, ambient light may be used to facilitate release of nitric oxide from one or more photolyzable nitric oxide donors 104 associated with the dressing 102. For example, in some embodiments, a dressing 102 may be configured with one or more transmissive backing sheets 106 through which ambient light may pass to facilitate release of nitric oxide from one or more photolyzable nitric oxide donors 104 associated with the dressing 102.

In some embodiments, a dressing 102 may be configured to deliver nitric oxide in a controlled manner. For example, in some embodiments, a dressing 102 that is configured as a patch that includes one or more photolyzable nitric oxide donors 104 may be applied to an individual 112 and then exposed to light to release nitric oxide onto the space between the patch and the surface of the individual 112. In some embodiments, a dressing 102 may be configured to deliver a preselected concentration of nitric oxide to a surface of an individual 112. For example, in some embodiments, a dressing 102 may be configured to include a quantity of one or more photolyzable nitric oxide donors 104 that release a predictable amount of nitric oxide upon being exposed to light. Accordingly, such dressings 102 may be constructed such that they deliver a known concentration of nitric oxide to the surface of an individual 112. For example, in some embodiments, a dressing 102 that is configured as a patch may be applied to an individual 112 such that the patch covers a known amount of surface area of an individual 112. In some embodiments, such a patch may be configured to create a closed airspace between the surface of an individual 112 and the patch. Accordingly, in such embodiments, one or more photolyzable nitric oxide donors 104 may be included within the patch that will release a quantity of nitric oxide within the closed airspace on the surface of the individual 112 that is therapeutic. For example, in some embodiments, a quantity of one or more photolyzable nitric oxide donors 104 may be included within a dressing 109 that is configured as a patch such that nitric oxide is released into the space between the patch and the surface of the individual 112 to which the patch is applied such that the nitric oxide concentration within the space is between about 160 ppm and about 400 ppm. Such a concentration range has been reported to reduce microbial infection within a wound site, reduce inflammation, and increase collagenase expression without inducing toxicity to healthy cells within the wound site (e.g., U.S. Patent Application No.: 2007/0088316). Accordingly, numerous concentrations of nitric oxide may be applied to the surface of an individual 112 through use of dressings 102 that are configured as a patch, bandage (e.g., U.S. Pat. No. 7,264,602), sleeve, glove, sock, hood, mitten, bag, condom, and the like.

Photolyzable Nitric Oxide Donor/Nitric Oxide

Numerous photolyzable nitric oxide donors 104 may be used within system 100. Examples of such photolyzable nitric oxide donors 104 include, but are not limited to, diazeniumdiolates (e.g., U.S. Pat. Nos. 7,105,502; 7,129,579; 6,673,338; herein incorporated by reference), trans-[RuCl([15]aneN4)NO]+2 (Ferezin et al., Nitric Oxide, 13:170-175 (2005), Bonaventura et al. Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney-et al., Br. J. Pharmacol., 107:842-848 (1999), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

In some embodiments, one or more photolyzable nitric oxide donors 104 may be used in association with additional nitric oxide donors that are not photolyzable. In some embodiments, one or more photolyzable nitric oxide donors 104 may be used in association with additional agents. Examples of such additional agents include, but are not limited to, enzyme inhibitors (e.g., U.S. Pat. No. 6,943,166; herein incorporated by reference), agents that increase the effects and/or concentration of nitric oxide 106 (e.g., methylene blue and N(w)-nitro-L-arginine (L-NOARG) (see Chen and Gillis, Biochem. Biophys. Res. Commun., 190, 559-563 (1993) and Kim et al., J. Vet. Sci., 1:81-86 (2000)), L-arginine (e.g., U.S. Published Patent Application No.: 20020068365 and U.S. Pat. No. 6,635,273; herein incorporated by reference), agents that stabilize nitric oxide donors (e.g., dimethyl sulfoxide and ethanol), agents that increase the half life of nitric oxide (e.g., U.S. Published Patent Application No.: 20030039697; herein incorporated by reference), and the like.

In some embodiments, one or more photolyzable nitric oxide donors may be associated with one or more antibacterial agents. In some embodiments, one or more photolyzable nitric oxide donors may be associated with one or more antiviral agents. In some embodiments, one or more photolyzable nitric oxide donors may be associated with one or more therapeutic agents (e.g., anti-thrombotics, coagulants, and the like).

Backing Sheet

Numerous types of backing sheets 106 may be used within system 100. Backing sheets 106 may be constructed from numerous types of materials and combinations of materials. Examples of such materials include, but are not limited to, metals, metal alloys, polymers, copolymers, ceramics, cloth, fabric, and the like. Backing sheets 106 may be configured in numerous ways. For example, in some embodiments, a backing sheet 106 may be one or more sheets of one or more materials to which one or more photolyzable nitric oxide donors 104 may be associated.

Backing sheets 106 may exhibit numerous physical characteristics. For example, in some embodiments, one or more backing sheets 106 may be transmissive backing sheets 106 that are substantially transparent to light that facilitates release of nitric oxide from one or more photolyzable nitric oxide donors 104. In some embodiments, one or more backing sheets 106 may be elastomeric. Methods to prepare elastomeric materials are known and have been reported (e.g., U.S. Pat. Nos. 6,639,007; 6,673,871; 7,105,607). In some embodiments, one or more backing sheets 106 may be inelastic. For example, in some embodiments, a backing sheet 106 may be fabricated from one or more metal foils. In some embodiments, one or more backing sheets 106 may be fabricated with pressure sensitive fibers. For example, in some embodiments, a backing sheet 106 may include one or more elastomeric materials that self-adhere. Accordingly, in some embodiments, a backing sheet 106 may be configured in the form of self-adhering athletic tape. In some embodiments, a backing sheet 106 may include one or more adhesives that are applied to one or more portions of the backing sheet 106. In some embodiments, one or more backing sheets 106 may include one or more films that are configured for energy conversion (e.g., U.S. Pat. No. 7,238,628). For example, in some embodiments, one or more backing sheets 106 may include one or more rare-earth elements. Accordingly, in some embodiments, one or more backing sheets 106 may be configured to convert ambient light into light that facilitates photolysis of one or more photolyzable nitric oxide donors 104.

Nitric Oxide Permeable Layer

Numerous types of nitric oxide permeable layers 108 may be used within system 100. Nitric oxide permeable layers 108 may be configured for application to an individual 1112. Nitric oxide permeable layers 108 may be configured to facilitate application of nitric oxide to a surface. In some embodiments, one or more nitric oxide permeable layers 108 may be configured to facilitate application of nitric oxide to one or more surfaces of an individual 112. For example, in some embodiments, one or more nitric oxide permeable layers 108 may be configured as a dressing 102 that may be positioned on a skin surface of an individual 112 to deliver nitric oxide to the skin surface. Examples of such dressings 102 include, but are not limited to, patches, bandages, gloves, hood, mittens, sleeves, and the like. In some embodiments, nitric oxide permeable layers 108 may be configured as bags. For example, in some embodiments, one or more nitric oxide permeable layers 108 may be configured as a bag that will enclose an individual 112 and/or a portion of an individual 112. In some embodiments, such a bag may be used to deliver nitric oxide to the surface of an individual 112. In some embodiments, one or more nitric oxide permeable layers 108 may be configured as a sleeve that will enclose a portion of a person. In some embodiments, such a sleeve may be used to deliver nitric oxide to the surface of an individual 112. In some embodiments, one or more nitric oxide permeable layers 108 may be configured to enclose at least a portion of one or more photolyzable nitric oxide donors 104.

Nitric oxide permeable layers 108 may be constructed of numerous types of materials and combinations of materials. Examples of such materials include, but are not limited to, ceramics, polymeric materials, metals, plastics, and the like. In some embodiments, nitric oxide permeable layers 108 may include numerous combinations of materials. For example, in some embodiments, a nitric oxide permeable layer 108 may include a nitric oxide impermeable material that is coupled to a nitric oxide permeable material. In some embodiments, a nitric oxide permeable layer 108 may include one or more nitric oxide permeable membranes (e.g., U.S. Patent Application No.: 20020026937). In some embodiments, a nitric oxide permeable layer 108 may include a selectively permeable membrane. For example, in some embodiments, a nitric oxide permeable layer 108 may include a selectively permeable membrane that is a hydrophilic polyester co-polymer membrane system that includes a copolymer with 70% polyester and 30% polyether (e.g., Sipatex™ 10 µm membrane, see Hardwick et al., Clinical Science, 100:395-400 (2001)). In some embodiments, a nitric oxide permeable layer 108 may include a scintered glass portion that is permeable to nitric oxide. Accordingly, nitric oxide permeable layers 108 may, include numerous types of porous ceramics that are permeable to nitric oxide. In some embodiments, a nitric oxide permeable layer 108 may include a porous metal portion that is permeable to nitric oxide. In some embodiments, a nitric oxide permeable layer 108 may include a nitric oxide permeable coating (e.g., U.S. Patent Application Nos.: 20050220838 and 20030093143).

Independent Light Source

Numerous light sources may be used within system 100. In some embodiments, one or more independent light sources 110 may be configured to emit light that facilitates release of nitric oxide from one or more nitric oxide donors. In some embodiments, one or more independent light sources 110 may be configured to emit light that facilitates release of nitric oxide from one or more specifically selected photolyzable nitric oxide donors 104. For example, in some embodiments, one or more independent light sources 110 may be selected that emit one or more wavelengths of light that facilitate photolysis of one or more photolyzable nitric oxide donors 104 and that do not emit one or more wavelengths of light that do not facilitate photolysis of the one or more photolyzable nitric oxide donors 104. Accordingly, independent light sources 110 and photolyzable nitric donors may be selected in a paired manner. In some embodiments, system 100 may include one or more independent light sources 110 that may be configured as a hand-held device. In some embodiments, one or more independent light sources 110 may be configured as a hand-held device that is configured to emit light onto one or more dressings 102. In some embodiments, one or more independent light sources 110 may be configured as a hand-held device that is configured to emit light onto a dressing 109 that may be configured as a patch. In some embodiments, one or more independent light sources 110 may be configured as a hand-held device that is configured to emit light onto a dressing 102 that may be configured as a bandage. Accordingly, an independent light source 110 may be configured in numerous ways to emit light onto one or more dressings 102.

Individual

A dressing 102 may be used to deliver nitric oxide to an individual 112. In some embodiments, an individual 112 may be a human. In some embodiments, a dressing 102 may be used to deliver nitric oxide to the skin of an individual 112. In some embodiments, such delivery may be for cosmetic purposes. In some embodiments, such delivery may be for therapeutic purposes. For example, in some embodiments, a dressing 102 may be used to deliver nitric oxide to a skin lesion, such as a skin ulcer, a burn, a cut, a puncture, a laceration, a blunt trauma, an acne lesion, a boil, and the like. In some embodiments, a dressing 102 may be used to deliver nitric oxide to a skin surface to increase the expression of endogenous collagenase. In some embodiments, a dressing 102 may be used to deliver nitric oxide to a skin surface to regulate the formation of collagen. In some embodiments, a dressing 102 may be used to deliver nitric oxide to reduce inflammation (e.g., reduce exudate secretion) at the site of a lesion (e.g., U.S. Patent Application No.: 2007/0088316). In some embodiments, a dressing 102 may be used to deliver nitric oxide to reduce the microbial burden within a wound site. For example, in some embodiments, a dressing 102 may be used to deliver nitric oxide as an antibacterial agent against methicillin-resistant *Staphylococcus aureus*. A dressing, 102 may deliver nitric oxide to an individual 112 at numerous concentrations. For example, in some embodiments, nitric oxide may be delivered at a concentration ranging from about 160 ppm to about 400 ppm. Such concentrations may be used without inducing toxicity in the healthy cells around a wound site (e.g., U.S. Patent Application No.: 2007/0088316).

Figure 2:
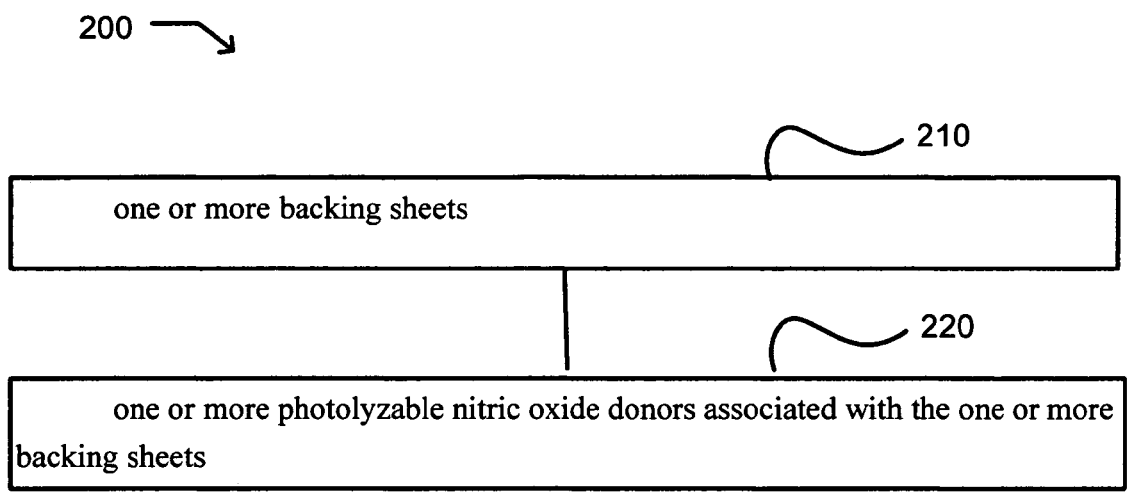
FIG. 2 illustrates embodiment 200 of dressing 102 within system 100.

FIG. 2 illustrates embodiment 200 of dressing 102 within system 100. In FIG. 2, discussion and explanation may be provided with respect to the above-described example of FIG. 1, and/or with respect to other examples and contexts. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 200 may include module 210 that includes one or more backing sheets. In some embodiments, dressing 102 may include one or more backing sheets 106. One or more backing sheets 106 may be fabricated from one or more materials. In some embodiments, one or more backing sheets 106 may include portions that are fabricated from different types of materials. For example, in some embodiments, a backing sheet 106 may include one or more portions that include one or more adhesive materials and one or more portions that include one or more nonadhesive materials. In some embodiments, a backing sheet 106 may include one or more portions that include one or more gas permeable materials and one or more portions that include one or more gas impermeable materials. Accordingly, one or more backing sheets 106 may include numerous combinations of materials that exhibit numerous properties. Examples of such material include, but are not limited to, elastic materials, inelastic materials, adhesive materials, nonadhesive materials, conductive materials, nonconductive materials, perforated materials, nonperforated materials, fluid permeable materials, fluid impermeable materials, gas permeable materials, gas impermeable materials, light permeable materials, selectively light permeable materials, light impermeable materials, and the like.

The embodiment 200 may include module 220 that includes one or more photolyzable nitric oxide donors associated with the one or more backing sheets. In some embodiments, dressing 102 may include one or more photolyzable nitric oxide donors 104 associated with one or more backing sheets 106. In some embodiments, one or more photolyzable nitric oxide donors 104 may include one or more diazeniumdiolates. In some embodiments, one or more photolyzable nitric oxide donors 104 may include one or more quantum dots. In some embodiments, one or more photolyzable nitric oxide donors 104 may include one or more fluorescent materials. In some embodiments, one or more photolyzable nitric oxide donors 104 may include one or more rare-earth materials. In some embodiments, one or more photolyzable nitric oxide donors 104 may include one or more fluorescent materials. In some embodiments, one or more photolyzable nitric oxide donors 104 may be associated with one or more polymeric materials.

Figure 3:
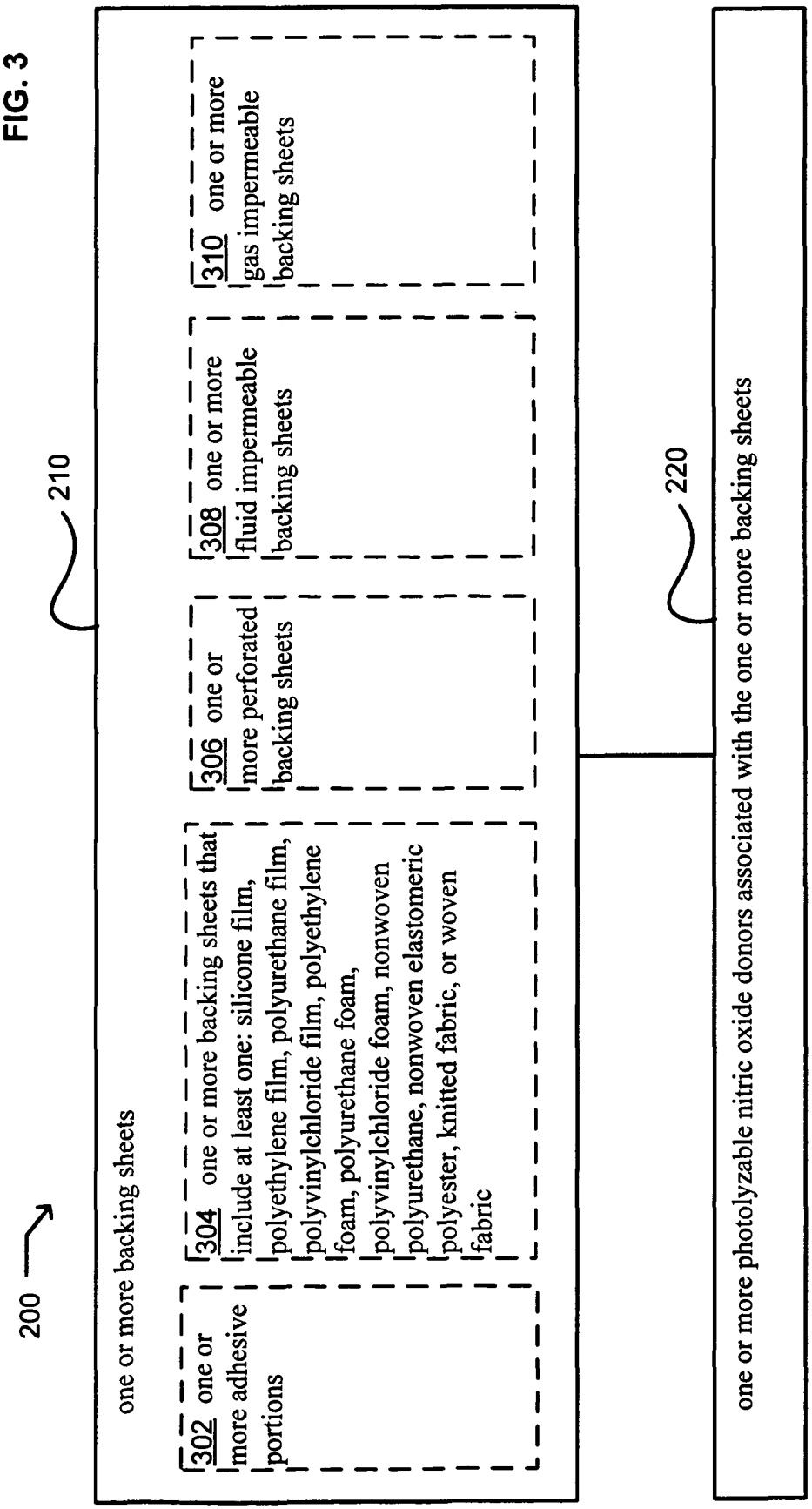
FIG. 3 illustrates alternate embodiments of embodiment 200 of dressing 102 within system 100.

FIG. 3 illustrates alternative embodiments of embodiment 200 of dressing 102 within system 100 of FIG. 2. FIG. 3 illustrates example embodiments of module 210. Additional embodiments may include an embodiment 302, an embodiment 304, an embodiment 306, an embodiment 308, and/or an embodiment 310.

At embodiment 309, module 210 may include one or more adhesive portions. In some embodiments, one or more backing sheets 106 may include one or more adhesive portions. Numerous types of adhesive materials may be associated with one or more backing sheets 106. Examples of such adhesive materials include, but are not limited to, UV-curable acrylic adhesives, rubber-based hot melt adhesives, and the like. One or more adhesive materials may be positioned on one or more backing sheets 106 in many conformations. In some embodiments, one or more adhesives may be positioned on a backing sheet 106 to form a pocket which will form a sealed space when attached to a surface. For example, in some embodiments, a backing sheet 106 may be configured as a circular patch with adhesive material positioned on the periphery of the circular patch such that the interior of the patch forms a sealed space when the patch is applied to a surface of an individual 112. Is some embodiments, such a patch may include one or more photolyzable nitric oxide donors 104 within the interior of the patch such that nitric oxide released from the one or more photolyzable nitric oxide donors 104 will be retained within the sealed space next to the surface of the individual 112. Accordingly, in such embodiments, patches may be used to deliver nitric oxide to a surface of an individual. Accordingly, numerous such adhesive and backing sheet 106 configurations may be used to fabricate dressings 102 that may be used to deliver nitric oxide to the surface of an individual 112.

At embodiment 304, module 210 may include one or more backing sheets that include at least one: silicone film, polyethylene film, polyurethane film, polyvinylchloride film, polyethylene foam, polyurethane foam, polyvinylchloride foam, nonwoven polyurethane, nonwoven elastomeric polyester, knitted fabric, or woven fabric. In some embodiments, one or more backing sheets 106 may include at least one: silicone film, polyethylene film, polyurethane film, polyvinylchloride film, polyethylene foam, polyurethane foam, polyvinylchloride foam, nonwoven polyurethane, nonwoven elastomeric polyester, knitted fabric, woven fabric, or substantially any combination thereof. Such materials are known and have been described.

At embodiment 306, module 210 may include one or more perforated backing sheets. In some embodiments, one or more backing sheets 106 may include one or more perforated backing sheets 106. In some embodiments, a dressing 102 may include one or more backing sheets 106 that are entirely perforated. In some embodiments, a dressing 102 may include one or more backing sheets 106 that are partially perforated. In some embodiments, a dressing 102 may include one or more backing sheets 106 having one or more portions that are perforated and one or more portions that are not perforated. For example, in some embodiments, a dressing 102 may be configured as a bandage that includes one or more nonperforated portions that form one or more sealed spaces when applied to a surface of an individual 12 and one or more perforated portions. Accordingly, in some embodiments, such a bandage may include one or more perforated portions that include one or more adhesives that serve to secure the bandage to the surface of an individual 112 and provide for exchange from the surface of the individual 112 that underlies the perforated portion. Examples of such exchange include, but are not limited to, exchange of gas, vapor, fluid, and the like. In addition, in such embodiments, the portion of the bandage that forms the sealed space may include one or more photolyzable nitric oxide donors 104 that release nitric oxide into the space and provide for delivery of nitric oxide to the surface of an individual 112. Dressings 102 may be configured in numerous ways that include one or more perforated backing sheets 106.

At embodiment 308, module 210 may include one or more fluid impermeable backing sheets. In some embodiments, one or more backing sheets 106 may include one or more fluid impermeable backing sheets 106. In some embodiments, a dressing 102 may include one or more backing sheets 106 that are entirely fluid impermeable. In some embodiments, a dressing 102 may include one or more backing sheets 106 that are partially fluid impermeable. In some embodiments, a dressing 102 may include one or more backing sheets 106 having one or more portions that are fluid impermeable and one or more portions that are fluid permeable. Numerous materials may be used to fabricate fluid impermeable backing sheets 106. Examples of such materials include, but are not limited to, polycarbonates, polystyrenes, latex, metals, ceramics, metal alloys, and the like. Fluid impermeable backing sheet 106 may be configured in numerous ways. In some embodiments, one or more backing sheets 106 may be selectively permeable. For example, in some embodiments, one or more backing sheets 106 may be fluid impermeable and vapor permeable.

At embodiment 310, module 210 may include one or more gas impermeable backing sheets. In some embodiments, one or more backing sheets 106 may include one or more gas impermeable backing sheets 106. In some embodiments, a dressing 102 may include one or more backing sheets 106 that are entirely gas impermeable. In some embodiments, a dressing 102 may include one or more backing sheets 106 that are partially gas impermeable. In some embodiments, a dressing 109 may include one or more backing sheets 106 having one or more portions that are gas impermeable and one or more portions that are gas permeable. Numerous materials may be used to fabricate gas impermeable substrates. Examples of such materials include, but are not limited to, polycarbonates, polystyrenes, latex, metals, ceramics, metal alloys, and the like. For example, in some embodiments, a dressing 102 may be configured as a bandage that includes one or more gas impermeable portions that form one or more sealed spaces when applied to a surface of an individual 112 and one or more gas permeable portions. Accordingly, the one or more gas impermeable portions may include one or more photolyzable nitric oxide donors 104 that release nitric oxide into the sealed space to facilitate delivery to a surface of an individual 112. Dressings 102 may be configured in numerous ways that include one or more gas impermeable backing sheets 106.

Figure 4:
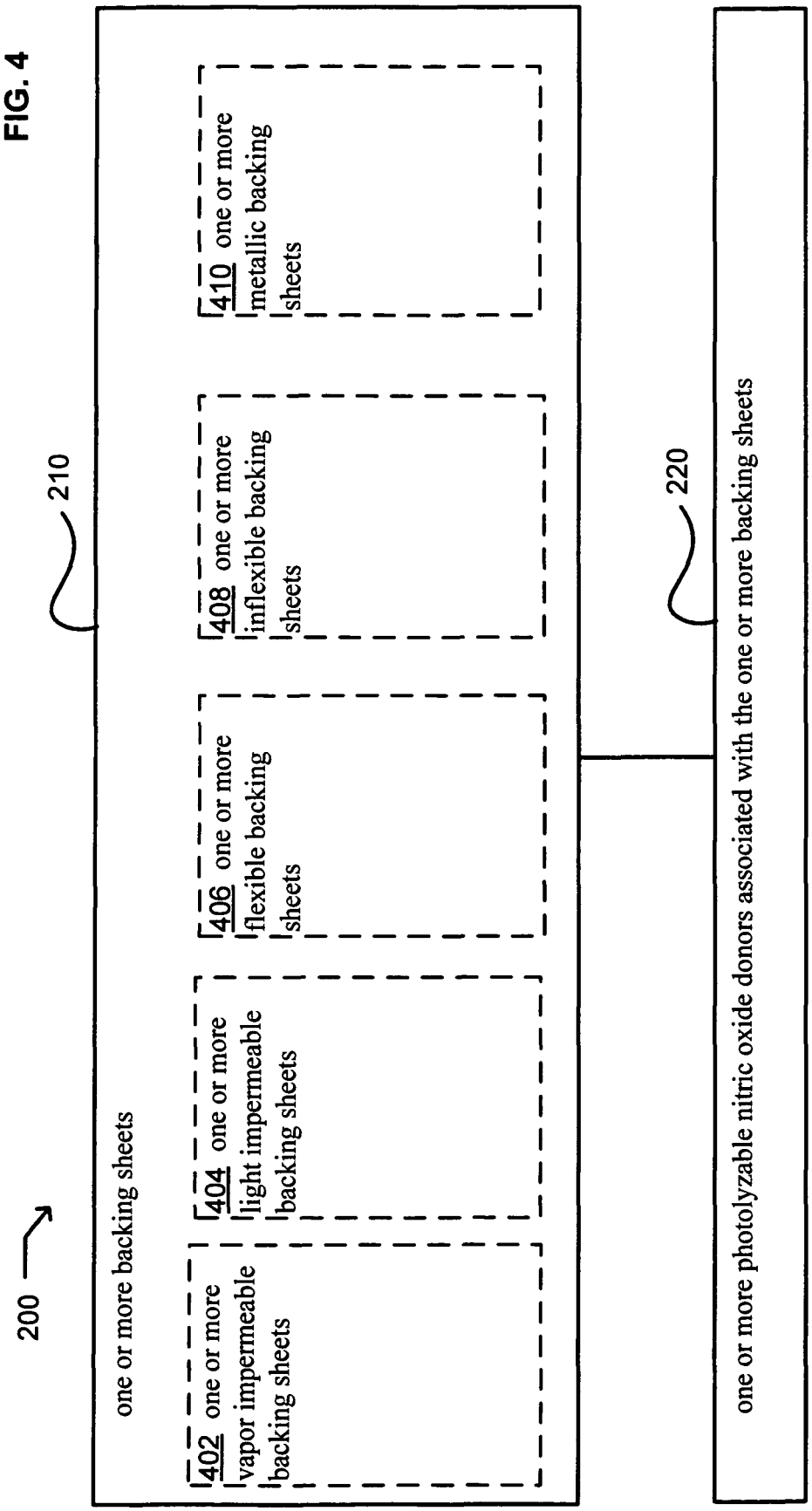
FIG. 4 illustrates alternate embodiments of embodiment 200 of dressing 102 within system 100.

FIG. 4 illustrates alternative embodiments of embodiment 200 of dressing 102 within system 100 of FIG. 2. FIG. 4 illustrates example embodiments of module 210. Additional embodiments may include an embodiment 402, an embodiment 404, an embodiment 406, an embodiment 408, and/or an embodiment 410.

At embodiment 402, module 210 may include one or more vapor impermeable backing sheets. In some embodiments, one or more backing sheets 106 may include one or more vapor impermeable backing sheets 106. In some embodiments, a dressing 102 may include one or more backing sheets 106 that are entirely vapor impermeable. In some embodiments, a dressing 102 may include one or more backing sheets 106 that are partially vapor impermeable. In some embodiments, a dressing 102 may include one or more backing sheets 106 having one or more portions that are vapor impermeable and one or more portions that are vapor permeable. Numerous materials may be used to fabricate vapor impermeable substrates. Examples of such materials include, but are not limited to, polycarbonates, polystyrenes, latex, metals, ceramics, metal alloys; and the like. Vapor impermeable backing sheet 106 may be configured in numerous ways. In some embodiments, one or more backing sheets 106 that are vapor impermeable may be configured to retain water vapor in one or more areas. For example, in some embodiments, one or more backing sheets 106 may be used to retain water vapor at a site to which nitric oxide is to be delivered. Accordingly, in some embodiments, one or more vapor impermeable backing sheet 106 may be configured as an outside surface of a dressing 102 that includes one or more photolyzable nitric oxide donors 104 that are associated with an inside surface of the dressing 102 such that water vapor is blocked from passage through the vapor impermeable backing sheet 106. For example, in some embodiments, a dressing 102 may be configured as a patch with one or more vapor impermeable backing sheet 106 forming an outside surface of the patch and one or more photolyzable nitric oxide donors 104 associated with the inside surface of the patch relative to a surface to which nitric oxide is to be delivered.

At embodiment 404, module 210 may include one or more light impermeable backing sheets. In some embodiments, one or more backing sheets 106 may include one or more light impermeable backing sheets 106. In some embodiments, a dressing 102 may include one or more backing sheets 106 that are entirely light impermeable. In some embodiments, a dressing 102 may include one or more backing sheets 106 that are partially light impermeable. In some embodiments, a dressing 102 may include one or more backing sheets 106 having one or more portions that are light impermeable and one or more portions that are light permeable. Numerous materials may be used to fabricate light impermeable backing sheets 106. In some embodiments, one or more backing sheets 106 may be selectively light impermeable. For example, in some embodiments, one or more backing sheets 106 may be impermeable to light that facilitates photolysis of one or more photolyzable nitric oxide donors 104. In some embodiments, one or more backing sheets 106 may be impermeable to ultraviolet light. In some embodiments, one or more backing sheets 106 may be selectively impermeable to light that causes damage to tissue. In some embodiments, a dressing 102 may include one or more backing sheets 106 that are removable. For example, in some embodiments, a dressing 102 may be configured as a bandage that includes one or more photolyzable nitric oxide donors 104 that are covered with a light impermeable backing sheet 106 that may be removed to facilitate entry of light to release nitric oxide from the one or more photolyzable nitric oxide donors 104.

At embodiment 406, module 210 may include one or more flexible backing sheets. In some embodiments, one or more backing sheets 106 may include one or more flexible backing sheets 106. In some embodiments, all portions of a backing sheet 106 may be flexible. In some embodiments, one or more portions of a backing sheet 106 may be flexible. In some embodiments, one or more portions of a backing sheet 106 may be flexible and one or more portions of the backing sheet 106 may be inflexible. In some embodiments, a dressing 102 may include one or more backing sheets 106 that include one or more inflexible portions that are configured to create a closed space above a surface without contacting the surface and one or more backing sheets 106 that include one or more flexible portions that allow the dressing 102 to be adhered to the surface. For example, in some embodiments, a dressing 102 may include an inflexible backing sheet 106 that is shaped like a dome to facilitate delivery of nitric oxide to a surface and a flexible backing sheet 106 that facilitates adhesion of the dressing 102 to the surface to which nitric oxide is to be delivered. Accordingly, a flexible backing sheet 106 may be configured in numerous ways.

At embodiment 408, module 210 may include one or more inflexible backing sheets. In some embodiments, one or more backing sheets 106 may include one or more inflexible backing sheets 106. In some embodiments, all portions of a backing sheet 106 may be inflexible. In some embodiments, one or more portions of a backing sheet 106 may be inflexible. For example, in some embodiments, a backing sheet 106 may include one or more inflexible portions and one or more flexible portions. In some embodiments, a dressing 102 may include one or more backing sheets 106 that include one or more inflexible portions that are configured to create a closed space above a surface and one or more backing sheets 106 that include one or more flexible portions that allow the dressing 102 to be adhered to the surface. For example, in some embodiments, a dressing 102 may include an inflexible backing sheet 106 that is shaped like a dome to facilitate delivery of nitric oxide to a surface and a-flexible backing sheet 106 that facilitates adhesion of the dressing 102 to the surface to which nitric oxide is to be delivered. Accordingly, a flexible backing sheet 106 may be configured in numerous ways.

At embodiment 410, module 210 may include one or more metallic backing sheets. In some embodiments, one or more backing sheets 106 may include one or more metallic backing sheets 106. For example, in some embodiments, a backing sheet 106 may be a metal foil. In some embodiments, a backing sheet 106 may be partially constructed with one or more metallic materials. For example, in some embodiments, a backing sheet 106 may include one or more portions that are metallic and one or more portions that are non-metallic.

Figure 5:
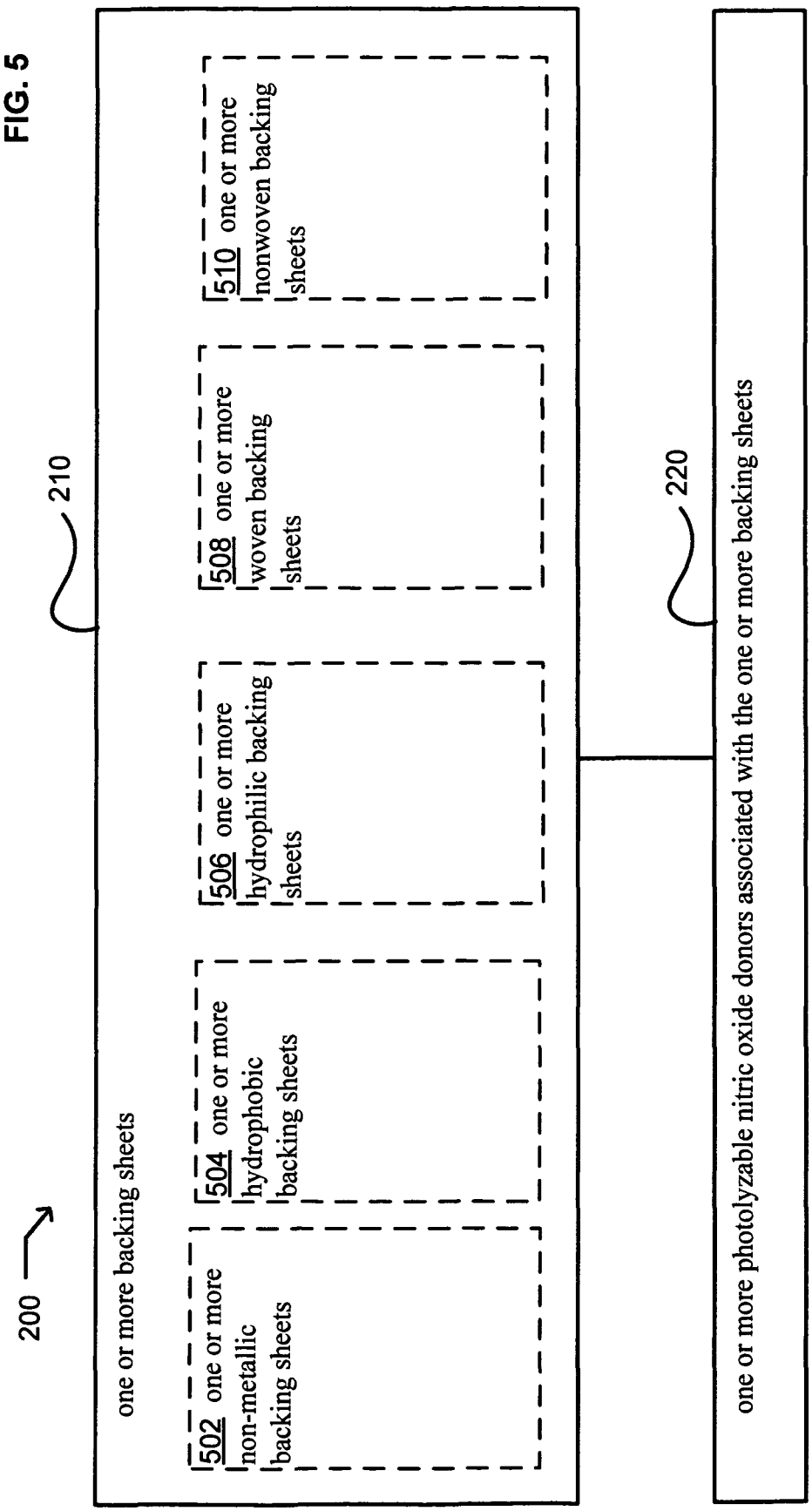
FIG. 5 illustrates alternate embodiments of embodiment 200 of dressing 102 within system 100.

FIG. 5 illustrates alternate embodiments of embodiment 200 of dressing 109 within system 100 of FIG. 2. FIG. 5 illustrates example embodiments of module 210. Additional embodiments may include an embodiment 502, an embodiment 504, all embodiment 506, an embodiment 508, and/or an embodiment 510.

At embodiment 502, module 210 may include one or more non-metallic backing sheets. In some embodiments, one or more backing sheets 106 may include one or more non-metallic backing sheets 106. In some embodiments, a backing sheet 106 may be entirely constructed with one or more non-metallic materials. In some embodiments, a backing sheet 106 may be partially constructed with one or more non-metallic materials. For example, in some embodiments, a backing sheet 106 may include one or more portions that are non-metallic and one or more portions that are metallic. In some embodiments, a backing sheet 106 may be a plastic backing sheet 106. In some embodiments, a backing sheet 106 may be constructed from woven ceramic fibers. In some embodiments, a backing sheet 106 may be constructed from woven natural fibers. Examples of such natural fibers include, but are not limited to, wool fibers, cotton fibers, silk fibers, and the like. In some embodiments, a backing sheet 106 may be constructed from woven synthetic fibers. Examples of such natural fibers include, but are not limited to, nylon fibers, rayon fibers, and the like.

At embodiment 504, module 210 may include one or more hydrophobic backing sheets. In some embodiments, one or more backing sheets 106 may include one or more hydrophobic backing sheets 106. In some embodiments, a backing sheet 106 may be entirely constructed with one or more hydrophobic materials. In some embodiments, a backing sheet 106 may be partially constructed with one or more hydrophobic materials. For example, in some embodiments, a backing sheet 106 may include one or more portions that are hydrophobic and one or more portions that are hydrophilic. Examples of hydrophobic materials include, but are not limited to, polytetrafluoroethylene, polytrifluorochloroethylene, and the like (e.g., U.S. Pat. No. 4,210,697).

At embodiment 506, module 210 may include one or more hydrophilic backing sheets. In some embodiments, one or more backing sheets 106 may include one or more hydrophilic backing sheets 106. In some embodiments, a backing sheet 106 may be entirely constructed with one or more hydrophilic materials. In some embodiments, a backing sheet 106 may be partially constructed with one or more hydrophilic materials. For example, in some embodiments, a backing sheet 106 may include one or more portions that are hydrophobic and one or more portions that are hydrophilic. Examples of hydrophilic materials include, but are not limited to, hydrophilic polyethylene sheets (e.g., U.S. Pat. No. 6,436,470), a cellulosic material such as regenerated cellulose rollstock film (e.g., U.S. Pat. No. 5,690,777), and the like.

At embodiment 508, module 210 may include one or more woven backing sheets. In some embodiments, one or more backing sheets 106 may include one or more woven backing sheets 106. Numerous materials may be used to construct a woven backing sheet 106. Examples of such materials include, but are not limited to, synthetic fibers, natural fibers, combinations of natural fibers and synthetic fibers, and the like. In some embodiments, one or more backing sheets 106 may include one or more portions that include woven backing sheet 106 and one or more portions that include non-woven backing sheets 106.

At embodiment 510, module 210 may include one or more nonwoven backing sheets. In some embodiments, one or more backing sheets 106 may include one or more non-woven backing sheets 106. Numerous materials may be used to construct a non-woven backing sheet 106. Examples of such materials include, but are not limited to, synthetic polymers, metals, metal alloys, silicates, ceramics, and the like. In some embodiments, non-woven backing sheet 106 may be fabricated through use of a spray process where material is sprayed onto a form. In some embodiments, non-woven backing sheet 106 may be fabricated though use of a sputtering process where material is sputtered onto a form. In some embodiments, one or more backing sheets 106 may include one or more portions that include woven backing sheet 106 and one or more portions that include non-woven backing sheets 106.

Figure 6:
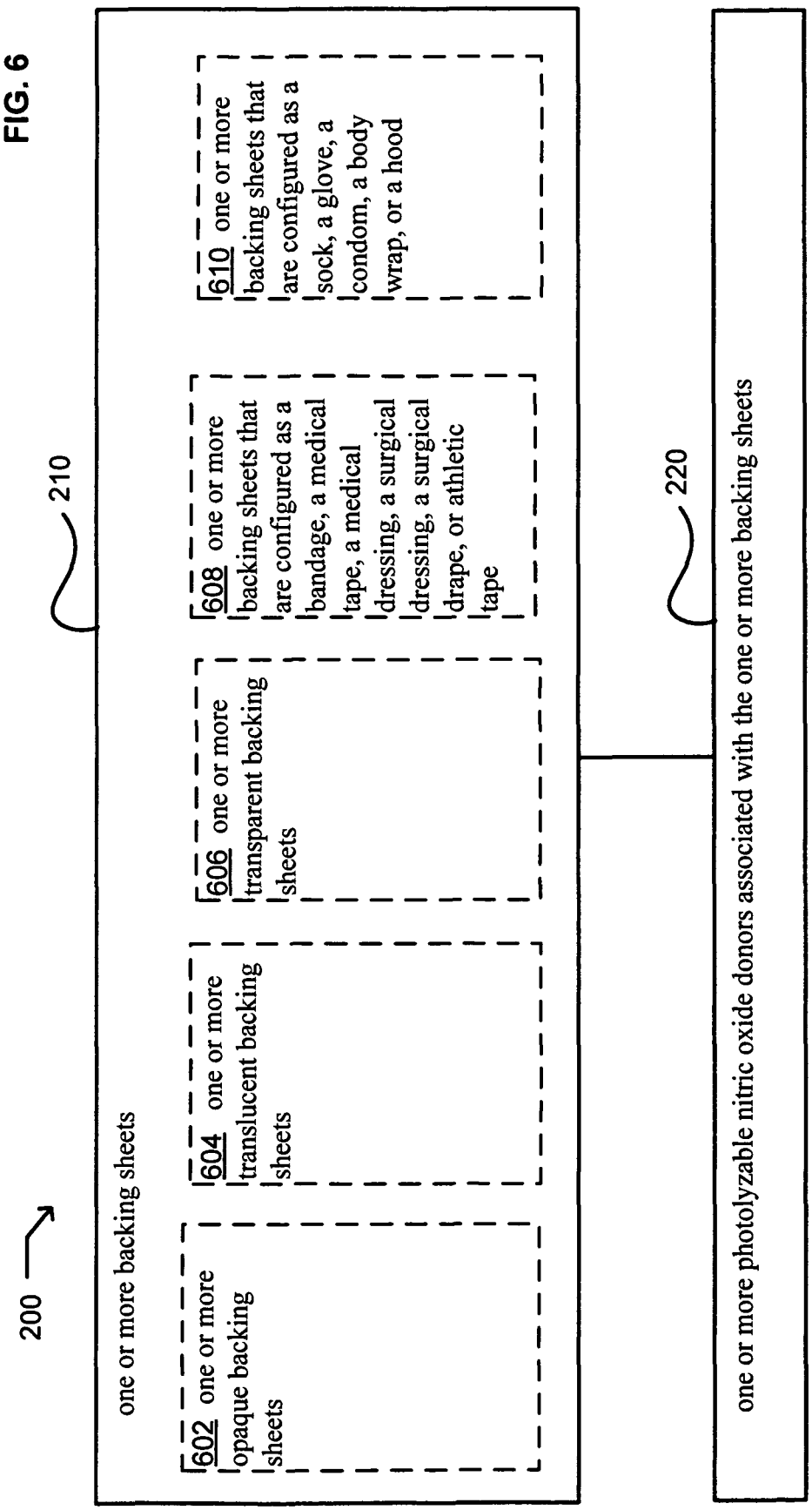
FIG. 6 illustrates alternate embodiments of embodiment 200 of dressing 102 within system 100.

FIG. 6 illustrates alternative embodiments of embodiment 200 of dressing 102 within system 100 of FIG. 2. FIG. 6 illustrates example embodiments of module 210. Additional embodiments may include an embodiment 602, an embodiment 604, an embodiment 606, an embodiment 608, and/or an embodiment 610.

At embodiment 602, module 210 may include one or more opaque backing sheets. In some embodiments, one or more backing sheets 106 may include one or more opaque backing sheets 106. Numerous materials may be used to construct an opaque backing sheet 106. Examples of such materials include, but are not limited to, polymethyl methacrylate treated so as to have a low transmission, a white vinyl chloride polymer, a white polyester, polyethylene, and the like (e.g., U.S. Pat. No. 7,183,001).

At embodiment 604, module 210 may include one or more translucent backing sheets. In some embodiments, one or more backing sheets 106 may include one or more translucent backing sheets 106. Numerous materials may be used to construct a translucent backing sheet 106. Examples of such materials include, but are not limited to, translucent polyvinyl butyral (PVB) (e.g., U.S. Pat. No. 7,253,953), matted polyethylene, and the like.

At embodiment 606, module 210 may include one or more transparent backing sheets. In some embodiments, one or more backing sheets 106 may include one or more transparent backing sheets 106. Numerous materials may be used to construct a transparent backing sheet 106. Examples of such materials include, but are not limited to, woven glass fibers, plastics, and the like.

At embodiment 608, module 210 may include one or more backing sheets that are configured as a bandage, a medical tape, a medical dressing, a surgical dressing, a surgical drape, or athletic tape. In some embodiments, one or more backing sheets 106 may include one or more backing sheets 106 that are configured as a patch, bandage, a medical tape, a medical dressing 102, a surgical dressing 102, a surgical drape, athletic tape, and the like.

At embodiment 610, module 210 may include one or more backing sheets that are configured as a sock, a glove, a condom, a body wrap, or a hood. In some embodiments, one or more backing sheets 106 may include one or more backing sheets 106 that are configured as a sock, a glove, a condom, a body wrap, or a hood.

Figure 7:
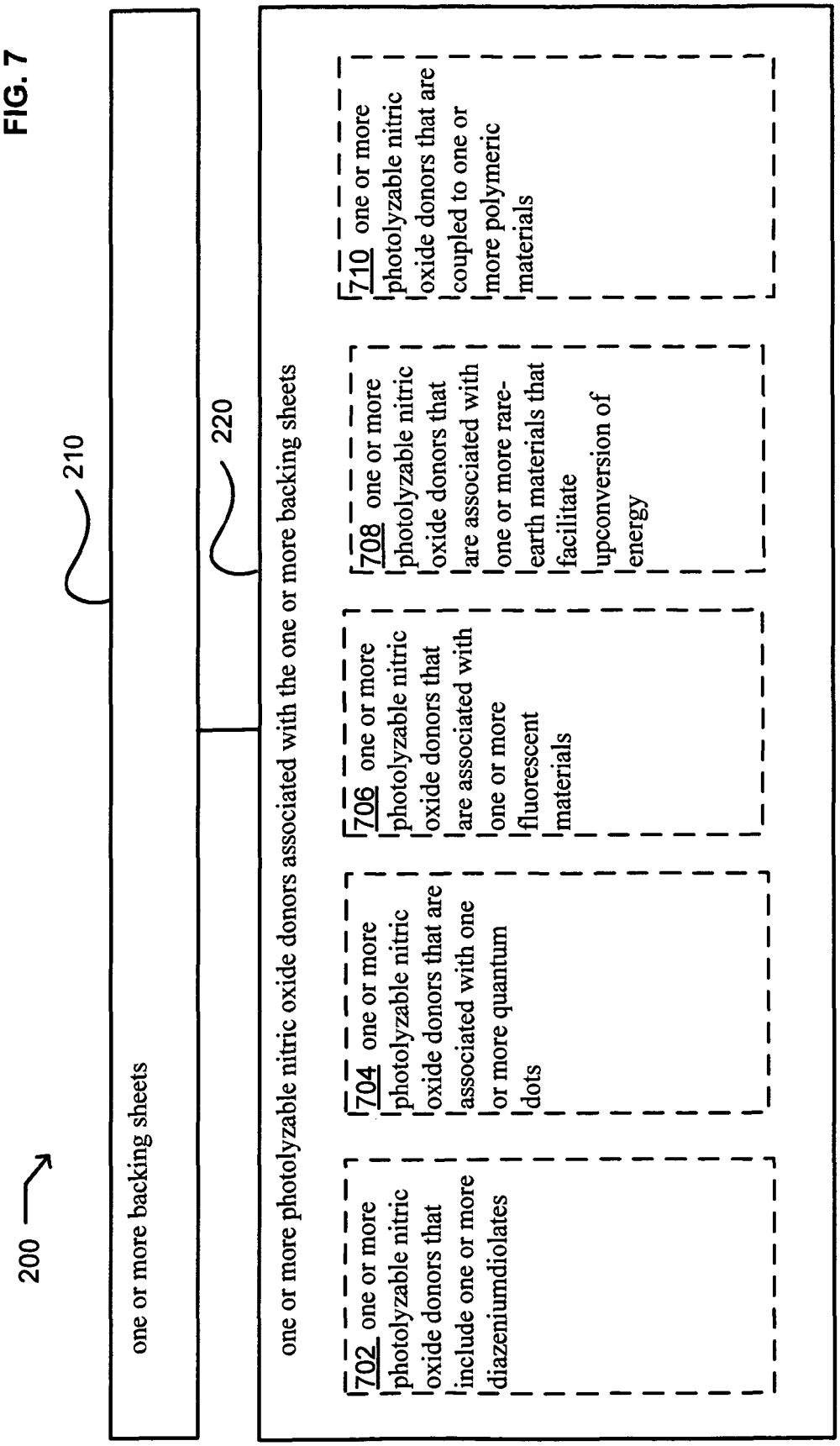
FIG. 7 illustrates alternate embodiments of embodiment 200 of dressing 102 within system 100.

FIG. 7 illustrates alternative embodiments of embodiment 200 of dressing 102 within system 100 of FIG. 2. FIG. 7 illustrates example embodiments of module 220. Additional embodiments may include an embodiment 709, an embodiment 704, an embodiment 706, an embodiment 708, and/or an embodiment 710.

At embodiment 709, module 220 may include one or more photolyzable nitric oxide donors that include one or more diazeniumdiolates. In some embodiments, one or more photolyzable nitric oxide donors 104 may include one or more photolyzable nitric oxide donors 104 that include one or more diazeniumdiolates. Many photolyzable nitric oxide donors 104 that are diazeniumdiolates are known and have been described (e.g., U.S. Pat. No. 7,199,529). Examples of such diazeniumdiolates include, but are not limited to, $O^2$-benzyl, $O^2$-naphthylmethyl substituted diazeniumdiolates and $O^2$-naphtylallyl substituted diazeniumdiolates.

At embodiment 704, module 220 may include one or more photolyzable nitric oxide donors that are associated with one or more quantum dots. In some embodiments, one or more photolyzable nitric oxide donors 104 may include one or more photolyzable nitric oxide donors 104 that are associated with one or more quantum dots. For example, in some embodiments, one or more diazeniumdiolates may be associated with one or more quantum dots. In some embodiments, one or more quantum dots may be tuned to emit light that facilitates photolysis of one or more nitric oxide donors. In some embodiments, a quantum dot may be tuned to emit light that specifically facilitates photolysis of one or more nitric oxide donors. For example, in some embodiments, one or more quantum dots may emit select wavelengths of light that correspond to wavelengths of light that cause photolysis of one or more nitric oxide donors. In some embodiments, one or more quantum dots may be selected that absorb light and emit light that facilitates photolysis of one or more nitric oxide donors.

At embodiment 706, module 220 may include one or more photolyzable nitric oxide donors that are associated with one or more fluorescent materials. In some embodiments, one or more photolyzable nitric oxide donors 104 may include one or more photolyzable nitric oxide donors 104 that are associated with one or more rare-earth materials. In some embodiments, one or more rare-earth materials may include one or more rare-earth elements. The rare-earth elements are a collection of sixteen chemical elements in the periodic table, namely scandium, yttrium, and fourteen of the fifteen lanthanoids (excluding promethium). In some embodiments, one or more rare-earth materials may include one or more rare-earth elements that fluoresce.

At embodiment 708, module 220 may include one or more photolyzable nitric oxide donors that are associated with one or more rare-earth materials that facilitate upconversion of energy. In some embodiments, one or more photolyzable nitric oxide donors 104 may include one or more photolyzable nitric oxide donors 104 that are associated with one or more rare-earth materials that facilitate upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more photolyzable nitric oxide donors 104 may be associated with one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more photolyzable nitric oxide donors 104 may be associated with $Nd^{3+}$ doped $KPb_2Cl_5$ crystals. In some embodiments, one or more photolyzable nitric oxide donors 104 may be associated with thiogallates doped with rare earths, such as $CaGa_2S_4:Ce^{3+}$ and $SrGa_2S_4:Ce^{3+}$. In some embodiments, one or more photolyzable nitric oxide donors 104 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

At embodiment 710, module 220 may include one or more photolyzable nitric oxide donors that are coupled to one or more polymeric materials. In some embodiments, one or more photolyzable nitric oxide donors 104 may include one or more photolyzable nitric oxide donors 104 that are coupled to one or more polymeric materials. For example, in some embodiments, one or more polymer matrices may be impregnated with one or more photolyzable nitric oxide donors 104 (e.g., U.S. Pat. No. 5,994,444). In some embodiments, one or more photolyzable nitric oxide donors 104 may be bound to a polymer. Methods that can be used to couple nitric oxide donors to a polymeric matrix have been reported (e.g., U.S. Pat. No. 5,405,919).

Figure 8:
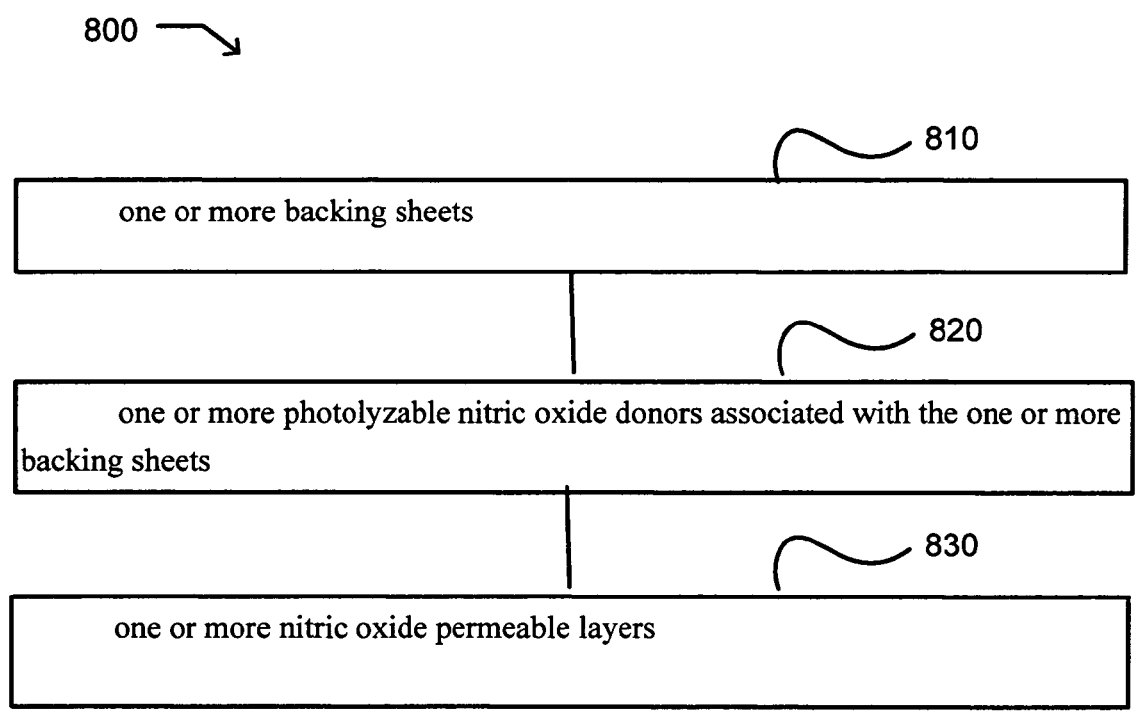
FIG. 8 illustrates embodiment 800 of dressing 102 within system 100.

FIG. 8 illustrates embodiment 800 of dressing 109 within system 100. In FIG. 8, discussion and explanation may be provided with respect to the above-described example of FIG. 1, and/or with respect to other examples and contexts. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 800 may include module 810 that includes one or more backing sheets. In some embodiments, dressing 102 may include one or more backing sheets 106. One or more backing sheets 106 may be fabricated from one or more materials. In some embodiments, one or more backing sheets 106 may include portions that are fabricated from different types of materials. For example, in some embodiments, a backing sheet 106 may include one or more portions that include one or more adhesive materials and one or more portions that include one or more nonadhesive materials. In some embodiments, a backing sheet 106 may include one or more portions that include one or more gas permeable materials and one or more portions that include one or more gas impermeable materials. Accordingly, one or more backing sheets 106 may include numerous combinations of materials that exhibit numerous properties. Examples of such material include, but are not limited to, elastic materials, inelastic materials, adhesive materials, nonadhesive materials, conductive materials, nonconductive materials, perforated materials, nonperforated materials, fluid permeable materials, fluid impermeable materials, gas permeable materials, gas impermeable materials, light permeable materials, light impermeable materials, and the like.

The embodiment 800 may include module 820 that includes one or more photolyzable nitric oxide donors associated with the one or more backing sheets. In some embodiments, dressing 102 may include one or more photolyzable nitric oxide donors 104 associated with one or more backing sheets 106. In some embodiments, one or more photolyzable nitric oxide donors 104 may include one or more diazeniumdiolates. In some embodiments, one or more photolyzable nitric oxide donors 104 may include one or more quantum dots. In some embodiments, one or more photolyzable nitric oxide donors 104 may include one or more fluorescent materials. In some embodiments, one or more photolyzable nitric oxide donors 104 may include one or more rare-earth materials. In some embodiments, one or more photolyzable nitric oxide donors 104 may include one or more fluorescent materials. In some embodiments, one or more photolyzable nitric oxide donors 104 may be associated with one or more polymeric materials.

The embodiment 800 may include module 830 that includes one or more nitric oxide permeable layers. In some embodiments, dressing 102 may include one or more nitric oxide permeable layers 108. A dressing 102 may include nitric oxide permeable layers 108 that are fabricated from numerous types of material. Examples of such materials include, but are not limited to, ceramics, polymeric materials, metals, plastics, and the like. In some embodiments, nitric oxide permeable layers 108 may include numerous combinations of materials. For example, in some embodiments, a nitric oxide permeable layer 108 may include a nitric oxide impermeable material that is coupled to a nitric oxide permeable material. In some embodiments, a nitric oxide permeable layer 108 may include one or more nitric oxide permeable membranes (e.g., U.S. Patent Application No.: 20020026937). In some embodiments, a nitric oxide permeable layer 108 may include a selectively permeable membrane. For example, in some embodiments, a nitric oxide permeable layer 108 may include a selectively permeable membrane that is a hydrophilic polyester co-polymer membrane system that includes a copolymer with 70% polyester and 30% polyether (e.g., Sympatex™ 10 μm membrane, see Hardwick et al., Clinical Science, 100:395-400 (2001)). In some embodiments, a nitric oxide permeable layer 108 may include a scintered glass portion that is permeable to nitric oxide. Accordingly, nitric oxide permeable layers 108 may include numerous types of porous ceramics that are permeable to nitric oxide. In some embodiments, a nitric oxide permeable layer 108 may include a porous metal portion that is permeable to nitric oxide. In some embodiments, a nitric oxide permeable layer 108 may include a nitric oxide permeable coating (e.g., U.S. Patent Application Nos.: 20050220838 and 20030093143).

Nitric oxide permeable layers 108 may be configured for application to an individual 112. Nitric oxide permeable layers 108 may be configured to facilitate application of nitric oxide to a surface. In some embodiments, one or more nitric oxide permeable layers 108 may be configured to facilitate application of nitric oxide to one or more surfaces of an individual 112. For example, in some embodiments, one or more nitric oxide permeable layers 108 may be configured as a sheet that may be positioned on a skin surface of an individual 112 to deliver nitric oxide to the skin surface. In some embodiments, a nitric oxide permeable layer 108 may be configured as a wearable article (e.g., hats, gloves, mittens, pants, shirts, hoods, patches, tapes, wraps, and the like). In some embodiments, nitric oxide permeable layers 108 may be configured as one or more bags. For example, in some embodiments, one or more nitric oxide permeable layers 108 may be included within a bag and/or sleeve that is configured to deliver nitric oxide to an individual 112. In some embodiments, one or more nitric oxide permeable layers 108 may be configured to enclose at least a portion of one or more photolyzable nitric oxide donors 104.

Figure 9:
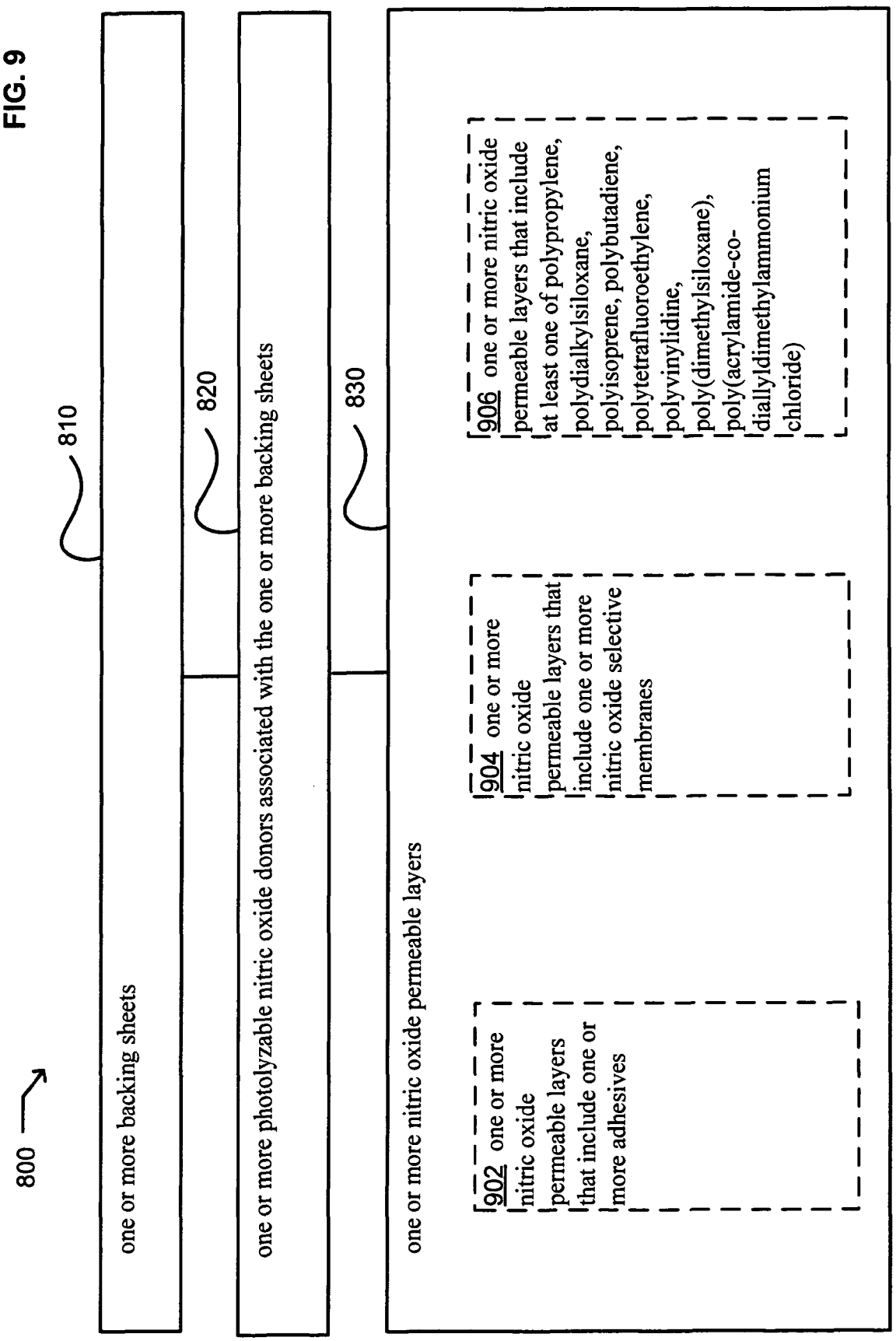
FIG. 9 illustrates alternate embodiments of embodiment 800 of dressing 102 within system 100.

FIG. 9 illustrates alternative embodiments of embodiment 800 of dressing 102 within system 800 of FIG. 8. FIG. 9 illustrates example embodiments of module 830. Additional embodiments may include an embodiment 902, an embodiment 904, and/or an embodiment 906.

At embodiment 902, module 830 may include one or more nitric oxide permeable layers that include one or more adhesives. In some embodiments, one or more nitric oxide permeable layers 108 may include one or more nitric oxide permeable layers 108 that include one or more adhesives. In some embodiments, one or more nitric oxide permeable layers 108 may include one or more adhesives that facilitate adhesion of at least a portion of a nitric oxide permeable layer 108 to a surface. For example, in some embodiments, a dressing 102 may include a nitric oxide permeable layer 108 that includes at least one portion which includes one or more adhesives and that is configured to deliver nitric oxide to a surface adjacent to the nitric oxide permeable layer. Accordingly, such an embodiment of dressing 102 may be used to deliver nitric oxide to a select surface by positioning the dressing 102 on and/or over the select surface and attaching the dressing 102 at points adjacent to the select surface with the one or more adhesives. In some embodiments, such an embodiment of dressing 102 may be configured as a patch, a bandage, tape, a body wrap, a sleeve, a surgical pad, and the like.

At embodiment 904, module 830 may include one or more nitric oxide permeable layers that include one or more nitric oxide selective membranes. In some embodiments, one or more nitric oxide permeable layers 108 may include one or more nitric oxide permeable layers 108 that include one or more nitric oxide selective membranes. In some embodiments, a nitric oxide permeable layer 108 may include a selectively permeable membrane. For example, in some embodiments, a nitric oxide permeable layer 108 may include a selectively permeable membrane that is a hydrophilic polyester co-polymer membrane system that includes a copolymer with 70% polyester and 30% polyether (e.g., Sympatex™ 10 μm membrane, see Hardwick et al., Clinical Science, 100:395-400 (2001)). Methods to fabricate nitric oxide permeable membranes are known (e.g., U.S. Patent Application No.: 20020026937).

At embodiment 906, module 830 may include one or more nitric oxide permeable layers that include at least one of polypropylene, polydialkylsiloxane, polyisoprene, polybutadiene, polytetrafluoroethylene, polyvinylidine, poly(dimethylsiloxane), poly(acrylamide-co-diallyldimethylammonium chloride). In some embodiments, one or more nitric oxide permeable layers 108 may include one or more nitric oxide permeable layers 108 that include at least one of polypropylene, polydialkylsiloxane, polyisoprene, polybutadiene, polytetrafluoroethylene, polyvinylidine, poly(dimethylsiloxane), poly(acrylamide-co-diallyldimethylammonium chloride).

Figure 10:
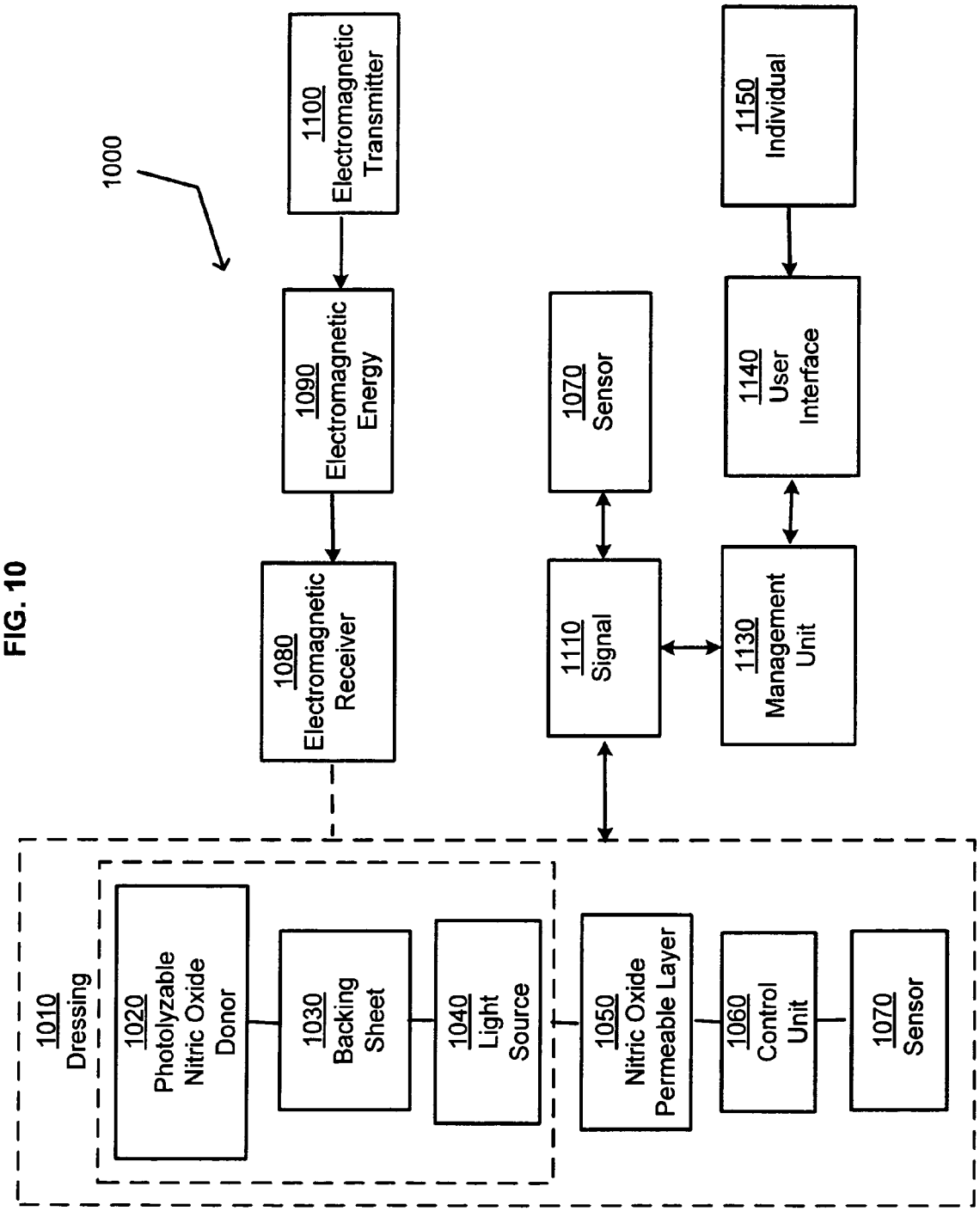
FIG. 10 illustrates an example system 1000 in which embodiments may be implemented.

FIG. 10 illustrates a system 1000 in which embodiments may be implemented. System 1000 may include a dressing 1010 that includes one or more light sources 1040, one or more backing sheets 1030, and one or more photolyzable nitric oxide donors 1020. In some embodiments, system 1000 may include a dressing 1010 that includes one or more control units 1060, one or more sensors 1070, and/or substantially any combination thereof. In some embodiments, system 1000 may include one or more light sources 1040, one or more backing sheets 1030, one or more photolyzable nitric oxide donors 1020, one or more control units 1060, one or more sensors 1070, and/or substantially any combination thereof.

In some embodiments, one or more photolyzable nitric oxide donors 1020 may be physically coupled with the one or more light sources 1040. For example, in some embodiments, the one or more light sources 1040 may be coated with the one or more photolyzable nitric oxide donors 1020. In some embodiments, the one or more light sources 1040 may include one or more polymeric materials that are coupled to at least one of the photolyzable nitric oxide donors 1090. In some embodiments, one or more light sources 1040 may be coated with a composition that includes one or more photolyzable nitric oxide donors 1020. In some embodiments, one or more light sources 1040 may be included within a backing sheet 1030 that is coated with one or more photolyzable nitric oxide donors 1020. Accordingly, in some embodiments one or more light sources 1040 may be in direct contact with one or more photolyzable nitric oxide donors 1020. In some embodiments, one or more light sources 1040 may be in indirect contact with one or more photolyzable nitric oxide donors 1020. In some embodiments, a dressing 1010 may include one or more operably coupled control units 1060. In some embodiments, the one or more control units 1060 may be operably coupled to the one or more light sources 1040. In some embodiments, the one or more control units 1060 may be operably coupled to the one or more light sources 1040 and may be used to control the operation of the one or more light sources 1040. In some embodiments, the one or more control units 1060 may be configured to receive one or more signals 1110. In some embodiments, the one or more control units 1060 may be configured to receive one or more signals 1110 from one or more transmitters. In some embodiments, the one or more control units 1060 may be configured to receive one or more signals 1110 from one or more sensors 1070. In some embodiments, one or more backing sheets 1030 may be configured to facilitate enclosure of one or more photolyzable nitric oxide donors 1020. In some embodiments, one or more backing sheets 1030 may be configured to facilitate enclosure of one or more photolyzable nitric oxide donors 1020 and one or more light sources 1040. In some embodiments, one or more backing sheets 1030 may be configured to facilitate enclosure of one or more photolyzable nitric oxide donors 1020, one or more light sources 1040, and one or more control units 1060. In some embodiments, one or more backing sheets 1030 may be configured to facilitate enclosure of one or more photolyzable nitric oxide donors 1020, one or more light sources 1040, one or more control units 1060, and one or more sensors 1070. In some embodiments, one or more backing sheets 1030 may be configured to facilitate enclosure of one or more photolyzable nitric oxide donors 1090, one or more light sources 1040, one or more control units 1060, one or more sensors 1070, or substantially any combination thereof. In some embodiments, one or more dressings 1010 may be operably coupled to one or more electromagnetic receivers 1080. In some embodiments, system 1000 may include one or more electromagnetic receivers 1080 that are configured to receive electromagnetic energy 1090. In some embodiments, system 1000 may include one or more electromagnetic receivers 1080 that are configured to receive electromagnetic energy 1090 that is transmitted by one or more electromagnetic transmitters 1100. In some embodiments, the one or more electromagnetic receivers 1080 may be operably coupled to a dressing 1010. In some embodiments, the one or more electromagnetic receivers 1080 may be operably coupled to one or more light sources 1040. In some embodiments, the one or more electromagnetic receivers 1080 may be operably coupled to the one or more light sources 1040 such that the one or more light sources 1040 are energized through receipt of electromagnetic energy 1090. In some embodiments, system 1000 may include one or more light sources 1040, one or more photolyzable nitric oxide donors 1020, one or more control units 1060, one or more backing sheets 1030, one or more sensors 1070, one or more electromagnetic receivers 1080, one or more electromagnetic transmitters 1100, or substantially any combination thereof.

Dressing

System 1000 includes one or more dressings 1010. A dressing 1010 may be configured in numerous ways. In some embodiments, a dressing 1010 may be configured to deliver nitric oxide to a surface of an individual 1150. In some embodiments, a dressing 1010 may be configured for application to an outside surface of an individual 1150. For example, in some embodiments, a dressing 1010 may be configured to deliver nitric oxide to the skin of an individual 1150. Accordingly, a dressing 1010 may be configured in numerous ways to deliver nitric oxide to a surface or region of an individual 1150. In some embodiments, a dressing 1010 may be configured to deliver nitric oxide as a therapeutic agent (e.g., U.S. Patent Application No.: 2007/0088316). For example, in some embodiments, a dressing 1010 may be configured to deliver nitric oxide to a person to combat infection. In some embodiments, a dressing 1010 may be configured to deliver nitric oxide to a person to assist in removal of necrotic tissue. In some embodiments, a dressing 1010 may be configured to deliver nitric oxide to a person to reduce inflammation. In some embodiments, a dressing 1010 may be configured to deliver nitric oxide to a person to upregulate the expression of collagenase. In some embodiments, a dressing 1010 may be configured to deliver nitric oxide to a person to facilitate vascularisation. In some embodiments, a dressing 1010 mall be configured to deliver nitric oxide to a person suffering from diabetes. For example, in some embodiments, a dressing 1010 may be configured to deliver nitric oxide to tissue lesions. In some embodiments, a dressing 1010 may be configured to deliver nitric oxide as a sanitizing agent. In some embodiments, a dressing 1010 may be configured to deliver nitric oxide to an accident victim. For example, in some embodiments, a dressing 1010 may be configured as a bandage and/or patch that may be applied to an individual 1150.

In some embodiments, a dressing 1010 may be applied to an individual 1150 and then irradiated with light to facilitate release of nitric oxide from one or more photolyzable nitric oxide donors 1020 associated with the dressing 1010. For example, in some embodiments, a dressing 1010 may be applied to an individual 1010 and then a Tight source 1040 may be used to irradiate the dressing 1010 to facilitate release of nitric oxide from one or more photolyzable nitric oxide donors 1090 associated with the dressing 1010. In some embodiments, ambient light may be used to facilitate release of nitric oxide from one or more photolyzable nitric oxide donors 1020 associated with the dressing 1010. For example, in some embodiments, a dressing 1010 may be configured with one or more transmissive backing sheets 1030 through which ambient light may pass to facilitate release of nitric oxide from one or more photolyzable nitric oxide donors 1020 associated with the dressing 1010. In some embodiments, a dressing 1010 may be applied to an individual 1150 and then irradiated width light emitted from one or more light sources 1040 that are associated with one or more backing sheets 1030 to facilitate release of nitric oxide for one or more photolyzable nitric oxide donors 1020 that are associated with the dressing 1010. For example, in some embodiments, a dressing 1010 may be applied to an individual 1150 and then a light source 1040 that is associated with one or more backing sheets 1030 may be used to irradiate one or more photolyzable nitric oxide donors 1020 associated with the dressing 1010 to facilitate release of nitric oxide.

In some embodiments, a dressing 1010 may be configured to deliver nitric oxide in a controlled manner. For example, in some embodiments, a dressing 1010 that is configured as a patch that includes one or more photolyzable nitric oxide donors 1010 may be applied to an individual 1150 and then exposed to light to release nitric oxide onto the space between the patch and the surface of the individual 1150. In some embodiments, a dressing 1010 may be configured to deliver a preselected concentration of nitric oxide to a surface of an individual 1150. For example, in some embodiments, a dressing 1010 may be configured to include a quantity of one or more photolyzable nitric oxide donors 1020 that release a predictable amount of nitric oxide upon being exposed to light. Accordingly, such dressings 1010 may be constructed such that they deliver a known concentration of nitric oxide to the surface of an individual 1150. For example, in some embodiments, a dressing 1010 that is configured as a patch may be applied to an individual 1150 such that the patch covers a known amount of surface area of an individual 1150. In some embodiments, such a patch may be configured to create a closed airspace between the surface of an individual 1150 and the patch. Accordingly, in such embodiments, one or more photolyzable nitric oxide donors 1020 may be included within the patch that will release a quantity of nitric oxide within the closed airspace on the surface of the individual 1150 that is therapeutic. For example, in some embodiments, a quantity of one or more photolyzable nitric oxide donors 1020 may be included within a dressing 1010 that is configured as a patch such that nitric oxide is released into the space between the patch and the surface of the individual 1150 to which the patch is applied such that the nitric oxide concentration within the space is between about 160 ppm and about 400 ppm. Such a concentration range has been reported to reduce microbial infection within a wound site, reduce inflammation, and increase collagenase expression without inducing toxicity to healthy cells within the wound site (e.g., U.S. Patent Application No.: 2007/0088316). Accordingly, numerous concentrations of nitric oxide may be applied to the surface of an individual 1150 through use of dressings 1010 that are configured as a patch, bandage (e.g., U.S. Pat. No. 7,264,602), sleeve, glove, sock, hood, mitten, bag, condom, and the like.

Backing Sheet

Numerous backing sheets 1030 may be used within system 1000. A backing sheet 1030 may be constructed firm numerous types of materials and combinations of materials. Examples of such materials include, but are not limited to, metals, metal alloys, polymers, copolymers, ceramics, cloth, fabric, and the like. Backing sheets 1030 may be configured in numerous ways. For example, in some embodiments, a backing sheet 1030 may include one or more sheets of one or more materials to which one or more light sources 1040 may be associated. In some embodiments, a backing sheet 1030 may include one or more sheets of one or more materials to which one or more photolyzable nitric oxide donors 1020 may be associated. In some embodiments, a backing sheet 1030 may include one or more sheets of one or more materials to which one or more light sources 1040 and one or more photolyzable nitric oxide donors 1020 may be associated. For example, in some embodiments, a backing sheet 1030 may include electrical connections that may be operably coupled to one or more light sources 1040. In some embodiments, a backing sheet 1030 may be configured to be associated with one or more power supplies. For example, in some embodiments, one or more backing sheets 1030 may be configured to associate with one or more solar cells. In some embodiments, one or more backing sheets 1030 may be configured to associate with one or more batteries (e.g., thin-film batteries). In some embodiments, one or more backing sheets 1030 may be configured to associate with one or more capacitors.

Backing sheets 1030 may exhibit numerous physical characteristics. For example, in some embodiments, one or more backing sheets 1030 may be substantially transparent to light that facilitates release of nitric oxide from one or more photolyzable nitric oxide donors 1020. In some embodiments, one or more backing sheets 1030 may substantially block transmission of light that facilitates release of nitric oxide from one or more photolyzable nitric oxide donors 1020.

In some embodiments, one or more backing sheets 1030 may be elastomeric. Methods to prepare elastomeric materials are known and have been reported (e.g., U.S. Pat. Nos. 6,639,007; 6,673,871; 7,105,607). In some embodiments, one or more backing sheets 1030 may be inelastic. For example, in some embodiments, a backing sheet 1030 may be fabricated from one or more metal foils. In some embodiments, one or more backing sheets 1030 may be fabricated with pressure sensitive fibers. For example, in some embodiments, a backing sheet 1030 may include one or more elastomeric materials that self-adhere. In some embodiments, a backing sheet 1030 may include one or more adhesives that are applied to one or more portions of the backing sheet 1030. In some embodiments, one or more backing sheets 1030 may include one or more films that are configured for energy conversion (e.g., U.S. Pat. No. 7,238,628). For example, in some embodiments, one or more backing sheets 1030 may include one or more rare-earth elements. Accordingly, in some embodiments, one or more backing sheets 1030 may be configured to convert light emitted from one or more light sources 1040 into light that facilitates release of nitric oxide from one or more photolyzable nitric oxide donors 1020.

Light Source

Numerous light sources 1040 may be used within system 1000. In some embodiments, one or more light sources 1040 may be used to facilitate release of nitric oxide from one or more photolyzable nitric oxide donors 1020. In some embodiments, one or more light sources 1040 may be configured to emit light of multiple wavelengths. In some embodiments, one or more light sources 1040 may be configured to emit light that is selected to facilitate release of nitric oxide from one or more photolyzable nitric oxide donors 1020. For example, in some embodiments, one or more light sources 1040 may be configured to emit one or more wavelengths of light that are selected to facilitate release of nitric oxide from one or more identified photolyzable nitric oxide donors 1020. In some embodiments, one or more light sources 1040 may emit one or more wavelengths of light that are selected based on the absorption spectrum of one or more photolyzable nitric oxide donors 1100. In some embodiments, one or more light sources 1040 may emit one or more wavelengths of light that are selected based on decomposition of one or more photolyzable nitric oxide donors 1020. For example, in some embodiments, one or more light sources 1040 may be configured to emit one or more wavelengths of light that cause decomposition of one or more photolyzable nitric oxide donors 1020 without causing injury to adjacent structures and/or tissues. In some embodiments, a first light source may be configured to emit one or more wavelengths of light that cause a first photolyzable nitric oxide donor 1020 to release nitric oxide and a second light source may be configured to emit one or more wavelengths of light that cause a second photolyzable nitric oxide donor 1090 to release nitric oxide. Accordingly, numerous light sources 1040 may be coupled with numerous types of photolyzable nitric oxide donors 1020 to provide for selective release of nitric oxide.

In some embodiments, one or more light sources 1040 may be associated with one or more quantum dots (e.g., U.S. Pat. No. 7,235,361; herein incorporated by reference). For example, in some embodiments, one or more light sources 1040 may be configured to emit one or more wavelengths of light that are absorbed by one or more quantum dots. In some embodiments, one or more quantum dots may be configured to absorb light and then emit one or more wavelengths of light that cause release of nitric oxide from one or more photolyzable nitric oxide donors 1020. Accordingly, in some embodiments, emission from one or more first quantum dots may be tuned to facilitate release of nitric oxide from one or more first photolyzable nitric oxide donors 1020 and emission from one or more second quantum dots may be tuned to facilitate release of nitric oxide from one or more second photolyzable nitric oxide donors 1020.

A light source 1040 may be configured in numerous ways. For example, in some embodiments, a light source 1040 may be configured as a sheet of light emitters (e.g., a sheet of light emitting diodes). In some embodiments, one or more light sources 1040 may be configured to include one or more energy sources (e.g., one or more batteries) and one or more light emitters (e.g., one or more light emitting diodes).

In some embodiments, light sources 1040 may be remotely controlled. For example, in some embodiments, one or more light sources 1040 may be configured to receive one or more signals 1110 that include instructions for operation of the one or more light sources 1040. Such instructions may be associated with emission of light, non-emission of light, time when light is emitted, length of light emission, intensity of light emission, wavelengths of emitted light, and the like.

In some embodiments, light sources 1040 may be configured to include one or more control units 1060. In some embodiments, one or more light sources 1040 may be configured to include a switch that may be used to turn the light source 1040 on and off. For example, in some embodiments, a light source 1040 may be configured to include a push button switch to turn the light source 1040 on and off.

In some embodiments, one or more light sources 1040 may include one or more light emitters that are coupled to one or more electromagnetic receivers 1080. The one or more electromagnetic receivers 1080 may be configured to couple with one or more electromagnetic transmitters 1100 that produce one or more electromagnetic fields that induce an electrical current to flow in the one or more electromagnetic receivers 1080 to energize the light emitters (e.g., U.S. Pat. No. 5,571, 152; herein incorporated by reference). Accordingly, in some embodiments, one or more light sources 1040 may be configured such that they are not directly coupled to an energy source.

A light source 1040 may be configured to emit numerous types of light. In some embodiments, emitted light may be visible light. In some embodiments, emitted light may be infrared light. In some embodiments, emitted light may be ultraviolet light. In some embodiments, emitted light may be substantially any combination of visible light, infrared light, and/or ultraviolet light. In some embodiments, one or more Tight sources 1040 may emit fluorescent light. In some embodiments, one or more light sources 1040 may emit phosphorescent light.

In some embodiments, one or more light sources 1040 may be configured to emit light continuously. In some embodiments, one or more light sources 1040 may be configured to emit light as a pulse. In some embodiments, one or more light sources 1040 may be configured to emit light as a flash. In some embodiments, one or more light sources 1040 may be configured to emit light continuously, as a pulse, as a flash, or substantially any combination thereof.

In some embodiments, one or more light emitters and/or light sources 1040 may be configured to provide for upconversion of energy. In some embodiments, infrared light may be upconverted to visible Tight (e.g., Mendioroz et al., Optical Materials, 26:351-357 (2004). In some embodiments, infrared light ma), be upconverted to ultraviolet light (e.g., Mendioroz et al., Optical Materials, 26:351-357 (2004). In some embodiments, one or more light sources 1040 may include one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more light sources 1040 may be associated with $Nd^{3+}$ doped $KPb_2Cl_5$ crystals. In some embodiments, one or more light sources 1040 may be associated with thiogallates doped with rare earths, such as $CaGa_2S_4:Ce^{3+}$ and $SrGa_2S_4:Ce^{3+}$. In some embodiments, one or more light sources 1040 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

Photolyzable Nitric Oxide Donor/Nitric Oxide

Numerous photolyzable nitric oxide donors 1020 may be used within system 1000. Examples of such photolyzable nitric oxide donors 1020 include, but are not limited to, diazeniumdiolates (e.g., U.S. Pat. Nos. 7,105,502; 7,122,529; 6,673,338; herein incorporated by reference), trans-[RuCl ([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 193:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al. Mol. Pharm., 46:709-715 (1994), Wang et al., Chem. Rest., 102:1091-1134 (2002)), imidazolyl derivatives (e.g., U.S. Pat. No. 5,374,710; herein incorporated by reference).

In some embodiments, one or more photolyzable nitric oxide donors 1020 may be used in association with additional nitric oxide donors that are not photolyzable. In some embodiments, one or more photolyzable nitric oxide donors 1020 may be used in association with additional agents. Examples of such additional agents include, but are not limited to, enzyme inhibitors (e.g., U.S. Pat. No. 6,943,166; herein incorporated by reference), agents that increase the effects and/or concentration of nitric oxide (e.g., methylene blue and N(w)-nitro-L-arginine (L-NOARG) (see Chem and Gillis, Biochem. Biophys. Res. Commun., 190, 559-563 (1993) and Kim et al., J. Vet. Sci., 1:81-86 (2000)), L-arginine (e.g., U.S. Published Patent Application No.: 20020068365 and U.S. Pat. No. 6,635,273; herein incorporated by reference), agents that stabilize nitric oxide donors (e.g., dimethyl sulfoxide and ethanol), agents that increase the half life of nitric oxide (e.g., U.S. Published Patent Application No.: 20030039697; herein incorporated by reference), and the like.

In some embodiments, one or more photolyzable nitric oxide donors may be associated with one or more antibacterial agents. In some embodiments, one or more photolyzable nitric oxide donors may be associated with one or more antiviral agents. In some embodiments, one or more photolyzable nitric oxide donors may be associated with one or more therapeutic agents (e.g., anti-thrombotics, coagulants, and the like).

Control Unit

Numerous types of control units 1060 may be used within system 1000. In some embodiments, one or more control units 1060 may be operably coupled with one or more light sources 1040, one or more sensors 1070, one or more electromagnetic receivers 1080, one or more electromagnetic transmitters 1100, or substantially any combination thereof. In some embodiments, one or more control units 1060 may be operably coupled to other components through use of one or more wireless connections, one or more hardwired connections, or substantially any combination thereof. Control units 1060 may be configured in numerous ways. For example, in some embodiments, a control unit 1060 may be configured as an on/off switch. Accordingly, in some embodiments, a control unit 1060 may be configured to turn a light source 1040 on and/or off. In some embodiments, a control unit 1060 may be configured to control the emission of light from one or more light sources 1040. For example, in some embodiments, one or more control units 1060 may regulate the intensity of light emitted from one or more light sources 1040, the duration of light emitted from one or more light sources 1040, the frequency of light emitted from one or more light sources 1040, wavelengths of light emitted from one or more light sources 1040, or substantially any combination thereof. In some embodiments, one or more control units 1060 may be configured to receive one or more signals 1110 from one or more sensors 1070. Accordingly, in some embodiments, one or more control units 1060 may be configured to control one or more light sources 1040 in response to one or more signals 1010 received from one or more sensors 1070. For example, in some embodiments, one or more sensors 1070 may sense a low concentration of nitric oxide in one or more tissues and send one or more signals 1110 to one or more control units 1060. The one or more control units 1060 may then turn one or more light sources 1040 on to facilitate release of nitric oxide from one or more photolyzable nitric oxide donors 1020. Accordingly, in some embodiments, one or more sensors 1070 may sense a high concentration of nitric oxide in one or more tissues and send one or more signals 1110 to one or more control units 1060. The one or more control units 1060 may then turn one or more light sources 1040 off to end release of nitric oxide from one or more photolyzable nitric oxide donors 1020. In some embodiments, one or more control units 1060 may be programmed to control one or more light sources 1040. For example, in some embodiments, one or more control units 1060 may be programmed to turn one or more light sources 1040 on for a predetermined amount of time and then turn the one or more light sources 1040 off. Accordingly, in some embodiments, one or more control units 1060 may be preprogrammed. In some embodiments, one or more control units 1060 may be dynamically programmed. For example, in some embodiments, one or more management units 1130 may receive one or more signals 1110 from one or more sensors 1070 and program one or more control units 1060 in response to the one or more signals 1110 received from the one or more sensors 1070. In some embodiments, one or more control units 1060 may include one or more receivers that are able to receive one or more signals 1110, one or more information packets, or substantially any combination thereof. Control units 1060 may be configured in numerous ways. For example, in some embodiments, one or more control units 1060 may be operably coupled to one or more light sources 1040 that include numerous light emitting diodes that emit light of different wavelengths. Accordingly, in some embodiments, one or more control units 1060 may control the wavelengths of light emitted by the one or more light sources 1040 by controlling the operation of light emitting diodes that emit light of the selected wavelength. Accordingly, control units 1060 may be configured in numerous ways and utilize numerous types of mechanisms.

Nitric Oxide Permeable Layer

Numerous types of nitric oxide permeable layers 1050 may be used within system 1000. Nitric oxide permeable layers 1050 may be configured for application to an individual 1150. Nitric oxide permeable layers 1050 may be configured to facilitate application of nitric oxide to a surface. In some embodiments, one or more nitric oxide permeable layers 1050 may be configured to facilitate application of nitric oxide to one or more surfaces of an individual 11150. For example, in some embodiments, one or more nitric oxide permeable layers 1050 may be configured as a dressing 1010 that may be positioned on a skin surface of an individual 1150 to deliver nitric oxide to the skin surface. Examples of such dressings 1010 include, but are not limited to, patches, bandages, gloves, condoms, hood, mittens, sleeves, and the like. In some embodiments, nitric oxide permeable layers 1050 may be configured as bags. For example, in some embodiments, one or more nitric oxide permeable layers 1050 may be configured as a bag that will enclose an individual 1150 and/or a portion of an individual 1150. In some embodiments, such a bag may be used to deliver nitric oxide to the surface of an individual 1150. In some embodiments, one or more nitric oxide permeable layers 1050 may be configured as a sleeve that will enclose a portion of a person. In some embodiments, such a sleeve may be used to deliver nitric oxide to the surface of an individual 1150. In some embodiments, one or more nitric oxide permeable layers 1050 may be configured to enclose at least a portion of one or more photolyzable nitric oxide donors 1020. In some embodiments, one or more nitric oxide permeable layers 1050 may be configured to enclose at least a portion of one or more light sources 1040. In some embodiments, one or more nitric oxide permeable layers 1050 may be configured to enclose at least a portion of one or more light sources 1040, one or more backing sheets 1030, one or more photolyzable nitric oxide donors 1070, one or more control units 1060, and/or one or more sensors 1070.

Nitric oxide permeable layers 1050 may be constructed of numerous types of materials and combinations of materials. Examples of such materials include, but are not limited to, ceramics, polymeric materials, metals, plastics, and the like. In some embodiments, nitric oxide permeable layers 1050 may include numerous combinations of materials. For example, in some embodiments, a nitric oxide permeable layer 1050 may include a nitric oxide impermeable material that is coupled to a nitric oxide permeable material. In some embodiments, a nitric oxide permeable layer 1050 may include one or more nitric oxide permeable membranes (e.g., U.S. Patent Application No.: 20020026937). In some embodiments, a nitric oxide permeable layer 1050 may include a selectively permeable membrane. For example, in some embodiments, a nitric oxide permeable layer 1050 may include a selectively permeable membrane that is a hydrophilic polyester co-polymer membrane system that includes a copolymer with 70% polyester and 30% polyether (e.g., Sympatex™ 10 μm membrane, see Hardwick et al. Clinical Science, 100:395-400 (2001)). In some embodiments, a nitric oxide permeable layer 1050 may include a scintered glass portion that is permeable to nitric oxide. Accordingly, nitric oxide permeable layers 1050 may include numerous types of porous ceramics that are permeable to nitric oxide. In some embodiments, a nitric oxide permeable layer 1050 may include a porous metal portion that is permeable to nitric oxide. In some embodiments, a nitric oxide permeable layer 1050 may include a nitric oxide permeable coating (e.g., U.S. Patent Application Nos.: 20050920838 and 20030093143).

Sensor

Numerous types of sensors 1070 may be used within system 1000. In some embodiments, one or more sensors 1070 may be used to determine the presence of nitric oxide in one or more tissues. In some embodiments, a sensor 1070 may be configured for use on an outside surface of an individual 1150. For example, in some embodiments, one or more sensors 1070 may be configured to detect the concentration of nitric oxide on the surface of skin, a wound, and the like. In some embodiments, one or more sensors 1070 may be configured to be included within one or more dressings 1010. In some embodiments, a sensor 1070 may be configured to utilize fluorescence to detect nitric oxide. For example, in some embodiments, a sensor 1070 may detect nitric oxide through use of one or more fluorescent probes, such as 4,5-diaminofluorescein diacetate (EMD Chemicals Inc., San Diego, Calif.). In some embodiments, a sensor 1070 may detect nitric oxide through use of one or more electrodes. For example, in some embodiments, a sensor 1070 may utilize an electrode that includes a single walled carbon nanotube and an ionic liquid to detect nitric oxide (e.g., Li et al. Electroanalysis, 18:713-718 (2006)). Numerous sensors 1070 are commercially available and have been described (e.g., World Precision Instruments, Inc., Sarasota, Fla., USA; U.S. Pat. Nos. 6,100,096; 6,280,604; 5,980,705). In some embodiments, a sensor 1070 may include one or more transmitters. In some embodiments, a sensor 1070 may include one or more receivers. In some embodiments, a sensor 1070 may be configured to transmit one or more signals 1110. In some embodiments, a sensor 1070 may be configured to receive one or more signals 1110. Manly types of sensors 1070 may be used within system 1000. Examples of such sensors 1070 include, but are not limited to, temperature sensors 1070, pressure sensors 1070 (e.g., blood pressure, hydrostatic pressure), pulse rate sensors 1070, sensors 1070, clocks, bacterial contamination sensors 1070, strain sensors 1070, light sensors 1070, nitric oxide sensors 1070, and the like.

Electromagnetic Receiver

Numerous types of electromagnetic receivers 1080 may be used within system 1000. In some embodiments, one or more electromagnetic receivers 1080 may be used to electromagnetically couple power to energize one or more light sources 1040 from an external power supply. Methods to construct such electromagnetic receivers 1080 have been described (e.g., U.S. Pat. No. 5,571,152). Briefly, in some embodiments, one or more electromagnetic receivers 1080 may be associated with one or more rectifier chips. The one or more electromagnetic receivers 1080 may include one or more cores about which are wrapped an electrical conductor. In some embodiments, cores may comprise a material, such as a ferrite material. However, other materials can be used for this purpose. In some embodiments, the electromagnetic receiver 1080 may be operably coupled to a light emitting diode.

Electromagnetic Transmitter

Numerous types of electromagnetic transmitters 1100 may be used within system 1000. Methods to construct electromagnetic transmitters 1100 have been described (e.g., U.S. Pat. No. 5,571,152). Briefly, in some embodiments, an electromagnetic transmitter 1100 may include a fenite core around which is wrapped an electrical conductor. Other types of material having high magnetic permeability and relatively low magnetic hysteresis may be used for the core. Insulating tape may be wrapped around the electrical conductor, or the electromagnetic transmitter 1100 may be dipped in a resin to form a coating that stabilizes and fixes the electrical conductor on the core. A return lead from one end of the electrical conductor may include one of two leads that are coupled to an AC power supply.

Electromagnetic Energy

Electrical power may be electromagnetically coupled from one or more electromagnetic transmitters 1100 with one or more electromagnetic receivers 1080. Accordingly, electrical power that is transferred to the one or more electromagnetic receivers 1080 may be used to power one or more operably linked light emitters. Methods and devices that may be used to transmit electrical power to a light emitter have been described (e.g., U.S. Pat. No. 5,571,159).

Management Unit

In some embodiments, system 1000 may include one or more management units 1130. In some embodiments, a management unit 1130 may be configured as a computer. Accordingly, in some embodiments, a management unit 1130 may be configured to accept input and provide output. For example, in some embodiments, a management unit 1130 may receive one or more signals 1110 from one or more sensors 1070, process the one or more signals 1110, and then transmit one or more signals 1110. In some embodiments, one or more transmitted signals 1110 may be received by one or more control units 1060. In some embodiments, one or more transmitted signals 1110 may be received by one or more light sources 1040. Accordingly, in some embodiments, a management unit 1130 may be configured to manage nitric oxide production by a dressing 1010. For example, in some embodiments, a management unit 1130 may include and execute a set of instructions for the operation of one or more control units 1060 that facilitate production of nitric oxide by one or more dressings 1010 at preselected times and for preselected concentrations. In some embodiments, such production may be regulated t-rough control of the intensity of light emitted by one or more light sources 1040, the duration of light emitted by one or more light sources 1040, the frequency of light emitted by one or more light sources 1040, and the like. In some embodiments, a management unit 1130 may dynamically control the production of nitric oxide by one or more dressings 1010. For example, in some embodiments, a management unit 1130 may be configured to maintain a nitric oxide concentration within a range of concentrations. Accordingly, the management unit 1130 may receive one or more signals 1110 from one or more sensors 1070 indicating a current concentration of nitric oxide. The management unit 1130 may then determine if the nitric oxide concentration is within a range of nitric oxide concentrations or out of a range of nitric oxide concentrations and then increase nitric oxide production, decrease nitric oxide production, or maintain nitric oxide production to cause the nitric oxide concentration to be maintained within a range. Accordingly, a management unit 130 may be used in numerous ways to regulate nitric oxide production.

Transmitter

The system 1000 may include one or more transmitters. In some embodiments, one or more transmitters may be operably coupled to one or more sensors 1070. In some embodiments, one or more transmitters may be operably coupled to one or more management units 1130. In some embodiments, one or more transmitters may be operably coupled to one or more control units 1060. In some embodiments, one or more transmitters may be operably coupled to one or more sensors 1070, one or more control units 1060, one or more management units 1130, or substantially any combination thereof. Numerous types of transmitters may be used in association with system 1000. Examples of such transmitters include, but are not limited to, transmitters that transmit one or more optical signals 110, radio signals 1110, wireless signals 1110, hardwired signals 1110, infrared signals 1110, ultrasonic signals 1110, and the like (e.g., U.S. Pat. No. RE39,785; U.S. Pat.Nos. 7,260,768; 7,260,764; 7,260,409; 7,257,327; 7,215,887; 7,218,900; herein incorporated by reference). In some embodiments, one or more transmitters may transmit one or more signals 1110 that are encrypted. Numerous types of transmitters are known and ha-e been described (e.g., U.S. Pat. Nos. 7,236,595; 7,760,155; 7,227,956; US2006/0280307; herein incorporated by reference).

Signal

Numerous types of signals 1110 may be used in association width system 1000. Examples of such signals 1110 include, but are not limited to, optical signals 1110, radio signals 1110, wireless signals 1110, hardwired signals 1110, infrared signals 1110, ultrasonic signals 1110, and the like.

In some embodiments, one or more signals 1110 may not be encrypted. In some embodiments, one or more signals 1110 may be encrypted. In some embodiments, one or more signals 1110 may be sent through use of a secure mode of transmission. In some embodiments, one or more signals 1110 may be coded for receipt by a specific individual 150. In some embodiments, such code may include anonymous code that is specific for an individual 1150. Accordingly, information included within one or more signals 1110 may be protected against being accessed by others who are not the intended recipient.

Receiver

System 1000 may include one or more receivers. In some embodiments, one or more receivers may be operably coupled to one or more sensors 1070. In some embodiments, one or more receivers may be operably coupled to one or more management units 1130. In some embodiments, one or more receivers may be operably coupled to one or more control units 1060. In some embodiments, one or more receivers may be operably coupled to one or more sensors 1070, one or more control units 1060, one or more management units 1130, or substantially any combination thereof. Numerous types of receivers may be used in association with system 1000. Examples of such receivers include, but are not limited to, receivers that receive one or more optical signals 1110, radio signals 1110, wireless signals 1110, hardwired signals 1110, infrared signals 1110, ultrasonic signals 1110, and the like. Such receivers are known and have been described (e.g., U.S. Pat. No. RE39,785; U.S. Pat.Nos. 7,218,900; 7,254,160; 7,245,894; 7,206,605; herein incorporated by reference).

User Interface/User

System 1000 may include numerous types of user interfaces 1140. For example, one or more users (e.g., individuals 1150) may interact through use of numerous user interfaces 1140 that utilize hardwired methods, such as through use of an on/off switch, a push button, a keyboard, and the like. In some embodiments, the user interface may utilize wireless methods, such as methods that utilize a transmitter and receiver, utilize the internet, and the like.

Individual

A dressing 1010 may be used to deliver nitric oxide to an individual 1150. In some embodiments, an individual 1150 may be a human. In some embodiments, an individual 1150 may be a human male. In some embodiments, an individual 1150 may be a human female. A dressing 1010 may be used within numerous contexts. For example, in some embodiments, a dressing 1010 may be used to deliver nitric oxide to an individual 1150 to treat sexual dysfunction. In some embodiments, a dressing 1010 may be used to deliver nitric oxide to the skin of an individual 1150. In some embodiments, such delivery may be for cosmetic purposes. In some embodiments, such delivery may be for therapeutic purposes. For example, in some embodiments, a dressing 1010 may be used to deliver nitric oxide to a skin lesion, such as a skin ulcer, a burn, a cut, a puncture, a laceration, a blunt trauma, an acne lesion, a boil, and the like. In some embodiments, a dressing 1010 may be used to deliver nitric oxide to a skin surface to increase the expression of endogenous collagenase. In some embodiments, a dressing 1010 may be used to deliver nitric oxide to a skin surface to regulate the formation of collagen. In some embodiments, a dressing 1010 may be used to deliver nitric oxide to reduce inflammation (e.g., reduce exudate secretion) at the site of a lesion (e.g., U.S. Patent Application No.: 2007/0088316). In some embodiments, a dressing 1010 may be used to deliver nitric oxide to reduce the microbial burden within a wound site. For example, in some embodiments, a dressing 1010 may be used to deliver nitric oxide as an antibacterial agent against methicillin-resistant *Staphylococcus aureus*. A dressing 1010 may deliver nitric oxide to an individual 1150 at numerous concentrations. For example, in some embodiments, nitric oxide may be delivered at a concentration ranging from about 160 ppm to about 400 ppm. Such concentrations may be used without inducing toxicity in the healthy cells around a wound site (e.g., U.S. Patent Application No.: 2007/0088-316).

Figure 11:
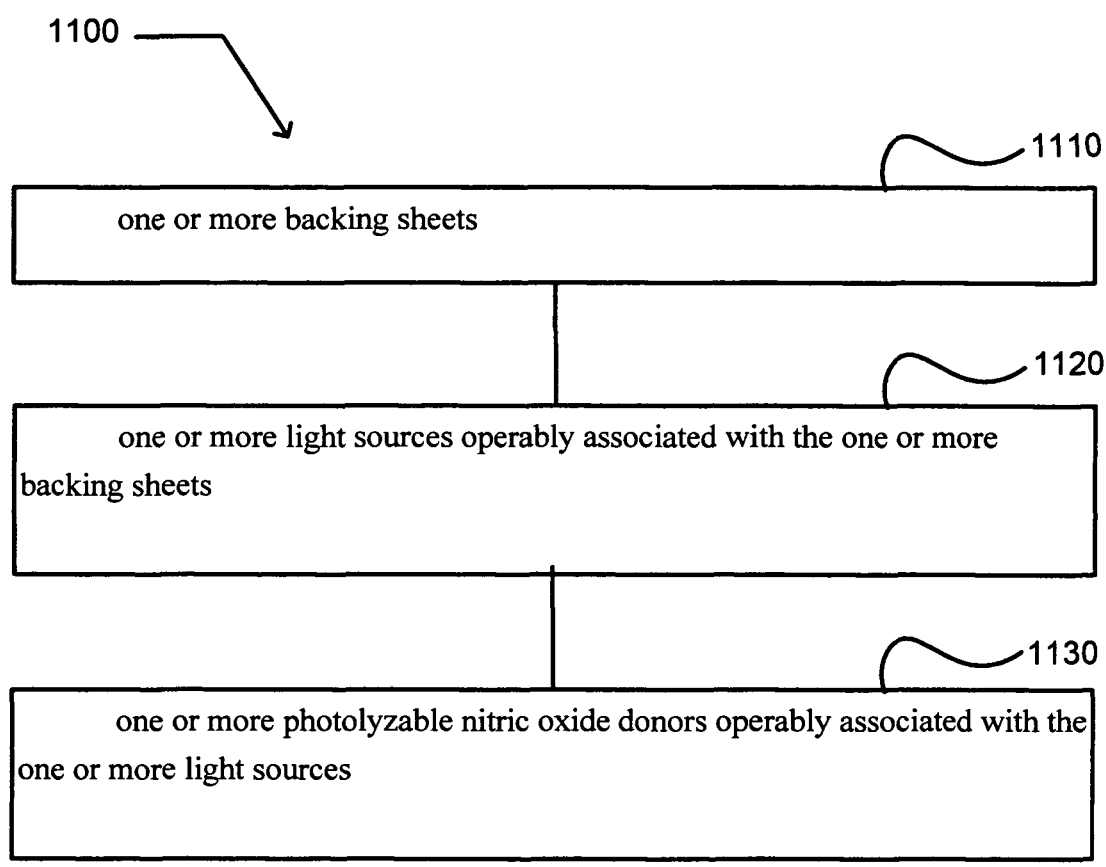
FIG. 11 illustrates embodiment 1100 of dressing 1010 within system 1000.

FIG. 11 illustrates embodiment 1100 of dressing 1010 within system 1000. In FIG. 11, discussion and explanation may be provided with respect to the above-described example of FIG. 10, and/or with respect to other examples and contexts. However, it should be understood that the modules may execute operations in a number of other environments and contexts, and/or modified versions of FIG. 10. Also, although the various modules are presented in the sequence(s) illustrated, it should be understood that the various modules may be configured in numerous orientations.

The embodiment 1100 mall include module 1110 that includes one or more backing sheets. In some embodiments, a dressing 1010 may include one or more backing sheets 1030. One or more backing sheets 1030 may be fabricated from one or more materials. In some embodiments, one or more backing sheets 1030 may, include portions that are fabricated from different types of materials. For example, in some embodiments, a backing sheet 1030 may include one or more portions that include one or more adhesive materials and one or more portions that include one or more nonadhesive materials. In some embodiments, a backing sheet 1030 may include one or more portions that include one or more gas permeable materials and one or more portions that include one or more gas impermeable materials. Accordingly, one or more backing sheets 1030 may include numerous combinations of materials that exhibit numerous properties. Examples of such material include, but are not limited to, elastic materials, inelastic materials, adhesive materials, nonadhesive materials, conductive materials, nonconductive materials, perforated materials, nonperforated materials, fluid permeable materials, fluid impermeable materials, gas permeable materials, gas impermeable materials, light permeable materials) selectively light permeable materials, light impermeable materials, and the like.

The embodiment 1100 may include module 1120 that includes one or more light sources operably associated with the one or more backing sheets. In some embodiments, a dressing 1010 may include one or more light sources 1040 operably associated with one or more backing sheets 1030. In some embodiments, a dressing 1010 may include one or more light sources 1040 that are operably associated with one or more photolyzable nitric oxide donors 1020. In some embodiments, one or more light sources 1040 may be directly coupled to one or more backing sheets 1030. For example, in some embodiments, one or more light sources 1040 may be integrated within one or more backing sheets 1030. In some embodiments, one or more light sources 1040 may be indirectly associated with one or more backing sheets 1030. For example, in some embodiments, one or more light sources 1040 may be associated with one or more backing sheets 1030 through attachment to one or more electrical connections associated with the one or more backing sheets 1030. In some embodiments) one or more light sources 1040 may be associated with one or more backing sheets 1030 through inclusion Within one or more compositions that include one or more photolyzable nitric oxide donors 1020 that are associated with one or more backing sheets 1030.

The embodiment 1100 may include module 1130 that includes one or more photolyzable nitric oxide donors operably associated with the one or more light sources. In some embodiments, a dressing 1010 may include one or more photolyzable nitric oxide donors 1020 operably associated wraith the one or more light sources 1040. In some embodiments, the one or more light sources 1040 may be directly coupled to one or more photolyzable nitric oxide donors 1020. For example, in some embodiments, the one or more photolyzable nitric oxide donors 1020 may be chemically coupled to a surface of the light source 1040 (e.g., chemically coupled to a polymer coating on the light source). In some embodiments, one or more photolyzable nitric oxide donors 1020 may be indirectly coupled to one or more light sources 1040. For example, in some embodiments, one or more photolyzable nitric oxide donors 1020 may be coupled to a material that is used to coat the one or more light sources 1040. Numerous photolyzable nitric oxide donors 1090 may be operably associated with one or more light sources 1040. Examples of such photolyzable nitric oxide donors 1020 include, but are not limited to, diazeniumdiolates (e.g., U.S. Pat. Nos. 7,105,502; 7,122,502; 6,673,338; herein incorporated by reference), trans-[RuC([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550: 819-828 (2003)), S-nitrosothiols (e.g., Andrews et al. British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rex., 102:1091-1134 (2002)), imidazolyl derivatives (e.g., U.S. Pat. No. 5,374,710; herein incorporated by reference).

Figure 12:
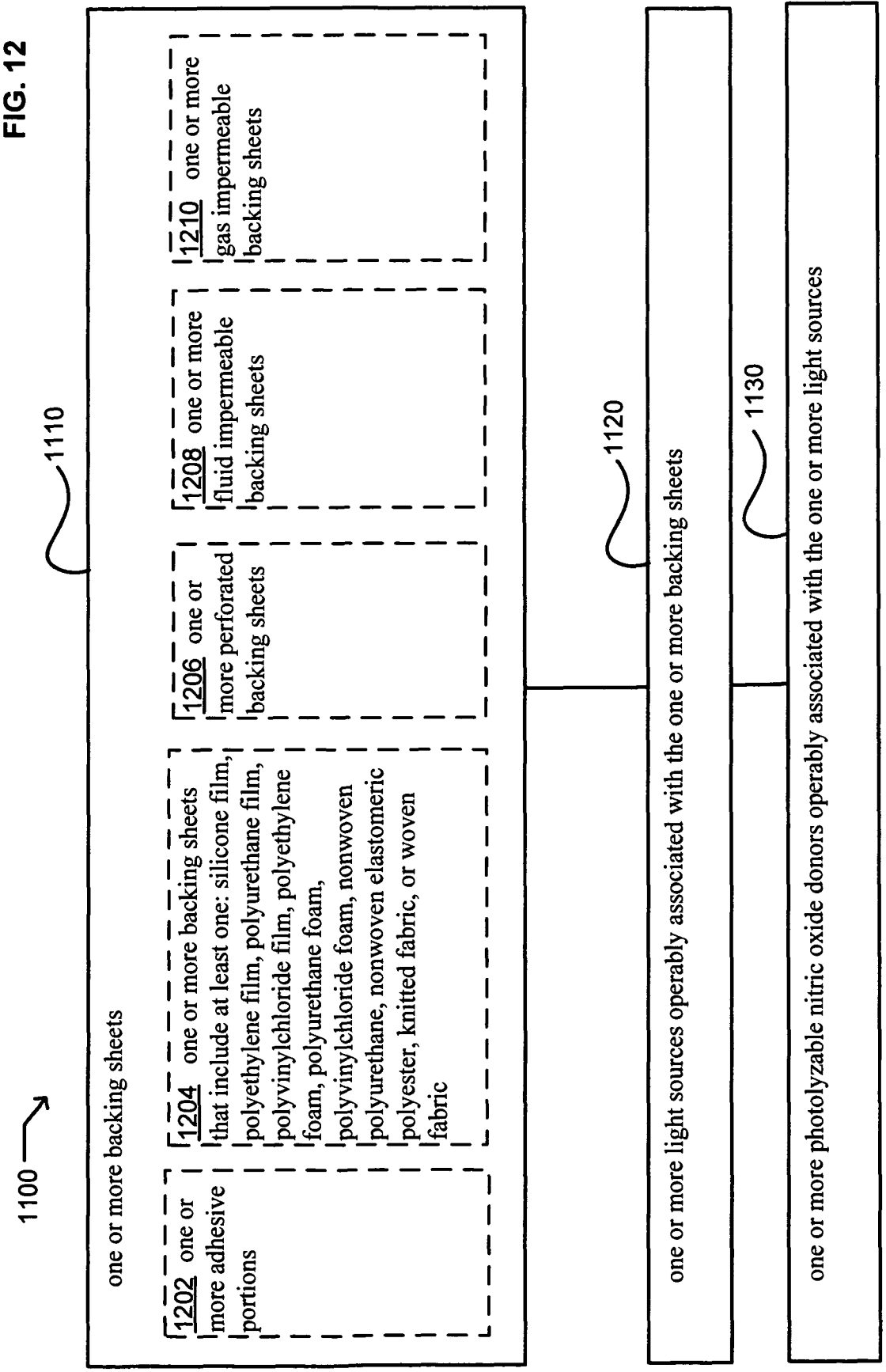
FIG. 12 illustrates alternate embodiments of embodiment 1100 of dressing 1010 within system 1000.

FIG. 12 illustrates alternative embodiments of embodiment 1110 of dressing 1010 within system 1000 of FIG. 11. FIG. 12 illustrates example embodiments of module 1110. Additional embodiments may include an embodiment 1202 an embodiment 1204, an embodiment 1206 an embodiment 1208, and/or an embodiment 1210.

At embodiment 2002, module 1110 may include one or more adhesive portions. In some embodiments, one or more backing sheets 1030 may include one or more adhesive portions. In some embodiments, one or more backing sheets 1030 may include one or more adhesive portions and one or more non-adhesive portions. In some embodiments, a dressing 1010 may include one or more backing sheets 1030 that include one or more adhesive portions that are configured to facilitate adhesion of the dressing 1010 to a surface. For example, in some embodiments, a dressing 1010 may be configured as a bandage that includes one or more backing sheets 1030 that include two adhesive portions that facilitate adhesion of the dressing 1010 onto a skin surface. In some embodiments, a dressing 1010 may be configured as a bandage and/or patch that includes one or more backing sheets 1030 that include an adhesive portion that produces a sealed space relative to a surface to which the dressing 1010 is adhered. In some embodiments of such a dressing 1010, one or more photolyzable nitric oxide donors 1020 and one or more light sources 1040 may be associated with the dressing 1010 such that nitric oxide released from the one or more photolyzable nitric oxide donors 1020 is retained in the sealed space relative to the surface. Accordingly, such embodiments may be used to deliver nitric oxide to a surface (e.g. a skin surface). In some embodiments, a dressing 1010 may include one or more adhesive portions that are configured in numerous ways.

At embodiment 1204, module 1110 may include one or more backing sheets that include at least one: silicone film, polyethylene film, polyurethane film, polyvinylchloride film, polyethylene foam, polyurethane foam, polyvinylchloride foam, nonwoven polyurethane, nonwoven elastomeric polyester, knitted fabric, or woven fabric. In some embodiments, one or more backing sheets 1030 may include one or more backing sheets 1030 that include at least one: silicone film, polyethylene film, polyurethane film, polyvinylchloride film polyethylene foam, polyurethane foam, polyvinylchloride foam, nonwoven polyurethane, nonwoven elastomeric polyester knitted fabric, woven fabric, or substantially any combination thereof.

At embodiment 1206, module 1110 may include one or more perforated backing sheets. In some embodiments, one or more backing sheets 1030 may include one or more perforated backing sheets 1030. In some embodiments, a dressing 1010 may include one or more backing sheets 1030 that include one or more perforated backing sheets 1030. In some embodiments, a dressing 1010 may be configured as a bandage that includes one or more perforated backing sheets 1030. For example, in some embodiments, a bandage may include one or more non-perforated portions of one or more backing sheets 1030 that are configured to facilitate delivery of nitric oxide to a surface (e.g., skin surface) and one or more perforated portions of one or more backing sheets 1030 that are configured to adhere the bandage to the surface and to provide for exchange of gas, moisture, and the like from the surface. Accordingly, a backing sheet 1030 may include one or more perforated portions and one or more non-perforated portions in numerous conformations.

At embodiment 108, module 1110 may include one or more fluid impermeable backing sheets. In some embodiments, one or more backing sheets 1030 may include one or more fluid impermeable backing sheets 1030. Numerous materials may be used to fabricate fluid impermeable backing sheets 1030. Examples of such materials include, but are not limited to, polycarbonates, polystyrenes, latex, metals, ceramics, metal alloys, and the like. In some embodiments, one or more backing sheets 1030 may be selectively permeable. For example, in some embodiments, one or more backing sheets 1030 may be fluid impermeable and vapor permeable. In some embodiments, a backing sheet may include a hydrophilic polyester co-polymer membrane system that includes a copolymer with 70% polyester and 30% polyether that is nitric oxide permeable (e.g., Sympatex™ 10 µm membrane, see Hardwick et al., Clinical Science, 100:395-400 (2001)).

At embodiment 1210, module 1110 may include one or more gas impermeable backing sheets. In some embodiments, one or more backing sheets 1030 may include one or more gas impermeable backing sheets 1030. Numerous materials may be used to fabricate a gas impermeable backing sheet 1030. Examples of such materials include, but are not limited to) polycarbonates, polystyrenes, latex, metals, ceramics, metal alloys, and the like. Gas impermeable backing sheets 1030 may be configured in numerous ways. In some embodiments, one or more backing sheets 1030 that are gas impermeable may be configured to retain nitric oxide in one or more areas. For example, in some embodiments, a gas impermeable backing sheet 1030 malt be configured in a dome-shape with one or more photolyzable nitric oxide donors 1020 associated with the inside of the dome. Accordingly, nitric oxide released from the one or more nitric oxide donors may be retained within the dome when the open end of the dome is placed against a surface. In some embodiments, such configurations may be used to deliver nitric oxide to a surface. In some embodiments, one or more gas impermeable backing sheets 1030 may be configured as an outside surface of a dressing 1010 having one or more photolyzable nitric oxide donors 1020 that are associated with an inside surface of the dressing 1010 such that nitric oxide released from the one or more photolyzable nitric oxide donors 1020 is blocked from passage through the gas impermeable backing sheet 1030. For example, in some embodiments, a dressing 1010 may be configured as a bandage having one or more gas impermeable backing sheets 1030 that form an outside surface of the bandage and one or more photolyzable nitric oxide donors 1020 associated with an inside surface of the bandage relative to a surface to which nitric oxide is to be delivered.

Figure 13:
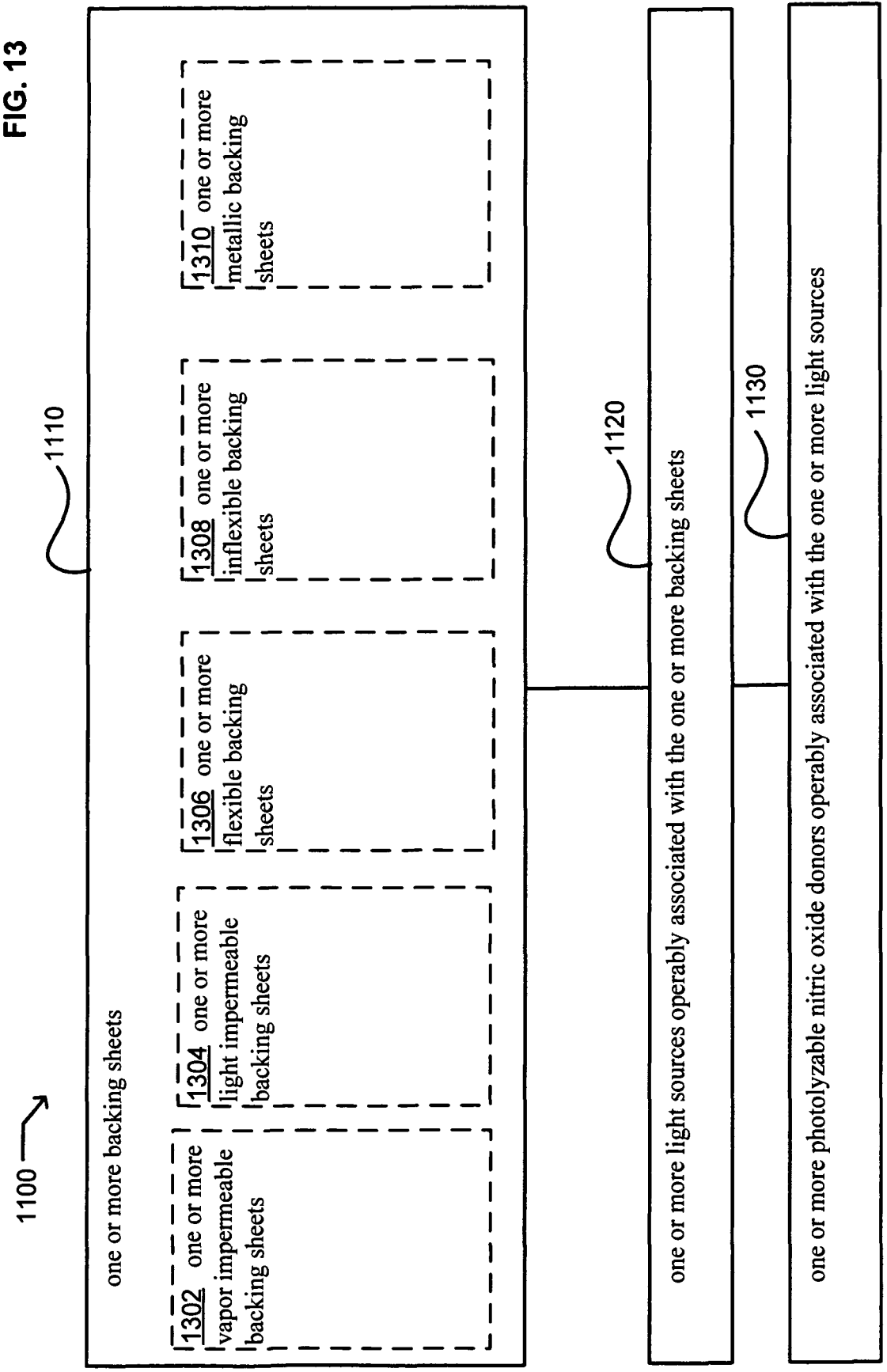
FIG. 13 illustrates alternate embodiments of embodiment 1100 of dressing 1010 within system 1000.

FIG. 13 illustrates alternative embodiments of embodiment 1110 of dressing 1010 within system 1000 of FIG. 11. FIG. 13 illustrates example embodiments of module 1110. Additional embodiments may include an embodiment 110, an embodiment 1304, an embodiment 1306, an embodiment 1308, and/or an embodiment 1310.

At embodiment 1302, module 1110 may include one or more vapor impermeable backing sheets. In some embodiments, one or more backing sheets 1030 may include one or more vapor impermeable backing sheets 1030. Numerous materials may be used to fabricate vapor impermeable backing sheets 1030. Examples of such materials include, but are not limited to, polycarbonates, polystyrenes, latex, metals, ceramics, metal alloys, and the like. Vapor impermeable backing sheets 1030 may be configured in numerous ways. In some embodiments, one or more backing sheets 1030 that are vapor impermeable may be configured to retain water vapor in one or more areas. For example, in some embodiments, one or more Vapor impermeable backing sheets 1030 may, be used to retain water vapor at a site to which nitric oxide is to be delivered. Accordingly, in some embodiments, one or more vapor impermeable backing sheets 1030 may be configured as an outside surface of a dressing 1010 that includes one or more photolyzable nitric oxide donors 1020 that are associated with an inside surface of the dressing 1010 such that water vapor is blocked from passage through the one or more vapor impermeable backing sheets 1030. For example, in some embodiments, a dressing 1010 may be configured as a patch with one or more vapor impermeable backing sheets 1030 forming an outside surface of the patch and one or more photolyzable nitric oxide donors 1020 associated with an inside surface of the patch relative to a surface to which nit-e oxide is to be delivered. In some embodiments, such a patch may be applied to a skin surface such that nitric oxide may be delivered to the skin su-face and moisture is retained at the site of the patch.

At embodiment 1304, module 1110 may include one or more light impermeable backing sheets. In some embodiments, one or more backing sheets 1030 may include one or more light impermeable backing sheets 1030. Numerous materials may be used to fabricate light impermeable backing sheets 1030. In some embodiments; one or more backing sheets 1030 may be selectively light impermeable. For example, in some embodiments, one or more backing sheets 1030 may be impermeable to light that facilitates photolysis of one or more photolyzable nitric oxide donors 1020. In some embodiments, one or more backing sheets 1030 may be impermeable to ultraviolet light. In some embodiments: one or more backing sheets 1030 may be selectively impermeable to light that causes damage to tissue. In some embodiments, a dressing 1010 may include one or more light impermeable backing sheets 1030 that are removable from the dressing 1010. For example, in some embodiments, a dressing 1010 may be configured as a bandage having a removable light impermeable backing. Accordingly; in some embodiments; such a bandage may be applied to a skin surface and then the light impermeable backing sheet 1030 may be removed to facilitate release of nitric oxide from one or more photolyzable nitric oxide donors 1020 associated with the bandage. Accordingly, in some embodiments, a light impermeable backing sheet 1030 may be configured as a protective covering to inhibit photolysis of one or more photolyzable nitric oxide donors 1020. In some embodiments; a light impermeable backing sheet 1030 may be configured as a protective covering for a surface. In some embodiments, one or more backing sheets 1030 may be configured to protect a surface against irradiation with light that facilitates release of nitric oxide from one or more photolyzable nitric oxide donors 1090. For example, in some embodiments, a dressing 1010 that is configured as a bandage having one or more photolyzable nitric oxide donors 1020 may be applied to a skin surface and then irradiated with light to facilitate release of nitric oxide from the bandage. Accordingly, in some embodiments, one or more light impermeable backing sheets 1030 malt serve to protect that skin underlying the bandage from irradiation.

At embodiment 1306, module 1110 may include one or more flexible backing sheets. In some embodiments, one or more backing sheets 1030 may include one or more flexible backing sheets 1030. In some embodiments, all portions of a backing sheet 1030 may be flexible. In some embodiments, one or more portions of a backing sheet 1030 may be flexible.

For example, in some embodiments, a backing sheet 1030 may include one or more inflexible portions and one or more flexible portions. In some embodiments, a dressing 1010 may include one or more backing sheets 1030 that include one or more inflexible portions that are configured to create a closed space above a surface without contacting the surface and one or more backing sheets 1030 that include one or more flexible portions that allow the dressing 1010 to be adhered to the surface. For example, in some embodiments, a dressing 1010 may include an inflexible backing sheet 1030 that is shaped like a dome to facilitate delivery of nitric oxide to a surface and a flexible backing sheet 1030 that facilitates adhesion of the dressing 1010 to the surface to which nitric oxide is to be delivered. Accordingly, a flexible backing sheet 1030 may be configured in numerous ways.

At embodiment 1308, module 1110 may include one or more inflexible backing sheets. In some embodiments, one or more backing sheets 1030 may include one or more inflexible backing sheets 1030. In some embodiments, all portions of a backing sheet 1030 may be inflexible. In some embodiments, one or more portions of a backing sheet 1030 may be inflexible. For example, in some embodiments, a backing sheet 1030 may include one or more inflexible portions and one or more flexible portions. In some embodiments, a dressing 1010 may include one or more backing sheets 1030 that include one or more inflexible portions that are configured to create a closed space above a surface without contacting the surface and one or more backing sheets 1030 that include one or more flexible portions that allow the dressing 1010 to be adhered to the surface. For example, in some embodiments, a dressing 1010 may be configured as a patch that includes an inflexible backing sheet 1030 that is shaped like a dome to facilitate delivery of nitric oxide to a surface and a flexible backing sheet 1030 that facilitates adhesion of the dressing 1010 to the surface to which nitric oxide is to be delivered. Accordingly, a flexible backing sheet 1030 may be configured in numerous ways.

At embodiment 1310, module 1110 may include one or more metallic backing sleets. In some embodiments, one or more backing sheets 1030 may include one or more metallic backing sheets 1030. In some embodiments, a backing sheet 1030 may be entirely constructed with one or more metallic materials. For example, in some embodiments, a backing sheet 1030 may be a metal foil. In some embodiments, a backing sheet 1030 may be partially constructed with one or more metallic materials. For example, in some embodiments, a backing sheet 1030 may include one or more portions that are metallic and one or more portions that are non-metallic. In some embodiments, a backing sheet 1030 may include metallic portions that are configured as one or more electrical connections. In some embodiments, a backing sheet 1030 may include metallic portions that include one or more electrical connections that are configured to associate with one or more light sources 1040. In some embodiments, a backing sheet 1030 may include metallic portions that include one or more electrical connections that are configured to associate with one or more sensors 1070. In some embodiments, a backing sheet 1030 may include metallic portions that include one or more electrical connections that are configured to associate with one or more control units 1060. In some embodiments, a backing sheet 1030 may include metallic portions that may be coupled to one or more nitric oxide donors that release nitric oxide in response to electrical current (e.g. Hou et al., Chem. Commun., 131-1832 (2000)).

Figure 14:
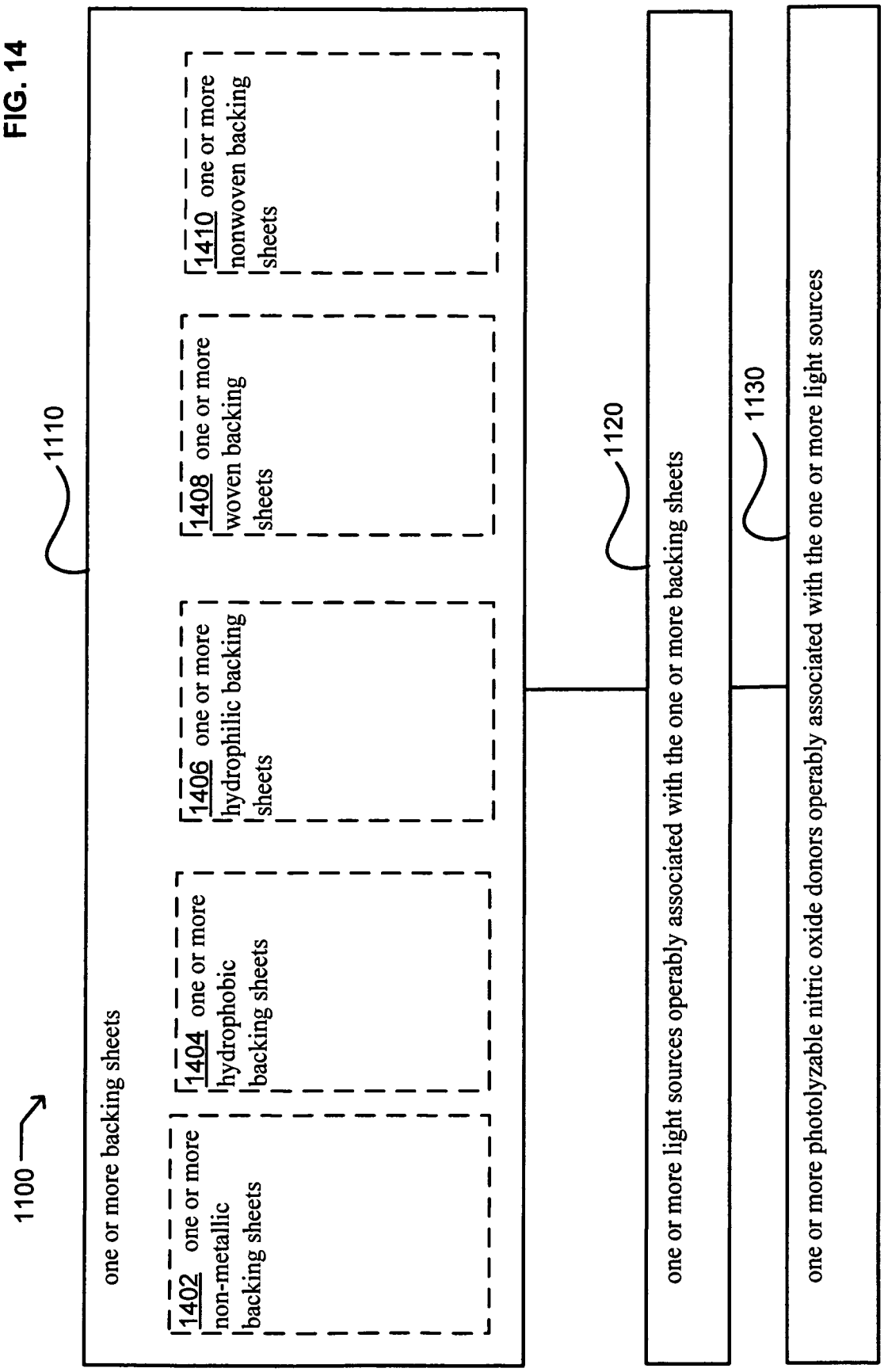
FIG. 14 illustrates alternate embodiments of embodiment 1100 of dressing 1010 within system 1000.

FIG. 14 illustrates alternative embodiments of embodiment 1110 of dressing 1010 within system 1000 of FIG. 11. FIG. 14 illustrates example embodiments of module 1110. Additional embodiments may include an embodiment 1408, an embodiment 1404, an embodiment 1406, an embodiment 1408, and/or an embodiment 1410.

At embodiment 1402, module 1110 may include one or more non-metallic backing sheets. In some embodiments, one or more backing sheets 1030 may include one or more non-metallic backing sheets 1030. In some embodiments, a backing sheet 1030 may be entirely constructed with one or more non-metallic materials. For example, in some embodiments, a backing sheet 1030 may be a plastic sheet. In some embodiments, a backing sheet 1030 may be partially constructed with one or more non-metallic materials. For example, in some embodiments, a backing sheet 1030 may include one or more portions that are non-metallic and one or more portions that are metallic. In some embodiments, a backing sheet 1030 may include one or more non-metallic portions that are configured as insulators for one or more metallic portions that are configured as electrical connections. Accordingly, in some embodiments, a backing sheet 1030 may include one or more non-metallic portions and one or more metallic portions that are configured as one or more electrical connections that may associate with one or more light sources 1040, one or more sensors 1070, one or more control units 1060, or substantially any combination thereof.

At embodiment 1404, module 1110 may include one or more hydrophobic backing sheets. In some embodiments, one or more backing sheets 1030 may include one or more hydrophobic backing sheets 1030. In some embodiments, a backing sheet 1030 may be entirely constructed with one or more hydrophobic materials. In some embodiments, a backing sheet 1030 may be partially constructed with one or more hydrophobic materials. For example, in some embodiments, a backing sheet 1030 may include one or more portions that are hydrophobic and one or more portions that are hydrophilic. Examples of hydrophobic materials include, but are not limited to, polytetrafluoroethylene, polytrifluorochloroethylene, and the like (e.g., U.S. Pat. No. 4,910,697).

At embodiment 1406, module 1110 may include one or more hydrophilic backing sheets. In some embodiments, one or more backing sheets 1030 may include one or more hydrophilic backing sheets 1030. In some embodiments, a backing sheet 1030 may be entirely constructed with one or more hydrophilic materials. In some embodiments, a backing sheet 1030 may be partially constructed with one or more hydrophilic materials. For example, in some embodiments, a backing sheet 1030 may include one or more portions that are hydrophobic and one or more portions that are hydrophilic. Examples of hydrophilic materials include, but are not limited to, hydrophilic polyethylene sheets (e.g., U.S. Pat. No. 6,436,470), a cellulosic material such as regenerated cellulose rollstock film (e.g., U.S. Pat. No. 5,690,777), and the like.

At embodiment 1408, module 1110 may include one or more woven backing sheets. In some embodiments, one or more backing sheets 1030 may include one or more woolen backing sheets 1030. Numerous materials may be used to construct a woven backing sheet 1030. Examples of such materials include, but are not limited to, synthetic fibers, natural fibers, combinations of natural fibers and synthetic fibers, and the like. In some embodiments, one or more backing sheets 1030 may include one or more portions that include woven backing sheets 1030 and one or more portions that include non-woven backing sheets 1030.

At embodiment 1410, module 1110 may include one or more nonwoven backing sheets. In some embodiments, one or more backing sheets 1030 may include one or more non-woven backing sheets 1030. Numerous materials may be used to construct a nonwoven backing sheet 1030. Examples of such materials include, but are not limited to, synthetic polymers, metals, metal alloys, silicates, ceramics, and the like. In some embodiments, nonwoven backing sheets 1030 may be fabricated through use of a spray process where material is sprayed onto a form. In some embodiments, nonwoven backing sheets 1030 may be fabricated through use of a sputtering process where material is sputtered onto a form. In some embodiments, one or more backing sheets 1030 may include one or more portions that include woven backing sheets 1030 and one or more portions that include nonwoven backing sheets 1030.

Figure 15:
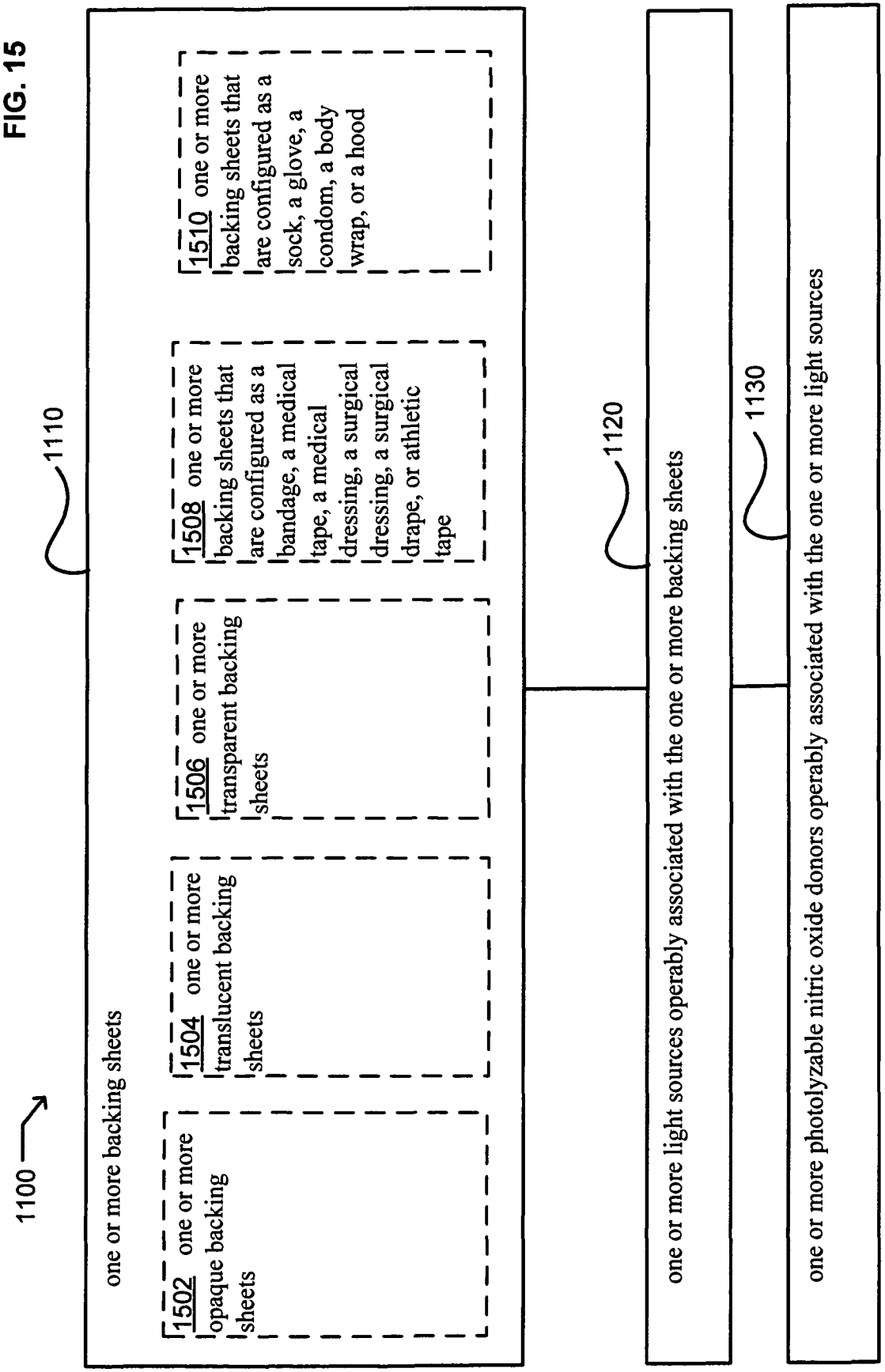
FIG. 15 illustrates alternate embodiments of embodiment 1100 of dressing 1010 within system 1000.

FIG. 15 illustrates alternative embodiments of embodiment 1110 of dressing 1010 within system 1000 of FIG. 11. FIG. 15 illustrates example embodiments of module 1110. Additional embodiments may include an embodiment 1502, an embodiment 1504, an embodiment 1506, an embodiment 1508, and/or an embodiment 1510.

At embodiment 1502, module 1110 may include one or more opaque backing sheets. In some embodiments, one or more backing sheets 1030 may, include one or more opaque backing sheets 1030. Numerous materials may be used to construct an opaque backing sheet 1030. Examples of such materials include, but are not limited to, polymethyl methacrylate treated so as to have a low, transmission, a white vinyl chloride polymer, a white polyester, polyethylene, and the like (e.g. U.S. Pat. No. 7,183,001).

At embodiment 1504, module 1110 may include one or more translucent backing sheets. In some embodiments, one or more backing sheets 1030 may include one or more translucent backing sheets 1030. Numerous materials may be used to construct a translucent backing sheet 1030. Examples of such materials include, but are not limited to, translucent polyvinylbutyral (PVB) (e.g., U.S. Pat. No. 7,395,953), matted polyethylene, and the like.

At embodiment 1506, module 110 may include one or more transparent backing sleets. In some embodiments, one or more backing sheets 1030 may include one or more transparent backing sheets 1030. Numerous materials may be used to construct a transparent backing sheet 1030. Examples of such materials include, but are not limited to, worsen class fibers, plastics, and the like.

At embodiment 1508, module 1110 may include one or more backing sheets that are configured as a bandage, a medical tape, a medical dressing, a surgical dressing, a surgical tape, or athletic tape. In some embodiments, one or more backing sheets 1030 may include one or more backing sheets 1030 that are configured as a patch, bandage, a medical tape, a medical dressing 1010, a surgical dressing 1010, a surgical drape, athletic tape, and the like.

At embodiment 1510, module 1110 may include one or more backing sheets that are configured as a sock, a glove, a condom, a body wrap, or a hood. In some embodiments, one or more backing sheets 1030 may include one or more backing sheets 1030 that are configured as a sock, a glove, a condom, a body wrap, or a hood.

Figure 16:
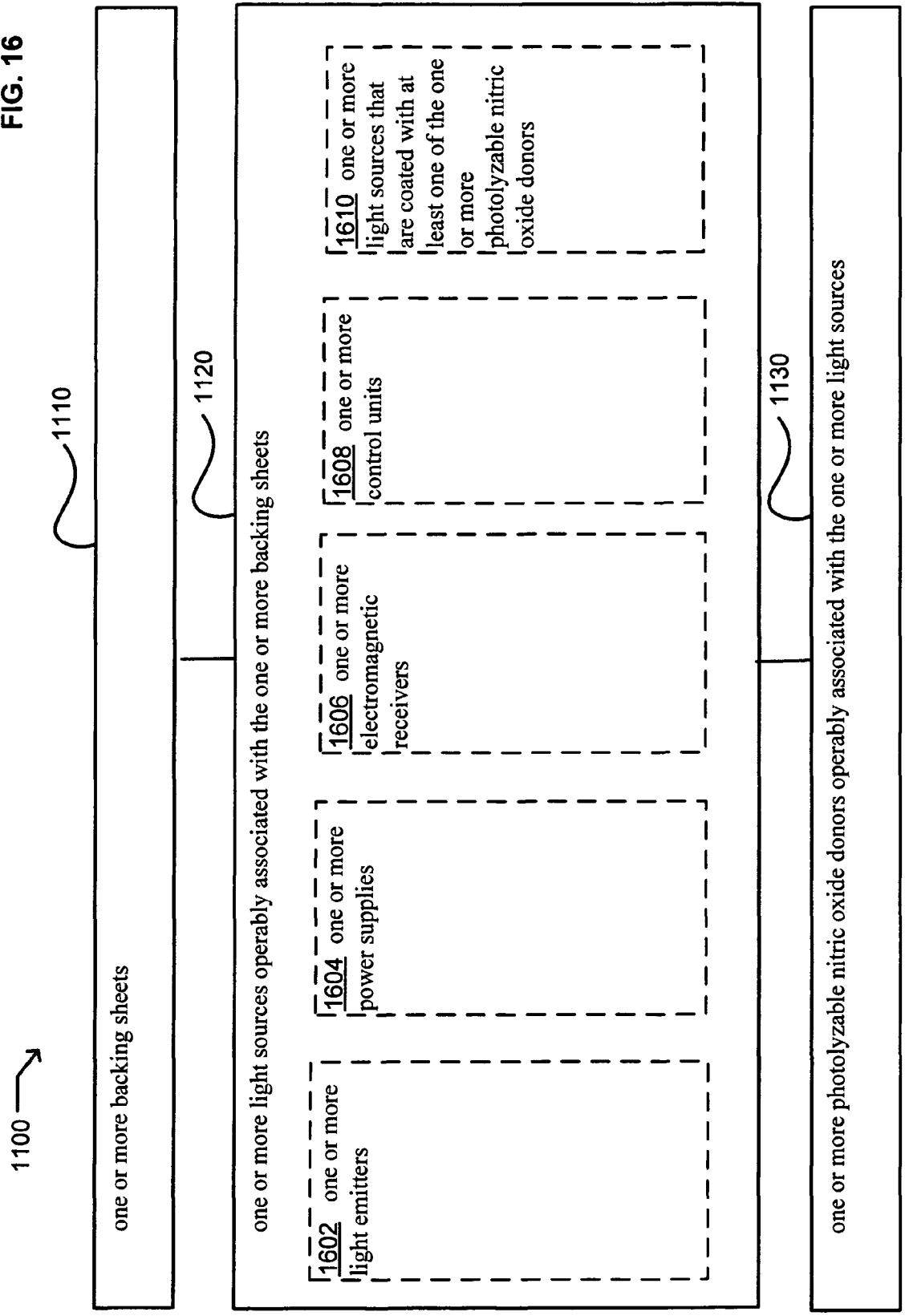
FIG. 16 illustrates alternate embodiments of embodiment 1100 of dressing 1010 within system 1000.

FIG. 16 illustrates alternative embodiments of embodiment 1120 of dressing 1010 within system 1000 of FIG. 11. FIG. 16 illustrates example embodiments of module 1120. Additional embodiments may include an embodiment 1602, an embodiment 1604, an embodiment 1606, an embodiment 1608, and/or an embodiment 1610.

At embodiment 1602, module 1120 may include one or more light emitters. In some embodiments, one or more light sources 1040 may include one or more light emitters. Numerous types of light emitters may be associated with one or more light sources 1040. Examples of such light emitters include, but are not limited to, light emitting diodes, filaments, arc lamps, fluorescent light emitters, phosphorescent light emitters, chemiluminescent emitters, and the like. In some embodiments, one or more light emitters may be coupled with one or more quantum dots. In some embodiments, one or more light emitters may be coupled with one or more rare-earth materials.

At embodiment 1604, module 190 may include one or more power supplies. In some embodiments, one or more light sources 1040 may include one or more power supplies. Numerous types of Power supplies may be associated with one or more light sources 1040. Examples of such power supplies include, but are not limited to, batteries (e.g., thin film batteries), electromagnetic receivers 1080, solar cells, capacitors, line power, and the like.

At embodiment 1606, module 1190 may include one or more electromagnetic receivers. In some embodiments, one or more light sources 1040 may include one or more electromagnetic receivers 1080. In some embodiments, one or more electromagnetic receivers 1080 may be used to receive electromagnetic energy 1090 for use in providing power to one or more Tight emitters. Methods to construct electromagnetic receivers 1080 have been described (e.g., U.S. Pat. No. 5,571, 152).

At embodiment 1608, module 1120 may include one or more control units. In some embodiments, one or more light sources 1040 may include one or more control units 1060. In some embodiments, the one or more control units 1060 may be operably associated with one or more light sources 1040 through use of a hardwired connection. In some embodiments, the one or more control units 1060 may be operably associated with one or more light sources 1040 through use of a wireless connection. In some embodiments, one or more control units 1060 may include numerous types of receivers. Examples of such receivers include, but are not limited to, receivers that receive one or more optical signals 1110, radio signals 1110, wireless signals 110, hardwired signals 1110, infrared signals 1110, ultrasonic signals 1110, and the like. Such receivers are known and have been described (e.g., U.S. Pat. No. RE39,785; U.S. Pat. Nos. 7,918,900; 7,954,160; 7,245,894; 7,206,605; herein incorporated by reference).

At embodiment 1610, module 1120 may include one or more light sources that are coated with at least one of the one or more photolyzable nitric oxide donors. In some embodiments, one or more light sources 1040 may include one or more light sources 1040 that are coated width at least one photolyzable nitric oxide donors 1090. For example, in some embodiments, a light source 1040 may be configured as a sheet that edits light which can be coated with one or more photolyzable nitric oxide donors 1020. In some embodiments, one or more light sources 1040 may be partially coated with one or more photolyzable nitric oxide donors 1020.

Figure 17:
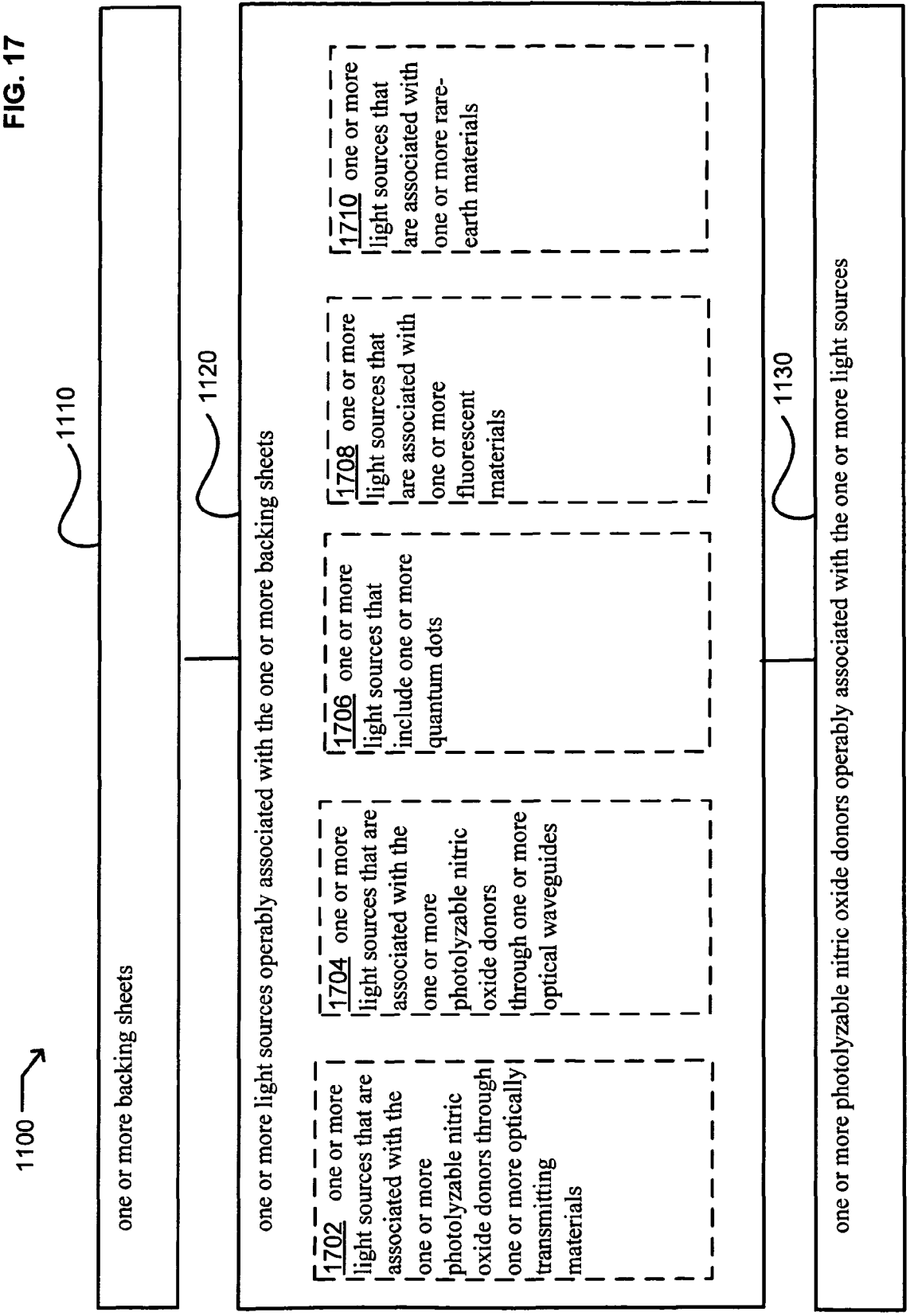
FIG. 17 illustrates alternate embodiments of embodiment 1100 of dressing 1010 within system 1000.

FIG. 17 illustrates alternate embodiments of embodiment 2120 of dressing 1010 within system 1000 of FIG. 11. FIG. 17 illustrates example embodiments of module 1120. Additional embodiments may include an embodiment 1702, an embodiment 1704, an embodiment 1706, an embodiment 1708, and/or an embodiment 1710.

At embodiment 1709, module 1120 may include one or more light sources that are associated with the one or more photolyzable nitric oxide donors through one or more optically transmitting materials. In some embodiments, one or more light sources 1040 may include one or more light sources 1040 that are associated with one or more photolyzable nitric oxide donors 1020 through one or more optically transmitting materials. In some embodiments, optically transmitting materials include all substances that function to alter or control electromagnetic radiation in the ultraviolet, visible, or infrared spectral regions. Such materials may be fabricated into optical elements such as lenses, minors, windows, prisms, polarizers, detectors, and modulators. These materials may reflect, reflect, transmit, disperse, polarize, detect, and/or transform-light Examples of optically transmitting materials include, but are not limited to, glass, crystalline materials, polymers, plastics, and the like. In some embodiments, one or more light sources 1040 may include fused silica which transmits to about 180 nm. In some embodiments, one or more light sources 1040 may include calcium fluoride which transmits into the ultraviolet region to about 140 nm. Accordingly, a light source 1040 may include numerous types of optically transmitting materials.

At embodiment 1704, module 1920 may include one or more light sources that are associated with the one or more photolyzable nitric oxide donors through one or more optical waveguides. In some embodiments, one or more light sources 1040 may include one or more light sources 1040 that are associated with one or more photolyzable nitric oxide donors 1020 through one or more optical waveguides. Numerous types of optical waveguides may be associated with one or more light sources 1040. For example, in some embodiments, a waveguide may be an optical fiber waveguide. In some embodiments, a waveguide may be a rectangular waveguide. In some embodiments, a waveguide may be a dielectric slab waveguide. In some embodiments, optical waveguides may include, but are not limited to, planar waveguides, strip waveguides, and/or fiber waveguides. In some embodiments, an optical waveguide may have a single-mode structure. In some embodiments, an optical waveguide may have a multi-mode structure. In some embodiments, an optical waveguide may exhibit a step refractive index distribution. In some embodiments, an optical waveguide may exhibit a gradient refractive index distribution. An optical waveguide may be constructed from numerous types of materials that include, but are not limited to, glass, polymers, semiconductors, and the like. Methods to construct optical waveguides have been described (e.g., U.S. Pat. No. 7,283,710).

At embodiment 1706, module 1110 may include one or more light sources that include one or more quantum dots. In some embodiments, one or more light sources 1040 may include one or more light sources 1040 that include one or more quantum dots. In some embodiments, one or more light sources 1040 may be associated with one or more quantum dots (e.g., U.S. Pat. No. 7,235,361; herein incorporated by reference). For example, in some embodiments, one or more light sources 1040 may be configured to emit one or more wavelengths of light that are absorbed by one or more quantum dots. In some embodiments, one or more quantum dots may be configured to absorb light and then emit one or more wavelengths of light that cause release of nitric oxide from one or more nitric oxide donors. Accordingly, in some embodiments, emission from one or more first quantum dots may be tuned to facilitate release of nitric oxide from one or more first photolyzable nitric oxide donors 1090 and emission from one or more second quantum dots may be tuned to facilitate release of nitric oxide from one or more second photolyzable nitric oxide donors 1020.

At embodiment 1708, module 1120 may include one or more light sources that are associated with one or more fluorescent materials. In some embodiments, one or more light sources 1040 may include one or more light sources 1040 that are associated with one or more fluorescent materials. Numerous fluorescent materials may be associated with one or more light sources 1040. Examples of such materials include, but are not limited to, 1,4-diphenylbutadiyne; 9,10-diphenylanthracene; benzene; biphenyl; ethyl-p-dimethylaminobenzoate; naphthalene; P-terphenyl; ethyl-p-dimethylaminobenzoate; stilbene; tryptophan; tyrosine; 1,2-diphenylacetylene; 7-methoxycoumarin-4-acetic acid; anthracene; indo-1; POPOP; P-quaterphenyl; pyrene; and the like.

At embodiment 1710, module 1120 may include one or more light sources that are associated with one or more rare-earth materials. In some embodiments, one or more light sources 1040 may include one or more light sources 1040 that are associated with one or more rare-earth materials. In some embodiments, one or more rare-earth materials malt include one or more rare-earth elements. The rare-earth elements are a collection of sixteen chemical elements in the periodic table, namely scandium, yttrium, and fourteen of the fifteen lanthanoids (excluding promethium). In some embodiments, one or more rare-earth materials may include one or more rare-earth elements that fluoresce.

Figure 18:
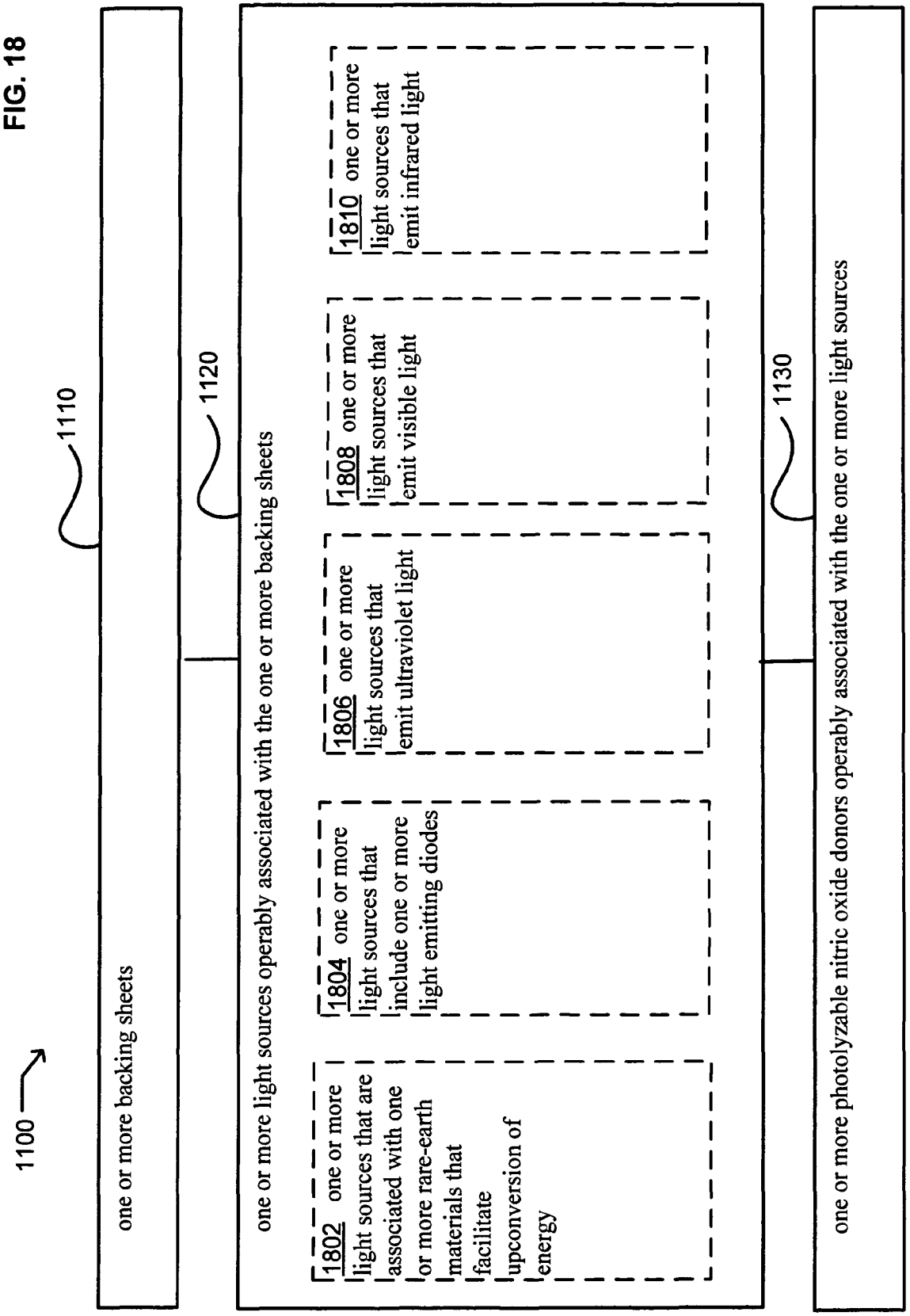
FIG. 18 illustrates alternate embodiments of embodiment 1100 of dressing 1010 within system 1000.

FIG. 18 illustrates alternative embodiments of embodiment 1120 of dressing 1010 within system 1000 of FIG. 11. FIG. 18 illustrates example embodiments of module 1110. Additional embodiments may include an embodiment 1802, an embodiment 1804, an embodiment 1806, an embodiment 1808, and/or an embodiment 1810.

At embodiment 1802, module 1120 may include one or more light sources that are associated with one or more rare-earth materials that facilitate upconversion of energy. In some embodiments, one or more light sources 1040 may include one or more light sources 1040 that are associated with one or more rare-earth materials that facilitate upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more light sources 1040 malt include one or more rare-earth materials (e.g., ytterbium-erbium, ytterbium-thulium, or the like) that facilitate upconversion of energy (e.g. U.S. Pat. No. 7,088,040; herein incorporated by reference). For example, in some embodiments, one or more light sources 1040 may be associated with Nd3+ doped KPb2Cl5 crystals. In some embodiments, one or more light sources 1040 may be associated with thiogallates doped with rare earths, such as CaGa2S4:Ce3+ and SrGa2S4:Ce3+. In some embodiments, one or more light sources 1040 may be associated with aluminates that are doped with rare earths, such as YAlO3:Ce3+, YGaO3:Ce3+, Y(Al,Ga)O3:Ce3+, and orthosilicates M2SiO5:Ce3+ (M:Sc, Y, Sc) doped with rare earths, such as, for example, Y2SiO5:Ce3+. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

At embodiment 1804, module 1120 may include one or more light sources that include one or more light emitting diodes. In some embodiments, one or more light sources 1040 may include one or more light sources 1040 that are associated with one or more light emitting diodes. One or more light sources 1040 may include one or more fight emitting diodes that are configured to emit light of select wavelengths. For example, light emitting diodes may be configured to emit infrared light, visible light, near-ultraviolet light, or ultraviolet light. In some embodiments, a light source 1040 may include a conventional light emitting diode that can include a variety of inorganic semiconductor materials. Examples of such materials and the emitting light include, but are not limited to, aluminium gallium arsenide (red and infrared), aluminium gallium phosphide (green), aluminium gallium indium phosphide (high-brightness orange-red, orange, yellowed, and green), gallium arsenide phosphide (red, orange-red, orange, and yellow), gallium phosphide (red, yellow and green), gallium nitride (green, pure green, emerald green, blue, and white (if it has an AlGaN Quantum Barrier)), indium gallium nitride (near ultraviolet, bluish-green and blue), silicon carbide (blue), silicon (blue), sapphire (blue), zinc selenide (blue), diamond (ultraviolet), aluminium nitride (near to far ultraviolet), aluminium gallium nitride (near to far ultraviolet), aluminium gallium indium nitride (near to far ultraviolet).

At embodiment 1806, module 1120 may include one or more light sources that emit ultraviolet light. In some embodiments, one or more light sources 1040 malt include one or more light sources 1040 that emit ultraviolet light. In some embodiments, one or more light sources 1040 may emit a broad spectrum of ultraviolet light. In some embodiments, one or more light sources 1040 may emit a narrow spectrum of ultraviolet light. In some embodiments, one or more light sources 1040 that emit one or more wavelengths of ultraviolet light that are specifically selected to release nitric oxide from one or more photolyzable nitric oxide donors 1020. In some embodiments, one or more light sources 1040 ma) emit ultraviolet light that does not include one or more wavelengths of light. In some embodiments, one or more light sources 1040 may emit ultraviolet light that is selected to avoid and/or reduce damage to structures and/or tissues of an individual 1150. For example, in some embodiments, one or more light sources 1040 may emit ultraviolet light that does not include wavelengths of light that are absorbed by nucleic acids. In some embodiments, one or more light sources 1040 may emit ultraviolet light that does not include wavelengths of light that are absorbed by polypeptides. In some embodiments, one or more light sources 1040 may emit light that does not include one or more wavelengths of ultraviolet light within the following range: 250-320 nm. For example, in some embodiments, one or more light sources 1040 may not emit 260 nm light. In some embodiments, one or more light sources 1040 may not emit 280 nm light. In some embodiments, one or more light sources 1040 may not emit 260 nm light or 280 nm light. Accordingly, numerous combinations of wavelengths of light may be excluded from emission by one or more light sources 1040. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof.

At embodiment 1808, module 1120 may include one or more light sources that emit visible light. In some embodiments, one or more light sources 1040 may include one or more light sources 1040 that emit visible light. In some embodiments, one or more light sources 1040 may emit a broad spectrum of visible light. In some embodiments, one or more light sources 1040 may emit a narrow spectrum of visible light. In some embodiments, one or more light sources 1040 may emit one or more wavelengths of visible light that are specifically selected to release nitric oxide from one or more photolyzable nitric oxide donors 1020. In some embodiments, one or more light sources 1040 maxi emit visible light that does not include one or more wavelengths of light. In some embodiments, one or more light sources 1040 may emit visible light that is selected to avoid and/or reduce damage to structures and/or tissues of an individual 1150. Accordingly, numerous combinations of wavelengths of light may be excluded from emission by one or more light sources 1040. In some embodiments light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof in some embodiments, visible light may be upconverted.

At embodiment 1810, module 1120 may include one or more light sources that emit infrared light. In some embodiments, one or more light sources 1040 may include one or more light sources 1040 that emit infrared light. In some embodiments, one or more light sources 1040 may emit a broad spectrum of infrared light. In some embodiments, one or more light sources 1040 may emit a narrow spectrum of infrared light. In some embodiments, one or more light sources 1040 may emit one or more wavelengths of infrared light that are specifically selected to release nitric oxide from one or more photolyzable nitric oxide donors 1020. In some embodiments, one or more light sources 1040 may emit infrared light that does not include one or more wavelengths of light. In some embodiments, one or more light sources 1040 may emit infrared light that is selected to avoid and/or reduce damage to structures and/or tissues of an individual 1150. Accordingly, numerous combinations of wavelengths of light may be excluded from emission by one or more light sources 1040. In some embodiments, light may be emitted continuously. In some embodiments, light may be emitted as a flash. In some embodiments, light may be emitted alternately as continuous light and a flash. In some embodiments, light may be emitted as a pulse. In some embodiments, light maid be emitted continuously, as a flash, as a pulse, or substantially any combination thereof. In some embodiments, infrared light may be upconverted.

Figure 19:
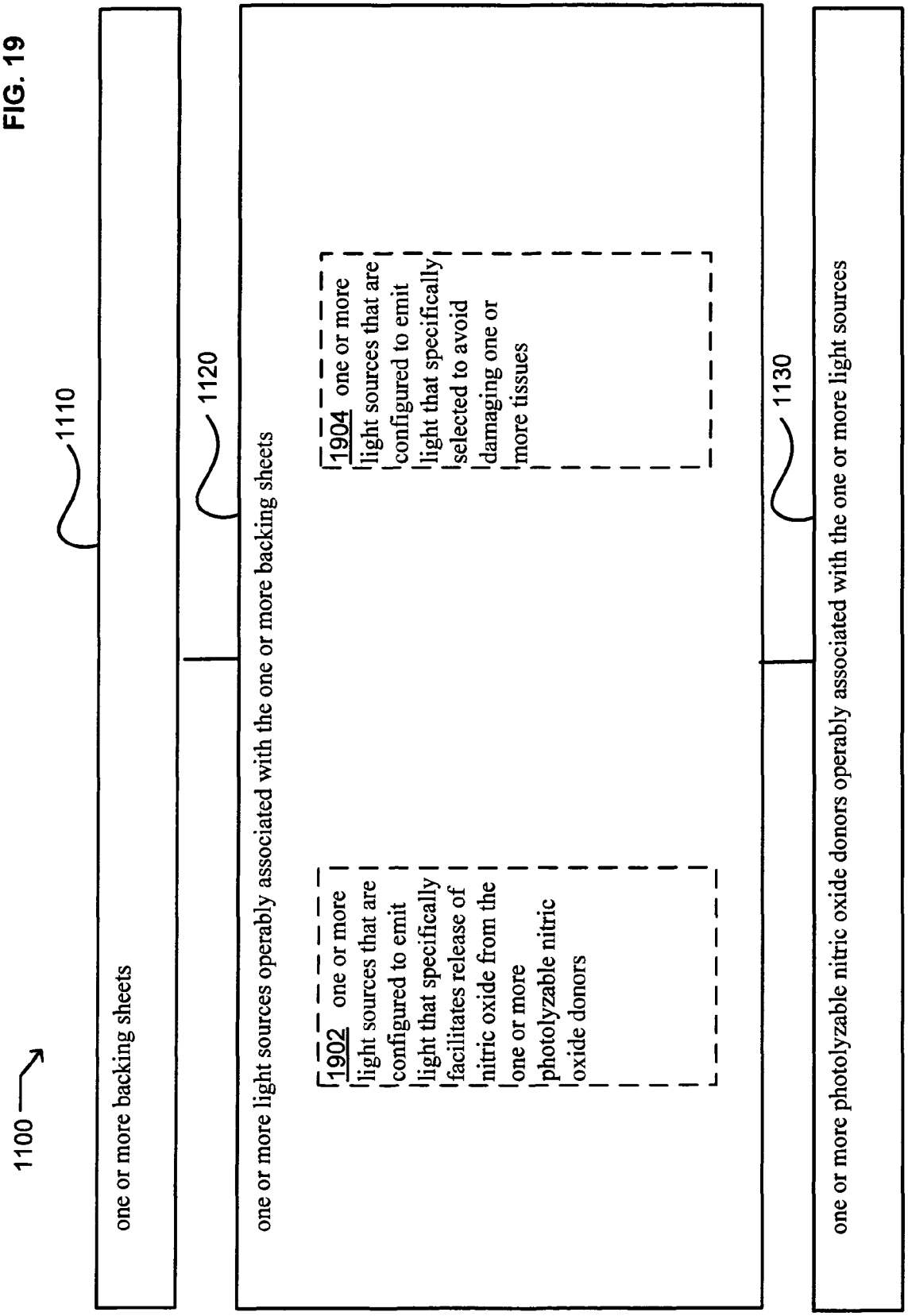
FIG. 19 illustrates alternate embodiments of embodiment 1100 of dressing 1010 within system 1000.

FIG. 19 illustrates alternative embodiments of embodiment 1120 of dressing 1010 within system 1000 of FIG. 11. FIG. 19 illustrates example embodiments of module 1120. Additional embodiments may include an embodiment 1902 and/or an embodiment 1904.

At embodiment 1902, module 1120 may include one or more light sources that are configured to emit light that specifically facilitates release of nitric oxide from the one or more photolyzable nitric oxide donors. In some embodiments one or more light sources 1040 math include one or more light sources 1040 that are configured to emit light that specifically facilitates release of nitric oxide from the one or more photolyzable nitric oxide donors 100. For example. In some embodiments one or more light sources 1040 may be configured to emit light that includes one or more wavelengths of light that correspond to the absorption maximum for one or more photolyzable nitric oxide donors 1020. Examples of nitric oxide donors and their associated $\lambda_{max}$ (nm) are provided in Table I below. Accordingly, one or more light sources 1040 may be configured to emit numerous wavelengths of light.

TABLE I

Example Nitric Oxide Donors

| Compound Name | $\lambda_{max}$ (nm) |
|---|---|
| $O^2$-(Acetoxymethyl) 1-(N,N-Diethylamino)diazen-1-ium-1,2-diolate | 230 |
| $O^2$-(Acetoxymethyl) 1-(Pyrrolidin-1-yl)diazen-1-ium-1,2-diolate | 256 |
| Sodium 1-(N-Benzyl-N-methylamino)diazen-1-ium-1,2-diolate | 252 |
| $O^2$-[(2,3,4,6-Tetra-O-acetyl)-β-D-glucosyl] 1-[4-(2,3-Dihydroxypropyl)piperazin-1 | 232 |
| Sodium 1-[4-(2,3-Dihydroxypropyl)piperazin-1-yl-]diazen-1-ium-1,2-diolate | 248.5 |
| $O^2$-Methyl 1-[(4-Carboxamido)piperidin-1-yl]diazen-1-ium-1,2-diolate | 241 |
| $O^2$-(2-Chloropyrimidin-4-yl) 1-(Pyrrolidin-1-yl)diazen-1-ium-1,2-diolate | 274 |
| $O^2$-(2,4-Dinitrophenyl) 1-[4-(N,N-Diethylcarboxamido)piperazin-1-yl]diazen-1-ium-1,2-diolate | 300 |
| $O^2$-(2,4-Dinitrophenyl) 1-(4-Nicotinylpiperazin-1-yl)diazen-1-ium-1,2-diolate | 300 |
| $O^2$-(2,4-Dinitrophenyl) 1-{4-[2-(4-{2-Methylpropyl}phenyl)propionyl]piperazin-1-yl}diazen-1-ium-1,2-diolate | 300 |
| Sodium 1-(4-Benzyloxycarbonylpiperazin-1-yl)diazen-1-ium-1,2-diolate | 252 |
| $O^2$-(2,4-Dinitrophenyl) 1-[4-(tert-Butoxycarbonyl)piperazin-1-yl]diazen-1-ium-1,2-diolate | 299 |
| $O^2$-(2,4-Dinitrophenyl) 1-(4-Acetylpiperazin-1-yl)diazen-1-ium-1,2-diolate | 394 |
| $O^2$-(2,4-Dinitrophenyl) 1-[4-(Succinimidoxycarbonyl)piperazin-1-yl]diazen-1-ium-1,2-diolate | 300 |
| $O^2$-(2,4-Dinitrophenyl) 1-(Piperazin-1-yl)diazen-1-ium-1,2-diolate, Hydrochloride Salt | 297 |
| $O^2$-(2,3,4,6-Tetra-O-acetyl-D-glucopyranosyl) 1-(N,N-Diethylamino)diazen-1-ium-1,2-diolate | 228 |
| $O^2$-(-D-Glucopyranosyl) 1-(N,N-Diethylamino)diazen-1-ium-1,2-diolate | 228 |
| Sodium (Z)-1-(N,N-Diethylamino)diazen-1-ium-1,2-diolate | 250 |
| 1-[N-(2-Aminoethyl)-N-(2-ammonioethyl)amino]diazen-1-ium-1,2-diolate | 252 |
| Sodium 1-(N,N-Dimethylamino)diazen-1-ium-1,2-diolate | 250 |
| $O^2$-(2,4-Dinitrophenyl) 1-(N,N-Diethylamino)diazen-1-ium-1,2-diolate | 302 |
| 1-[N-(3-Aminopropyl)-N-(3-ammoniopropyl]diazen-1-ium-1,2-diolate | 252 |
| 1-[N-(3-Aminopropyl)-N-(3-ammoniopropyl]diazen-1-ium-1,2-diolate | 252 |
| Bis-diazeniumdiolated benzyl imidate dehydrate | 264 |
| p-Bisdiazeniumdiolated benzene | 316 |
| Methane Trisdiazeniumdiolate trihydrate | 316 |
| $O^2$-(β-D-Glucopyranosyl) 1-(Isopropylamino)diazen-1-ium-1,2-diolate | 278 |
| Sodium 1-[4-(5-Dimethylamino-1-naphthalenesulfonyl)piperazin-1-yl]diazen-1-ium-1,2-diolate | 344 |
| 1-(2-Methyl-1-propenyl)piperidine diazeniumdiolate | 246 |
| 1-(2-Methyl-1-propenyl)pyrrolidine diazeniumdiolate | 246 |
| $O^2$-Vinyl 1-(Pyrrolidin-1-yl)diazen-1-ium-1,2-diolate | 268 |
| 1-{N-[3-Aminopropyl]-N-[4-(3-aminopropylammoniobutyl)]}diazen-1-ium-1,2-diolate | 252 |
| Disodium 1-[(2-Carboxylato)pyrrolidin-1-yl]diazen-1-ium-1,2-diolate | 252 |
| 1-[N-(3-Ammoniopropyl)-N-(n-propyl)amino]diazen-1-ium-1,2-diolate | 250 |
| (Z)-1-{N-Methyl-N-[6-(N-methylammoniohexyl)amino]}diazen-1-ium-1,2-diolate | 250 |
| $O^2$-(2,4-Dinitrophenyl) 1-[(4-Ethoxycarbonyl)piperazin-1-yl]diazen-1-ium-1,2-diolate | 300 |

At embodiment 1904, module 1120 mail include one or more light sources that are configured to emit light that specifically selected to avoid damaging one or more tissues. In some embodiments, one or more light sources 1040 may include one or more light sources 1040 that are configured to emit light that specifically selected to avoid damaging one or more tissues. In some embodiments, one or more light sources 1040 may emit light that is selected to avoid and/or reduce damage to structures and/or tissues of an individual 11150. For example. In some embodiments, one or more light sources 1040 may emit light that does not include wavelengths of light that are absorbed by nucleic acids. In some embodiments, one or more light sources 1040 may emit light that does not include wavelengths of light that are absorbed by polypeptides. In some embodiments, one or more light sources 1040 may emit light that does not include one or more wavelengths of light within the following range: 250-320 nm. For example, in some embodiments, one or more light sources 1040 may not emit 260 nm light. In some embodiments, one or more light sources 1040 may not emit 280 nm light. In some embodiments, one or more light sources 1040 may not emit 260 nm light or 280 nm light. Accordingly, numerous combinations of wavelengths of light may be excluded from emission by one or more light sources 1040. In some embodiments, light may be emitted continuously. In some embodiments, list may be emitted as a flash. In some embodiments, light may be emitted alternately, as continuous light and a flash. In some embodiments, light may be emitted as a pulse.

Figure 20:
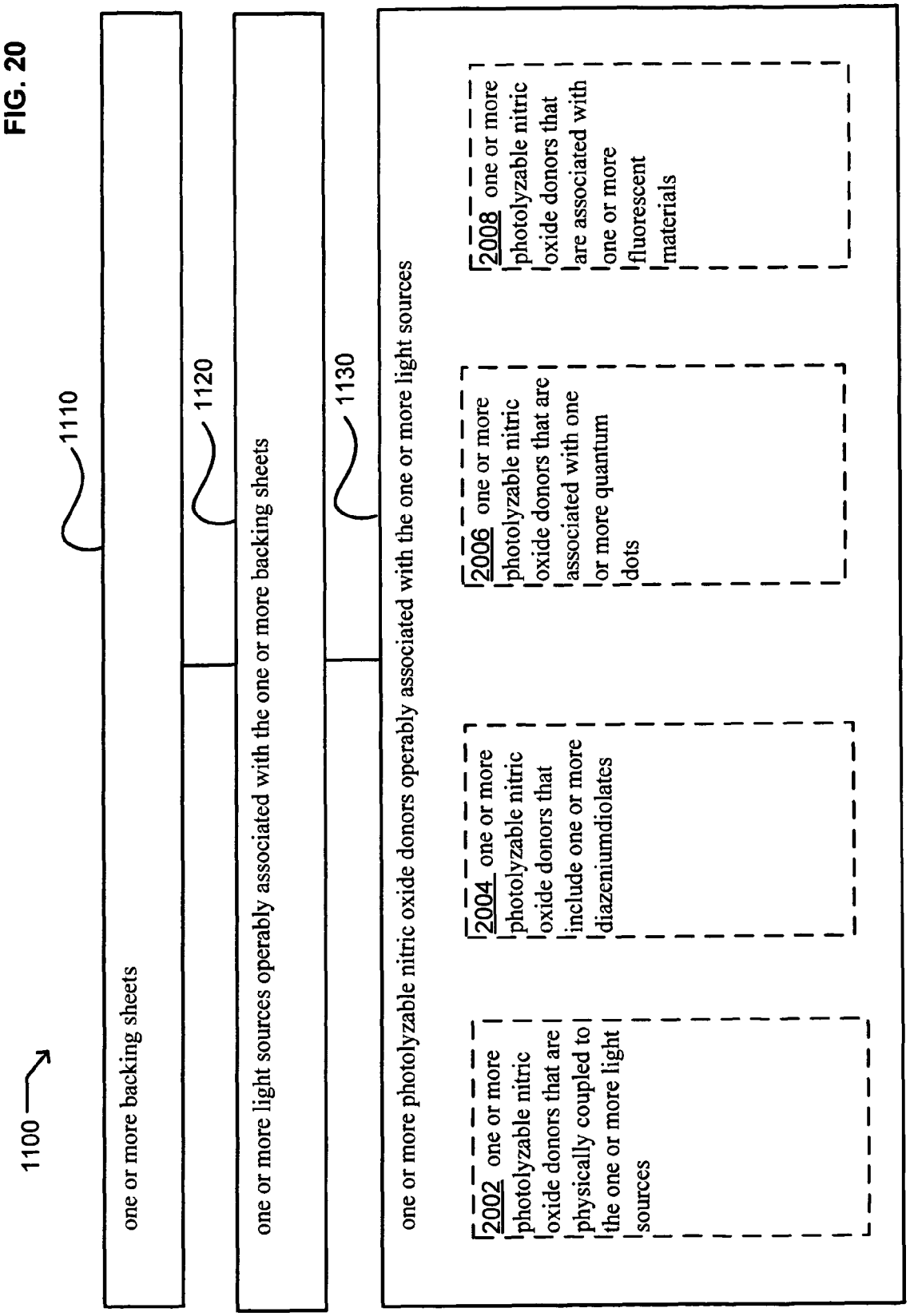
FIG. 20 illustrates alternate embodiments of embodiment 1100 of dressing 1010 within system 1000.

FIG. 20 illustrates alternative embodiments of embodiment 1130 of dressing 1010 within system 1000 of FIG. 11. FIG. 20 illustrates example embodiments of module 1130.

Additional embodiments may include an embodiment 2002, an embodiment 2004, an embodiment 2006, and/or an embodiment 2008.

At embodiment 2002, module 1130 may include one or more photolyzable nitric oxide donors that are physically coupled to the one or more light sources. In some embodiments, one or more photolyzable nitric oxide donors 1020 may include one or more photolyzable nitric oxide donors 1020 that are physically coupled to one or more light sources 1040. In some embodiments, the one or more light sources 1040 may be directly coupled to one or more photolyzable nitric oxide donors 1020. For example, in some embodiments, the one or more photolyzable nitric oxide donors 1020 may be chemically coupled to a surface of the light source 1040 (e.g., chemically coupled to a polymer coating on the light source). In some embodiments, one or more photolyzable nitric oxide donors 1020 may be indirectly coupled to one or more light sources 1040. For example, in some embodiments, one or more photolyzable nitric oxide donors 1090 may be coupled to a material that is used to coat the one or more light sources 1040.

At embodiment 2004, module 1130 may include one or more photolyzable nitric oxide donors that include one or more diazeniumdiolates. In some embodiments, one or more photolyzable nitric oxide donors 1020 may, include one or more photolyzable nitric oxide donors 1090 that include one or more diazeniumdiolates. Many photolyzable nitric oxide donors 1020 that are diazeniumdiolates are known and halve been described (e.g., U.S. Pat. No. 7,122,529). Examples of such diazeniumdiolates include, but are not limited to, $O^2$-benzyl, $O^2$-naphthylmethyl substituted diazeniumdiolates and $O_2$-naphthylallyl substituted diazeniumdiolates.

At embodiment 2006, module 1130 may include one or more photolyzable nitric oxide donors that are associated Keith one or more quantum dots. In some embodiments, one or more photolyzable nitric oxide donors 1090 may include one or more photolyzable nitric oxide donors 1020 that are associated with one or more quantum dots. For example. In some embodiments, one or more diazeniumdiolates may be associated with one or more quantum dots. In some embodiments, one or more quantum dots may be tuned to emit light that facilitates photolysis of one or more nitric oxide donors. In some embodiments, a quantum dot ma) be tuned to emit light that specifically facilitates photolysis of one or more nitric oxide donors. For example, in some embodiments, one or more quantum dots may emit select wavelengths of light that correspond to wavelengths of light that cause photolysis of one or more nitric oxide donors. In some embodiments, one or more quantum clots may be selected that absorb light emitted by one or more light sources 1040 and emit light that facilitates photolysis of one or more nitric oxide donors in some embodiments, one or more photolyzable nitric oxide donors 1020 may include one or more photolyzable nitric oxide donors 1020 that are associated with one or more quantum dots. For example, in some embodiments, one or more diazeniumdiolates may be associated with one or more quantum dots. In some embodiments, one or more quantum dots may be tuned to emit light that facilitates photolysis of one or more nitric oxide donors. In some embodiments, a quantum dot may be tuned to emit light that specifically facilitates photolysis of one or more nitric oxide donors. For example, in some embodiments, one or more quantum dots may emit select wavelengths of light that correspond to wavelengths of light that cause photolysis of one or more nitric oxide donors. In some embodiments, one or more quantum dots may be selected that absorb light emitted by one or more light sources 1040 and emit light that facilitates photolysis of one or more nitric oxide donors.

At embodiment 2008, module 1130 may include one or more photolyzable nitric oxide donors that are associated with one or more fluorescent materials. In some embodiments, one or more photolyzable nitric oxide donors 1020 may include one or more photolyzable nitric oxide donors 1020 that are associated with one or more fluorescent materials. Numerous fluorescent materials may be associated with one or more photolyzable nitric oxide donors 1020. Examples of such materials include, but are not limited to 1,4-diphenylbutadiyne; 9,10-diphenylanthracene; benzene; biphenyl; ethyl-p-dimethylaminobenzoate; naphthalene; P-terphenyl; ethyl-p-dimethylaminobenzoate; stilbene; tryptophan; tyrosine; 1,2-diphenyl acetylene; 7-methoxycoumarin-4-acetic acid; anthracene; indo-1; POPOP; P-quaterphenyl; pyrene; and the like.

Figure 21:
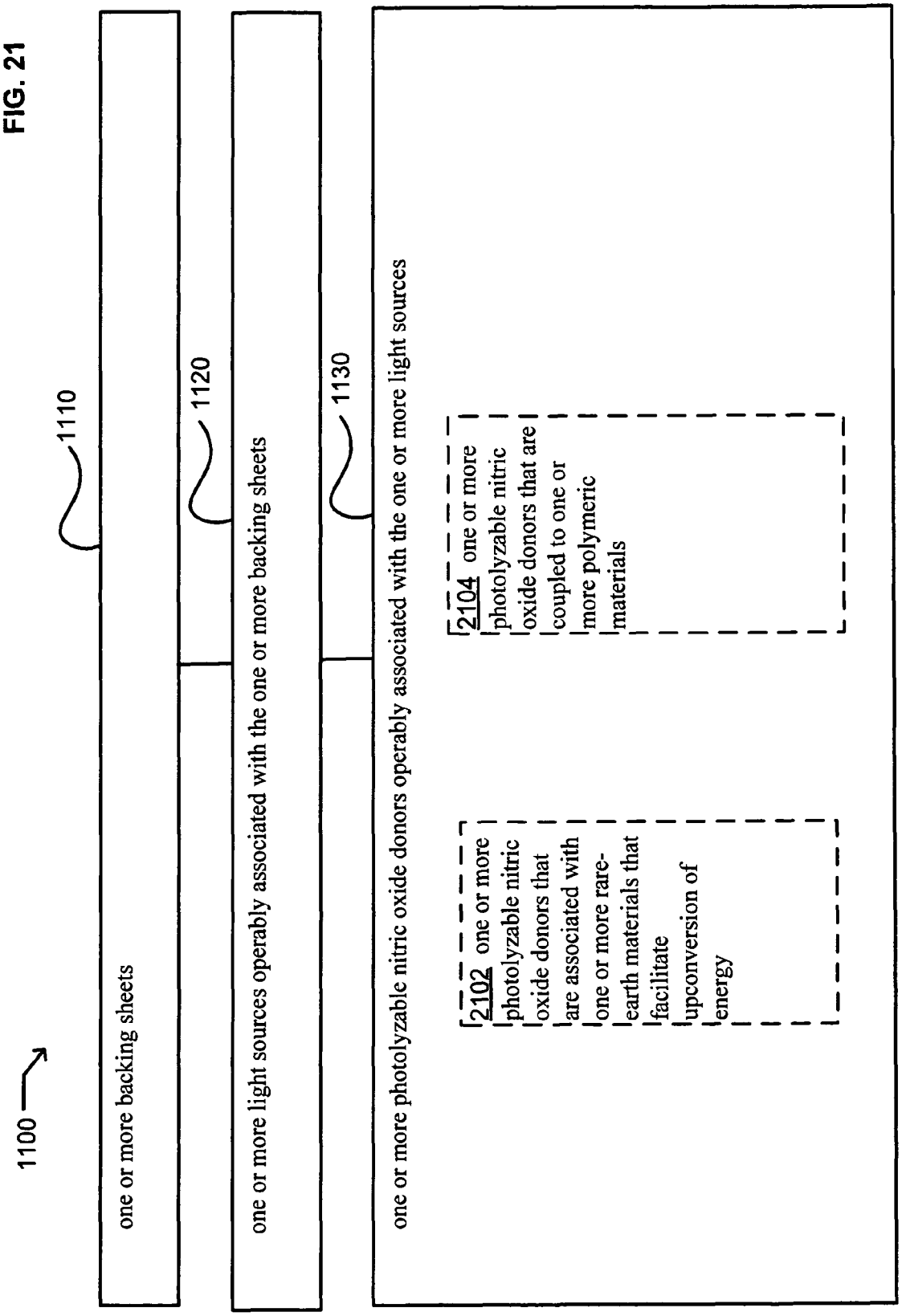
FIG. 21 illustrates alternate embodiments of embodiment 1100 of dressing 1010 within system 1000.

FIG. 21 illustrates alternative embodiments of embodiment 1130 of dressing 1010 within system 1000 of FIG. 11. FIG. 21 illustrates example embodiments of module 1130. Additional embodiments may include an embodiment 2102 and/or an embodiment 2104.

At embodiment 2102, module 1130 may include one or more photolyzable nitric oxide donors that are associated with one or more rare-earth materials that facilitate upconversion of energy. In some embodiments one or more photolyzable nitric oxide donors 1020 may include one or more photolyzable nitric oxide donors 1020 that are associated with one or more rare-earth materials that facilitate upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more photolyzable nitric oxide donors 1020 may be associated with one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more photolyzable nitric oxide donors 1020 may be associated with $Nd^{3+}$ doped $KPb_2Cl_5$ crystals. In some embodiments, one or more photolyzable nitric oxide donors 1020 may be associated with thiogallates doped with rare earths, such as $CaGa_2S_4:Ce^{3+}$ and $SrGa_2S_4:Ce^{3+}$. In some embodiments, one or more photolyzable nitric oxide donors 100 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

At embodiment 2104, module 1130 may include one or more photolyzable nitric oxide donors that are coupled to one or more polymeric materials. In some embodiments one or more photolyzable nitric oxide donors 1020 may include one or more photolyzable nitric oxide donors 1090 that are coupled to one or more polymeric materials. For example, in some embodiments, one or more polymer matrices may be impregnated with one or more photolyzable nitric oxide donors 1020 (e.g., U.S. Pat. No. 5,994,444). In some embodiments, one or more photolyzable nitric oxide donors 1020 may be bound to a polymer. Methods that can be used to couple nitric oxide donors to a polymeric matrix have been reported (e.g., U.S. Pat. No. 5,405,919).

Figure 22:
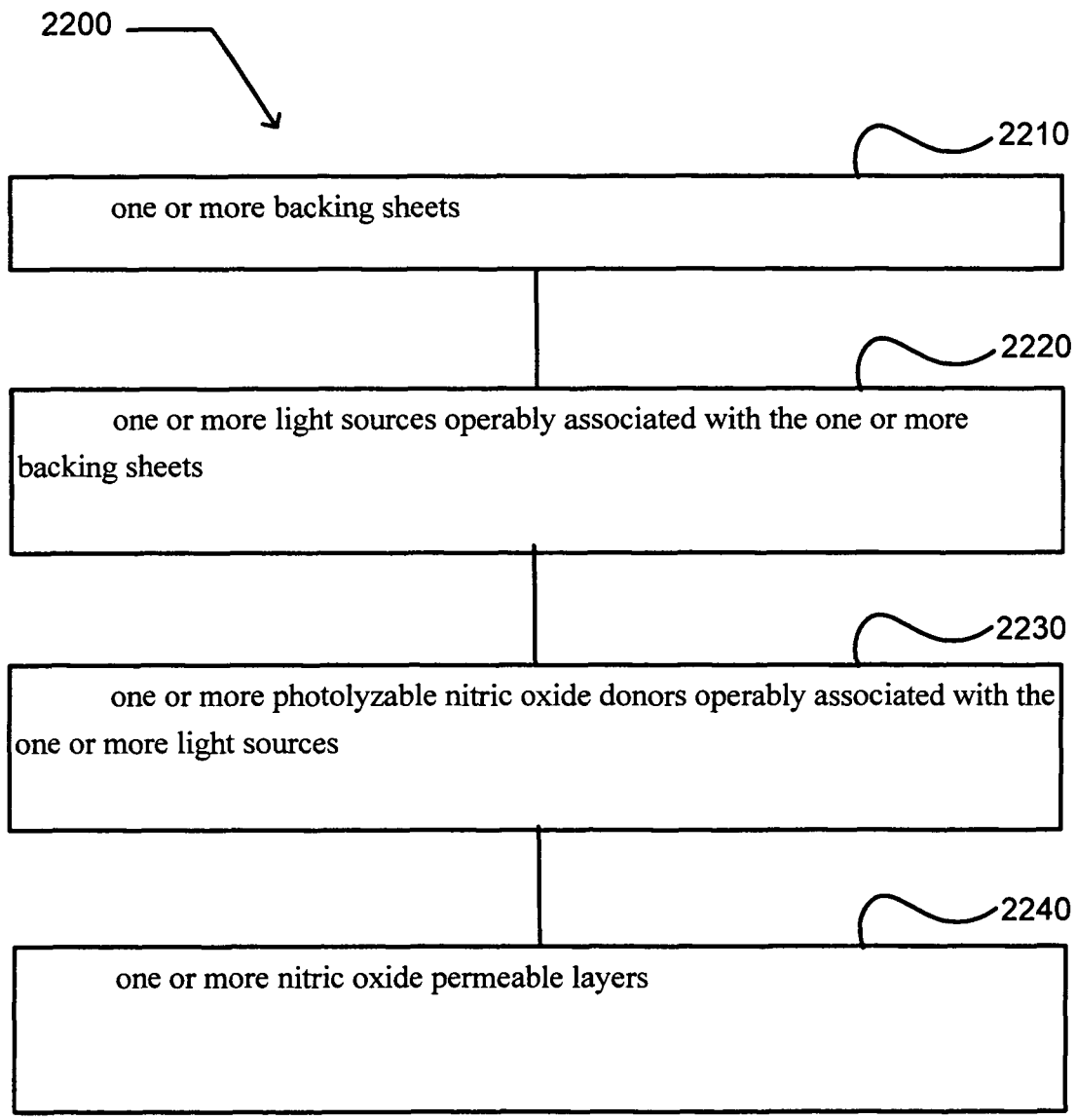
FIG. 22 illustrates embodiment 2200 of dressing 1010 within system 1000.

FIG. 22 illustrates embodiment 2200 of dressing 1010 within system 1000. In FIG. 22, discussion and explanation may be provided with respect to the above-described example of FIG. 10, and/or with respect to other examples and contexts. However, it should be understood that the modules may execute operations in a number of other environments and contexts, and/or modified versions of FIG. 10. Also, although the various modules are presented in the sequence(s) illustrated, it should be understood that the various modules may be configured in numerous orientations.

The embodiment 2200 may include module 2210 that includes one or more backing sheets. In some embodiments, a dressing 1010 may include one or more backing sheets 1030. One or more backing sheets 1030 may be fabricated from one or more materials. In some embodiments, one or more backing sheets 1030 may include portions that are fabricated from different types of materials. For example in some embodiments, a backing sheet 1030 may include one or more portions that include one or more adhesive, materials and one or more portions that include one or more nonadhesive materials. In some embodiments, a backing sheet 1030 may include one or more portions that include one or more gas permeable materials and one or more portions that include one or more (as impermeable materials. Accordingly, one or more backing sheets 1030 may include numerous combinations of materials that exhibit numerous properties. Examples of such material include, but are not limited to, elastic materials, inelastic materials, adhesive materials, nonadhesive materials, conductive materials, nonconductive materials, perforated materials, nonperforated materials, fluid permeable materials, fluid impermeable materials, gas permeable materials, gas impermeable materials, light permeable materials, selectively light permeable materials, light impermeable materials, and the like.

The embodiment 2200 may include module 2220 that includes one or more light sources operably associated with the one or more backing sheets. In some embodiments, a dressing 1010 may include one or more light sources 1040 operably associated with one or more backing sheets 1030. In some embodiments, a dressing 1010 may include one or more light sources 1040 that are operably associated with one or more photolyzable nitric oxide donors 1020. In some embodiments one or more light sources 1040 may be directly coupled to one or more backing sheets 1030. For example in some embodiments, one or more light sources 1040 may be integrated within one or more backing sheets 1030. In some embodiments, one or more light sources 1040 may be indirectly associated with one or more backing sheets 1030. For example, in some embodiments, one or more light sources 1040 may be associated with one or more backing sheets 1030 through attachment to one or more electrical connections associated with the one or more backing sheets 1030. In some embodiments, one or more light sources 1040 may be associated with one or more backing sheets 1030 through inclusion within one or more compositions that include one or more photolyzable nitric oxide donors 1020 that are associated with one or more backing sheets 1030.

The embodiment 2200 may include module 2230 that includes one or more photolyzable nitric oxide donors operably associated with the one or more light sources. In some embodiments, a dressing 1010 may include one or more photolyzable nitric oxide donors 1090 operably associated with the one or more light sources 1040. In some embodiments, the one or more light sources 1040 made be directly coupled to one or more photolyzable nitric oxide donors 1020. For example, in some embodiments, the one or more photolyzable nitric oxide donors 1090 may be chemically coupled to a surface of the light source 1040 (e.g., chemically coupled to a polymer coating on the light source). In some embodiments, one or more photolyzable nitric oxide donors 1020 may be indirectly coupled to one or more light sources 1040. For example, in some embodiments, one or more photolyzable nitric oxide donors 1020 may be coupled to a material that is used to coat the one or more light sources 1040. Numerous photolyzable nitric oxide donors 1020 ma be operably associated with one or more light sources 1040. Examples of such photolyzable nitric oxide donors 1090 include, but are not limited to, diazeniumdiolates (e.g.; U.S. Pat. Nos. 7,105,502; 7,122,529; 6,673,338; herein incorporated by reference), trans-[RuCl([15]aneN4)NO]+2 (Ferezin et al. Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 13:8669-8666 (2001)), S-nitroso-glutathione (e.g., Rotta et al., Braz. J. Med. Res., 36:587-594 (2003), Flitney and Megson, J. Physiol., 550: 819-828 (2003)), S-nitrosothiols (e.g., Andrews et al., British Journal of Pharmacology, 138:939-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102: 1091-1134 (2002)), imidazolyl derivatives (e.g., U.S. Pat. No. 5,374,710; herein incorporated by reference).

The embodiment 2200 may include module 2240 that includes one or more nitric oxide permeable layers. In some embodiments, a dressing 1010 may include one or more nitric oxide permeable layers 1050. A dressing 1010 ma include one or more nitric oxide permeable layers 1050 that are fabricated from numerous types of material. Examples of such materials include, but are not limited to, ceramics, polymeric materials, metals, plastics, and the like. In some embodiments, a nitric oxide permeable layer 1050 may include numerous combinations of materials. For example, in some embodiments, a nitric oxide permeable layer 1050 may include a nitric oxide impermeable material that is coupled to a nitric oxide permeable material. In some embodiments, a nitric oxide permeable layer 1050 may include one or more nitric oxide permeable membranes (e.g., U.S. Patent Application No.: 20020026937). In some embodiments, a nitric oxide permeable layer 1050 may include a selectively permeable membrane. For example, in some embodiments, a nitric oxide permeable layer 1050 may include a selectively permeable membrane that is a hydrophilic polyester co-polymer membrane system that includes a copolymer with 70% polyester and 30% polyether (e.g., Sympatex™ 10 μm membrane, see Hardwick et al., Clinical Science, 100:395-400 (2001)). In some embodiments, a nitric oxide permeable layer 1050 may include a scintered glass portion that is permeable to nitric oxide. Accordingly, nitric oxide permeable layers 1050 may include numerous types of porous ceramics that are permeable to nitric oxide. In some embodiments, a nitric oxide permeable layer 1050 may include a porous metal portion that is permeable to nitric oxide. In some embodiments, a nitric oxide permeable layer 1050 may include a nitric oxide permeable coating (e.g., U.S. Patent Application Nos.: 20050220838 and 20030093143).

Nitric oxide permeable layers 1050 may be configured for application to an individual 1150. Nitric oxide permeable layers 1050 may be configured to facilitate application of nitric oxide to a surface. In some embodiments, one or more nitric oxide permeable layers 1050 may be configured to facilitate application of nitric oxide to one or more surfaces of an individual 1150. For example, in some embodiments, one or more nitric oxide permeable layers 1050 may be configured as part of a bandage and/or patch that may be positioned on a skin surface of an individual 1150 to deliver nitric oxide to the skin surface. In some embodiments, a nitric oxide permeable layer 1050 may be configured as a bag. For example, in some embodiments, one or more nitric oxide permeable layers 1050 may be included within a bag and/or sleeve that is configured to deliver nitric oxide to an individual 1150.

In some embodiments, one or more nitric oxide permeable layers 1050 may be configured to enclose at least a portion of one or more photolyzable nitric oxide donors 1020. In some embodiments, one or more nitric oxide permeable layers 1050 may be configured to enclose at least a portion of one or more light sources 1040, at least a portion of one or more control units 1060, at least a portion of one or more sensors 1070, at least a portion of one or more electromagnetic receivers 1080, or substantially any combination thereof.

Figure 23:
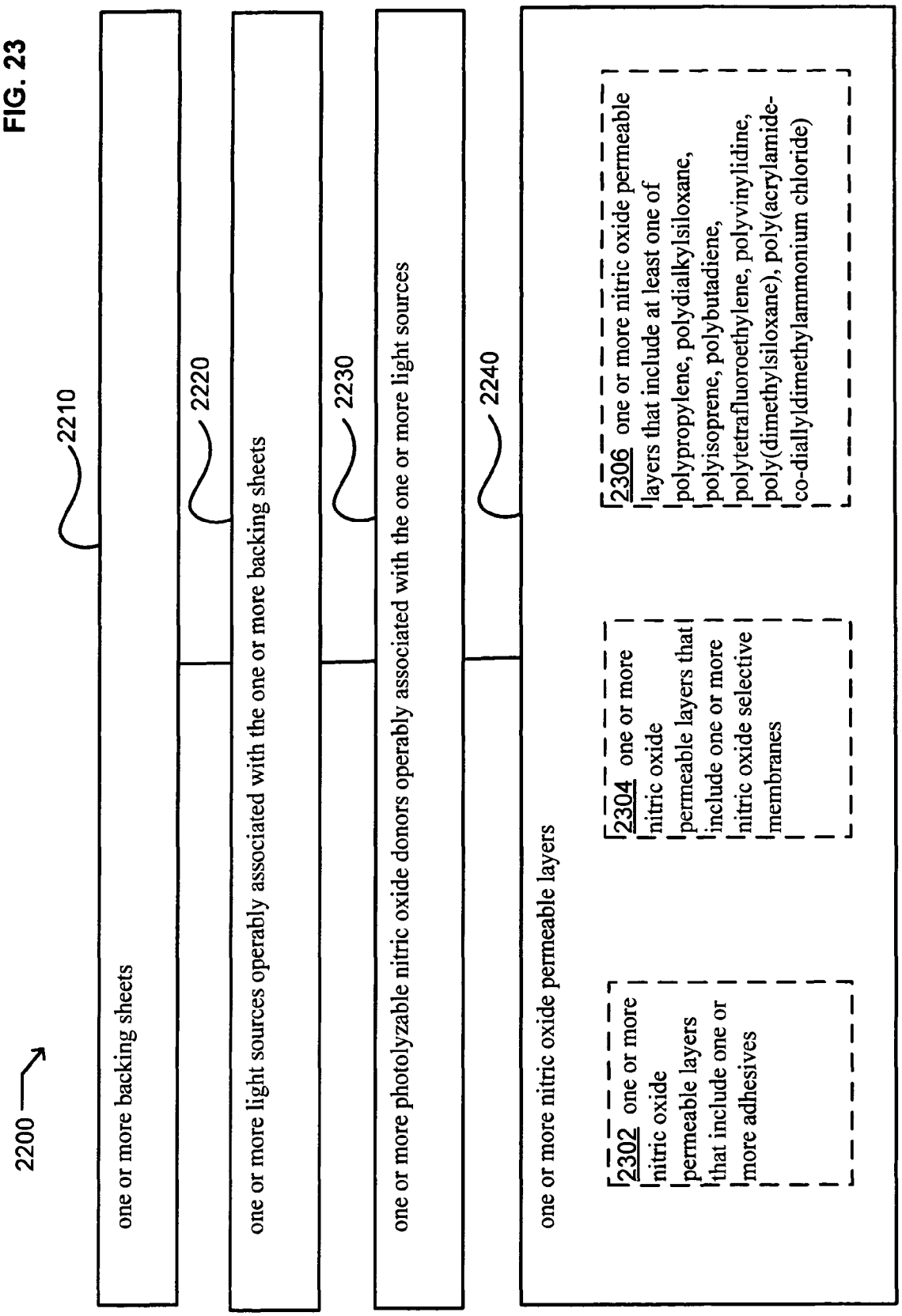
FIG. 23 illustrates alternate embodiments of embodiment 2200 of dressing 1010 within system 1000.

FIG. 23 illustrates alternative embodiments of embodiment 2200 of dressing 1010 within system 1100 of FIG. 11. FIG. 23 illustrates example embodiments of module 2240. Additional embodiments may include an embodiment 2302, an embodiment 2304, and/or an embodiment 2306.

At embodiment 2302, module 2240 may, include one or more nitric oxide permeable layers that include one or more adhesives. In some embodiments, one or more nitric oxide permeable layers 1050 may include one or more nitric oxide permeable layers 1050 that include one or more adhesives. In some embodiments, a dressing 1010 may include one or more nitric oxide permeable layers 1050 that include one or more adhesives that facilitate adhesion of at least a portion of a nitric oxide permeable layer 1050 to a surface. For example, in some embodiments, a dressing 1010 may include a nitric oxide permeable layer 1050 that includes at least one portion which includes one or more adhesives and that is configured to deliver nitric oxide to a surface adjacent to the nitric oxide permeable layer 1050. For example, in some embodiments, a dressing 1010 may be configured as a bandage that includes a nitric oxide permeable membrane on the portion of the bandage that is to be placed on a skin surface of an individual 11150. In some embodiments, adhesive may enclose a space on the surface of the nitric oxide permeable layer 1050 such that a sealed space is formed on the skin when the bandage is adhered to the skin surface. Accordingly, such an embodiment of a dressing 1010 may be used to deliver nitric oxide to a select surface by positioning the dressing 1010 on and/or over the select surface and attaching the dressing 1010 at points adjacent to the select surface with the one or more adhesives. In some embodiments, such an embodiment of dressing 1010 may be configured as a bandage, a patch, and the like.

At embodiment 2304, module 2240 may include one or more nitric oxide permeable layers that include one or more nitric oxide selective membranes. In some embodiments, one or more nitric oxide permeable layers 1050 may include one or more nitric oxide permeable layers 1050 that include one or more nitric oxide selective membranes. In some embodiments, a nitric oxide permeable layer 1050 may include a selectively permeable membrane. For example, in some embodiments, a nitric oxide permeable layer 1050 may include a selectively permeable membrane that is a hydrophilic polyester co-polymer membrane system that includes a copolymer with 70% polyester and 30% polyether (e.g., Sympatex™ 10 μm membrane, see Hardwick et al., Clinical Science, 100:395-400 (2001)). Methods to fabricate nitric oxide permeable membranes are known (e.g., U.S. Patent Application No.: 20020026937).

At embodiment 2306, module 2240 may include one or more nitric oxide permeable layers that include at least one of polypropylene, polydialkylsiloxane, polyisoprene, polybutadiene, polytetrafluoroethylene, polyvinylidine, poly(dimethylsiloxane), poly(acrylamide-co-diallyldimethylammonium chloride). In some embodiments, one or more nitric oxide permeable layers 1050 may include one or more nitric oxide permeable layers 1050 that include at least one of polypropylene, polydialkylsiloxane, polyisoprene, polybutadiene, polytetrafluoroethylene, polyvinylidine, poly(dimethylsiloxane), poly(acrylamide-co-diallyldimethylammonium chloride).

Figure 24:
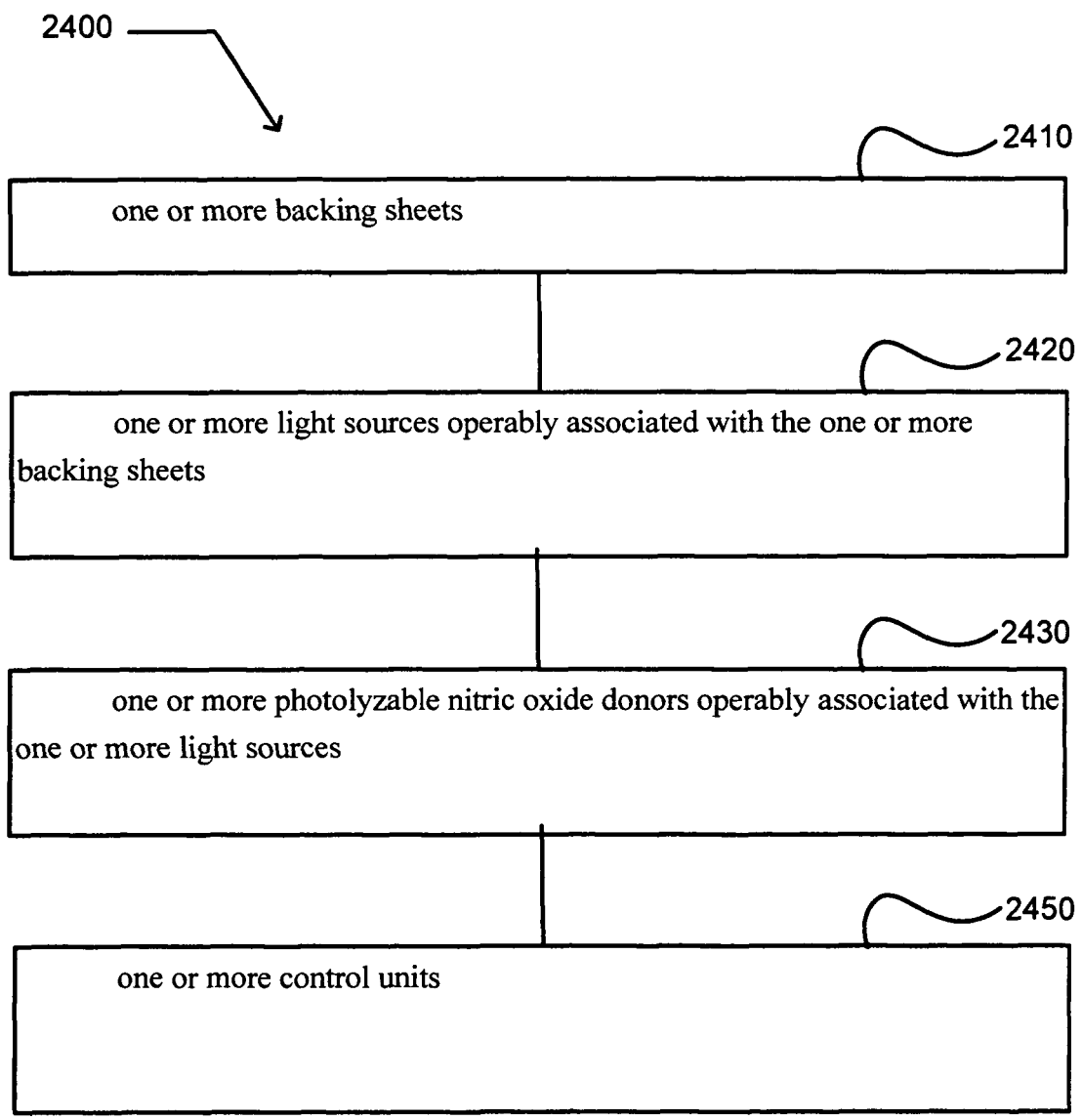
FIG. 24 illustrates embodiment 2400 of dressing 1010 within system 1000.

FIG. 24 illustrates embodiment 2400 of dressing 1010 within system 1000. In FIG. 24, discussion and explanation may be provided with respect to the above-described example of FIG. 10, and/or with respect to other examples and contexts. However, it should be understood that the modules may execute operations in a number of other environments and contexts, and/or modified versions of FIG. 10. Also, although the various modules are presented in the sequence(s) illustrated, it should be understood that the various modules may be configured in numerous orientations.

The embodiment 2400 may include module 2410 that includes one or more backing sheets. In some embodiments, a dressing 1010 may include one or more backing sheets 1030. One or more backing sheets 1030 may be fabricated from one or more materials. In some embodiments, one or more backing sheets 1030 may include portions that are fabricated from different types of materials. For example, in some embodiments, a backing sheet 1030 may include one or more portions that include one or more adhesive materials and one or more portions that include one or more nonadhesive materials. In some embodiments, a backing sheet 1030 may include one or more portions that include one or more gas permeable materials and one or more portions that include one or more gas impermeable materials. Accordingly: one or more backing sheets 1030 may include numerous combinations of materials that exhibit numerous properties. Examples of such material include, but are not limited to, elastic materials, inelastic materials, adhesive materials, nonadhesive materials, conductive materials, nonconductive materials, perforated materials, nonperforated materials, fluid permeable materials, fluid impermeable materials, gas permeable materials, gas impermeable materials, light permeable materials, selectively light permeable materials, light impermeable materials, and the like.

The embodiment 2400 may include module 2420 that includes one or more light sources operably associated with the one or more backing sheets. In some embodiments, a dressing 1010 may include one or more light sources 1040 operably associated with one or more backing sheets 1030. In some embodiments, a dressing 1010 may include one or more light sources 1040 that are operably associated with one or more photolyzable nitric oxide donors 1020. In some embodiments, one or more light sources 1040 may be directly coupled to one or more backing sheets 1030. For example, in some embodiments, one or more light sources 1040 may be integrated within one or more backing sheets 1030. In some embodiments, one or more light sources 1040 may be indirectly associated with one or more backing sheets 1030. For example, in some embodiments, one or more light sources 1040 may be associated wraith one or more backing sheets 1030 through attachment to one or more electrical connections associated with the one or more backing sheets 1030. In some embodiments, one or more light sources 1040 may be associated with one or more backing sheets 1030 through inclusion within one or more compositions that include one or more photolyzable nitric oxide donors 1020 that are associated with one or more backing sheets 1030.

The embodiment 2400 may include module 2430 that includes one or more photolyzable nitric oxide donors operably associated with the one or more light sources. In some embodiments, a dressing 1010 may include one or more photolyzable nitric oxide donors 1020 operably associated with the one or more light sources 1040. In some embodiments, the one or more light sources 1040 may be directly coupled to one or more photolyzable nitric oxide donors 1020. For example, in some embodiments, the one or more photolyzable nitric oxide donors 1020 may be chemically coupled to a surface of the light source 1040 (e.g., chemically coupled to a polymer coating on the light source). In some embodiments, one or more photolyzable nitric oxide donors 1020 may be indirectly coupled to one or more light sources 1040. For example, in some embodiments, one or more photolyzable nitric oxide donors 1020 may be coupled to a material that is used to coat the one or more light sources 1040. Numerous photolyzable nitric oxide donors 1020 may be operably associated with one or more light sources 1040. Examples of such photolyzable nitric oxide donors 1020 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol. 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc. 123:8662-8666 (2001)), S-nitroso-glutathione (e.g., Rotta et al., Braz. J. Med. Res., 36:597-594 (2003), Flitney and Megson, J. Physiol., 550: 819-898 (2003)), S-nitrosothiols (e.g., Andrews et al., British Journal of Pharmacology, 138:932-940 (2003), Singh et al.; FEBS Lett., 360:47-51 (1995)), 2-Methyl-2-nitrosopropane (e.g., Pou et al., Mol. Pharm., 46:709-715 (1994), Wang et al., Chem. Res., 102:1091-1134 (2002)), imidazolyl derivatives (e.g., U.S. Pat. No. 5,374,710; herein incorporated by reference).

The embodiment 2400 may include module 2450 that includes one or more control units. In some embodiments, a dressing 1010 may include one or more control units 1060. A dressing 1010 may include numerous types of control units 1060. In some embodiments, one or more control units 1060 may be operably coupled with one or more light sources 1040, one or more sensors 1070, one or more electromagnetic receivers 1080, one or more electromagnetic transmitters 1100, or substantially any combination thereof. In some embodiments, one or more control units 1060 may be operably coupled to other components through use of one or more wireless connections, one or more hardwired connections, or substantially any combination thereof. A control unit 1060 may be configured in numerous ways. For example, in some embodiments, a control unit 1060 may be configured as an on/off switch. Accordingly, in some embodiments, a control unit 1060 may be configured to turn a light source 1040 on and/or off. In some embodiments, a control unit 1060 may be configured to control the emission of light from one or more light sources 1040. For example, in some embodiments, one or more control units 1060 may regulate the intensity of light emitted from one or more light sources 1040, the duration of light emitted from one or more light sources 1040, the frequency of light emitted from one or more light sources 1040, wavelengths of light emitted from one or more light sources 1040, times when light is emitted from one or more light sources 1040, or substantially any combination thereof. In some embodiments, one or more control units 1060 may be configured to receive one or more signals 1110 from one or more sensors 1070. Accordingly, in some embodiments, one or more control units 1060 may be configured to control one or more light sources 1040 in response to one or more signals 1110 received from one or more sensors 1070. For example, in some embodiments, one or more sensors 1070 may sense a low concentration of nitric oxide in one or more tissues and send one or more signals 1110 to one or more control units 1060. The one or more control units 1060 may then tuna one or more light sources 1040 on to facilitate release of nitric oxide from one or more photolyzable nitric oxide donors 1020. Accordingly, in some embodiments, one or more sensors 1070 may sense a high concentration of nitric oxide in one or more tissues and send one or more signals 1110 to one or more control units 1060. The one or more control units 1060 may then turn one or more light sources 1040 off to end release of nitric oxide from one or more photolyzable nitric oxide donors 1020. In some embodiments, one or more control units 1060 may be programmed to control one or more light sources 1040. For example, in some embodiments, one or more control units 1060 may be programmed to turn one or more light sources 1040 on for a predetermined amount of time and then turn off. Accordingly, in some embodiments, one or more control units 1060 may be preprogrammed. In some embodiments, one or more control units 1060 may be dynamically programmed. For example, in some embodiments, one or more management units 1130 may receive one or more signals 1110 from one or more sensors 1070 and program one or more control units 1060 in response to the one or more signals 1110 received from the one or more sensors 1070. In some embodiments, one or more control units 1060 may include one or more receivers that are able to receive one or more signals 1110, one or more information packets, or substantially any combination thereof. Control units 1060 may be configured in numerous ways. For example, in some embodiments, one or more control units 1060 may be operably coupled to one or more light sources 1040 that include numerous light emitting diodes that emit light of different wavelengths. Accordingly, in some embodiments, one or more control units 1060 may control the wavelengths of light emitted by the one or more light sources 1040 by controlling the operation of light emitting diodes that emit light of the selected wavelength. Accordingly, control units 1060 may be configured in numerous ways and utilize numerous types of mechanisms.

Figure 25:
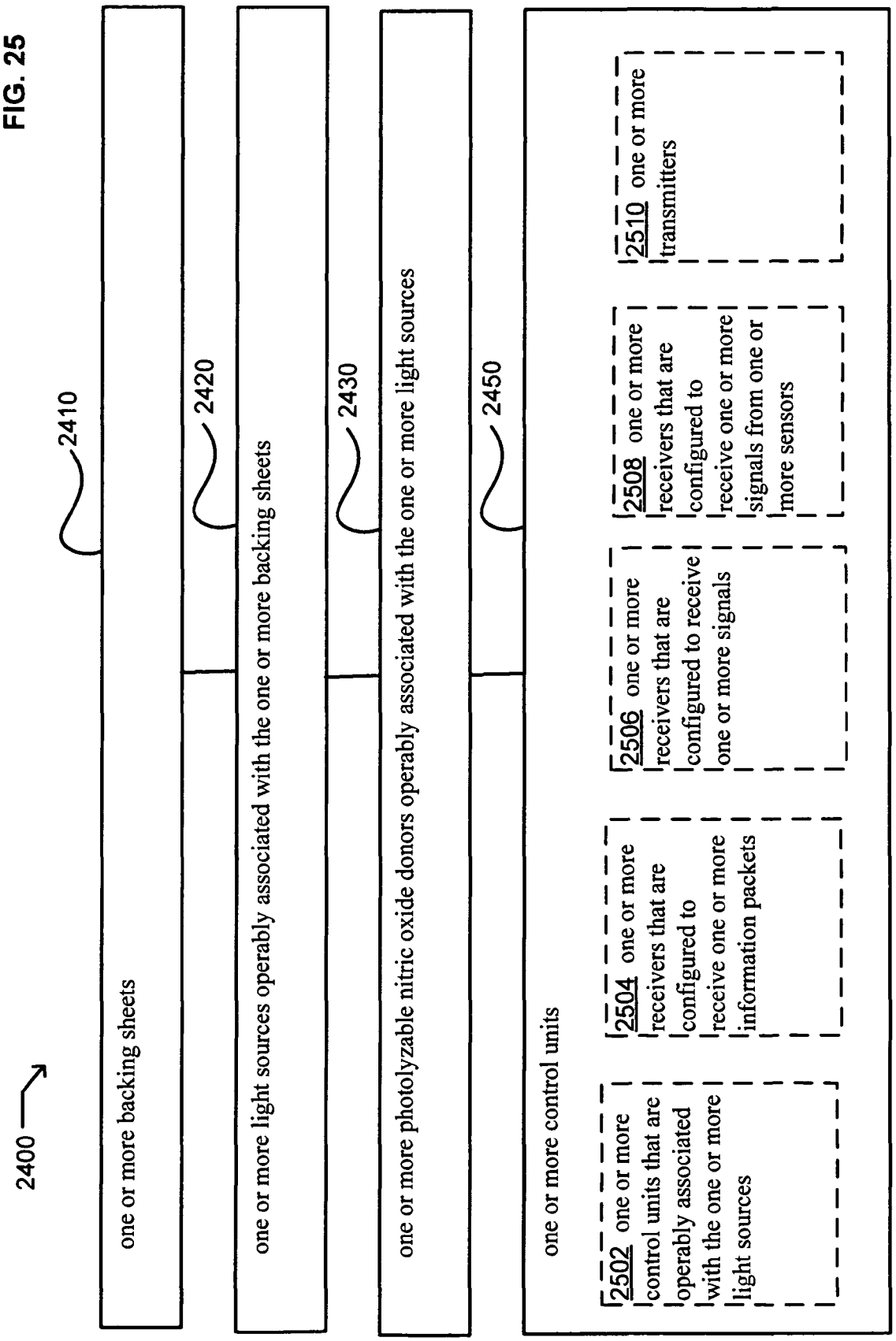
FIG. 25 illustrates alternate embodiments of embodiment 2400 of dressing 1010 within system 1000.

FIG. 25 illustrates alternative embodiments of embodiment 2400 of dressing 1010 within system 1000 of FIG. 10. FIG. 25 illustrates example embodiments of module 2450. Additional embodiments may include an embodiment 2502, an embodiment 2504, an embodiment 2506, an embodiment 2508, and/or an embodiment 2510.

At embodiment 2509, module 2450 may include one or more control units that are operably associated with the one or more light sources. In some embodiments, one or more control units 1060 may include one or more control units 1060 that are operably associated with the one or more light sources 1040. In some embodiments, the one or more control units 1060 may be operably associated with one or more light sources 1040 through use of a hardwired connection. In some embodiments, the one or more control units 1060 may be operably associated with one or more light sources 1040 through use of a wireless connection. In some embodiments, one or more control units 1060 may include numerous types of receivers. Examples of such receivers include, but are not limited to, receivers that receive one or more optical signals 1110, radio signals 110, wireless signals 1110, hardwired signals 1110, infrared signals 1110, ultrasonic signals 1110, and the like. Such receivers are known and have been described (e.g., U.S. Pat. No. RE39,785; U.S. Pat. Nos. 7,218,900; 7,254,160; 7,945,894; 7,906,605; herein incorporated by reference).

At embodiment 2504, module 2450 may include one or more receivers that are configured to receive one or more information packets. In some embodiments, one or more control units 1060 may include one or more receivers that are configured to receive one or more information packets. In some embodiments, one or more control units 1060 may be configured to receive one or more information packets that include numerous types of information. Examples of such information include, but are not limited to, intensity of light to be emitted by one or more light sources 1040, duration of light to be emitted by one or more light sources 1040, frequency of light to be emitted by one or more light sources 1040, wavelengths of light to be emitted by one or more light sources 1040, and the like.

At embodiment 2506, module 2450 may include one or more receivers that are configured to receive one or more signals. In some embodiments, one or more control units 1060 may include one or more receivers that are configured to receive one or more signals 1110. A control unit 1060 may include a receiver that is configured to receive numerous types of signals 1110. Examples of such signals 1110 include, but are not limited to, optical signals 1110, radio signals 1110, wireless signals 1110, hardwired signals 1110, infrared signals 1110, ultrasonic signals 1110, and the like. In some embodiments, one or more signals 1110 may not be encrypted. In some embodiments, one or more signals 1110 may be encrypted. In some embodiments, one or more signals 1110 may be sent through use of a secure mode of transmission. In some embodiments, one or more signals 1110 may be coded for receipt by a specific individual 1150. In some embodiments, such code may include anonymous code that is specific for an individual 1150. Accordingly, information included within one or more signals 1110 may be protected against being accessed by others who are not the intended recipient.

At embodiment 2508, module 2450 may include one or more receivers that are configured to receive one or more signals from one or more sensors. In some embodiments, one or more control units 1060 may include one or more receivers that are configured to receive one or more signals 1110 from one or more sensors 1070. In some embodiments, one or more control units 1060 may include one or more receivers that are configured to receive one or more signals 1110 from one or more sensors 1070. Control units 1060 may be configured to receive one or more signals 1110 from numerous types of sensors 1070. Examples of such sensors 1070 include, but are not limited to, temperature sensors 1070, blood pressure sensors 1070, pulse rate sensors 1070, hydrostatic pressure sensors 1070, clocks, and the like.

At embodiment 2510, module 2450 may include one or more transmitters. In some embodiments, one or more control units 1060 may be associated with one or more transmitters. In some embodiments, one or more control units 1060 may transmit one or more signals 1110. In some embodiments, one or more control units 1060 may transmit one or more information packets. Accordingly, in some embodiments, control units 1060 may be configured to operate within a feedback scheme that can receive information and transmit information to regulate the generation of nitric oxide. For example, in some embodiments, one or more control units 1060 may regulate one or more light sources 1040 to generate nitric oxide and then transmit information related to the operation of the one or more light sources 1040.

Figure 26:
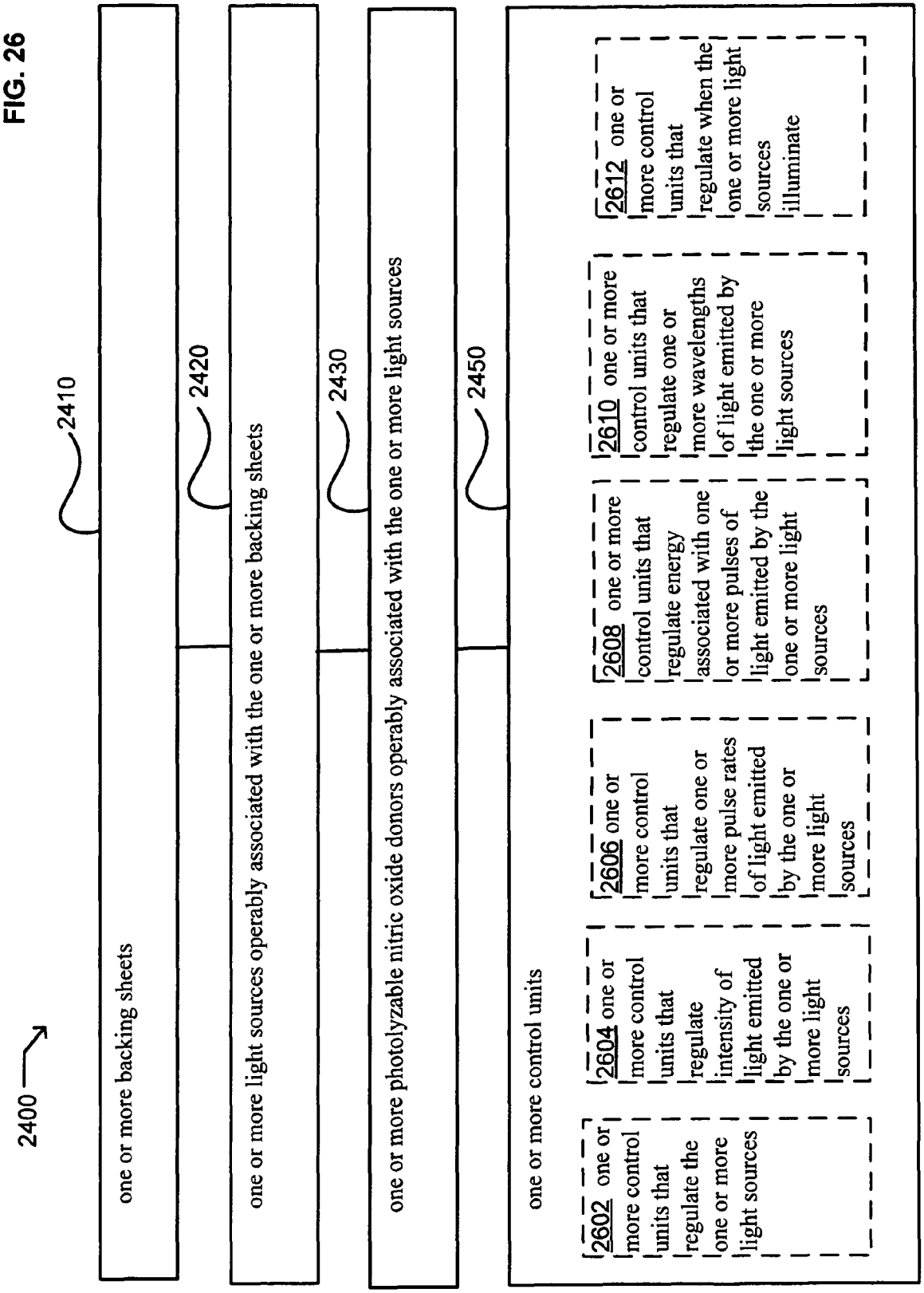
FIG. 26 illustrates alternate embodiments of embodiment 2400 of dressing 1010 within system 1000.

FIG. 26 illustrates alternative embodiments of embodiment 2400 of dressing 1010 within system 1000 of FIG. 24. FIG. 26 illustrates example embodiments of module 2450. Additional embodiments may include an embodiment 2602, an embodiment 2604, an embodiment 2606, an embodiment 2608, an embodiment 2608, and/or an embodiment 2612.

At embodiment 2602, module 2450 may include one or more control units that regulate the one or more light sources. In some embodiments, one or more control units 1060 may include one or more control units 1060 that regulate one or more light sources 1040. One or more control units 1060 may regulate numerous aspects of one or more light sources 1040. Examples of such aspects include, but are not limited to, intensity of emitted light, duration of emitted light, pulse frequency of emitted light, wavelengths of emitted light, and the like.

At embodiment 2604, module 2450 may include one or more control units that regulate intensity of light emitted by the one or more light sources. In some embodiments, one or more control units 1060 may include one or more control units 1060 that regulate the intensity of light emitted by one or more light sources 1040. For example, in some embodiments, one or more control units 1060 may regulate the current flowing through a light source 1040 to regulate the intensity of light emitted from the light source 1040. For example, in some embodiments, one or more control units 1060 may include a potentiometer.

At embodiment 2606, module 2450 may include one or more control units that regulate one or more pulse rates of light emitted by the one or more light sources. In some embodiments, one or more control units 1060 may include one or more control units 1060 that regulate one or more pulse rates of light emitted by the one or more light sources 1040. For example, in some embodiments, one or more control units 1060 may cause a light source 1040 to emit light in short pulses (e.g., nanosecond pulses, microsecond pulses). In some embodiments, one or more control units 1060 may cause a light source 1040 to emit light in medium pulses (e.g., second pulses, minute pulses). In some embodiments, one or more control units 1060 may cause a light source 1040 to emit light in medium pulses (e.g., hour pulses, day long pulses).

At embodiment 2608, module 2450 may include one or more control units that regulate energy associated width one or more pulses of light emitted by the one or more light sources. In some embodiments, one or more control units 1060 may include one or more control units 1060 that regulate energy associated with one or more pulses of light emitted by the one or more light sources 1040. For example, in some embodiments, one or more control units 1060 may regulate the current flowing through a light source 1040 to regulate the energy associated with one or more pulses of light emitted by the one or more light sources 1040. In some embodiments, one or more control units 1060 may regulate what wavelengths of light are emitted by a light source 1040 to regulate the energy associated with one or more pulses of light emitted by the one or more light sources 1040.

At embodiment 2610, module 2450 may include one or more control units that regulate one or more wavelengths of light emitted by the one or more light sources. In some embodiments, one or more control units 1060 may include one or more control units 1060 that regulate one or more wavelengths of light emitted by one or more light sources 1040. For example, in some embodiments, one or more control units 1060 may be coupled to a light source 1040 that includes numerous light emitting diodes that emit light of different wavelengths. Accordingly, in some embodiments, one or more control units 1060 may regulate wavelengths of light emitted from the light source 1040 by selectively illuminating light emitting diodes that emit the desired wavelengths of light.

At embodiment 2612, module 2450 may include one or more control units that regulate when the one or more light sources illuminate. In some embodiments, one or more control units 1060 may include one or more control units 1060 that regulate when the one or more light sources 1040 illuminate. In some embodiments, one or more control units may regulate one or more start times for one or more light sources. For example, in some embodiments, one or more control units may turn on one or more light sources at a certain time. In some embodiments, one or more control units may turn off one or more light sources at a certain time.

Figure 27:
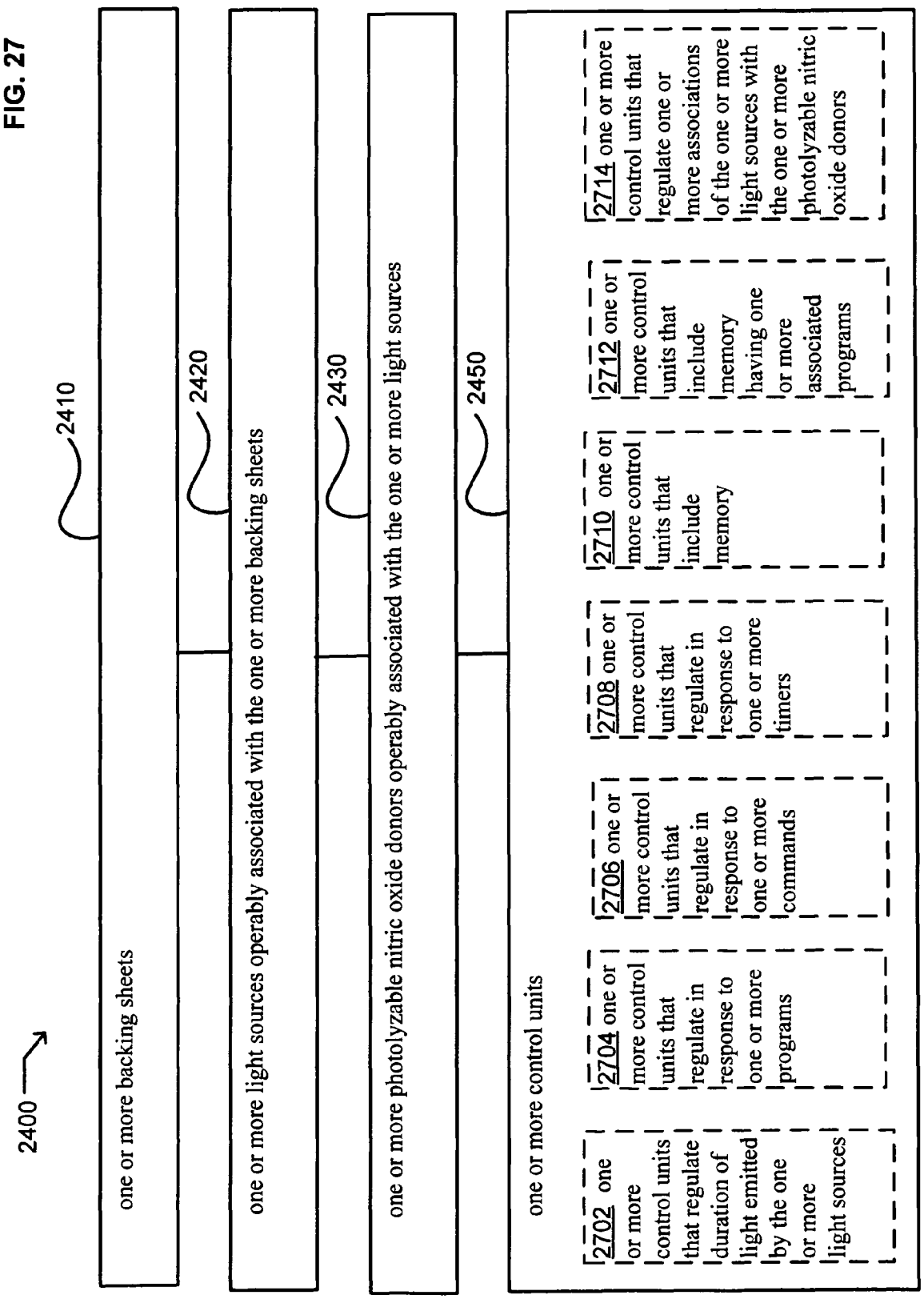
FIG. 27 illustrates alternate embodiments of embodiment 2400 of dressing 1010 within system 1000.

FIG. 27 illustrates alternative embodiments of embodiment 2400 of dressing 1010 within system 1000 of FIG. 24. FIG. 27 illustrates example embodiments of module 2450. Additional embodiments may include an embodiment 2702, an embodiment 2704, an embodiment 2706, an embodiment 2708, an embodiment 2710, an embodiment 2712, and/or an embodiment 2714.

At embodiment 2709, module 2450 may include one or more control units that regulate duration of light emitted by the one or more light sources. In some embodiments, one or more control units 1060 may include one or more control units 1060 that regulate the duration of light emitted by one or more light sources 1040. For example, one or more control units 1060 may cause one or more light sources 1040 to emit light for a period of nanoseconds, microseconds, milliseconds, seconds, minutes, hours, days, and the like.

At embodiment 2704, module 2450 may include one or more control units that regulate in response to one or more programs. In some embodiments, one or more control units 1060 may include one or more control units 1060 that are responsive to one or more programs. For example, in some embodiments, one or more control units 1060 may be responsive to a programmed set of instructions. In some embodiments, the one or more control units 1060 may be directly programmed. For example, in some embodiments, one or more control units 1060 may include a programmable memory that can include instructions. In some embodiments, the one or more control units 1060 may receive instructions from a program that is associated with one or more management units 1130.

At embodiment 2706, module 2450 may include one or more control units that regulate in response to one or more commands. In some embodiments, one or more control units 1060 mats include one or more control units 1060 that are responsive to one or more commands. For example, in some embodiments, one or more control units 1060 may receive one or more signals 1110 that act as commands for the one or more control units 1060. In some embodiments, one or more control units 1060 may receive one or more information packets that act as commands for the one or more control units 1060.

At embodiment 2708, module 2450 may include one or more control units that regulate in response to one or more timers. In some embodiments, one or more control units 1060 may include one or more control units 1060 that are responsive to one or more timers. In some embodiments, one or more control units 1060 may be configured to include one or more timers to which the one or more control units 1060 are responsive. In some embodiments, one or more control units 1060 may be responsive to one or more timers that are remote from the one or more control units 1060. For example, in some embodiments, one or more control units 1060 malt be responsive to one or more timers that are associated with one or more management units 1130 that send instructions to the one or more control units 1060.

At embodiment 2710, module 2450 may include one or more control units that include memory. In some embodiments, one or more control units 1060 may include one or more control units 1060 that include memory. Numerous types of memory may be associated with one or more control units 1060. Examples of such memory include, but are not limited to, magnetic memory, semiconductor memory, and the like.

At embodiment 2712, module 2450 may include one or more control units that include memory having one or more associated programs. In some embodiments, one or more control units 1060 may include one or more control units 1060 that include memory having one or more associated programs. In some embodiments, one or more control units 1060 may include memory that includes a program that provides instructions for operating one or more light sources 1040. For example, in some embodiments, one or more control units 1060 may receive information with regard to a current concentration of nitric oxide within an area and then process the information with one or more programs to determine one or more operating parameters for one or more light sources 1040. In some embodiments, one or more control units 1060 may receive information with regard to bacterial contamination within an area and then process the information with one or more programs to determine one or more operating parameters for one or more light sources 1040. Accordingly, one or more control units 1060 may include one or more programs that may be configured to respond to numerous types of information.

At embodiment 2714, module 2450 may include one or more control units that regulate one or more associations of the one or more light sources with the one or more photolyzable nitric oxide donors. In some embodiments, one or more control units 1060 may include one or more control units 1060 that regulate one or more associations of one or more light sources 1040 with one or more photolyzable nitric oxide donors 1020. For example, in some embodiments, one or more control units 1060 may regulate one or more connections that couple one or more light sources 1040 with one or more optical fibers that are associated with one or more photolyzable nitric oxide donors 1020. Accordingly, in some embodiments, one or more control units 1060 may regulate light emission through regulation of the coupling of one or more light sources 104 with one or more optically transmitting materials that are associated with one or more photolyzable nitric oxide donors 1090.

Figure 28:
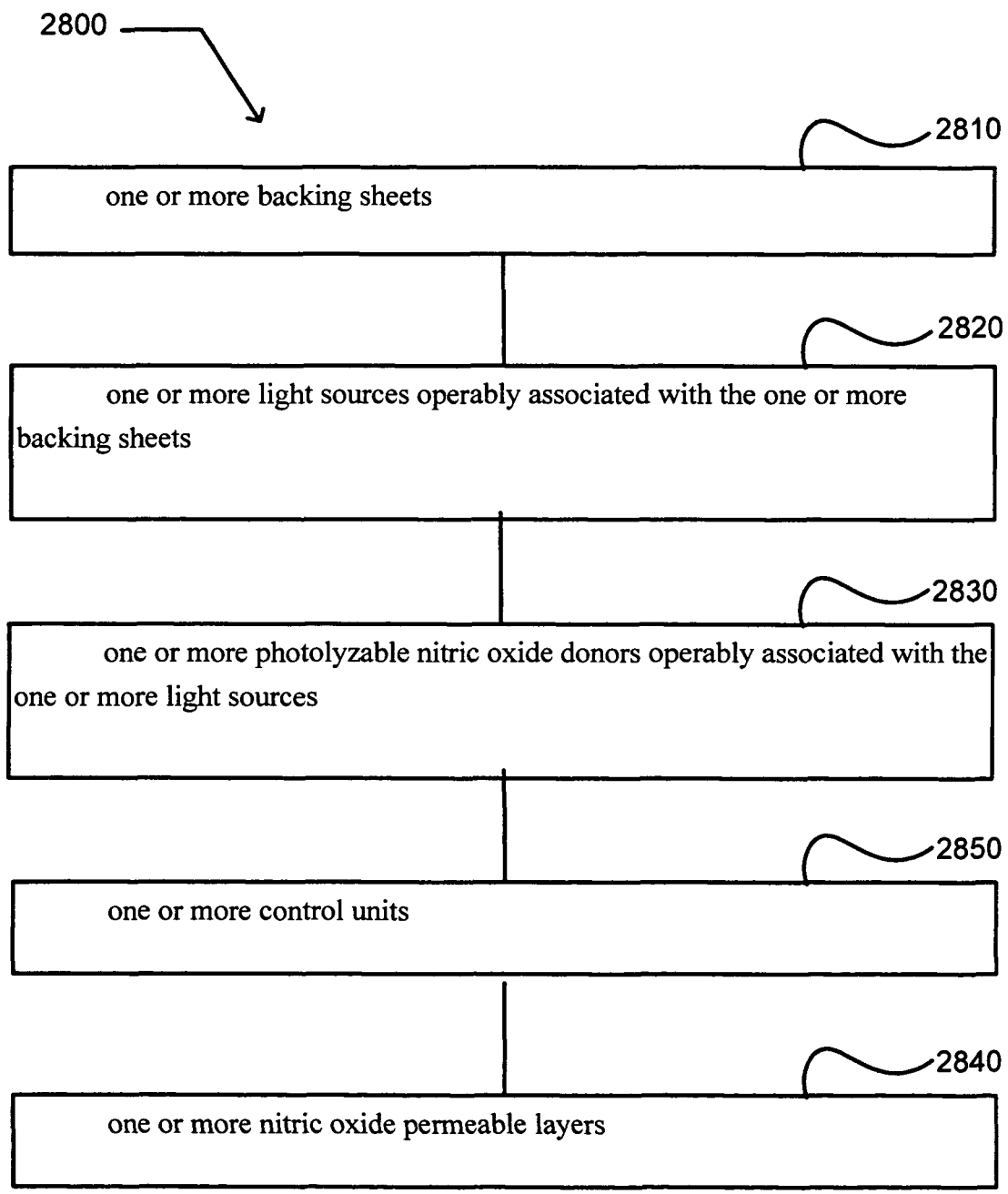
FIG. 28 illustrates embodiment 2800 of dressing 1010 within system 1000.

FIG. 28 illustrates embodiment 2800 of dressing 1010 within system 1000. In FIG. 28, discussion and explanation may be provided with respect to the above-described example of FIG. 10, and/or with respect to other examples and contexts. However, it should be understood that the modules may execute operations in a number of other environments and contexts, and/or modified versions of FIG. 10. Also, although the various modules are presented in the sequence(s) illustrated, it should be understood that the various modules may be configured in numerous orientations.

The embodiment 2800 may include module 2810 that includes one or more backing sheets. In some embodiments, a dressing 1010 may include one or more backing sheets 1030. One or more backing sheets 1030 may be fabricated from one or more materials. In some embodiments, one or more backing sheets 1030 may include portions that are fabricated from different types of materials. For example, in some embodiments, a backing sheet 1030 may include one or more portions that include one or more adhesive materials and one or more portions that include one or more nonadhesive materials. In some embodiments, a backing sheet 1030 may include one or more portions that include one or more gas permeable materials and one or more portions that include one or more gas impermeable materials. Accordingly, one or more backing sheets 1030 may include numerous combinations of materials that exhibit numerous properties. Examples of such material include, but are not limited to, elastic materials, inelastic materials, adhesive materials, nonadhesive materials, conductive materials, nonconductive materials, perforated materials, nonperforated materials, fluid permeable materials, fluid impermeable materials, gas permeable materials, gas impermeable materials, light permeable materials, selectively light permeable materials, light impermeable materials, and the like.

The embodiment 2800 may include module 2820 that includes one or more light sources operably associated with the one or more backing sheets. In some embodiments, a dressing 1010 may include one or more light sources 1040 operably associated with one or more backing sheets 1030. In some embodiments, a dressing 1010 may include one or more light sources 1040 that are operably associated with one or more photolyzable nitric oxide donors 1020. In some embodiments, one or more light sources 1040 may be directly coupled to one or more backing sheets 1030. For example in some embodiments, one or more light sources 1040 may be integrated within one or more backing sheets 1030. In some embodiments, one or more light sources 1040 may be indirectly associated with one or more backing sheets 1030. For example, in some embodiments, one or more light sources 1040 may be associated with one or more backing sheets 1030 through attachment to one or more electrical connections associated with the one or more backing sheets 1030. In some embodiments, one or more light sources 1040 may be associated with one or more backing sheets 1030 through inclusion within one or more compositions that include one or more photolyzable nitric oxide donors 1020 that are associated with one or more backing sheets 1030.

The embodiment 2800 may include module 2830 that includes one or more photolyzable nitric oxide donors operably associated width the one or more light sources. In some embodiments, a dressing 1010 may include one or more photolyzable nitric oxide donors 1020 operably associated with the one or more light sources 1040. In some embodiments, the one or more light sources 1040 may be directly coupled to one or more photolyzable nitric oxide donors 1020. For example, in some embodiments, the one or more photolyzable nitric oxide donors 1020 may be chemically coupled to a surface of the light source 1040 (e.g., chemically coupled to a polymer coating on the tight source 1040). In some embodiments, one or more photolyzable nitric oxide donors 1020 may be indirectly coupled to one or more light sources 1040. For example, in some embodiments, one or more photolyzable nitric oxide donors 1020 may be coupled to a material that is used to coat the one or more light sources 1040. Numerous photolyzable nitric oxide donors 1020 may be operably associated with one or more light sources 1040. Examples of such photolyzable nitric oxide donors 1020 include, but are not limited to, diazeniumdiolates (e.g., U.S. Pat. Nos. 7,105,502; 7,122,529; 6,673.338: herein incorporated by reference), trans-[RuCl([15]aneN4)NO]+2 (Ferezin et al., Nitric Oxide, 13:170-175 (2005), Bonaventura et al. Nitiic Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 17:1549-1557 (1996), Matthews et al., Br. J. Pharmacol., 13:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550: 819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

The embodiment 2800 may include module 2850 that includes one or more control units. In some embodiments, a dressing 1010 may include one or more control units 1060. A dressing 1010 may include numerous types of control units 1060. In some embodiments, one or more control units 1060 may be operably coupled with one or more light sources 1040, one or more sensors 1070, one or more electromagnetic receivers 1080, one or more electromagnetic transmitters 1100, or substantially any combination thereof. In some embodiments, one or more control units 1060 may be operably coupled to other components through use of one or more wireless connections, one or more hardwired connections, or substantially any combination thereof. A control unit 1060 may be configured in numerous ways. For example, in some embodiments, a control unit 1060 may be configured as an on/off switch. Accordingly, in some embodiments, a control unit 1060 may be configured to turn a light source 1040 on and/or off. In some embodiments, a control unit 1060 may be configured to control the emission of light from one or more light sources 1040. For example, in some embodiments, one or more control units 1060 may regulate the intensity of light emitted from one or more light sources 1040, the duration of light emitted from one or more light sources 1040, the frequency of light emitted from one or more light sources 1040, wavelengths of light emitted from one or more light sources 1040, times when light is emitted from one or more light sources 1040, or substantially any combination thereof. In some embodiments, one or more control units 1060 may be configured to receive one or more signals 110 from one or more sensors 1070. Accordingly, in some embodiments, one or more control units 1060 may be configured to control one or more light sources 1040 in response to one or more signals 1110 received from one or more sensors 1070. For example, in some embodiments, one or more sensors 1070 may sense a low concentration of nitric oxide in one or more tissues and send one or more signals 1110 to one or more control units 1060. The one or more control units 1060 may then turn one or more light sources 1040 on to facilitate release of nitric oxide from one or more photolyzable nitric oxide donors 100. Accordingly, in some embodiments, one or more sensors 1070 may sense a high concentration of nitric oxide in one or more tissues and send one or more signals 1110 to one or more control units 1060. The one or more control units 1060 may then turn one or more light sources 1040 off to end release of nitric oxide from one or more photolyzable nitric oxide donors 1090. In some embodiments, one or more control units 1060 may be programmed to control one or more light sources 1040. For example, in some embodiments, one or more control units 1060 may be programmed to turn one or more light sources 1040 on for a predetermined amount of time and then turn off. Accordingly, in some embodiments, one or more control units 1060 may be preprogrammed. In some embodiments, one or more control units 1060 may be dynamically programmed. For example, in some embodiments, one or more management units 1130 may receive one or more signals 1110 from one or more sensors 1070 and program one or more control units 1060 in response to the one or more signals 1110 received from the one or more sensors 1070. In some embodiments, one or more control units 1060 may include one or more receivers that are able to receive one or more signals 1110, one or more information packets, or substantially any combination thereof. Control units 1060 may be configured in numerous ways. For example, in some embodiments, one or more control units 1060 may be operably coupled to one or more light sources 1040 that include numerous light emitting diodes that emit light of different wavelengths. Accordingly, in some embodiments, one or more control units 1060 may control the wavelengths of light emitted by the one or more light sources 1040 by controlling the operation of light emitting diodes that emit light of the selected wavelength. Accordingly, control units 1060 may be configured in numerous ways and utilize numerous types of mechanisms.

The embodiment 2800 may include module 2840 that includes one or more nitric oxide permeable layers. In some embodiments, a dressing 1010 may include one or more nitric oxide permeable layers 1050. A dressing 1010 may include nitric oxide permeable layers 1050 that are fabricated from numerous types of material. Examples of such materials include, but are not limited to, ceramics, polymeric materials, metals, plastics, and the like. In some embodiments, nitric-oxide permeable layers 1050 may include numerous combinations of materials. For example, in some embodiments, a nitric oxide permeable layer 1050 may include a nitric oxide impermeable material that is coupled to a nitric oxide permeable material. In some embodiments, a nitric oxide permeable layer 1050 may include one or more nitric oxide permeable membranes (e.g., U.S. Patent Application No.: 20020026937). In some embodiments, a nitric oxide permeable layer 1050 may include a selectively permeable membrane. For example, in some embodiments, a nitric oxide permeable layer 1050 may include a selectively permeable membrane that is a hydrophilic polyester co-polymer membrane system that includes a copolymer with 70% polyester and 30% polyether (e.g., Sympatex™ 10 μm membrane, see Hardwick et al., Clinical Science, 100:395-400 (2001)). In some embodiments, a nitric oxide permeable layer 1050 may include a scintered glass portion that is permeable to nitric oxide. Accordingly, nitric oxide permeable layers 1050 may include numerous types of porous ceramics that are permeable to nitric oxide. In some embodiments, a nitric oxide permeable layer 1050 may include a porous metal portion that is permeable to nitric oxide. In some embodiments, a nitric oxide permeable layer 1050 may include a nitric oxide permeable coating (e.g., U.S. Patent Application Nos.: 20050220838 and 20030093143).

Nitric oxide permeable layers 1050 may be configured for application to an individual 1150. Nitric oxide permeable layers 1050 may be configured to facilitate application of nitric oxide to a surface. In some embodiments, one or more nitric oxide permeable layers 1050 may be configured to facilitate application of nitric oxide to one or more surfaces of an individual 1150. For example, in some embodiments, one or more nitric oxide permeable layers 1050 may be configured as a sheet that may be positioned on a skin surface of an individual 1150 to deliver nitric oxide to the skin surface. In some embodiments, nitric oxide permeable layers 1050 may be configured as a bandage, a patch, and the like.

Figure 29:
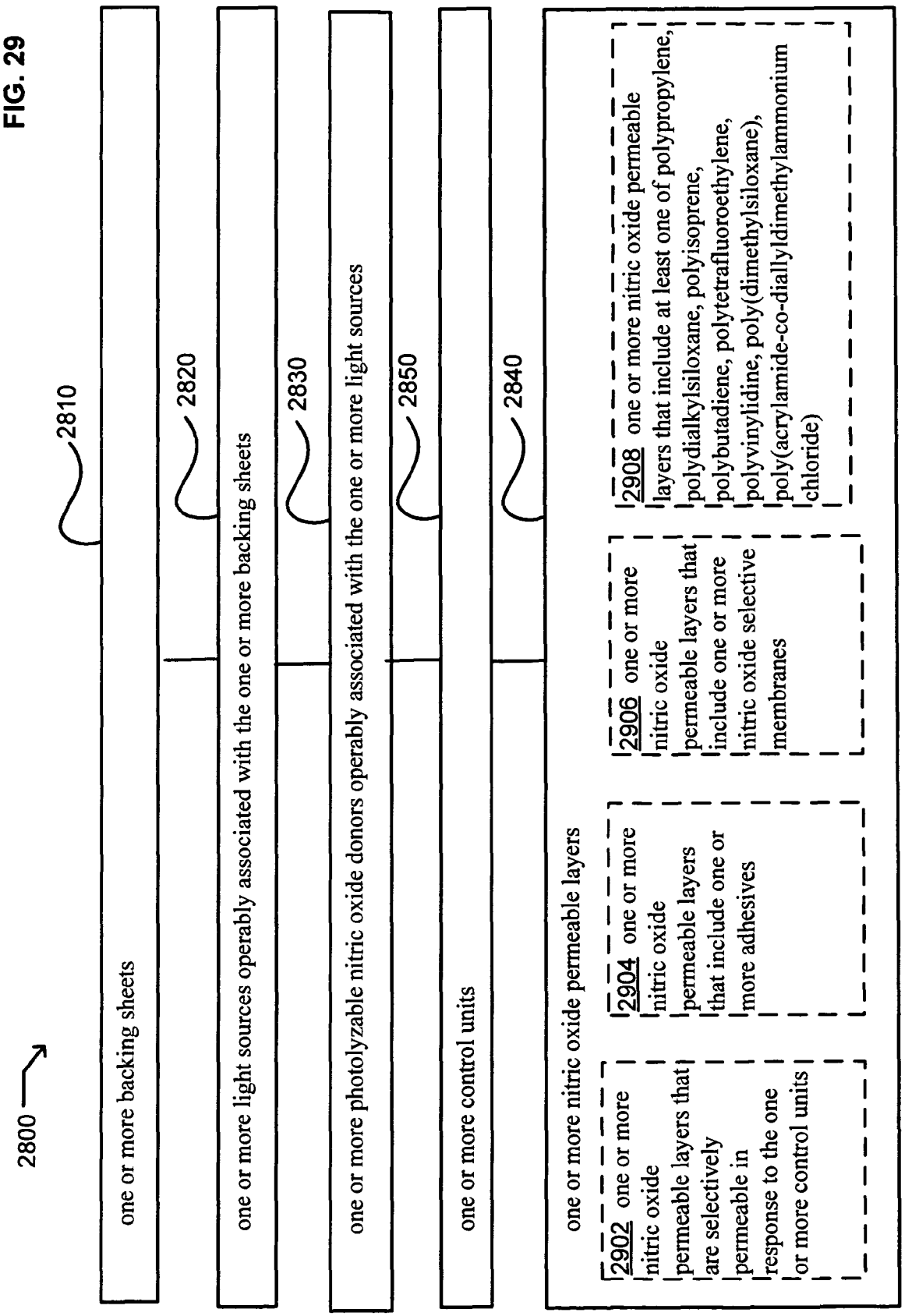
FIG. 29 illustrates alternate embodiments of embodiment 2800 of dressing 1010 within system 1000.

FIG. 29 illustrates alternative embodiments of embodiment 2800 of dressing 1010 within system 1000 of FIG. 28. FIG. 29 illustrates example embodiments of module 2840. Additional embodiments may include an embodiment 2902, an embodiment 2904, an embodiment 2906, and/or an embodiment 2908.

At embodiment 2902, module 2840 may include one or more nitric oxide permeable layers that are selectively permeable in response to the one or more control units. In some embodiments, one or more nitric oxide permeable layers 1050 may include one or more nitric oxide permeable layers 1050 that are selectively permeable in response to one or more control units 1060. In some embodiments, one or more nitric oxide permeable layers 1050 may be selectively permeable to light in response to one or more control units 1060. For example, in some embodiments, one or more nitric oxide permeable layers 1050 may be fabricated from electrochromic polymers. Accordingly, in some embodiments, the permeability of the one or more layers may be altered by one or more control units 1060 (e.g., U.S. Pat. No. 7,256,923). In some embodiments, one or more control units 1060 may control electrical charge distribution on one or more permeable layers. Accordingly, in some embodiments, one or more control units 1060 may alter passage of charged and uncharged molecules through one or more layers.

At embodiment 2904, module 2840 may include one or more nitric oxide permeable layers that include one or more adhesives. In some embodiments, one or more nitric oxide permeable layers 1050 may include one or more nitric oxide permeable layers 1050 that include one or more adhesives. In some embodiments, a dressing 1010 may include one or more nitric oxide permeable layers 1050 that include one or more adhesives that facilitate adhesion of at least a portion of a nitric oxide permeable layer 1050 to a surface. For example, in some embodiments, a dressing 1010 may include a nitric oxide permeable layer 1050 that includes at least one portion which includes one or more adhesives and that is configured to deliver nitric oxide to a surface adjacent to the nitric oxide permeable layer 1050. For example, in some embodiments, a dressing 1010 may be configured as a bandage that includes a nitric oxide permeable membrane on the portion of the bandage that is to be placed on a skin surface of an individual 1150. In some embodiments, adhesive may enclose a space on the surface of the nitric oxide permeable layer 1050 such that a sealed space is formed on the skin when the bandage is adhered to the skin surface. Accordingly, such an embodiment of a dressing 1010 may be used to deliver nitric oxide to a select surface by positioning the dressing 1010 on and/or offer the select surface and attaching the dressing 1010 at points adjacent to the select surface with the one or more adhesives. In some embodiments, such an embodiment of dressing 1010 may be configured as a bandage, a patch, and the like.

At embodiment 2906, module 2840 may include one or more nitric oxide permeable layers that include one or more nitric oxide selective membranes. In some embodiments, one or more nitric oxide permeable layers 1050 may include one or more nitric oxide permeable layers 1050 that include one or more nitric oxide selective membranes. In some embodiments, a nitric oxide permeable layer 1050 may include a selectively permeable membrane. For example, in some embodiments, a nitric oxide permeable layer 1050 may include a selectively permeable membrane that is a hydrophilic polyester co-polymer membrane system that includes a copolymer with 70% polyester and 30% polyether (e.g., Sympatex™ 10 µm membrane, see Hardwick et al., Clinical Science, 100:395-400 (2001)). Methods to fabricate nitric oxide permeable membranes are known (e.g., U.S. Patent Application No.: 20020026937).

At embodiment 2908, module 2840 may include one or more nitric oxide permeable layers that include at least one of polypropylene, polydialkylsiloxane, polyisoprene, polybutadiene, polytetrafluoroethylene, polyvinylidine, poly(dimethylsiloxane), poly(acryl amide-co-diallyldimethylammonium chloride). In some embodiments, one or more nitric oxide permeable layers 1050 may include one or more nitric oxide permeable layers 1050 that include at least one of polypropylene, polydialkylsiloxane, polyisoprene, polybutadiene, polytetrafluoroethylene, polyvinylidine, poly(dimethylsiloxane), poly(acrylamide-co-diallyldimethylammonium chloride).

Figure 30:
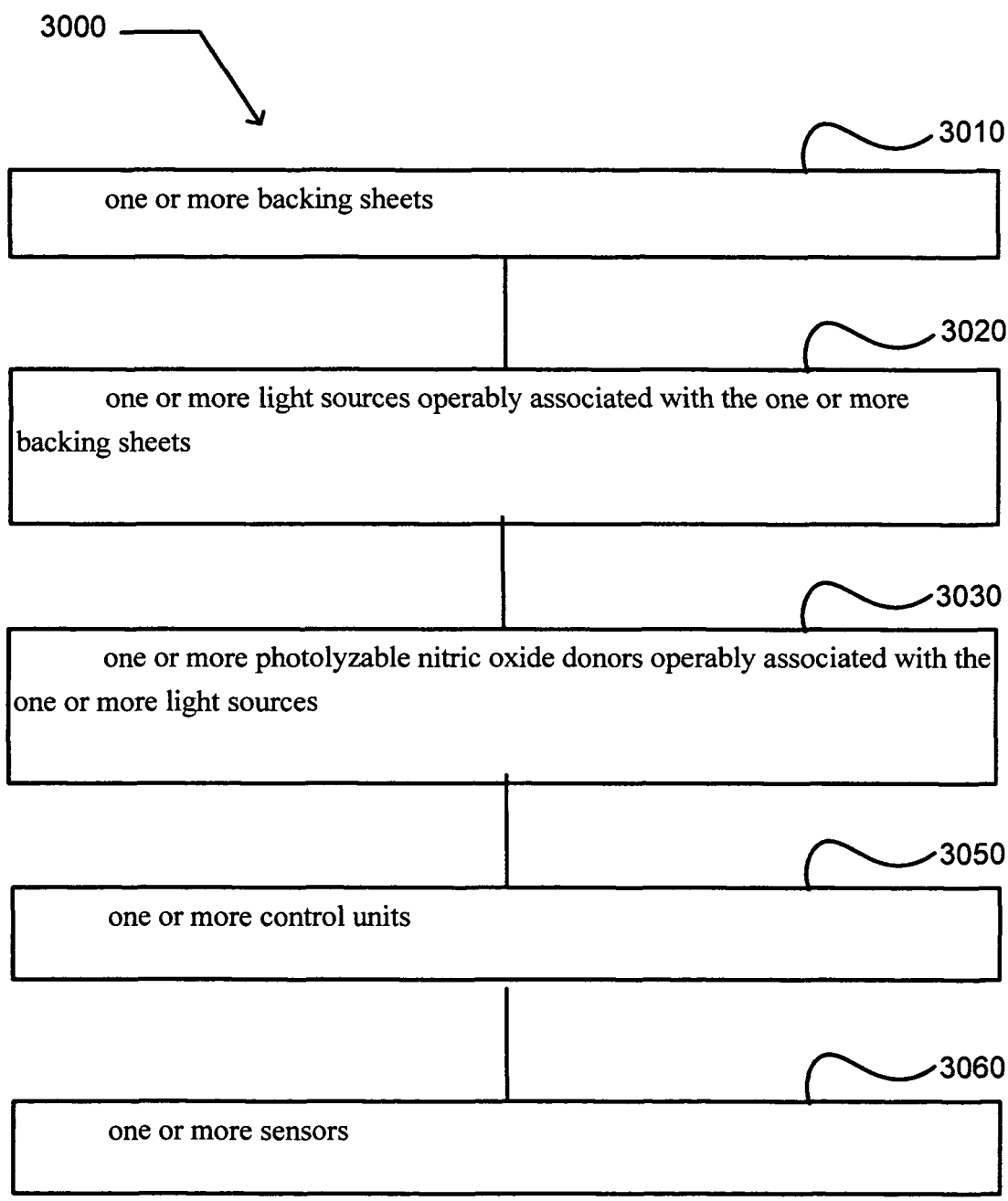
FIG. 30 illustrates embodiment 3000 of dressing 1010 within system 1000.

FIG. 30 illustrates embodiment 3000 of dressing 1010 within system 1000. In FIG. 30, discussion and explanation may be provided with respect to the above-described example of FIG. 10, and/or with respect to other examples and contexts. However, it should be understood that the modules may execute operations in a number of other environments and contexts, and/or modified versions of FIG. 10. Also, although the various modules are presented in the sequence(s) illustrated, it should be understood that the various modules may be configured in numerous orientations.

The embodiment 3000 may include module 3010 that includes one or more backing sheets. In some embodiments, a dressing 1010 may include one or more backing sheets 1030. One or more backing sheets 1030 may be fabricated from one or more materials. In some embodiments, one or more backing sheets 1030 may include portions that are fabricated from different types of materials. For example, in some embodiments, a backing sheet 1030 may include one or more portions that include one or more adhesive materials and one or more portions that include one or more nonadhesive materials. In some embodiments, a backing sheet 1030 may include one or more portions that include one or more gas permeable materials and one or more portions that include one or more gas impermeable materials. Accordingly, one or more backing sheets 1030 may include numerous combinations of materials that exhibit numerous properties. Examples of such material include, but are not limited to, elastic materials, inelastic materials, adhesive materials, nonadhesive materials, conductive materials, nonconductive materials, perforated materials, nonperforated materials, fluid permeable materials, fluid impermeable materials, gas permeable materials, gas impermeable materials, light permeable materials, selectively light permeable materials, light impermeable materials, and the like.

The embodiment 3000 may include module 3020, that includes one or more light sources operably associated with the one or more backing sheets. In some embodiments, a dressing 1010 may include one or more light sources 1040 operably associated with one or more backing sheets 1030. In some embodiments, a dressing 1010 may include one or more light sources 1040 that are operably associated with one or more photolyzable nitric oxide donors 1020. In some embodiments, one or more light sources 1040 may be directly coupled to one or more backing sheets 1030. For example, in some embodiments, one or more light sources 1040 may be integrated within one or more backing sheets 1030. In some embodiments, one or more light sources 1040 may be indirectly associated with one or more backing sheets 1030. For example, in some embodiments, one or more light sources 1040 may be associated with one or more backing sheets 1030 through attachment to one or more electrical connections associated smith the one or more backing sheets 1030. In some embodiments, one or more light sources 1040 may be associated with one or more backing sheets 1030 through inclusion within one or more compositions that include one or more photolyzable nitric oxide donors 1020 that are associated with one or more backing sheets 1030.

The embodiment 3000 may include module 3030 that includes one or more photolyzable nitric oxide donors operably associated with the one or more light sources. In some embodiments, a dressing 1010 may include one or more photolyzable nitric oxide donors 1020 operably associated with the one or more light sources 1040. In some embodiments, the one or more light sources 1040 may be directly coupled to one or more photolyzable nitric oxide donors 1020. For example, in some embodiments, the one or more photolyzable nitric oxide donors 1020 may be chemically coupled to a surface of the light source 1040 (e.g., chemically coupled to a polymer coating on the light source 1040). In some embodiments, one or more photolyzable nitric oxide donors 1020 may be indirectly coupled to one or more light sources 1040. For example, in some embodiments, one or more photolyzable nitric oxide donors 1020 may be coupled to a material that is used to coat the one or more light sources 1040. Numerous photolyzable nitric oxide donors 1020 may be operably associated with one or more light sources 1040. Examples of such photolyzable nitric oxide donors 1020 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson. J. Physiol., 550: 819-828 (2003)), S-nitrosothiols (e.g., Andrews et al., British Journal of Pharmacology, 138:932-940 (2003), Singh et al., FEBS Lett. 360:47-51 (1995)), 2-Methyl-2-nitrosopropane (e.g., Pou et al., Mol. Pharm., 46:709-715 (1994), Wang et al. Chem. Rev., 102:1091-1134 (2002)), imidazolyl derivatives (e.g., U.S. Pat. No. 5,374,710; herein incorporated by reference).

The embodiment 3000 may include module 3050 that includes one or more control units. In some embodiments, a dressing 1010 mail include one or more control units 1060. A dressing 1010 may include numerous types of control units 1060. In some embodiments, one or more control units 1060 may be operably coupled with one or more light sources 1040, one or more sensors 1070, one or more electromagnetic receivers 1080, one or more electromagnetic transmitters 1100, or substantially any combination thereof. In some embodiments, one or more control units 1060 may be operably coupled to other components through use of one or more wireless connections, one or more hardwired connections, or substantially any combination thereof. A control unit 1060 may be configured in numerous ways. For example, in some embodiments, a control unit 1060 may be configured as an on/off switch. Accordingly, in some embodiments, a control unit 1060 may be configured to turn a light source 1040 on and/or off. In some embodiments, a control unit 1060 may be configured to control the emission of light from one or more light sources 1040. For example, in some embodiments, one or more control units 1060 may regulate the intensity of light emitted from one or more light sources 1040, the duration of light emitted from one or more light sources 1040, the frequency of light emitted from one or more light sources 1040, wavelengths of light emitted from one or more light sources 1040, times when light is emitted from one or more light sources 1040, or substantially any combination thereof. In some embodiments, one or more control units 1060 may be configured to receive one or more signals 1110 from one or more sensors 1070. Accordingly, in some embodiments, one or more control units 1060 may be configured to control one or more light sources 1040 in response to one or more signals 1110 received from one or more sensors 1070. For example, in some embodiments, one or more sensors 1070 may sense a low concentration of nitric oxide in one or more tissues and send one or more signals 1110 to one or more control units 1060. The one or more control units 1060 may then turn one or more light sources 1040 on to facilitate release of nitric oxide from one or more photolyzable nitric oxide donors 1020. Accordingly. In some embodiments, one or more sensors 1070 may sense a high concentration of nitric oxide in one or more tissues and send one or more signals 1110 to one or more control units 1060. The one or more control units 1060 may then turn one or more light sources 1040 off to end release of nitric oxide from one or more photolyzable nitric oxide donors 1020. In some embodiments, one or more control units 1060 may be programmed to control one or more light sources 1040. For example, in some embodiments, one or more control units 1060 may be programmed to turn one or more light sources 1040 on for a predetermined amount of time and then turn off. Accordingly, in some embodiments, one or more control units 1060 may be preprogrammed. In some embodiments, one or more control units 1060 may be dynamically programmed. For example, in some embodiments, one or more management units 1130 may receive one or more signals 1110 from one or more sensors 1070 and program one or more control units 1060 in response to the one or more signals 1110 received from the one or more sensors 1070. In some embodiments, one or more control units 1060 may include one or more receivers that are able to receive one or more signals 1110, one or more information packets, or substantially any combination thereof. Control units 1060 may be configured in numerous ways. For example, in some embodiments, one or more control units 1060 may be operably coupled to one or more light sources 1040 that include numerous light emitting diodes that emit light of different wavelengths. Accordingly, in some embodiments, one or more control units 1060 may control the wavelengths of light emitted by the one or more light sources 1040 by controlling the operation of light emitting diodes that emit light of the selected wavelength. Accordingly, control units 1060 may be configured in numerous ways and utilize numerous types of mechanisms.

The embodiment 3000 may include module 3060 that includes one or more sensors. In some embodiments, a dressing 1010 may include one or more sensors 1070. In some embodiments, one or more sensors 1070 may be integrated within one or more dressings 1010. In some embodiments, one or more sensors 1070 may be associated with one or more surfaces of one or more dressings 1010. In some embodiments, one or more sensors 1070 may be associated with one or more electrical connections associated with one or more backing sheets 1030. Numerous types of sensors 1070 may be associated with one or more dressings 1010. Examples of such sensors 1070 include, but are not limited to, temperature sensors 1070, pressure sensors 1070 (e.g. blood pressure, hydrostatic pressure), pulse rate sensors 1070, sensors 1070, clocks, bacterial contamination sensors 1070, strain sensors 1070, light sensors 1070, nitric oxide sensors 1070, and the like.

Figure 31:
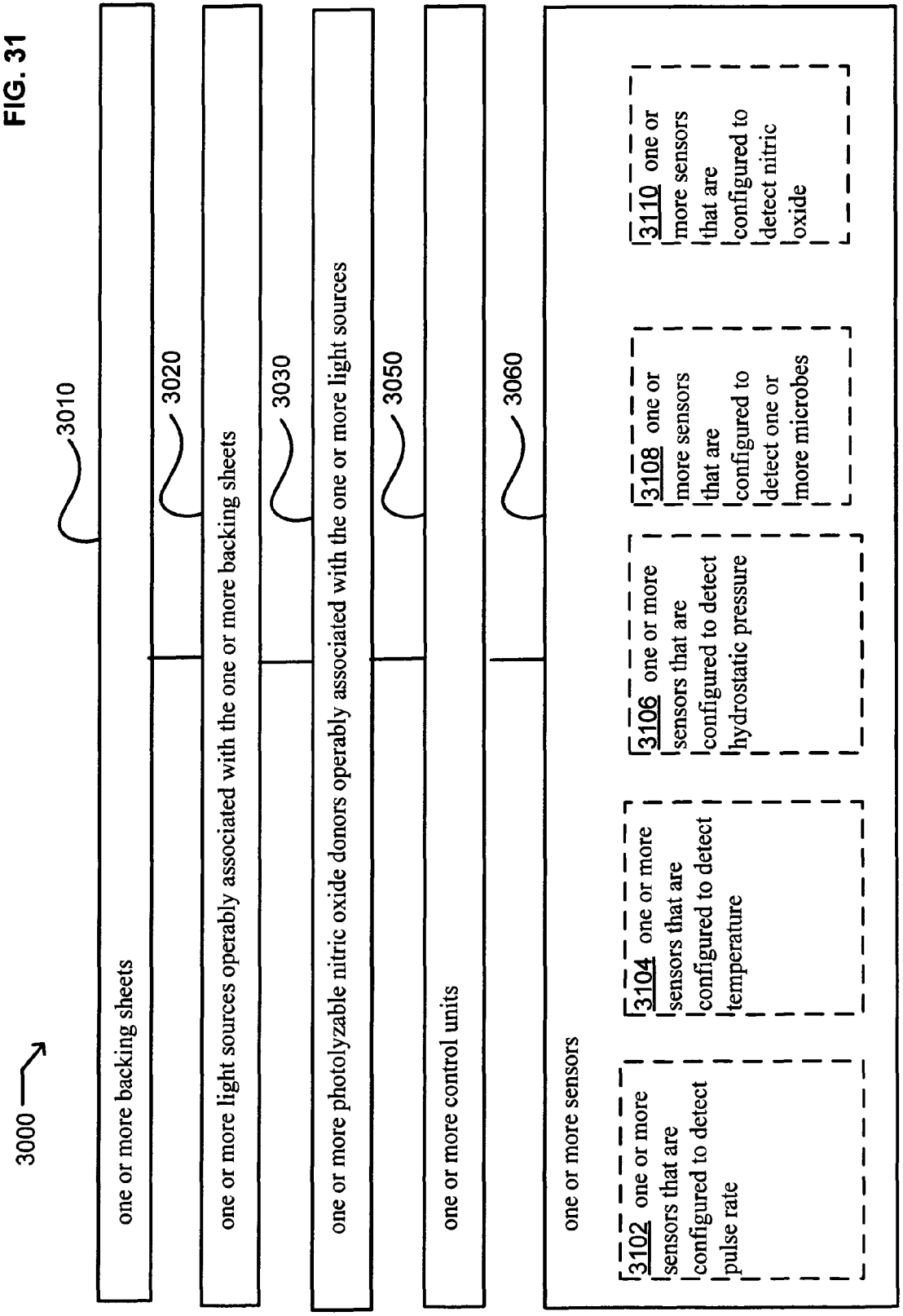
FIG. 31 illustrates alternate embodiments of embodiment 3000 of dressing 1010 within system 1000.

FIG. 31 illustrates alternative embodiments of embodiment 3000 of dressing 1010 within system 1000 of FIG. 30. FIG. 31 illustrates example embodiments of module 3060. Additional embodiments may include an embodiment 3102, an embodiment 3104, an embodiment 3106, an embodiment 3108, and/or an embodiment 3110.

At embodiment 310, module 3060 may include one or more sensors that are configured to detect pulse rate. In some embodiments, one or more sensors 1070 may include one or more sensors 1070 that are configured to detect pulse rate. In some embodiments, a pulse rate detector may utilize infrared radiation to measure pulse rate. For example, in some embodiments, a pulse surface (e.g., a skin surface) may be irradiated with infrared light which may be variably reflected to an infrared sensor to provide an electrical pulse-rate signal that correlates to a pulse rate (e.g., U.S. Pat. No. 6,080,110). In some embodiments, a sensor 1070 may be configured to include a cuff to measure pulse rate. Accordingly, one or more sensors 1070 may be configured in numerous ways to facilitate detection of pulse rate.

At embodiment 3104, module 3060 may include one or more sensors that are configured to detect temperature. In some embodiments, one or more sensors 1070 may include one or more sensors 1070 that are configured to detect temperature. In some embodiments, one or more sensors 1070 may be configured to include a thermocouple to facilitate detection of temperature. In some embodiments, one or more sensors 1070 may include one or more thermally conductive materials that produce a signal 1110 that is responsive to temperature (e.g., U.S. Pat. No. 7,303,333). Accordingly, one or more sensors 1070 may be configured in numerous ways to facilitate detection of temperature.

At embodiment 3106, module 3060 may include one or more sensors that are configured to detect hydrostatic pressure. In some embodiments, one or more sensors 1070 may include one or more sensors 1070 that are configured to detect hydrostatic pressure. In some embodiments, one or more sensors 1070 may be configured to utilize one or more stress/strain monitors to detect hydrostatic pressure. In some embodiments, one or more pressure sensors 1070 may be configured to detect hydrostatic pressure. Accordingly, one or more sensors 1070 may be configured in numerous ways to facilitate detection of hydrostatic pressure.

At embodiment 3108, module 3060 may include one or more sensors that are configured to detect one or more microbes. In some embodiments, one or more sensors 1070 may include one or more sensors 1070 that are configured to detect one or more microbes. In some embodiments, one or more sensors 1070 may utilize a dye that undergoes a detectable color change in the presence of one or more microbes (e.g., U.S. Patent Application No.: 20060134728). In some embodiments, one or more sensors 1070 may utilize an array that binds to microbes and provides for their detection. Accordingly, one or more sensors 1070 may be configured in numerous ways to facilitate detection of one or more microbes.

At embodiment 3110, module 3060 may include one or more sensors that are configured to detect nitric oxide. In some embodiments, one or more sensors 1070 may include one or more sensors 1070 that are configured to detect nitric oxide. In some embodiments, one or more sensors 1070 may be integrated within one or more dressings 1010. In some embodiments, one or more sensors 1070 may be associated with one or more surfaces of one or more dressings 1010. In some embodiments, one or more sensors 1070 may be associated with one or more electrical connections associated with one or more dressings 1010. In some embodiments, a sensor 1070 that is configured to detect nitric oxide may be configured for use on the outside surface of an individual 1150. For example, in some embodiments, one or more sensors 1070 that are configured to detect nitric oxide may be configured to detect the concentration of nitric oxide on the surface of skin, a wound, and the like. In some embodiments, a sensor 1070 that is configured to detect nitric oxide may be configured to utilize fluorescence to detect nitric oxide. For example, in some embodiments, a sensor 1070 may detect nitric oxide through use of one or more fluorescent probes, such as 4,5-diaminofluorescein diacetate (EMD Chemicals Inc., San Diego, Calif.). In some embodiments, a sensor 1070 may detect nitric oxide through use of one or more electrodes. For example, in some embodiments, a sensor 1070 may utilize an electrode that includes a single walled carbon nanotube and an ionic liquid to detect nitric oxide (e.g., Li et al., Electroanalysis, 18:713-718 (2006)). Numerous sensors 1070 are commercially available and haste been described (e.g., World Precision Instruments, Inc., Sarasota, Fla., USA; U.S. Pat. Nos. 6,100,096; 6,280,604; 5,980,705). In some embodiments, a sensor 1070 that is configured to detect nitric oxide may include one or more transmitters. In some embodiments, a sensor 1070 that is configured to detect nitric oxide may include one or more receivers. In some embodiments, a sensor 1070 that is configured to detect nitric oxide may be configured to transmit one or more signals 1110. In some embodiments, a sensor 1070 that is configured to detect nitric oxide may be configured to receive one or more signals 1110.

Figure 32:
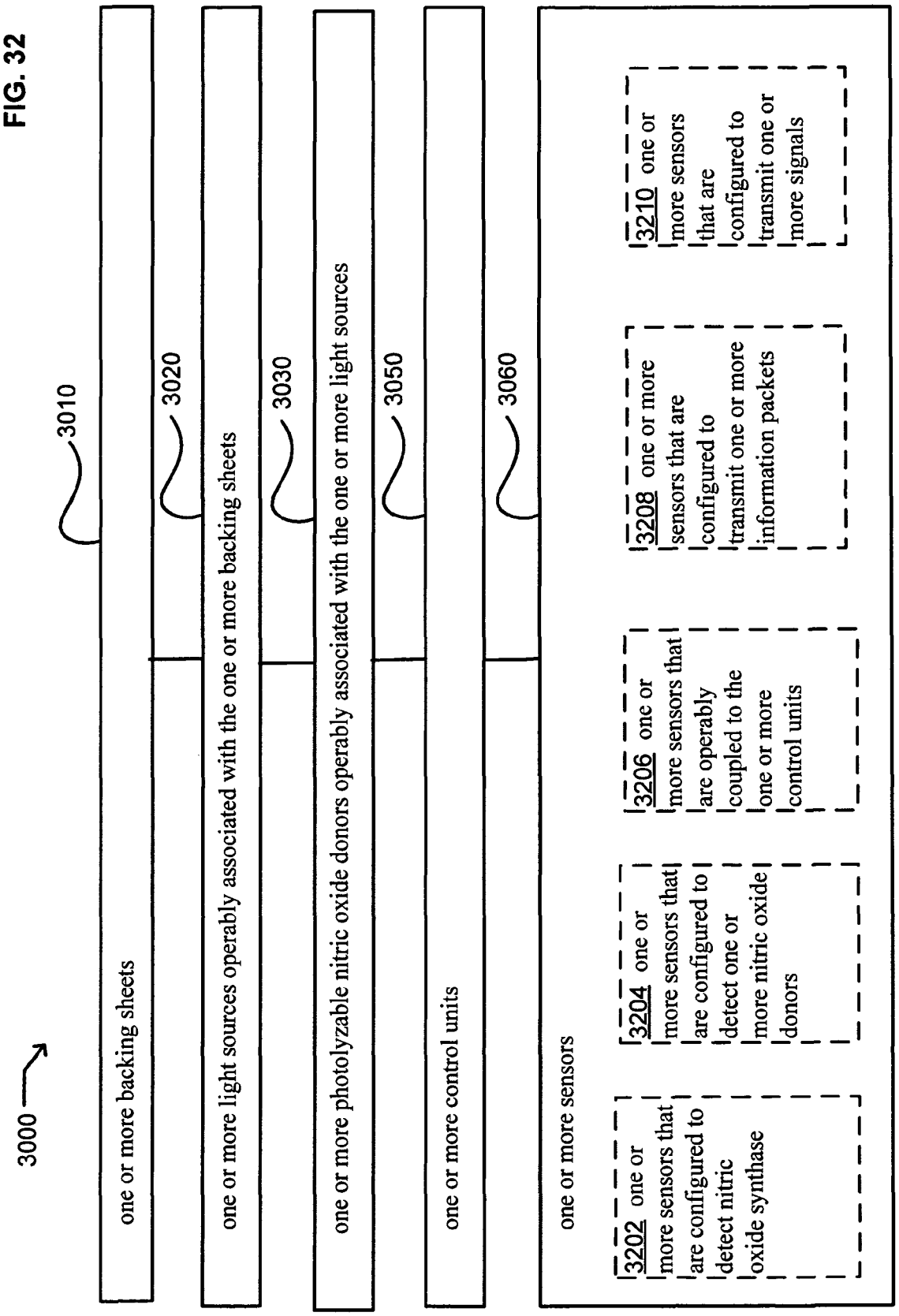
FIG. 32 illustrates alternate embodiments of embodiment 3000 of dressing 1010 within system 1000.

FIG. 32 illustrates alternative embodiments of embodiment 3000 of dressing 1010 within system 1000 of FIG. 30. FIG. 32 illustrates example embodiments of module 3060. Additional embodiments may include an embodiment 3702, an embodiment 3904, an embodiment 3206, an embodiment 3208, and/or an embodiment 3210.

At embodiment 3202, module 3060 may include one or more sensors that are configured to detect nitric oxide synthase. In some embodiments, one or more sensors 1070 may include one or more sensors 1070 that are configured to detect nitric oxide synthase. In some embodiments, one or more sensors 1070 may be configured to detect nitric oxide synthase activity. Nitric oxide synthase detection kits are commercially available (e.g., Cell Technology, Inc., Mountain View, Calif.). In some embodiments, one or more sensors 1070 may be configured to detect nitric oxide synthase messenger ribonucleic acid (mRNA). Methods that may be used to detect such mRNA have been reported (e.g., Sonoki et al., Leukemia, 13:713-718 (1999)). In some embodiments, one or more sensors 1070 may be configured to detect nitric oxide synthase through immunological methods. Methods that may be used to detect nitric oxide synthase directly been reported (e.g., Burrell et al., J. Histochem. Cytochem., 44:339-346 (1996) and Hattenbach et al., Opthalmologica, 216:209-714 (2002)). In some embodiments, microelectromechanical systems may be used to detect nitric oxide synthase. In some embodiments, antibodies and/or aptamers that bind to nitric oxide synthase may be used within one or more microelectromechanical systems to detect nitric oxide synthase. Methods to construct microelectromechanical detectors have been described (e.g., Gau et al., Biosensors & Bioelectronics, 16:745-755 (2001)). Accordingly, sensors 1070 may be configured in numerous ways to detect one or more nitric oxide synthases.

At embodiment 3204, module 3060 may include one or more sensors that are configured to detect one or more nitric oxide donors. In some embodiments, one or more sensors 1070 may include one or more sensors 1070 that are configured to detect one or more nitric oxide donors. In some embodiments, one or more sensors 1070 may include one or more surface plasmon resonance chemical electrodes that are configured to detect one or more nitric oxide donors. For example, in some embodiments, one or more sensors 1070 may include one or more surface plasmon resonance chemical electrodes that include antibodies and/or aptamers that bind to one or more nitric oxide donors. Accordingly, such electrodes may be used to detect the one or more nitric oxide donors through, use of surface plasmon resonance. Methods to construct surface plasmon resonance chemical electrodes are known and have been described (e.g., U.S. Pat. No. 5,858, 799; Lin et al., Applied Optics, 46:800-806 (2007)). In some embodiments, antibodies and/or aptamers that bind to one or more nitric oxide donors may be used within one or more microelectromechanical systems to detect one or more nitric oxide donors. Methods to construct microelectromechanical detectors have been described (e.g., Gau et al., Biosensors & Bioelectronics, 16:745-755 (2001)).

At embodiment 3206, module 3060 may include one or more sensors that are operably coupled to the one or more control units. In some embodiments, one or more sensors 1070 may include one or more sensors 1070 that are operably coupled to one or more control units 1060. In some embodiments, one or more sensors 1070 may be operably associated with one or more control units 1060 through a hardwired connection. In some embodiments, one or more sensors 1070 may be operably associated with one or more control units 1060 through a wireless connection. In some embodiments, one or more sensors 1070 may be configured to send one or more signals 1110 to one or more control units 1060. In some embodiments, one or more sensors 1070 may be configured to receive one or more signals 1110 from one or more control units 1060.

At embodiment 3208, module 3060 may include one or more sensors that are configured to transmit one or more information packets. In some embodiments, one or more sensors 1070 may include one or more sensors 1070 that are configured to transmit one or more information packets. In some embodiments, one or more sensors 1070 may be configured to transmit one or more information packets to one or more control units 1060. Information packets may include numerous types of information. Examples of such information include, but are not limited to, nitric oxide concentration, temperature, time, pulse, blood pressure, bacterial contamination, and the like.

At embodiment 310, module 3060 may include one or more sensors that are configured to transmit one or more signals. In some embodiments, one or more sensors 1070 may include one or more sensors 1070 that are configured to transmit one or more signals 1110. In some embodiments, one or more sensors 1070 may be configured to transmit one or more signals 1110. Numerous types of signals 1110 may be transmitted. Examples of such signals 1110 include, but are not limited to, optical signals 1110, radio signals 1110, wireless signals 1110, hardwired signals 110, infrared signals 1110, ultrasonic signals 110, and the like.

Figure 33:
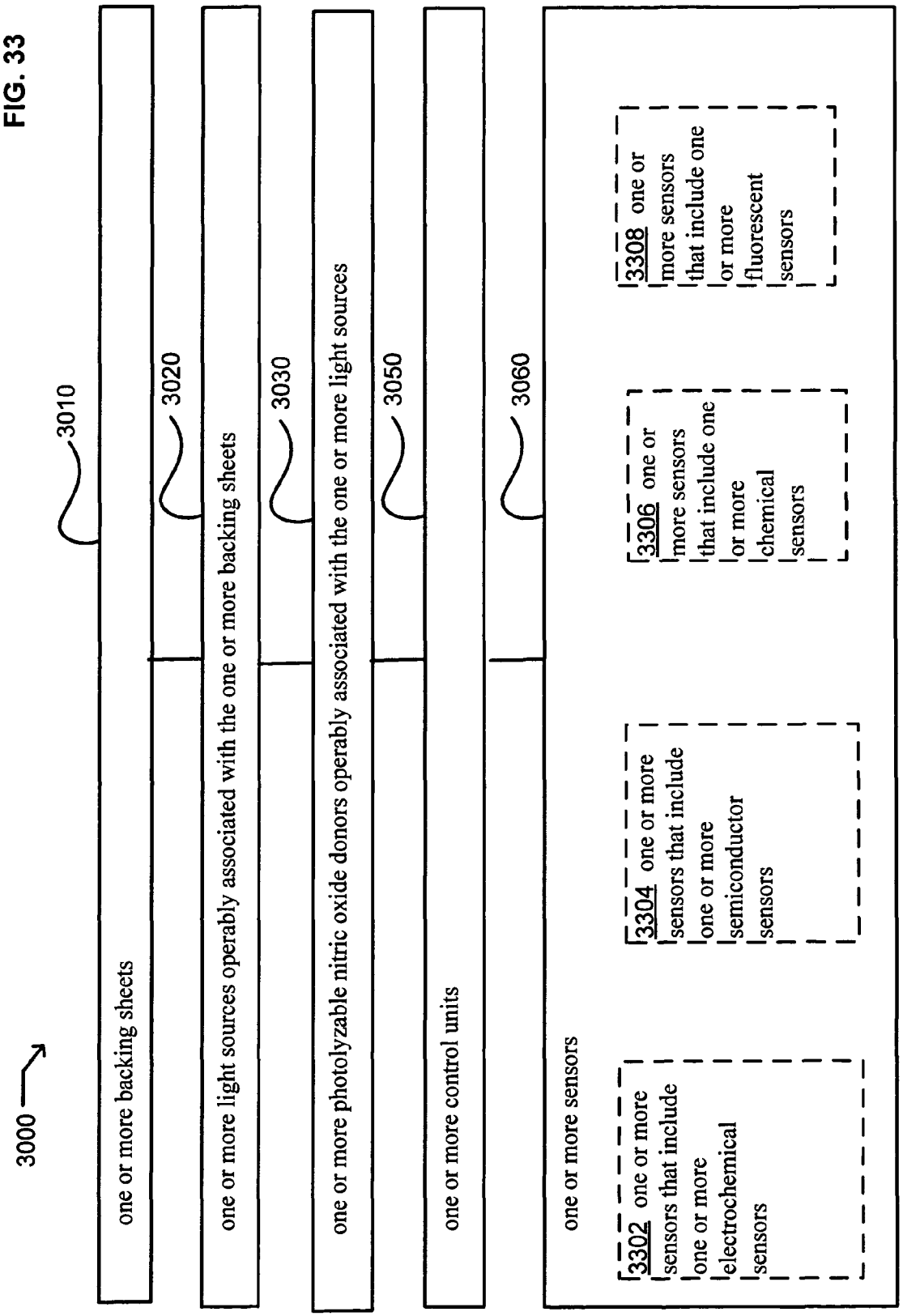
FIG. 33 illustrates alternate embodiments of embodiment 3000 of dressing 1010 within system 1000.

FIG. 33 illustrates alternative embodiments of embodiment 3000 of dressing 1010 within system 1000 of FIG. 30. FIG. 33 illustrates example embodiments of module 3060. Additional embodiments may include an embodiment 3302, an embodiment 3304, an embodiment 3306, and/or an embodiment 3308.

At embodiment 3302, module 3060 may include one or more sensors that include one or more electrochemical sensors. In some embodiments, one or more sensors 1070 may include one or more sensors 1070 that include one or more electrochemical sensors 1070. Sensors 1070 may include numerous types of electrochemical sensors 1070. For example, in some embodiments, an electrochemical sensor may be configured as a nitric oxide specific electrode. In some embodiments, a nitric oxide specific electrode may include ruthenium and/or at least one oxide of ruthenium. Methods to construct such electrodes are known and have been described (e.g., U.S. Pat. Nos. 6,280,604; 5,980,705). In some embodiments, a sensor 1070 may include an amperometric sensor that includes a sensing electrode that is configured to oxidize nitric oxide complexes to generate an electrical current that indicates the concentration of nitric oxide. Methods to construct such electrodes are known and have been described (e.g., U.S. Patent Application No.: 20070181444 and Ikeda et al., Sensors, 5:161-170 (2005)). Numerous types of electrochemical sensors 1070 may be associated with one or more sensors 1070 (e.g., Li et al., Electroanalysis 18:713-718 (2006)). Electrodes that may be used to detect nitric oxide are commercially available (World Precision Instruments, Sarasota, Fla.). In some embodiments, such electrodes may be used to detect nitric oxide at concentrations of about 0.5 nanomolar and above, and may be about 100 micrometers in diameter (World Precision Instruments, Sarasota, Fla.).

At embodiment 3304, module 3060 may include one or more sensors that include one or more semiconductor sensors. In some embodiments, one or more sensors 1070 may include one or more sensors 1070 that include one or more semiconductor sensors 1070. In some embodiments, the sensor may be a molecular controlled semiconductor resistor of a multilayered GaAs structure to which a layer of multifunctional NO-binding molecules are adsorbed. Such nitric oxide binding molecules may include, but are not limited to, vicinal diamines, metalloporphyrins, metallophthalocyanines, and iron-dithiocarbamate complexes that contain at least one functional group selected from carboxyl, thiol, acyclic sulfide, cyclic disulfide, hydroxamic acid, trichlorosilane or phosphate (e.g., U.S. Published Patent Application No.: 20040072360). In some embodiments, a semiconductive sensor may employ a polycrystalline-oxide semiconductor material that is coated with porous metal electrodes to form a semiconductor sandwich. In some embodiments, the semiconductor material may be formed of $SnO_2$ or ZnO. The porous electrodes may be formed with platinum and used to measure the conductivity of the semiconductor material. In some embodiments, the conductivity of the semiconductor material changes when nitric oxide is absorbed on the surface of the semiconductor material (e.g., U.S. Pat. No. 5,580,433; International Application Publication Number WO 02/057738). One or more sensors 1070 may include numerous other types of semiconductor sensors 1070.

At embodiment 3306, module 3060 may include one or more sensors that include one or more chemical sensors. In some embodiments, one or more sensors 1070 may include one or more sensors 1070 that include one or more chemical sensors 1070. For example, in some embodiments, one or more sensors 1070 may include one or more chemical sensors 1070 that include a reagent solution that undergoes a chemiluminescent reaction with nitric oxide. Accordingly, one or more photodetectors may be used to detect nitric oxide. Methods to construct such detectors are known and have been described (e.g., U.S. Pat. No. 6,100,096). In some embodiments, ozone may be reacted with nitric oxide to produce light in proportion to the amount of nitric oxide present. The light produced may be measured with a photodetector. In some embodiments, sensors 1070 may include one or more charge-coupled devices to detect photonic emission.

At embodiment 3308, module 3060 may include one or more sensors that include one or more fluorescent sensors. In some embodiments, one or more sensors 1070 may include one or more sensors 1070 that include one or more fluorescent sensors 1070. In some embodiments, a fluorescent sensor may include one or more fluorescent probes that may be used to detect nitric oxide. For example, in some embodiments, 4,5-diaminofluorescein may be used to determine nitric oxide concentration (e.g., Rathel et al., Biol. Proced. Online, 5:136-142 (2003)). Probes that may be used to detect nitric oxide are commercially available (EMD Chemicals Inc., San Diego, Calif.).

Figure 34:
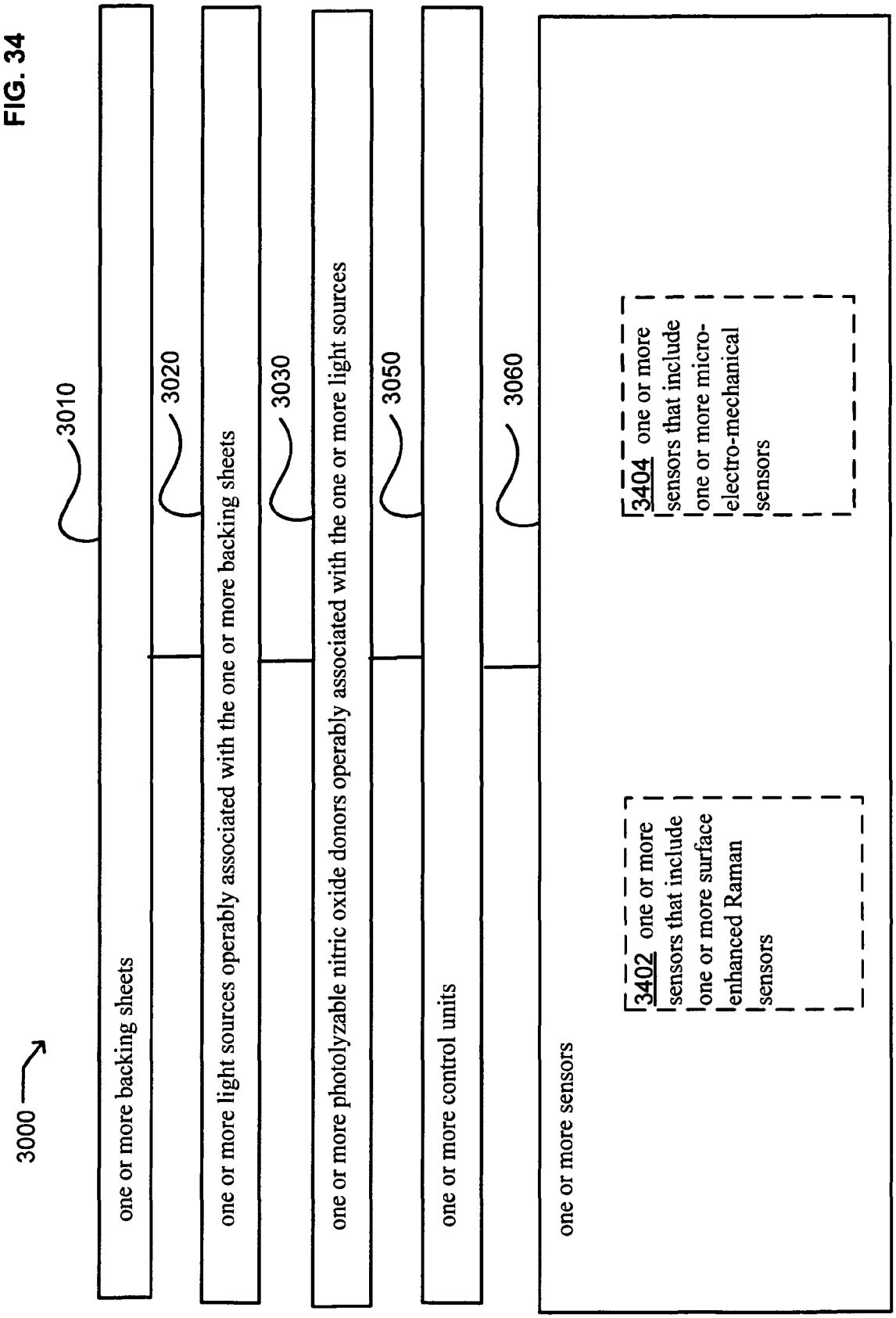
FIG. 34 illustrates alternate embodiments of embodiment 3000 of dressing 1010 within system 1000.

FIG. 34 illustrates alternative embodiments of embodiment 3000 of dressing 1010 within system 1000 of FIG. 30. FIG. 34 illustrates example embodiments of module 3060. Additional embodiments may include an embodiment 3402 and/or an embodiment 3404.

At embodiment 3402, module 3060 may include one or more sensors that include one or more surface enhanced Raman sensors. In some embodiments, one or more sensors 1070 may include one or more sensors 1070 that include one or more Raman sensors 1070. Methods to use Raman spectroscopy to detect nitric oxide are known and have been described (e.g., U.S. Patent Application No.: 20060074282). In addition, Raman spectrometers are commercially available (e.g., Raman Systems, Austin, Tex. and B&W Tek, Inc., Newark, Del.).

At embodiment 3404, module 3060 may include one or more sensors that include one or more micro-electro-mechanical sensors. In some embodiments, one or more sensors 1070 may include one or more sensors 1070 that include one or more micro-electro-mechanical sensors 1070. In some embodiments, microelectromechanical systems may be used to detect nitric oxide synthase. In some embodiments, antibodies and/or aptamers that bind to nitric oxide synthase may be used within one or more microelectromechanical systems to detect nitric oxide synthase. Methods to construct microelectromechanical detectors have been described (e.g., Gau et al., Biosensors & Bioelectronics, 16:745-755 (2001)). Accordingly, sensors 1070 may be configured in numerous ways to detect one or more nitric oxide synthases.

Figure 35:
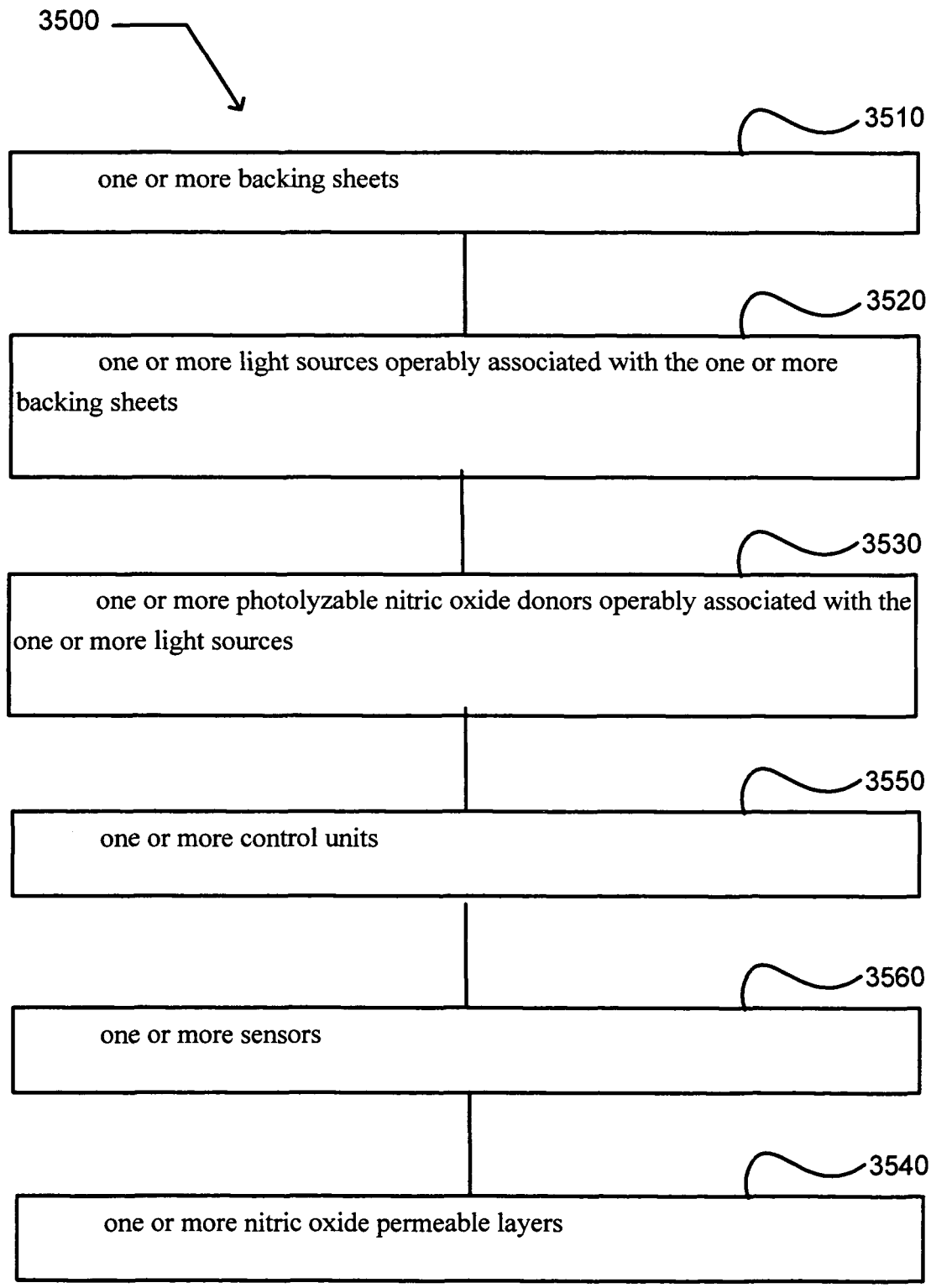
FIG. 35 illustrates embodiment 3500 of dressing 1010 within system 1000.

FIG. 35 illustrates embodiment 3500 of dressing 1010 within system 1000. In FIG. 35, discussion and explanation may be provided with respect to the above-described example of FIG. 10, and/or with respect to other examples and contexts. However, it should be understood that the modules may execute operations in a number of other environments and contexts, and/or modified versions of FIG. 10. Also, although the various modules are presented in the sequence(s) illustrated, it should be understood that the various modules may be configured in numerous orientations.

The embodiment 3500 may include module 3510 that includes one or more backing sheets. In some embodiments, a dressing 1010 may include one or more backing sheets 1030. One or more backing sheets 1030 may be fabricated from one or more materials. In some embodiments, one or more backing sheets 1030 may include portions that are fabricated from different types of materials. For example, in some embodiments, a backing sheet 1030 may include one or more portions that include one or more adhesive materials and one or more portions that include one or more nonadhesive materials. In some embodiments, a backing sheet 1030 may include one or more portions that include one or more gas permeable materials and one or more portions that include one or more gas impermeable materials. Accordingly, one or more backing sheets 1030 may include numerous combinations of materials that exhibit numerous properties. Examples of such material include, but are not limited to, elastic materials, inelastic materials, adhesive materials, nonadhesive materials, conductive materials, nonconductive materials, perforated materials, nonperforated materials, fluid permeable materials, fluid impermeable materials, gas permeable materials, gas impermeable materials, light permeable materials, selectively light permeable materials, light impermeable materials, and the like.

The embodiment 3500 may include module 3520 that includes one or more light sources operably associated with the one or more backing sheets. In some embodiments, a dressing 1010 may include one or more light sources 1040 operably associated with one or more backing sheets 1030. In some embodiments, a dressing 1010 may include one or more light sources 1040 that are operably associated with one or more photolyzable nitric oxide donors 1020. In some embodiments, one or more light sources 1040 may be directly coupled to one or more backing sheets 1030. For example. In some embodiments, one or more light sources 1040 may be integrated within one or more backing sheets 1030. In some embodiments, one or more light sources 1040 may be indirectly associated with one or more backing sheets 1030. For example, in some embodiments, one or more light sources 1040 may be associated with one or more backing sheets 1030 through attachment to one or more electrical connections associated with the one or more backing sheets 1030. In some embodiments, one or more light sources 1040 may be associated with one or more backing sheets 1030 through inclusion within one or more compositions that include one or more photolyzable nitric oxide donors 1020 that are associated with one or more backing sheets 1030.

The embodiment 3500 may include module 3530 that includes one or more photolyzable nitric oxide donors operably associated with the one or more light sources. In some embodiments, a dressing 1010 may include one or more photolyzable nitric oxide donors 1020 operably associated with the one or more light sources 1040. In some embodiments, the one or more light sources 1040 may be directly coupled to one or more photolyzable nitric oxide donors 1020. For example, in some embodiments, the one or more photolyzable nitric oxide donors 1020 may be chemically coupled to a surface of the light source 1040 (e.g., chemically coupled to a polymer coating on the light source 1040). In some embodiments, one or more photolyzable nitric oxide donors 1020 may be indirectly coupled to one or more light sources 1040. For example, in some embodiments, one or more photolyzable nitric oxide donors 1020 may be coupled to a material that is used to coat the one or more light sources 1040. Numerous photolyzable nitric oxide donors 1020 may be operably associated with one or more light sources 1040. Examples of such photolyzable nitric oxide donors 1020 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al. Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 1117:1549-1557 (1996), Matthews et al., Br. J. Pharmacol., 113:87-94 (1994)), 6-Nitrobenzo[a]pyrene (e.g., Fukuhara et al., J. An. Chem. Soc., 123:8662-8666 (2001)), S-nitroso-glutathione (e.g., Rotta et al., Braz. J. Med. Res., 36:587-594 (2003), Flitney and Megson, J. Physiol., 550: 819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

The embodiment 3500 may include module 3550 that includes one or more control units. In some embodiments, a dressing 1010 may include one or more control units 1060. A dressing 1010 may include numerous types of control units 1060. In some embodiments, one or more control units 1060 may be operably coupled with one or more light sources 1040, one or more sensors 1070, one or more electromagnetic receivers 1080, one or more electromagnetic transmitters 1100, or substantially any combination thereof. In some embodiments, one or more control units 1060 may be operably coupled to other components through use of one or more wireless connections, one or more hardwired connections, or substantially any combination thereof. A control unit 1060 may be configured in numerous ways. For example, in some embodiments, a control unit 1060 may be configured as an on/off switch. Accordingly, in some embodiments, a control unit 1060 may be configured to turn a light source 1040 on and/or off. In some embodiments, a control unit 1060 may be configured to control the emission of light from one or more light sources 1040. For example, in some embodiments, one or more control units 1060 may regulate the intensity of light emitted from one or more light sources 1040, the duration of light emitted from one or more light sources 1040, the frequency of light emitted from one or more light sources 1040, wavelengths of light emitted from one or more light sources 1040, times when light is emitted from one or more light sources 1040, or substantially any combination thereof. In some embodiments, one or more control units 1060 may be configured to receive one or more signals 110 from one or more sensors 1070. Accordingly, in some embodiments, one or more control units 1060 may be configured to control one or more light sources 1040 in response to one or more signals 110 received from one or more sensors 1070. For example, in some embodiments, one or more sensors 1070 may sense a low concentration of nitric oxide in one or more tissues and send one or more signals 1110 to one or more control units 1060. The one or more control units 1060 may then turn one or more light sources 1040 on to facilitate release of nitric oxide from one or more photolyzable nitric oxide donors 1020. Accordingly, in some embodiments, one or more sensors 1070 may sense a high concentration of nitric oxide in one or more tissues and send one or more signals 1110 to one or more control units 1060. The one or more control units 1060 may then turn one or more light sources 1040 off to end release of nitric oxide from one or more photolyzable nitric oxide donors 1020. In some embodiments, one or more control units 1060 may be programmed to control one or more light sources 1040. For example, in some embodiments, one or more control units 1060 may be programmed to turn one or more light sources 1040 on for a predetermined amount of time and then turn off. Accordingly, in some embodiments, one or more control units 1060 may be preprogrammed. In some embodiments, one or more control units 1060 may be dynamically programmed. For example, in some embodiments, one or more management units 1130 may receive one or more signals 1110 from one or more sensors 1070 and program one or more control units 1060 in response to the one or more signals 1110 received from the one or more sensors 1070. In some embodiments, one or more control units 1060 may include one or more receivers that are able to receive one or more signals 1110, one or more information packets, or substantially any combination thereof. Control units 1060 may be configured in numerous ways. For example, in some embodiments, one or more control units 1060 may be operably coupled to one or more light sources 1040 that include numerous light emitting diodes that emit light of different wavelengths. Accordingly, in some embodiments, one or more control units 1060 may control the wavelengths of light emitted by the one or more light sources 1040 by controlling the operation of light emitting diodes that emit light of the selected wavelength. Accordingly, control units 1060 may be configured in numerous ways and utilize numerous types of mechanisms.

The embodiment 3500 may include module 3560 that includes one or more sensors. In some embodiments, a dressing 1010 may include one or more sensors 1070. In some embodiments, one or more sensors 1070 may be integrated within one or more dressings 1010. In some embodiments, one or more sensors 1070 may be associated with one or more surfaces of one or more dressings 1010. In some embodiments, one or more sensors 1070 may be associated with one or more electrical connections associated with one or more backing sheets 1030. Numerous types of sensors 1070 may be associated with one or more dressings 1010. Examples of such sensors 1070 include, but are not limited to, temperature sensors 1070, pressure sensors 1070 (e.g., blood pressure, hydrostatic pressure), pulse rate sensors 1070, sensors 1070, clocks, bacterial contamination sensors 1070, strain sensors 1070, light sensors 1070, nitric oxide sensors 1070, and the like.

The embodiment 3500 may include module 3540 that includes one or more nitric oxide permeable layers. In some embodiments, a dressing 1010 may include one or more nitric oxide permeable layers 1050. A dressing 1010 may include nitric oxide permeable layers 1050 that are fabricated from numerous types of material. Examples of such materials include, but are not limited to, ceramics, polymeric materials, metals, plastics, and the like. In some embodiments, nitric oxide permeable layers 1050 may include numerous combinations of materials. For example, in some embodiments, a nitric oxide permeable layer 1050 may include a nitric oxide impermeable material that is coupled to a nitric oxide permeable material. In some embodiments, a nitric oxide permeable layer 1050 may include one or more nitric oxide permeable membranes (e.g., U.S. Patent Application No.: 20020026937). In some embodiments, a nitric oxide permeable layer 1050 may include a selectively permeable membrane. For example, in some embodiments, a nitric oxide permeable layer 1050 may include a selectively permeable membrane that is a hydrophilic polyester co-polymer membrane system that includes a copolymer with 70% polyester and 30% polyether (e.g., Sympatex™ 10 µm membrane, see Hardwick et al., Clinical Science, 100:395-400 (2001)). In some embodiments, a nitric oxide permeable layer 1050 may include a scintered glass portion that is permeable to nitric oxide. Accordingly, nitric oxide permeable layers 1050 may include numerous types of porous ceramics that are permeable to nitric oxide. In some embodiments, a nitric oxide permeable layer 1050 may include a porous metal portion that is permeable to nitric oxide. In some embodiments, a nitric oxide permeable layer 1050 may include a nitric oxide permeable coating (e.g., U.S. Patent Application Nos.: 20050220838 and 20030093143).

Nitric oxide permeable layers 1050 may be configured for application to an individual 1150. Nitric oxide permeable layers 1050 may be configured to facilitate application of nitric oxide to a surface. In some embodiments, one or more nitric oxide permeable layers 1050 may be configured to facilitate application of nitric oxide to one or more surfaces of an individual 1150. For example, in some embodiments, one or more nitric oxide permeable layers 1050 may be configured as a sheet that may be positioned on a skin surface of an individual 150 to deliver nitric oxide to the skin surface. In some embodiments, nitric oxide permeable layers 1050 may be configured as a bandage, a patch, and the like.

Figure 36:
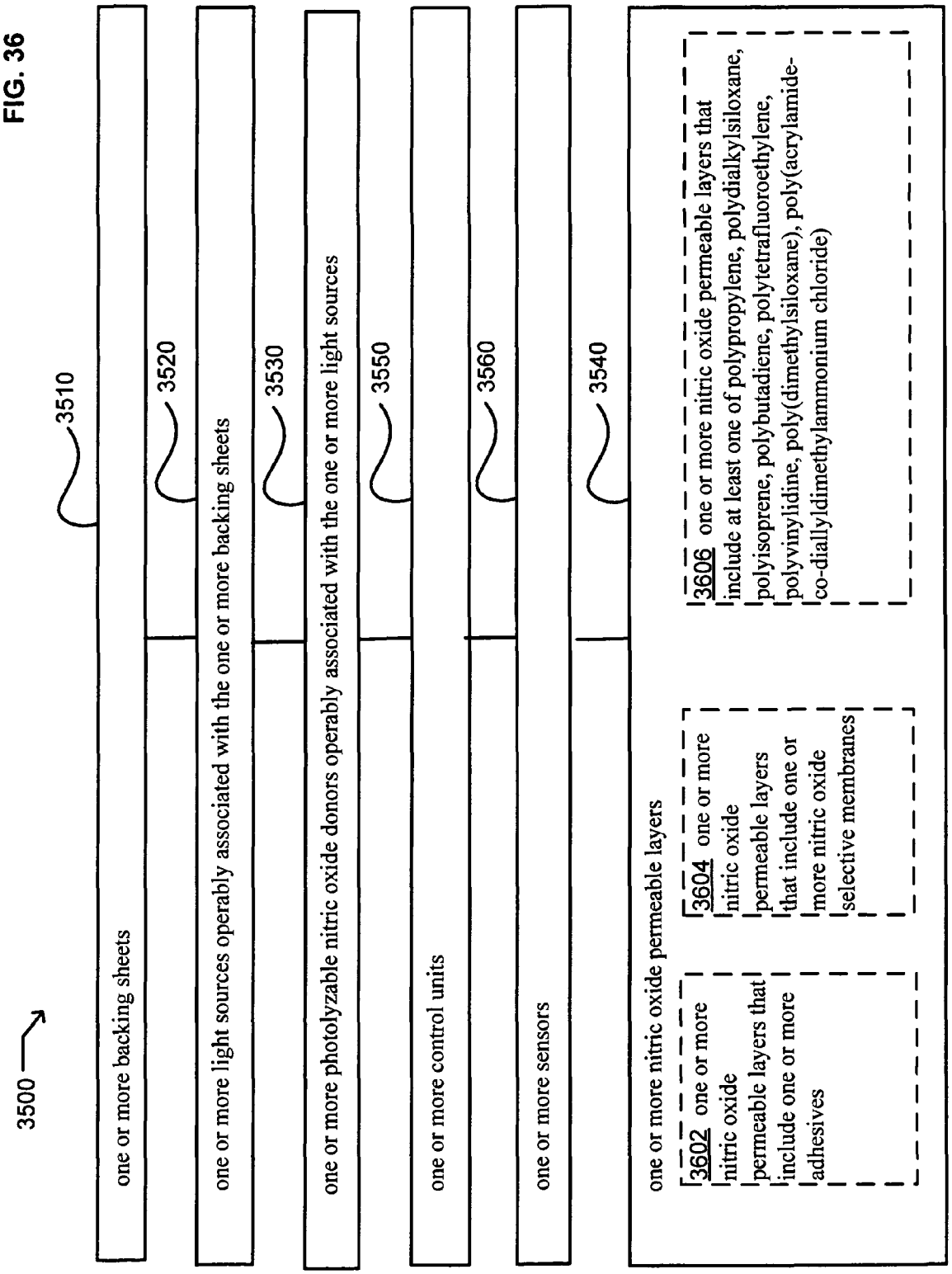
FIG. 36 illustrates alternate embodiments of embodiment 3500 of dressing 1010 within system 1000.

FIG. 36 illustrates alternative embodiments of embodiment 3500 of dressing 1010 within system 1000 of FIG. 35. FIG. 36 illustrates example embodiments of module 3540. Additional embodiments may include an embodiment 3609, an embodiment 3604, and/or an embodiment 3606.

At embodiment 3602, module 3540 may include one or more nitric oxide permeable layers that include one or more adhesives. In some embodiments, one or more nitric oxide permeable layers 1050 may include one or more nitric oxide permeable layers 1050 that include one or more adhesives. In some embodiments, a dressing 1010 may include one or more nitric oxide permeable layers 1050 that include one or more adhesives that facilitate adhesion of at least a portion of a nitric oxide permeable layer 1050 to a surface. For example, in some embodiments, a dressing 1010 may include a nitric oxide permeable layer 1050 that includes at least one portion which includes one or more adhesives and that is configured to deliver nitric oxide to a surface adjacent to the nitric oxide permeable layer 1050. For example, in some embodiments, a dressing 1010 may be configured as a bandage that includes a nitric oxide permeable membrane on the portion of the bandage that is to be placed on a skin surface of an individual 1150. In some embodiments, adhesive may enclose a space on the surface of the nitric oxide permeable layer 1050 such that a sealed space is formed on the skin Ashen the bandage is adhered to the skin surface. Accordingly, such an embodiment of a dressing 1010 may be used to deliver nitric oxide to a select surface by positioning the dressing 1010 on and/or over the select surface and attaching the dressing 1010 at points adjacent to the select surface with the one or more adhesives. In some embodiments, such an embodiment of dressing 1010 may be configured as a bandage, a patch, and the like.

At embodiment 3604, module 3540 may include one or more nitric oxide permeable layers that include one or more nitric oxide selective membranes. In some embodiments, one or more nitric oxide permeable layers 1050 may include one or more nitric oxide permeable layers 1050 that include one or more nitric oxide selective membranes. In some embodiments, a nitric oxide permeable layer 1050 may include a selectively permeable membrane. For example, in some embodiments, a nitric oxide permeable layer 1050 may include a selectively permeable membrane that is a hydrophilic polyester co-polymer membrane system that includes a copolymer with 70% polyester and 30% polyether (e.g., Sympatex™ 10 µm membrane, see Hardwick et al., Clinical Science, 100:395-400 (2001)). Methods to fabricate nitric oxide permeable membranes are known (e.g., U.S. Patent Application No.: 20020026937).

At embodiment 3606, module 3540 may include one or more nitric oxide permeable layers that include at least one of polypropylene, polydialkylsiloxane, polyisoprene, polybutadiene, polytetrafluoroethylene, polyvinylidine, poly(dimethylsiloxane), poly(acrylamide-co-diallyldimethyl ammonium chloride). In some embodiments, one or more nitric oxide permeable layers 1050 may include one or more nitric oxide permeable layers 1050 that include at least one of polypropylene, polydialkyl siloxane, polyisoprene, polybutadiene, polytetrafluoroethylene, polyvinylidine, poly(dimethylsiloxane), poly(acrylamide-co-diallyldimethylammonium chloride).

Figure 37:
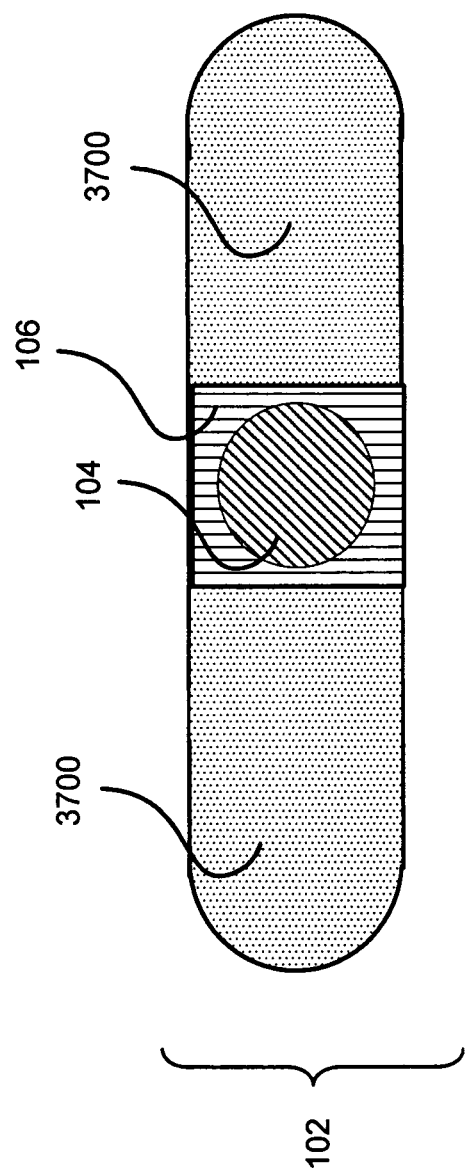
FIG. 37 illustrates embodiment of dressing 102 within system 100.

FIG. 37 illustrates an embodiment of dressing 102. In FIG. 37, an embodiment of dressing 102 is configured as a bandage. A backing sheet 106 that is light transmissive is shown operably associated with one or more photolyzable nitric oxide donors 104. The backing sheet 106 that is light transmissive and the one or more photolyzable nitric oxide donors 104 are shown operably associated with a second backing sheet 3700. In some embodiments, the second backing sheet 3700 may be transmissive to light. In some embodiments, the second backing sheet 3700 may be non-transmissive to light. In some embodiments, the second backing sheet 3700 may include one or more adhesives. In some embodiments, the second backing sheet 3700 may be porous.

Figure 38A:
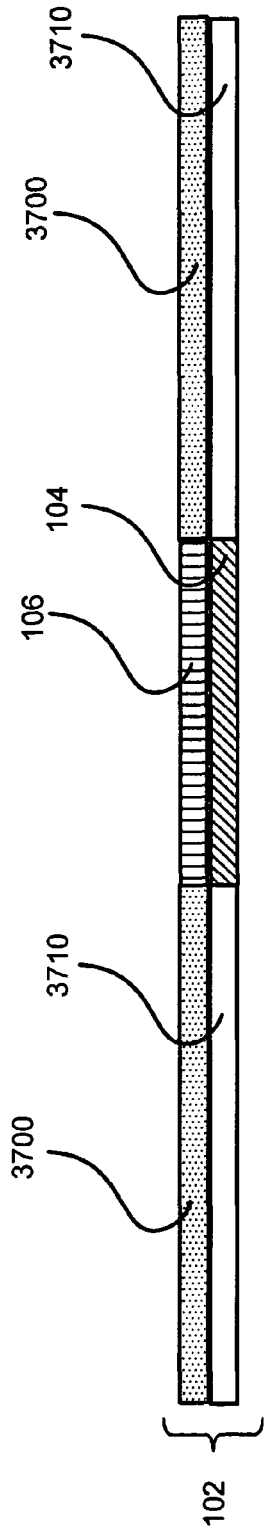
FIG. 38A illustrates a side-view of an embodiment of dressing 102 within system 100 as illustrated in FIG. 37.

FIG. 38A illustrates a side-view of an embodiment of dressing 102 as illustrated in FIG. 37. A backing sheet 106 that is transmissive to light is shown operably associated with one or more photolyzable nitric oxide donors 104. The backing sheet 106 that is transmissive to light is shown operably associated with second backing sheet 3700 that includes one or more adhesives 3710. In some embodiments, the second backing sheet 3700 may be transmissive to light. In some embodiments, the second backing sheet 3700 may be non-transmissive to light.

Figure 38B:
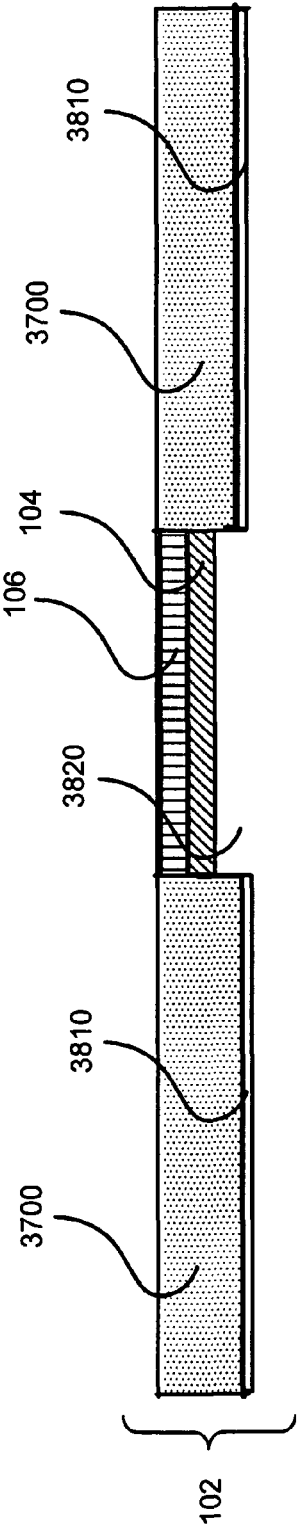
FIG. 38B illustrates a side-view of an embodiment of dressing 102 within system 100 as illustrated in FIG. 37.

FIG. 38B illustrates a side-view of an embodiment of dressing 102 as illustrated in FIG. 37. A backing sheet 106 that is transmissive to light is shown operably associated with one or more photolyzable nitric oxide donors 104. The backing sheet 106 that is transmissive to light is shown operably associated with second backing sheet 3700 that includes one or more adhesives 3810. A closed space 3820 is shown adjacent to the one or more photolyzable nitric oxide donors 104. In some embodiments, the second backing sheet 3700 may be transmissive to light. In some embodiments, the second backing sheet 3700 may be non-transmissive to light.

Figure 38C:
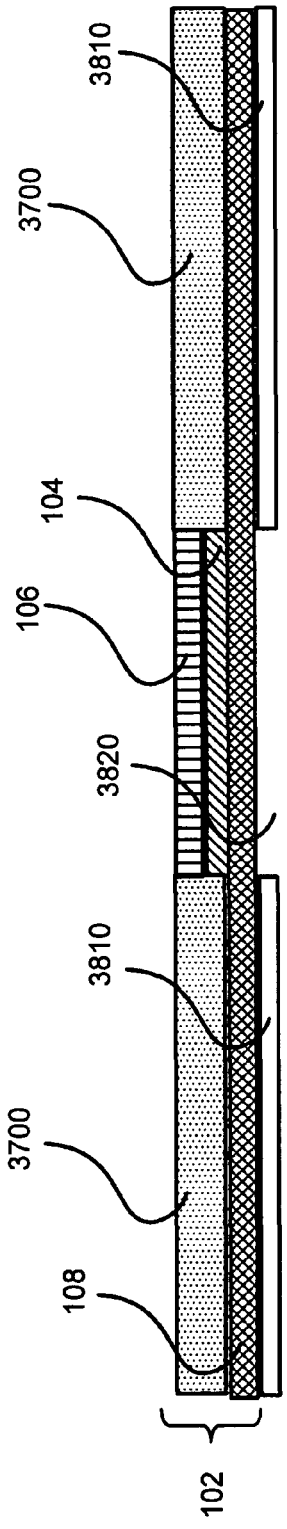
FIG. 38C illustrates a side-view of an embodiment of dressing 102 within system 100 as illustrated in FIG. 37.

FIG. 38C illustrates a side-view of an embodiment of dressing 102 as illustrated in FIG. 37. A backing sheet 106 that is transmissive to light is shown operably associated with one or more photolyzable nitric oxide donors 104. The backing sheet 106 that is transmissive to light is shown operably associated with second backing sheet 3700. In some embodiments, the second backing sheet 3700 may be transmissive to light. In some embodiments, the second backing sheet 3700 may be non-transmissive to light. A nitric oxide permeable layer 108 is shown operably associated with the backing sheet 3700 and one or more adhesives 3810. A closed space 3820 is shown proximate to the nitric oxide permeable layer 108.

Figure 39:
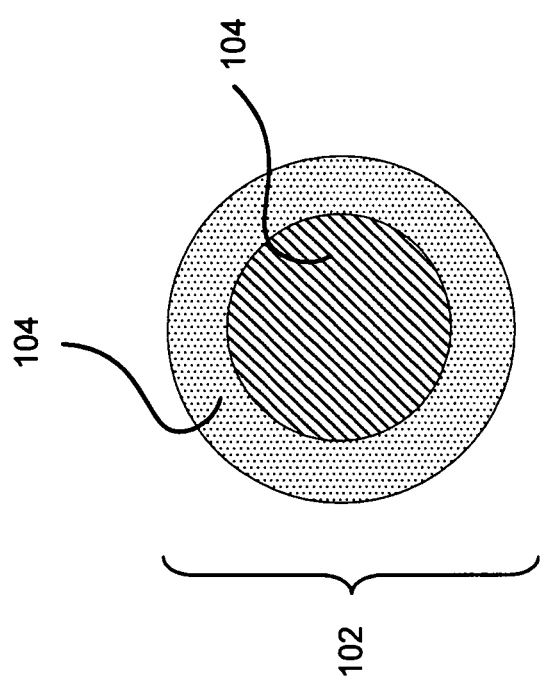
FIG. 39 illustrates embodiment of dressing 102 within system 100.

FIG. 39 illustrates an embodiment of dressing 102. In FIG. 39, an embodiment of dressing 102 is configured as a patch. A backing sheet 106 is shown operably associated with one or more photolyzable nitric oxide donors 104. In some embodiments, the backing sheet 106 may include one or more adhesives. In some embodiments, the backing sheet 106 may be porous.

Figure 40A:
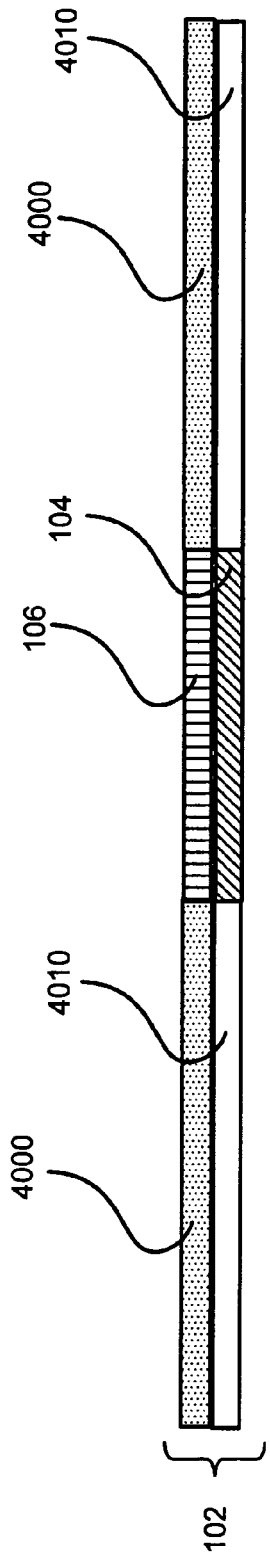
FIG. 40A illustrates a side-view of an embodiment of dressing 102 within system 100 as illustrated in FIG. 39.

FIG. 40A illustrates a side-view, of an embodiment of dressing 102 as illustrated in FIG. 39. Backing sheet 106 that is transmissive to light is shown operably associated with one or more photolyzable nitric oxide donors 104. Backing sheet 106 that is transmissive to light is shown operably associated with backing sheet 4000 that includes one or more adhesives 4010. In some embodiments, the second backing sheet 4000 may be transmissible to light. In some embodiments, the second backing sheet 4000 may be non-transmissive to light.

Figure 40B:
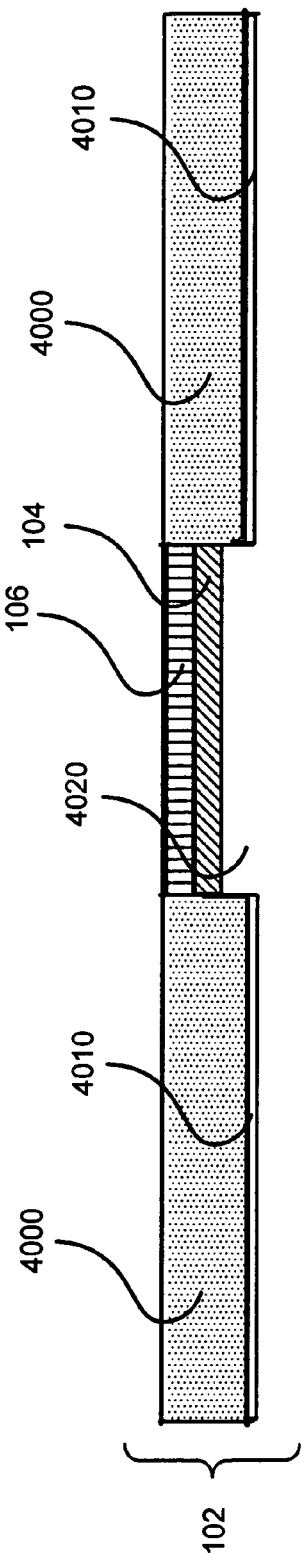
FIG. 40B illustrates a side-view of an embodiment of dressing 102 within system 100 as illustrated in FIG. 39.

FIG. 40B illustrates a side-view of an embodiment of dressing 102 as illustrated in FIG. 39. Backing sheet 106 that is transmissive to light is shown operably associated with one or more photolyzable nitric oxide donors 104. Backing sheet 106 that is transmissive to light is shown operably associated with backing sheet 4000 that includes one or more adhesives 4010. In some embodiments, backing sheet 4000 may be transmissive to light. In some embodiments, backing sheet 4000 may be non-transmissive to light. A closed space 4020 is shown adjacent to the one or more photolyzable nitric oxide donors 104.

Figure 40C:
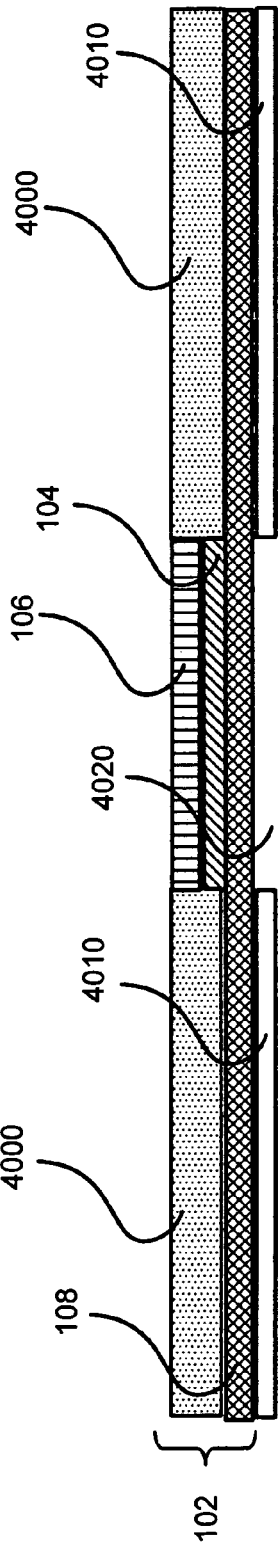
FIG. 40C illustrates a side-view of an embodiment of dressing 102 within system 100 as illustrated in FIG. 39.

FIG. 40C illustrates a side-view of an embodiment of dressing 102 as illustrated in FIG. 39. Backing sheet 106 that is transmissive to light is shown operably associated Keith one or more photolyzable nitric oxide donors 104. Backing sheet 106 that is transmissive to light is shown operably associated with backing sheet 4000. In some embodiments, backing sheet 4000 may be transmissive to light. In some embodiments, backing sheet 4000 may be non-transmissive to light. A nitric oxide permeable layer 108 is shown operably associated with backing sheet 4000 and one or more adhesives 4010. A closed space 4020 is shown adjacent to the nitric oxide permeable layer 108.

FIG. 41 illustrates an embodiment of dressing 1010. In FIG. 41, an embodiment of dressing 1010 is configured as a bandage. A backing sheet 1030 and a light source 1040 are shown operably associated with one or more photolyzable nitric oxide donors 1020. Adhesive 4110 is illustrated as encircling the one or more photolyzable nitric oxide donors 1020.

FIG. 42A illustrates a side-view of an embodiment of dressing 1010 as illustrated in FIG. 41. Backing sheet 1030 is shown operably associated with a light source 1040 that is operably associated with one or more photolyzable nitric oxide donors 1090. Backing sheet 1030 is shown associated with one or more adhesives 4110.

FIG. 42B illustrates a side-view of an embodiment of dressing 1010 as illustrated in FIG. 41. Backing sheet 1030 is shown operably associated with a light source 1040 that is operably associated with one or more photolyzable nitric oxide donors 1020. Backing sheet 1030 is shown associated with one or more adhesives 4110. A closed space 4220 is shown adjacent to the one or more photolyzable nitric oxide donors 1020.

FIG. 42C illustrates a side-view of an embodiment of dressing 1010 as illustrated in FIG. 41. Backing sheet 1030 is shown operably associated with a light source 1040 that is operably associated with one or more photolyzable nitric oxide donors 1020. Backing sheet 1030 is shown associated with a nitric oxide permeable layer 1050 that includes one or more adhesives 4110.

Figure 43:
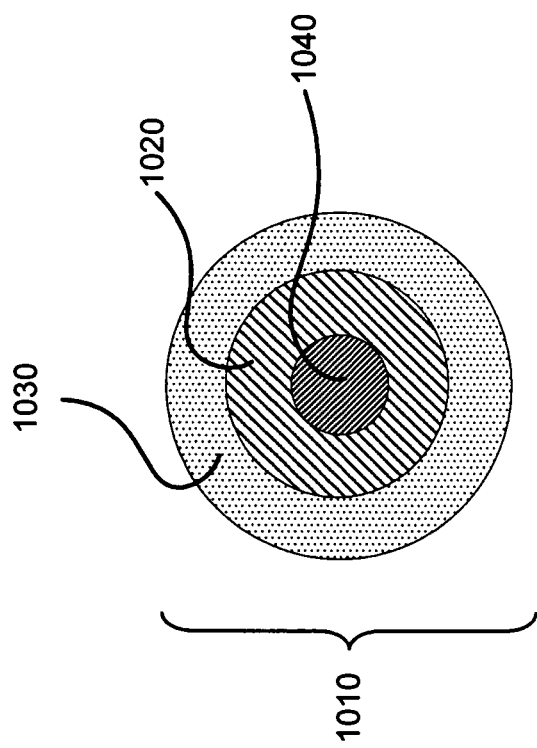
FIG. 43 illustrates embodiment of dressing 1010 within system 1000.

FIG. 43 illustrates an embodiment of dressing 1010. In FIG. 43, an embodiment of dressing 1010 is configured as a patch. A backing sheet 1030 is shown operably associated with one or more photolyzable nitric oxide donors 1020 that are operably associated with a light source 1040.

Figure 44A:
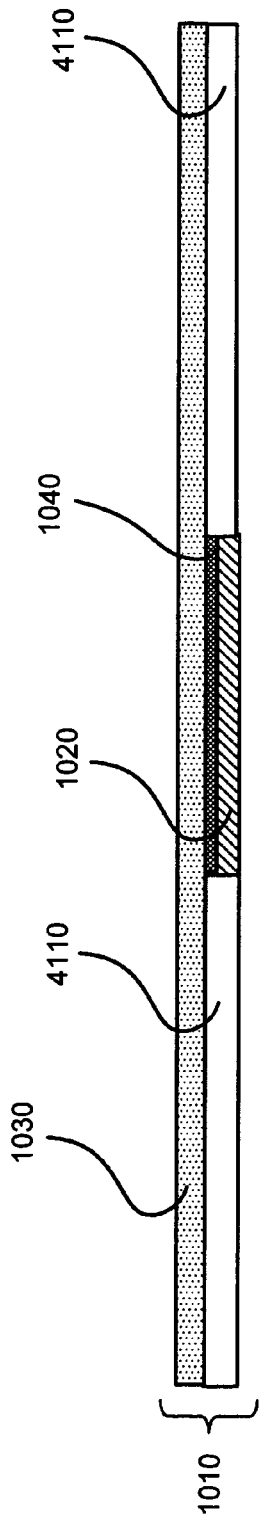
FIG. 44A illustrates a side-view of an embodiment of dressing 1010 within system 1000 as illustrated in FIG. 43.

FIG. 44A illustrates a side-view of an embodiment of dressing 1010 as illustrated in FIG. 43. Backing sheet 1030 is shown operably associated with a light source 1040 that is operably associated with one or more photolyzable nitric oxide donors 1020. Backing sheet 1030 is shown associated with one or more adhesives 4110.

Figure 44B:
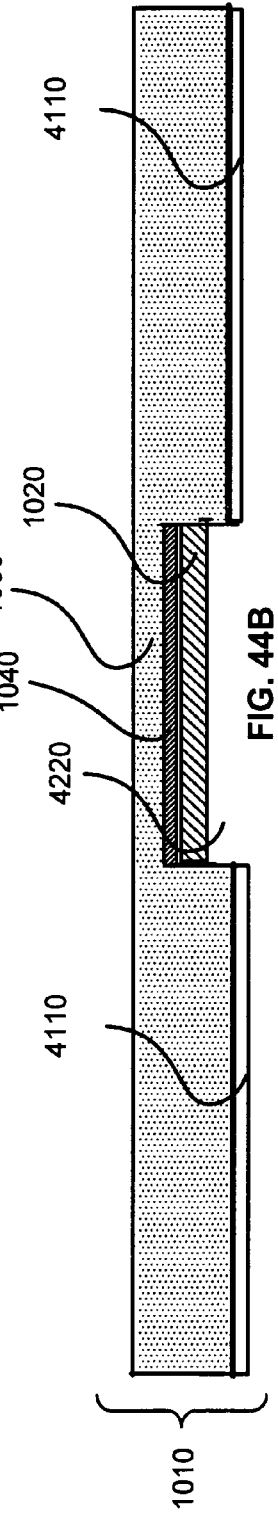
FIG. 44B illustrates a side-view of an embodiment of dressing 1010 within system 1000 as illustrated in FIG. 43.

FIG. 44B illustrates a side-view of an embodiment of dressing 1010 as illustrated in FIG. 43. Backing sheet 1030 is shown operably associated with a light source 1040 that is operably associated with one or more photolyzable nitric oxide donors 1020. Backing sheet 1030 is shown associated with one or more adhesives 4110. A closed space 4220 is shown adjacent to the one or more photolyzable nitric oxide donors 1020.

Figure 44C:
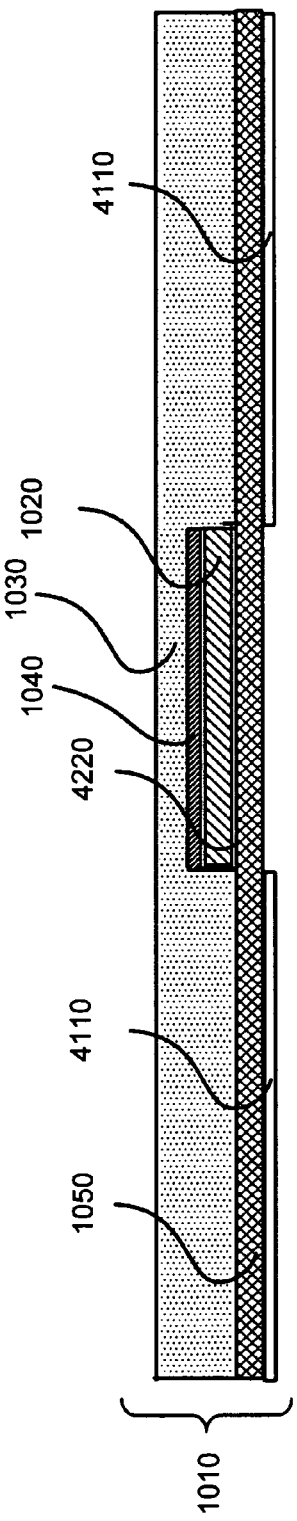
FIG. 44C illustrates a side-view of an embodiment of dressing 1010 within system 1000 as illustrated in FIG. 43.

FIG. 44C illustrates a side-view of an embodiment of dressing 1010 as illustrated in FIG. 43. Backing sheet 1030 is shown operably associated with a light source 1040 that is operably associated with one or more photolyzable nitric oxide donors 1020. Backing sheet 1030 is shown associated with a nitric oxide permeable layer 1050 that includes one or more adhesives 4110.

Figure 45:
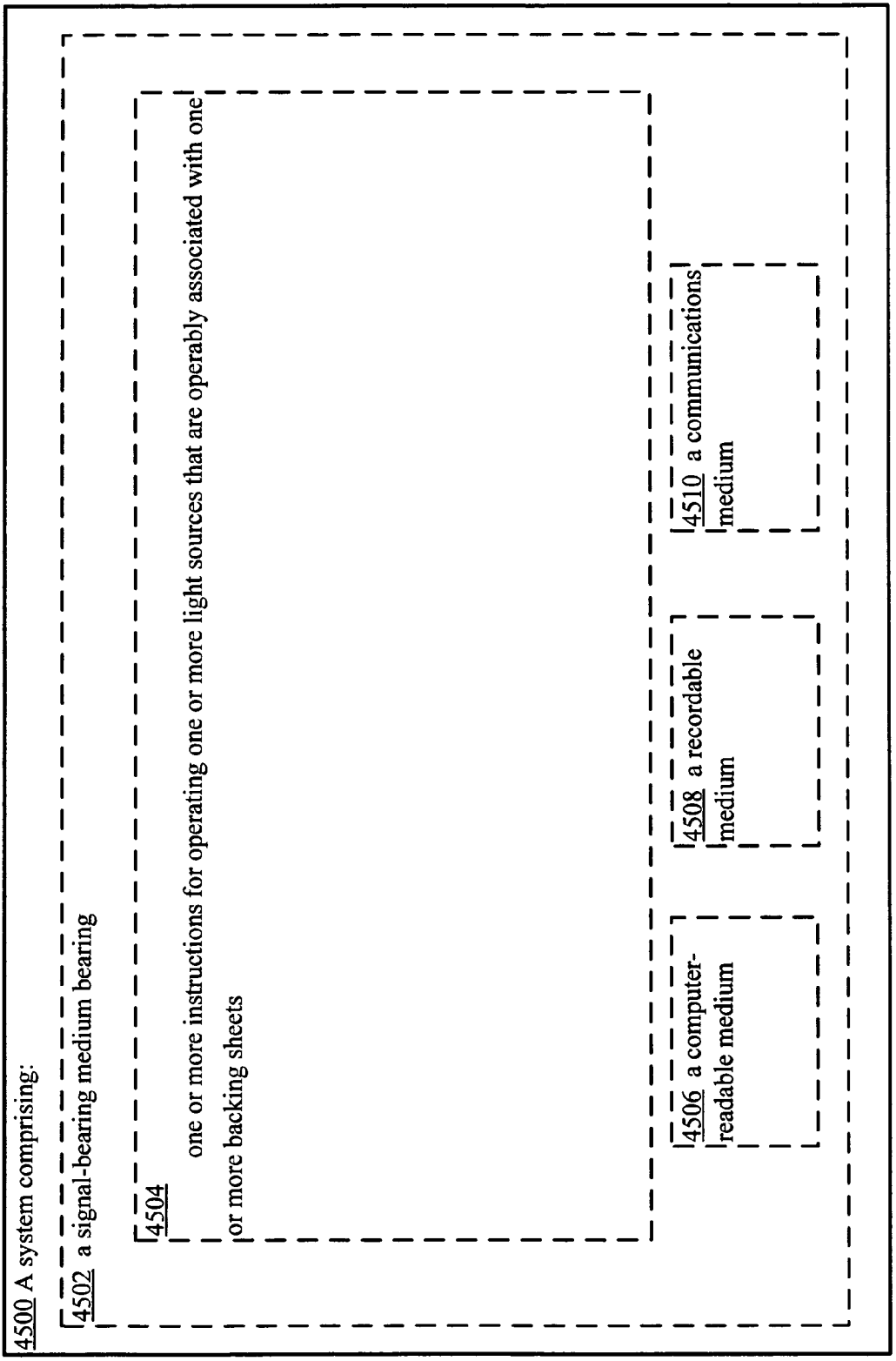
FIG. 45 illustrates a partial view of a system 4500 that includes a computer program for executing a computer process on a computing device.

FIG. 45 illustrates a partial view of a system 4500 that includes a computer program 4504 for executing a computer process on a computing device. An embodiment of system 4500 is provided using a signal-bearing medium 4502 bearing one or more instructions for operating one or more light sources that are operably associated with one or more backing sheets. The one or more instructions may be, for example, computer executable and/or logic-implemented instructions. In some embodiments, the signal-bearing medium 4502 may include a computer-readable medium 4506. In some embodiments, the signal bearing medium 4502 may include a recordable medium 4508. In some embodiments, the signal bearing medium 4502 may include a communications medium 4510.

Figure 46:
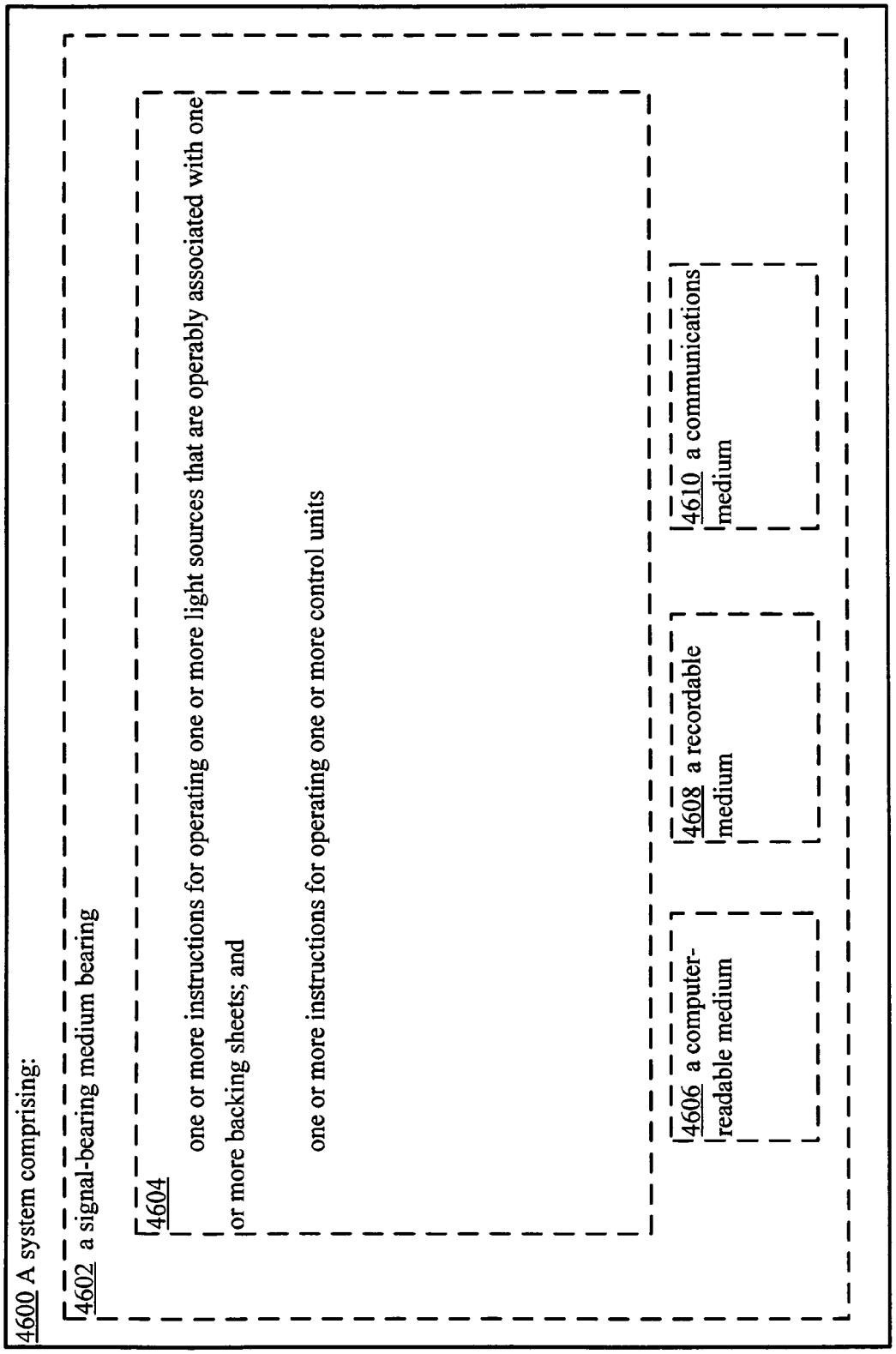
FIG. 46 illustrates a partial view of a system 4600 that includes a computer program for executing a computer process on a computing device.

FIG. 46 illustrates a partial view of a system 4600 that includes a computer program 4604 for executing a computer process on a computing device. An embodiment of system 4600 is provided using a signal-bearing medium 4602 bearing one or more instructions for operating one or more light sources that are operably associated with one or more backing sheets and one or more instructions for operating one or more control units. The one or more instructions may be, for example, computer executable and/or logic-implemented instructions. In some embodiments, the signal-bearing medium 4602 may include a computer-readable medium 4606. In some embodiments, the signal bearing medium 4602 may include a recordable medium 4608. In some embodiments, the signal bearing medium 4602 may include a communications medium 4610.

Figure 47:
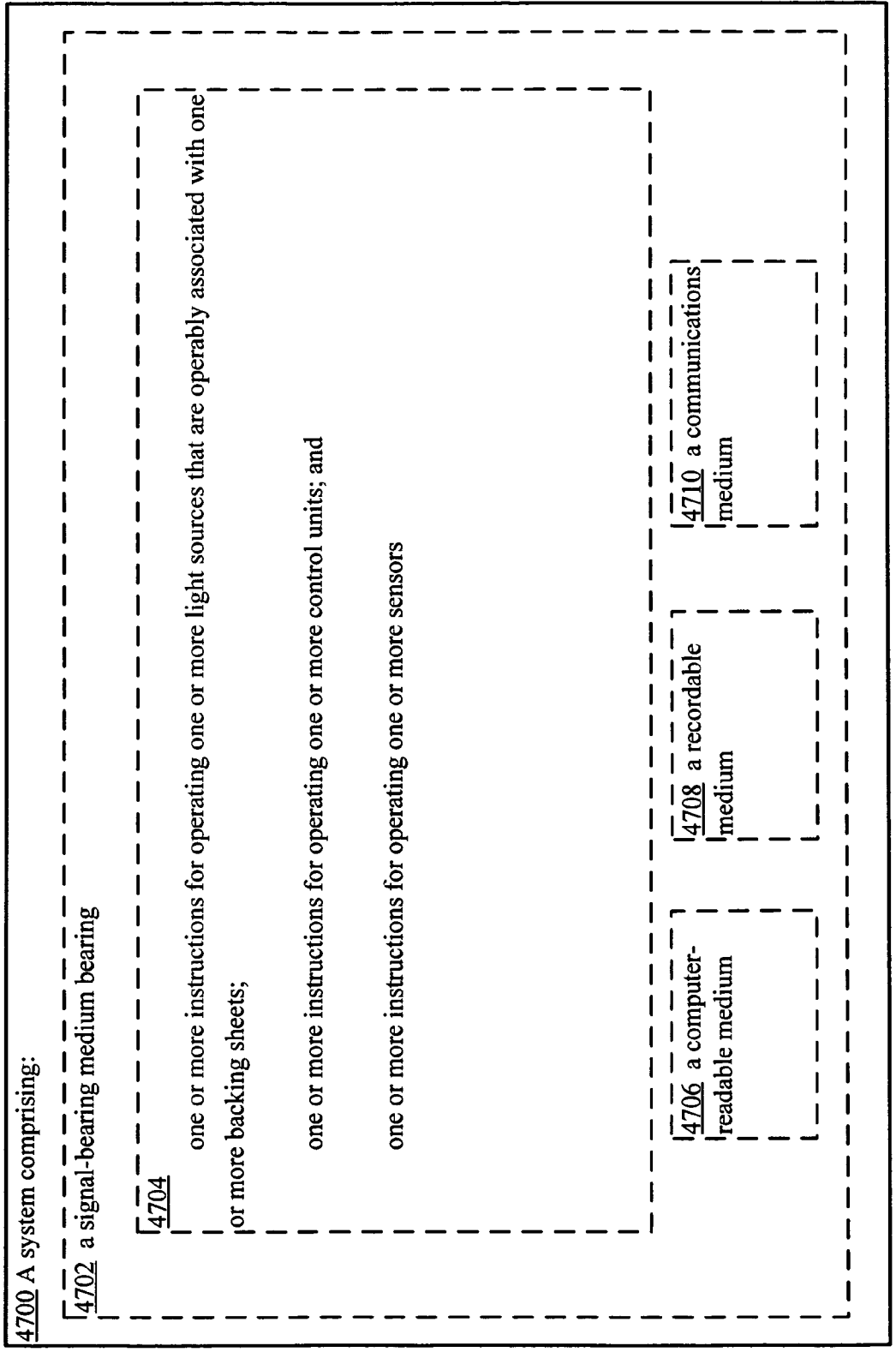
FIG. 47 illustrates a partial view of a system 4700 that includes a computer program for executing a computer process on a computing device.

FIG. 47 illustrates a partial view of a system 4700 that includes a computer program 4704 for executing a computer process on a computing device. All embodiment of system 4700 is provided using a signal-bearing medium 4702 bearing one or more instructions for operating one or more light sources that are operably associated with one or more backing sheets, one or more instructions for operating one or more control units, and one or more instructions for operating one or more sensors. The one or more instructions may be, for example, computer executable and/or logic-implemented instructions. In some embodiments, the signal-bearing medium 4702 may include a computer-readable medium 4706. In some embodiments, the signal bearing medium 4702 may include a recordable medium 4708. In some embodiments, the signal bearing medium 4702 may include a communications medium 4710.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer ma) opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DEAD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electromechanical systems having a wide range of electrical components such as hardware, software, firmware, or digitally any combination thereof; and a wide range of components that may impart mechanical force or motion such as rigid bodies, spring or torsional bodies, hydraulics, and electro-magnetically actuated devices, or Virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electromechanical systems include but are not limited to a variety of consumer electronics systems, as well as other systems such as motorized transport systems, factory automation systems, security systems, and communication/computing systems. Those skilled in the art will recognize that electromechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or an), combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.) (f) a business entity (e.g., an Internet Service Provider (ISP) entity such as Comcast Cable Quest, Southwestern Bell, etc), or (g) a wired/wireless services entity (e.g., such as Sprint, Cingular, Nextel, etc.), etc.

Although the user interface 1140 is shown/described herein as a single illustrated figure that is associated with an individual 150, those skilled in the art will appreciate that a user interface 1140 may be utilized by a user that is a representative of a human user, a robotic user (e.g., computational entity), and/or substantially any combination thereof (e.g., a user may be assisted by one or more robotic based systems). In addition, a user as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, anti two components so associated can also be viewed as being "operably collected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A dressing comprising:
    one or more photolyzable nitric oxide donors;
    one or more light sources configured to emit light that facilitates release of nitric oxide from at least some of the one or more photolyzable nitric oxide donors; and
    at least one control unit configured to operate at least some of the one or more light sources that are configured to emit light that facilitates release of nitric oxide from at least some of the one or more photolyzable nitric oxide donors.

2. The dressing of claim 1, further comprising:
    one or more power supplies.

3. The dressing of claim 1, further comprising:
    one or more optical waveguides.

4. The dressing of claim 1, further comprising:
    one or more quantum dots.

5. The dressing of claim 1, further comprising:
    one or more rare-earth materials.

6. The dressing of claim 1, wherein the one or more light sources configured to emit light that facilitates release of nitric oxide from at least some of the one or more photolyzable nitric oxide donors comprises:
    one or more light emitting diodes configured to emit light that facilitates release of nitric oxide from at least some of the one or more photolyzable nitric oxide donors.

7. The dressing of claim 1, wherein the one or more light sources configured to emit light that facilitates release of nitric oxide from at least some of the one or more photolyzable nitric oxide donors comprises:
    one or more light sources configured to emit visible light that facilitates release of nitric oxide from at least some of the one or more photolyzable nitric oxide donors.

8. The dressing of claim 1, wherein the one or more light sources configured to emit light that facilitates release of nitric oxide from at least some of the one or more photolyzable nitric oxide donors comprises:
    one or more light sources configured to emit infrared light that facilitates release of nitric oxide from at least some of the one or more photolyzable nitric oxide donors.

9. The dressing of claim 1, further comprising:
    one or more receivers.

10. The dressing of claim 1, further comprising:
    one or more transmitters.

11. The dressing of claim 1, wherein the at least one control unit configured to operate at least some of the one or more light sources that are configured to emit light that facilitates release of nitric oxide from at least some of the one or more photolyzable nitric oxide donors comprises:
    at least one control unit configured to regulate at least some of the one or more light sources that are configured to emit light that facilitates release of nitric oxide from at least some of the one or more photolyzable nitric oxide donors.

12. The dressing of claim 1, wherein the at least one control unit configured to operate at least some of the one or more light sources that are configured to emit light that facilitates release of nitric oxide from at least some of the one or more photolyzable nitric oxide donors comprises:
    at least one control unit configured to regulate in response to one or more programs at least some of the one or more light sources that are configured to emit light that facilitates release of nitric oxide from at least some of the one or more photolyzable nitric oxide donors.

13. The dressing of claim 1, wherein the at least one control unit configured to operate at least some of the one or more light sources that are configured to emit light that facilitates release of nitric oxide from at least some of the one or more photolyzable nitric oxide donors comprises:
    at least one control unit configured to regulate in response to one or more commands at least some of the one or more light sources that are configured to emit light that facilitates release of nitric oxide from at least some of the one or more photolyzable nitric oxide donors.

14. The dressing of claim 1, further comprising:
    one or more sensors.

15. The dressing of claim 14, wherein the one or more sensors comprises:
    one or more sensors configured to detect temperature.

16. The dressing of claim 14, wherein the one or more sensors comprises:
    one or more sensors configured to detect hydrostatic pressure.

17. The dressing of claim 14, wherein the one or more sensors comprises:
one or more sensors configured to detect one or more microbes.

18. The dressing of claim 14, wherein the one or more sensors comprises:
one or more sensors configured to detect nitric oxide.

19. The dressing of claim 14, wherein the one or more sensors comprises:
one or more sensors configured to detect the one or more photolyzable nitric oxide donors.

20. The dressing of claim 14, wherein the one or more sensors comprises:
one or more sensors operably coupled to the at least one control unit.

21. The dressing of claim 14, wherein the one or more sensors comprises:
one or more sensors configured to transmit one or more signals.

22. The dressing of claim 14, wherein the one or more sensors comprises:
one or more electrochemical sensors.

23. The dressing of claim 14, wherein the one or more sensors comprises:
one or more semiconductor sensors.

24. The dressing of claim 14, wherein the one or more sensors comprises:
one or more chemical sensors.

25. The dressing of claim 14, wherein the one or more sensors comprises:
one or more pulse rate sensors.

26. The dressing of claim 1, further comprising:
one or more user interfaces.

27. The dressing of claim 1, wherein the one or more light sources configured to emit light that facilitates release of nitric oxide from at least some of the one or more photolyzable nitric oxide donors comprises:
one or more light sources configured to emit ultraviolet light that facilitates release of nitric oxide from at least some of the one or more photolyzable nitric oxide donors.

28. The dressing of claim 1, wherein the dressing is at least one of the following: patch, bandage, tape, drape, sock, glove, condom, wrap, and/or hood.

29. The dressing of claim 1, wherein the at least one control unit configured to operate at least some of the one or more light sources that are configured to emit light that facilitates release of nitric oxide from at least some of the one or more photolyzable nitric oxide donors comprises:
at least one control unit configured to regulate at least one of intensity, pulse rate, wavelength, and/or timing of light emitted from at least some of the one or more light sources.

30. The dressing of claim 1, wherein the at least one control unit configured to operate at least some of the one or more light sources that are configured to emit light that facilitates release of nitric oxide from at least some of the one or more photolyzable nitric oxide donors comprises:
at least one control unit configured to regulate in response to one or more timers at least some of the one or more light sources that are configured to emit light that facilitates release of nitric oxide from at least some of the one or more photolyzable nitric oxide donors.

31. The dressing of claim 1, further comprising:
at least one backing sheet.

32. The dressing of claim 31, wherein the at least one backing sheet comprises:
at least one backing sheet that includes one or more adhesive portions.

33. The dressing of claim 31, wherein the at least one backing sheet comprises:
at least one flexible backing sheet.

34. The dressing of claim 31, wherein the at least one backing sheet comprises:
at least one inflexible backing sheet.

35. The dressing of claim 31, wherein the at least one backing sheet comprises:
at least one of the following types of backing sheets: film, foam, fabric, perforated, fluid impermeable, gas impermeable, vapor impermeable, light impermeable, metallic, non-metallic, hydrophobic, hydrophilic, woven, non-woven, opaque, translucent, transparent, and/or polymeric.

36. The dressing of claim 1, further comprising:
at least one nitric oxide permeable layer.

37. The dressing of claim 36, wherein the at least one nitric oxide permeable layer comprises:
at least one nitric oxide permeable layer that includes one or more adhesive portions.

38. The dressing of claim 36, wherein the at least one nitric oxide permeable layer comprises:
at least one nitric oxide selective membrane.

39. A dressing comprising:
one or more light sources configured to emit light that facilitates release of nitric oxide from one or more photolyzable nitric oxide donors; and
at least one control unit configured to operate at least some of the one or more light sources that are configured to emit light that facilitates release of nitric oxide from one or more photolyzable nitric oxide donors.

40. A system comprising:
one or more light sources configured to emit light that facilitates release of nitric oxide from one or more photolyzable nitric oxide donors onto one or more skin surfaces; and
at least one control unit configured to operate at least some of the one or more light sources that are configured to emit light that facilitates release of nitric oxide from one or more photolyzable nitric oxide donors onto one or more skin surfaces.

* * * * *